United States Patent
Cheng et al.

(10) Patent No.: US 10,189,836 B2
(45) Date of Patent: Jan. 29, 2019

(54) THERAPEUTIC COMPOUNDS, COMPOSITIONS AND METHODS OF USE THEREOF

(71) Applicant: Genentech, Inc., South San Francisco, CA (US)

(72) Inventors: Yun-Xing Cheng, Beijing (CN); Rongbao Hua, Beijing (CN); Terry Kellar, Burlingame, CA (US); Wei Li, Beijing (CN); Paul Gibbons, San Francisco, CA (US); Mark Edward Zak, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/009,596

(22) Filed: Jun. 15, 2018

(65) Prior Publication Data

US 2018/0297997 A1     Oct. 18, 2018

Related U.S. Application Data

(63) Continuation of application No. PCT/EP2016/081553, filed on Dec. 16, 2016.

(30) Foreign Application Priority Data

Dec. 18, 2015   (WO) ................ PCT/CN2015/097932

(51) Int. Cl.
   *C07D 471/04*    (2006.01)
   *C07D 519/00*    (2006.01)
   *A61P 11/06*     (2006.01)

(52) U.S. Cl.
   CPC ............ *C07D 471/04* (2013.01); *A61P 11/06* (2018.01); *C07D 519/00* (2013.01)

(58) Field of Classification Search
   CPC ...... C07D 471/04; C07D 519/00; A61P 11/06
   USPC ..................................... 514/210.18
   See application file for complete search history.

(56) References Cited

FOREIGN PATENT DOCUMENTS

WO    WO-2015032286 A1 * 3/2015 ........... C07D 471/04

* cited by examiner

*Primary Examiner* — Kristin A Vajda
(74) *Attorney, Agent, or Firm* — Tamara A. Kale

(57) ABSTRACT

Compounds of Formula (I) and methods of use as Janus kinase inhibitors are described herein.

15 Claims, No Drawings

THERAPEUTIC COMPOUNDS, COMPOSITIONS AND METHODS OF USE THEREOF

CROSS-REFERENCE TO RELATED APPLICATIONS

This application is a continuation of International Application No. PCT/EP2016/081553, filed Dec. 16, 2016, which claims the benefit of priority to International Application No. PCT/CN2015/097932, filed Dec. 18, 2015, each of which is incorporated by reference herein in its entirety.

FIELD OF THE INVENTION

The field of the invention pertains to compounds that are inhibitors of a Janus kinase, such as JAK1, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3 and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFNgamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIF receptor signalling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) has been approved by the European Commission for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Annu. Rev. Immunol. 22:789-815). IL-4 and IL-13 induce increased mucus production, recruitment of eosinophils to the lung, and increased production of IgE (Kasaian et al., 2008, Biochem. Pharmacol. 76(2): 147-155). IL-9 leads to mast cell activation, which exacerbates the asthma symptoms (Kearley et al., 2011, Am. J. Resp. Crit. Care Med., 183(7): 865-875). The IL-4Rα chain activates JAK1 and binds to either IL-4 or IL-13 when combined with the common gamma chain or the IL-13Rα1 chain respectively (Pernis et al., 2002, J. Clin. Invest. 109(10):1279-1283). The common gamma chain can also combine with IL-9Rα to bind to IL-9, and IL-9Rα activates JAK1 as well (Demoulin et al., 1996, Mol. Cell Biol. 16(9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18(3):314-323). Inhibition of IL-4, IL-13 and IL-9 signaling by blocking the JAK/STAT signaling pathway can alleviate asthmatic symptoms in pre-clinical lung inflammation models (Mathew et al., 2001, J. Exp. Med. 193(9): 1087-1096; Kudlacz et. al., 2008, Eur. J. Pharmacol. 582(1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signalling. A fully human monoclonal antibody targeting the shared p40 subunit of the IL-12 and IL-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

Currently there remains a need for additional compounds that are inhibitors of Janus kinases. For example, there is a need for compounds that possess useful potency as inhibitors of one or more Janus kinases (e.g., JAK1) in combination with other pharmacological properties that are necessary to achieve a useful therapeutic benefit. For example, there is a need for potent compounds that demonstrate selectivity for one Janus kinase over other kinases in general. There is also a need for potent compounds that demonstrate selectivity for one Janus kinase over other Janus kinases (e.g., selectivity for JAK1 over other Janus kinases). Kinases demonstrating selectivity for JAK1 could provide a therapeutic benefit, with fewer side effects, in conditions responsive to the inhibition of JAK1. Additionally there is currently a need for potent JAK1 inhibitors that possess other properties (e.g., melting point, pK, solubility, etc.) necessary for formulation and administration by inhalation. Such compounds would be particularly useful for treating conditions such as, for example, asthma.

SUMMARY OF INVENTION

One aspect of the invention includes a compound of Formula (I):

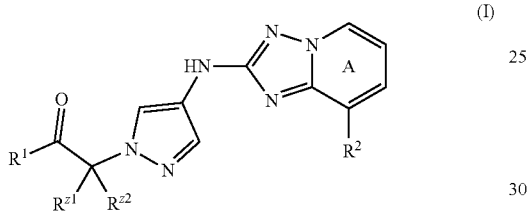

(I)

or a salt or stereoisomer thereof, wherein:
R$^1$ is a 3-11 membered heterocyclyl that is optionally substituted with one or more R$^a$;
R$^2$ is selected from the group consisting of:

(a)
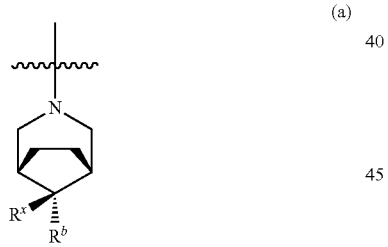

(b)
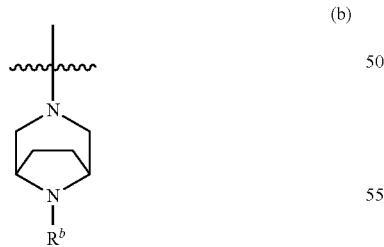

(c)
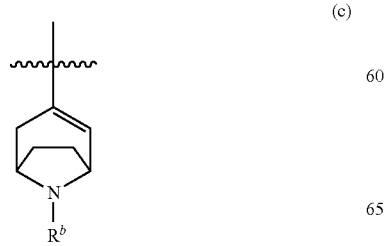

(d)
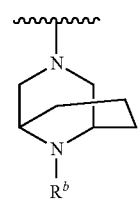

(e)
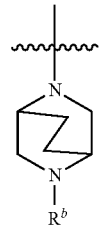

(f)
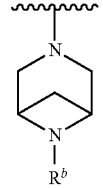

(g)
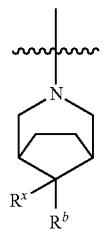

(h)
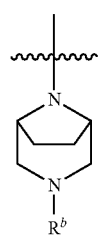

(i)
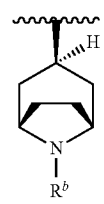

(j)
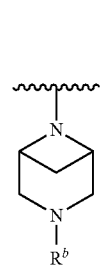

(o)

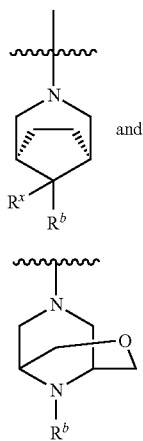

and (p)

each $R^a$ is independently selected from the group consisting of OH, halo, $C_1$-$C_6$alkyl, $C_3$-$C_8$cycloalkyl, 6-10 membered aryl, 3-11 membered heterocyclyl, C(O)NR$^c$R$^d$, NR$^c$R$^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, ($C_1$-$C_6$alkyl)S—, $C_3$-$C_8$cycloalkyl, 3-11 membered heterocyclyl that is optionally substituted with one or more groups independently selected from the group consisting of —C(O)—NR$^c$R$^d$, —C(O)—OR$^k$, —($C_1$-$C_6$alkyl)-C(O)—NR$^c$R$^d$, and —($C_1$-$C_6$alkyl)-C(O)—OR$^k$, and $C_1$-$C_6$alkyl that is optionally substituted with one or more groups independently selected from the group consisting of halo, $C_1$-$C_6$alkoxy, and $C_3$-$C_8$cycloalkyl; $R^b$ is selected from the group consisting of hydrogen, —OR$^k$, —CN, $C_1$-$C_6$alkyl, $C_3$-$C_8$cycloalkyl, 6-10 membered aryl, 3-11 membered heterocyclyl, —NR$^s$R$^t$, —C(O)NR$^f$R$^g$, —S(O)$_n$R$^e$, —S(O)$_2$NR$^f$R$^g$, —NR$^c$C(O)R$^m$, and —C(O)R$^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from R$^h$; and R$^x$ is selected from the group consisting of hydrogen and $C_1$-$C_6$alkyl that is optionally substituted with one or more groups independently selected from halo, cyano, and $C_1$-$C_6$alkoxy; or $R^b$ and $R^x$ taken together form a $C_1$-$C_6$alkenylene that is optionally substituted with one or more groups independently selected from halo, cyano, and $C_1$-$C_6$alkoxy;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl; or alternatively $R^c$ and $R^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, cyano, hydroxy, $C_1$-$C_6$alkoxy, —SH, ($C_1$-$C_6$alkyl)S—, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, R$^p$, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively $R^f$ and $R^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, ($C_1$-$C_6$alkyl)S—, cyano, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, cyano, S(O)$_2$NR$^f$R$^g$, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, —S(O)$_2$($C_1$-$C_6$alkyl), $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, 6-10 membered aryl and 3-11 membered heterocyclyl, wherein any said 6-10 aryl and 3-11 membered heterocyclyl is optionally substituted with halo, cyano, ($C_1$-$C_6$alkyl)$_2$NC(O)—, or $C_1$-$C_6$alkyl that is optionally substituted with one or more groups independently selected from the group consisting of halo, $C_1$-$C_6$alkoxy, cyano, hydroxy, and $C_3$-$C_8$cycloalkyl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl is optionally substituted with one or more groups R$^n$;

each $R^n$ is independently selected from the group consisting of halo, cyano, hydroxy, $C_1$-$C_6$alkyl, $C_1$-$C_6$alkoxy, $C_3$-$C_8$cycloalkyl, —SH, —NR$^u$R$^v$, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano;

each $R^p$ is independently selected from the group consisting of $C_3$-$C_8$cycloalkyl, 6-10 membered aryl, and 3-11 membered heterocyclyl, wherein any $C_3$-$C_8$cycloalkyl, 6-10 membered aryl, and 3-11 membered heterocyclyl is optionally substituted with one or more groups independently selected from the group consisting of halo, cyano, hydroxy, $C_1$-$C_6$alkoxy, $C_3$-$C_8$cycloalkyl, —SH, ($C_1$-$C_6$alkyl)S—, and $C_1$-$C_6$alkyl that is optionally substituted with one or more groups independently selected from the group consisting of halo, hydroxy, $C_1$-$C_6$alkoxy, cyano, and $C_3$-$C_8$cycloalkyl;

$R^s$ and $R^t$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl;

$R^u$ and $R^o$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl;

n is 0, 1, or 2;

$R^{z1}$ and $R^{z2}$ are each independently selected from hydrogen and $C_1$-$C_6$alkyl; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl. In some embodiments, ring A is not optionally substituted.

Also provided is a pharmaceutical composition that comprises a compound of the invention and a pharmaceutically acceptable carrier, diluent or excipient.

Another aspect includes a compound of the invention for use in therapy, such as the treatment of an inflammatory disease or cancer.

Another aspect includes a method of preventing, treating or lessening the severity of a disease or condition responsive to the inhibition of a Janus kinase, such as JAK1 kinase, in a patient. The method can comprise administering to the patient a therapeutically effective amount of a compound of the invention.

Another aspect includes the use of a compound of the invention in the manufacture of a medicament for the treatment of a disease responsive to the inhibition of a Janus kinase, such as JAK1 kinase.

Another aspect includes a kit for treating a disease or disorder responsive to the inhibition of a Janus kinase, such as JAK1 kinase. The kit can comprise a first pharmaceutical composition comprising a compound of the invention, and instructions for use.

Certain compounds of the invention possess beneficial potency as inhibitors of one or more Janus kinase (e.g., JAK1). Certain compounds are also, a) selective for one Janus kinase over other kinases, b) selective for JAK1 over other Janus kinases, and/or c) possess other properties (e.g., melting point, pK, solubility, etc.) necessary for formulation and administration by inhalation. Certain compounds of Formula (I) may be particularly useful for treating conditions such as asthma.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_8$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl. In some embodiments, substituents for "optionally substituted alkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "$C_1$-$C_6$alkenylene" refers to a linear or branched-chain divalent hydrocarbon radical (e.g. $C_1$-$C_5$alkyl)CH= and ($C_1$-$C_4$alkyl)($CH_3$)C=), wherein the alkenylene radical may be optionally substituted.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy) phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl) phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

The terms "compound(s) of the invention," and "compound(s) of the present invention" and the like, unless otherwise indicated, include compounds of Formula (I), (I-I), (I-II), (Ia), (Ib), (Ic), (Id), (Ie), (If), (Ig), (Ih), (Ii), (Ij), (Im), (In), (Io), (Ip), (Iq) and the compounds of Tables 1 and 2 herein, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1] heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heterocyclic group", "heterocyclic", "heterocycle", "heterocyclyl", or "heterocyclo" are used interchangeably and refer to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl$, $[NR_4]^+OH$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13th ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy.

The term "alkanoyl" refers to group (alkyl)-C(=O)—, wherein alkyl is as defined herein. For example, $C_1$-$C_6$alkanoyl refers to a group of formula ($C_1$-$C_5$alkyl)-C(=O)—. Alkanoyl groups include, formyl, acetyl, propanoyl, isopropanoyl, butanoyl, isobutanoyl, pentanoyl, 3-methylpentanoyl, and hexanoyl.

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line "⁓" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$—$R^2$—$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethyl aminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the invention can exist in unsolvated forms as well as solvated forms, including hydrated forms. A "solvate" refers to an association or complex of one or more solvent molecules and a compound of the present invention.

Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4''-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl) methylsilyl)ethyl, p-toluenesulfonyl ethyl, 4-nitrobenzyl sulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silyl-ethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, P3-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarb onyloxymethyl, N—($C_1$-$C_6$)alkoxycarbonylaminomethyl, succinoyl, ($C_1$-$C_6$)alkanoyl, alpha-amino($C_1$. $C_4$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase. In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

In some embodiments, a compound of Formula (I) is selective for inhibition of JAK1 over JAK3 and TYK2. In some embodiments, a compound of Formula (I) is selective for inhibition of JAK1 over JAK2, JAK3, or TYK2, or any combination of JAK2, JAK3, or TYK2. In some embodiments, a compound of Formula (I) is selective for inhibition of JAK1 and JAK2 over JAK3 and TYK2. In some embodiments, a compound of Formula (I) is selective for inhibition of JAK1 over JAK3. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of a particular Janus kinase (e.g., JAK1) activity compared to another particular Janus kinase (e.g., JAK3) activity, or is at least a 2-, 3-, 4-, 5-, 10-, 25-, 50-, 100-, 250-, or 500-fold better inhibitor of a particular Janus kinase (e.g., JAK1) activity compared to another particular Janus kinase (e.g., JAK3) activity.

"Therapeutically effective amount" means an amount of a compound of the present invention, such as a compound of Formula (I), (I-I), (I-II), (Ia), (Ib), (Ic), (Id), (Ie), (If), (Ig), (Ih), (Ii), (Ij), (Im), (In), (Io), (Ip), or (Iq), or a compound of Table 1 or 2, that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula (I), (I-I), (I-II), (Ia), (Ib), (Ic), (Id), (Ie), (If), (Ig), (Ih), (i), (Ij), (Im), (In), (Io), (Ip), or (Iq), or a compound of Table 1 or 2, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

Unless otherwise stated, structures depicted herein are also meant to include compounds that differ only in the presence of one or more isotopically enriched atoms.

Exemplary isotopes that can be incorporated into compounds of the invention, include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of the invention, one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention.

Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

As noted, one aspect of the invention includes a compound of Formula (I):

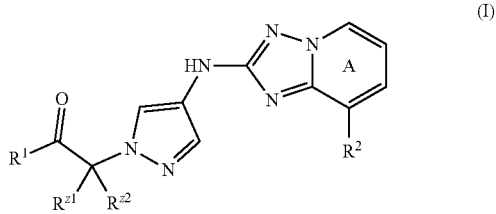

or a salt or stereoisomer thereof, wherein:

$R^1$ is a 3-11 membered heterocyclyl that is optionally substituted with one or more $R^a$;

$R^2$ is selected from the group consisting of:

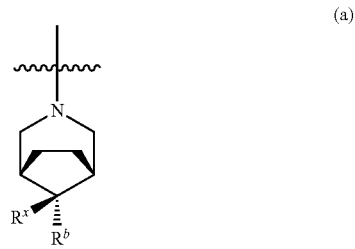

(a)

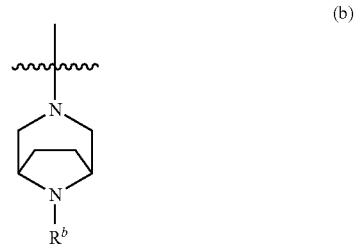

(b)

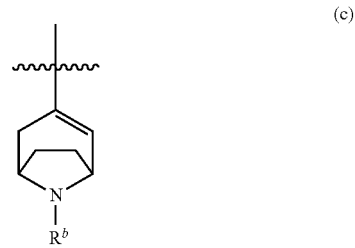

(c)

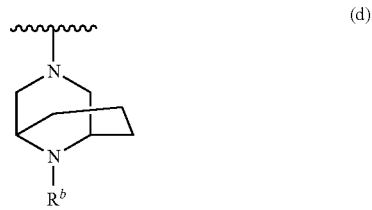

(d)

(e) 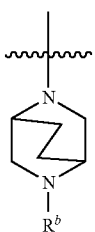

(f) 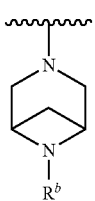

(g) 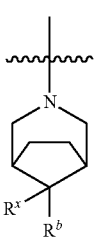

(h) 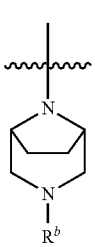

(i) 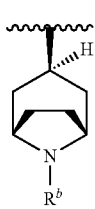

(j) 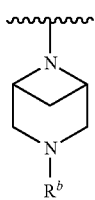

(o) 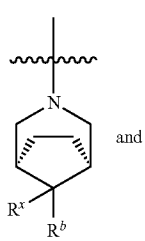 and (p) 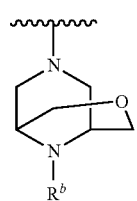

each $R^a$ is independently selected from the group consisting of OH, halo, $C_1$-$C_6$alkyl, $C_3$-$C_8$cycloalkyl, 6-10 membered aryl, 3-11 membered heterocyclyl, $C(O)NR^cR^d$, $NR^cR^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, $(C_1$-$C_6$alkyl)S—, $C_3$-$C_8$cycloalkyl, 3-11 membered heterocyclyl that is optionally substituted with one or more groups independently selected from the group consisting of —C(O)—$NR^cR^d$, —C(O)—$OR^k$, —($C_1$-$C_6$alkyl)-C(O)—$NR^cR^d$, and —($C_1$-$C_6$alkyl)-C(O)—$OR^k$, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —$OR^k$, —CN, $C_1$-$C_6$alkyl, $C_3$-$C_8$cycloalkyl, 6-10 membered aryl, 3-11 membered heterocyclyl, —$NR^sR^t$, —C(O)$NR^fR^g$, —$S(O)_nR^e$, —$S(O)_2NR^fR^g$, —$NR^cC(O)R^m$, and —$C(O)R^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from $R^h$; and $R^x$ is selected from the group consisting of hydrogen and $C_1$-$C_6$alkyl that is optionally substituted with one or more groups independently selected from halo, cyano, and $C_1$-$C_6$alkoxy; or $R^b$ and $R^x$ taken together form a $C_1$-$C_6$alkenylene that is optionally substituted with one or more groups independently selected from halo, cyano, and $C_1$-$C_6$alkoxy;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl; or alternatively $R^c$ and $R^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, cyano, hydroxy, $C_1$-$C_6$alkoxy, —SH, $(C_1$-$C_6$alkyl)S—, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, $R^p$, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively $R^f$ and $R^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, ($C_1$-$C_6$alkyl)S—, cyano, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, cyano, $S(O)_2NR^fR^g$, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, —S(O)$_2$($C_1$-$C_6$alkyl), $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, 6-10 membered aryl and 3-11 membered heterocyclyl, wherein any said 6-10 aryl and 3-11 membered heterocyclyl is optionally substituted with halo, cyano, ($C_1$-$C_6$alkyl)$_2$NC(O)—, or $C_1$-$C_6$alkyl that is optionally substituted with one or more groups independently selected from the group consisting of halo, $C_1$-$C_6$alkoxy, cyano, hydroxy, and $C_3$-$C_8$cycloalkyl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl is optionally substituted with one or more groups $R^n$;

each $R^n$ is independently selected from the group consisting of halo, cyano, hydroxy, $C_1$-$C_6$alkyl, $C_1$-$C_6$alkoxy, $C_3$-$C_8$cycloalkyl, —SH, —NR$^u$R$^v$, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano;

each $R^p$ is independently selected from the group consisting of $C_3$-$C_8$cycloalkyl, 6-10 membered aryl, and 3-11 membered heterocyclyl, wherein any $C_3$-$C_8$cycloalkyl, 6-10 membered aryl, and 3-11 membered heterocyclyl is optionally substituted with one or more groups independently selected from the group consisting of halo, cyano, hydroxy, $C_1$-$C_6$alkoxy, $C_3$-$C_8$cycloalkyl, —SH, ($C_1$-$C_6$alkyl)S—, and $C_1$-$C_6$alkyl that is optionally substituted with one or more groups independently selected from the group consisting of halo, hydroxy, $C_1$-$C_6$alkoxy, cyano, and $C_3$-$C_8$cycloalkyl;

$R^s$ and $R^t$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl;

$R^u$ and $R^v$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl;

n is 0, 1, or 2;

$R^{z1}$ and $R^{z2}$ are each independently selected from hydrogen and $C_1$-$C_6$alkyl; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl. In some embodiments, ring A is not optionally substituted.

Another aspect of the invention includes a compound of Formula (I-0):

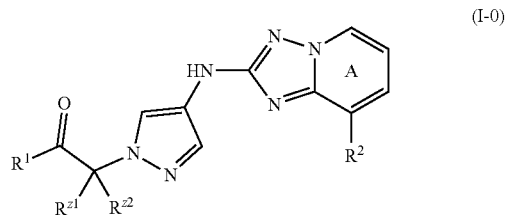

(I-0)

or a salt or stereoisomer thereof, wherein:

$R^1$ is a 3-11 membered heterocyclyl that is optionally substituted with one or more $R^a$;

$R^2$ is selected from the group consisting of:

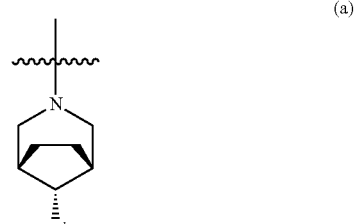

(a)

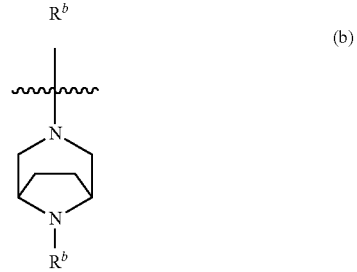

(b)

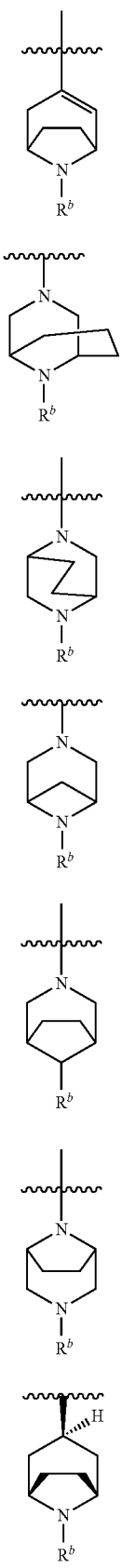
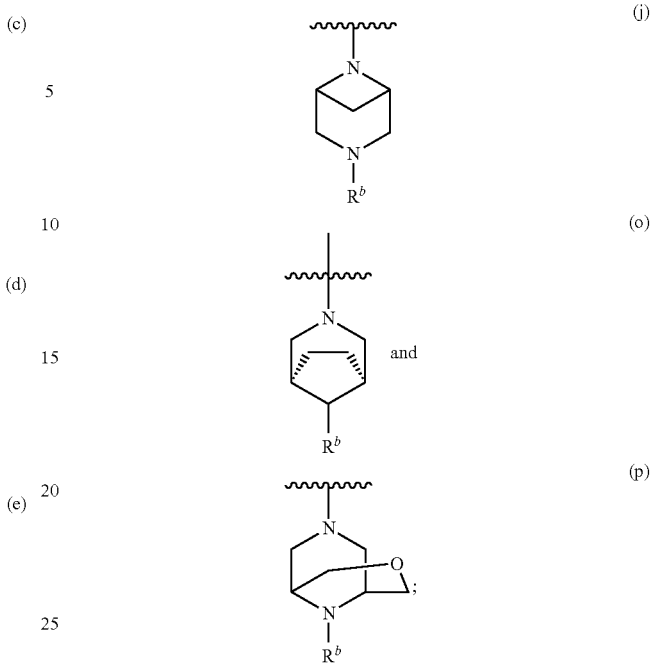

each $R^a$ is independently selected from the group consisting of OH, halo, $C_1$-$C_6$alkyl, $C_3$-$C_8$cycloalkyl, 6-10 membered aryl, 3-11 membered heterocyclyl, $C(O)NR^cR^d$, $NR^cR^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, $C_3$-$C_8$cycloalkyl, 3-11 membered heterocyclyl that is optionally substituted with —($C_1$-$C_6$alkyl)-C(O)—$NR^cR^d$ or —($C_1$-$C_6$alkyl)-C(O)—$OR^k$, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —$OR^k$, —CN, $C_1$-$C_6$alkyl, $C_3$-$C_8$cycloalkyl, 6-10 membered aryl, 3-11 membered heterocyclyl, $NR^cR^d$, —C(O) $NR^fR^g$, —S(O)$_n$$R^e$, —S(O)$_2$$NR^fR^g$, and —C(O)$R^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from $R^h$;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl; or alternatively $R^c$ and $R^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, $C_1$-$C_6$alkoxy, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively $R^f$ and $R^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, cyano, $S(O)_2NR^fR^g$, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, 6-10 membered aryl and 3-11 membered heterocyclyl, wherein any said 6-10 aryl and 3-11 membered heterocyclyl is optionally substituted with halo, cyano, or $C_1$-$C_6$alkyl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl is optionally substituted with one or more groups $R^n$;

each $R^n$ is independently selected from the group consisting of halo, cyano, $C_1$-$C_6$alkyl, $C_1$-$C_6$alkoxy, $C_3$-$C_8$cycloalkyl, —SH, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano;

n is 0, 1, or 2;

$R^{z1}$ and $R^{z2}$ are each independently selected from hydrogen and $C_1$-$C_6$alkyl; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl. In some embodiments, ring A is not optionally substituted.

Also provided is a compound of Formula (I) that further defined as a compound of Formula (I-I):

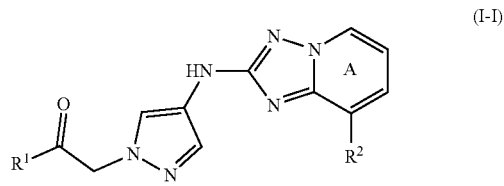

(I-I)

or a salt or stereoisomer thereof, wherein:

$R^1$ is a 3-11 membered heterocyclyl that is optionally substituted with one or more $R^a$;

$R^2$ is selected from the group consisting of:

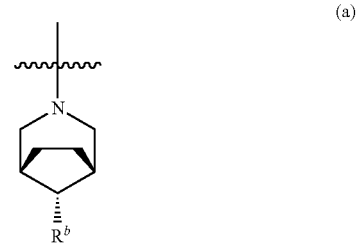

(a)

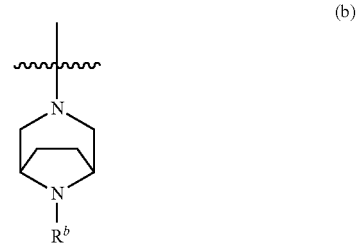

(b)

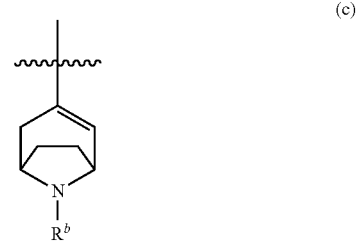

(c)

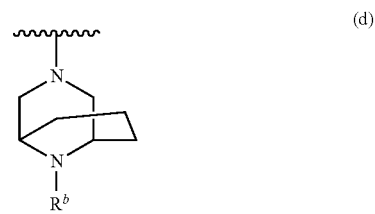

(d)

-continued (e)
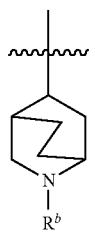

(f)
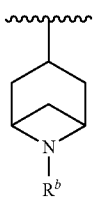

(g)
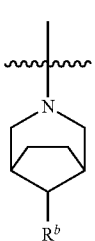

(h)
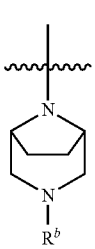

(i)

and (j)
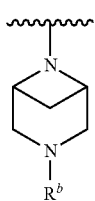

each $R^a$ is independently selected from the group consisting of OH, halogen, $C_1$-$C_6$alkyl, $C_3$-$C_8$cycloalkyl, 6-10 membered aryl, 3-11 membered heterocyclyl, C(O)NR$^c$R$^d$, NR$^c$R$^d$, and $C_1$-$C_6$alkanoyl, wherein said alkyl, cycloalkyl, alkanoyl, 6-10 membered aryl, 3-11 membered heterocyclyl are optionally substituted with one or more groups independently selected from the group consisting of halo, $C_1$-$C_6$alkoxy, $C_3$-$C_8$cycloalkyl, 3-11 membered heterocyclyl, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —OR$^k$, —CN, $C_1$-$C_6$alkyl, $C_3$-$C_8$cycloalkyl, 6-10 membered aryl, 3-11 membered heterocyclyl, —C(O)NR$^f$R$^g$, —S(O)$_n$R$^e$, —S(O)$_2$NR$^f$R$^g$, and —C(O)R$^m$, wherein said $C_1$-$C_6$alkyl, $C_3$-$C_8$cycloalkyl, $C_1$-$C_6$alkanoyl, 6-10 membered aryl, and 3-11 membered heterocyclyl, are each independently optionally substituted with one or more groups independently selected from R$^h$;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively $R^c$ and $R^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, $C_1$-$C_6$alkoxy, $C_3$-$C_8$cycloalkyl, and $C_1$-$C_6$alkyl that is optionally substituted with one or more groups independently selected from the group consisting of halo, $C_1$-$C_6$alkoxy, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively $R^f$ and $R^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, and 6-10 membered aryl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl of R''' is optionally substituted with one or more groups R'';

each R'' is independently selected from the group consisting of halo, cyano, $C_1$-$C_6$alkyl, $C_1$-$C_6$alkoxy, $C_3$-$C_8$cycloalkyl, —SH, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano;

n is 0, 1, or 2; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl. In some embodiments, ring A is not optionally substituted.

In some embodiments, $R^{z1}$ and $R^{z2}$ are each hydrogen. In some embodiments, $R^{z1}$ is hydrogen and $R^{z2}$ is $C_1$-$C_6$alkyl.

Also provided is a compound selected from Examples 1-199 of Table 1. Although specific salts may be shown in Table 1, it is to be understood that other salts are contemplated, such as described herein.

In one embodiment a compound of Formula (Ia):

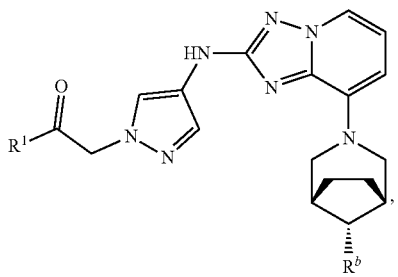

(Ia)

or a salt or stereoisomer thereof is provided.

In one embodiment a compound of Formula (Ib):

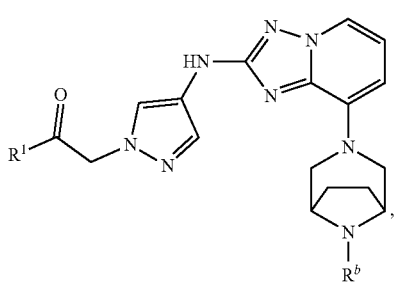

(Ib)

or a salt or stereoisomer thereof is provided.

In one embodiment a compound of Formula (Ic):

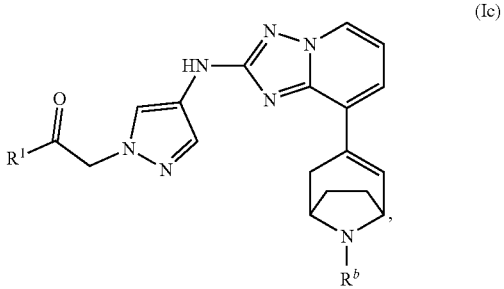

(Ic)

or a salt or stereoisomer thereof is provided.

In one embodiment a compound of Formula (Id):

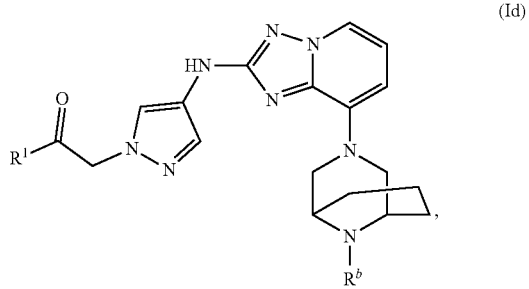

(Id)

or a salt or stereoisomer thereof is provided.

In one embodiment a compound of Formula (Ie):

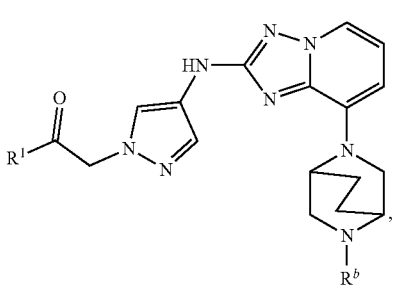

(Ie)

or a salt or stereoisomer thereof is provided.

In one embodiment a compound of Formula (If):

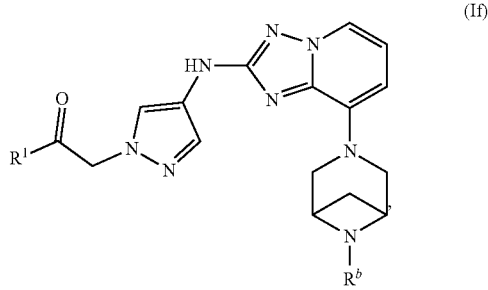

(If)

or a salt or stereoisomer thereof is provided.

In one embodiment a compound of Formula (Ig):

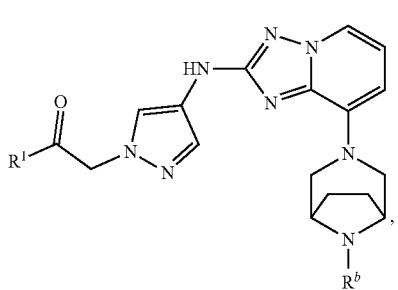

(Ig)

or a salt or stereoisomer thereof is provided.

In one embodiment a compound of Formula (Ih):

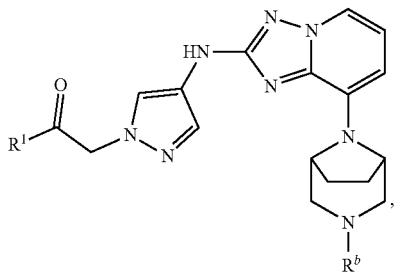

(Ih)

or a salt or stereoisomer thereof is provided.

In one embodiment a compound of Formula (Ii):

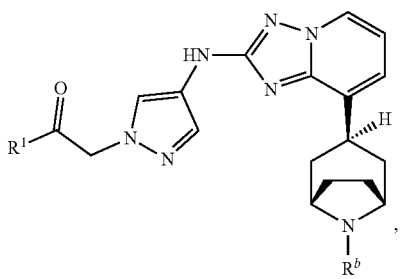

(Ii)

or a salt or stereoisomer thereof is provided.

In one embodiment a compound of Formula (Ij):

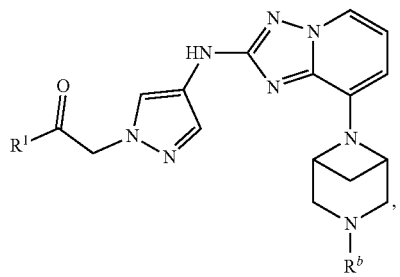

(Ij)

or a salt or stereoisomer thereof is provided.

In one embodiment a compound of Formula (Io):

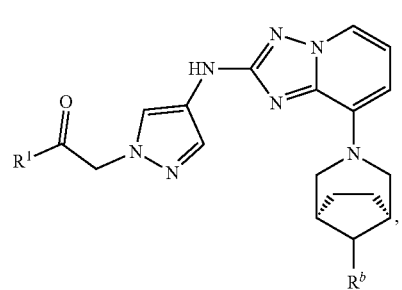

(Io)

or a salt or stereoisomer thereof is provided.

In one embodiment a compound of Formula (Ip):

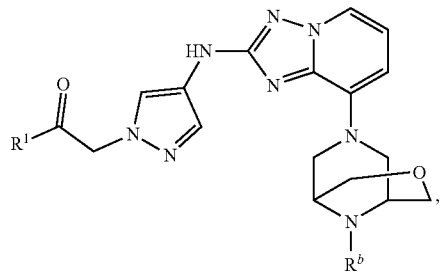

(Ip)

or a salt or stereoisomer thereof is provided.

In one embodiment a compound of Formula (Iaa):

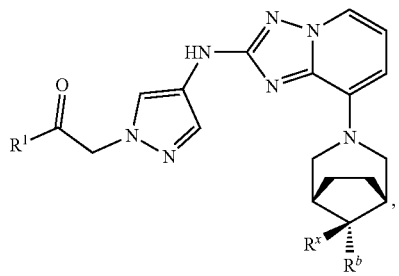

(Iaa)

or a salt or stereoisomer thereof is provided.

In one embodiment a compound of Formula (Igg):

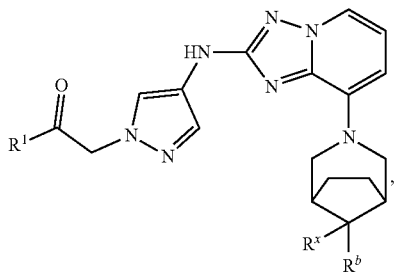

(Igg)

or a salt or stereoisomer thereof is provided.

In one embodiment a compound of Formula (Ioo):
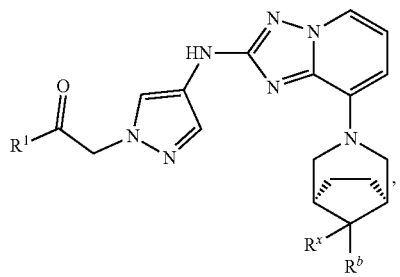
or a salt or stereoisomer thereof is provided.
In one embodiment $R^1$ of a compound, salt or stereoisomer of Formula (I) is selected from the group consisting of:
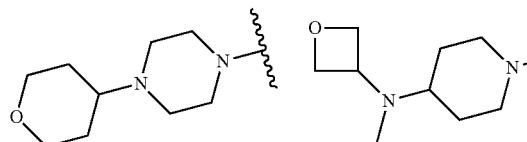
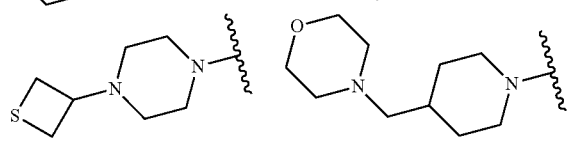
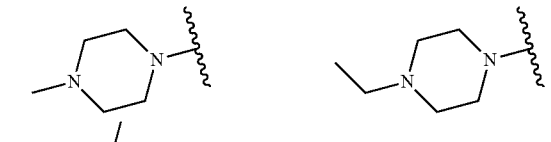
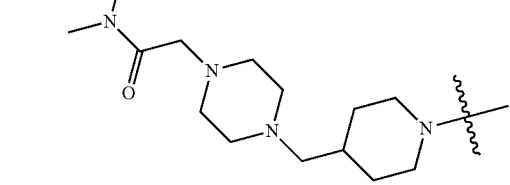
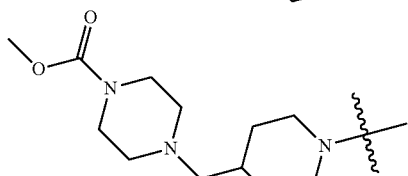
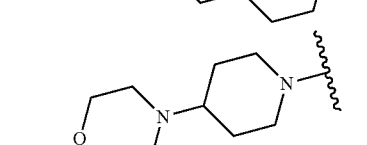
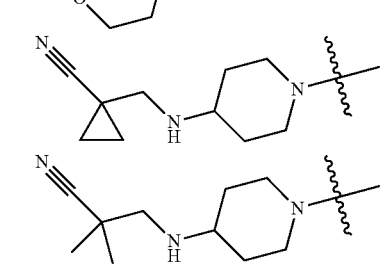
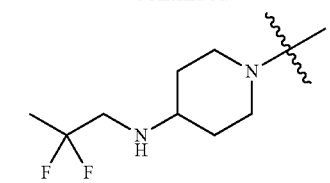
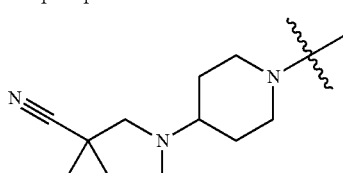
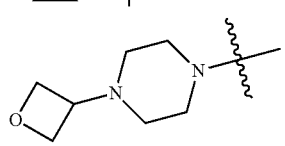
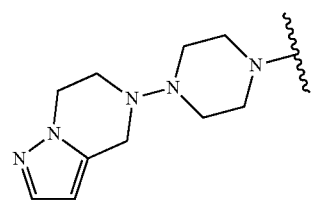
and
In one embodiment $R^1$ of a compound, salt or stereoisomer of Formula (I) is selected from the group consisting of:
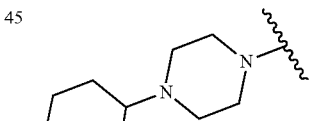
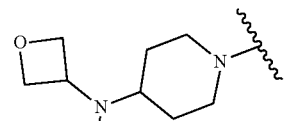
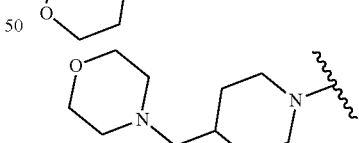
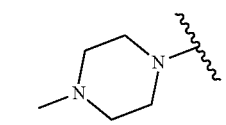
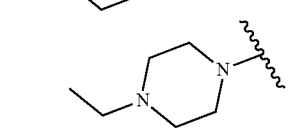
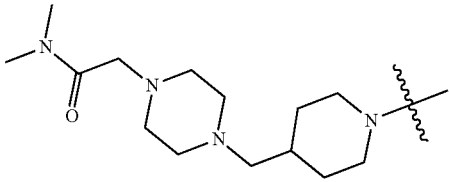
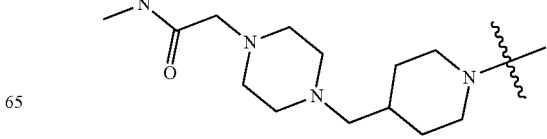

-continued
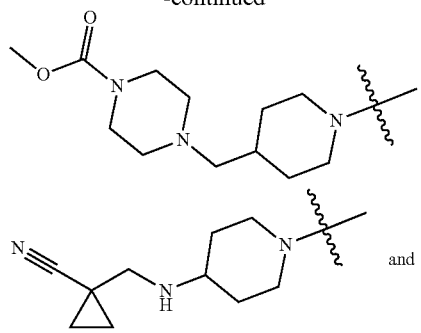
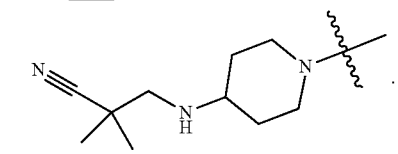
In one embodiment R¹ of a compound, salt or stereoisomer of Formula (I) is selected from the group consisting of:
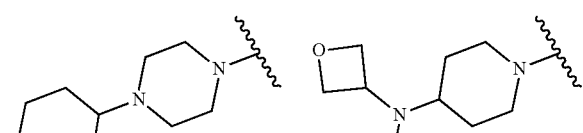
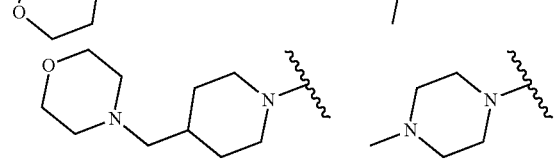
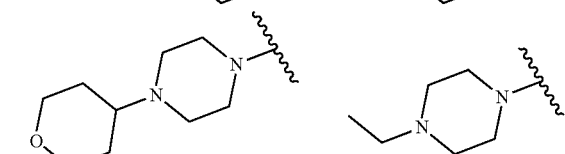
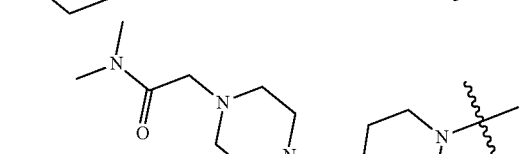
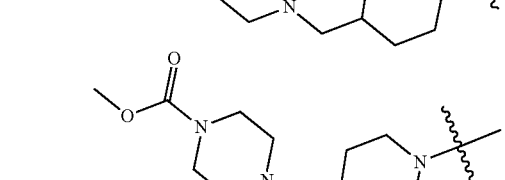
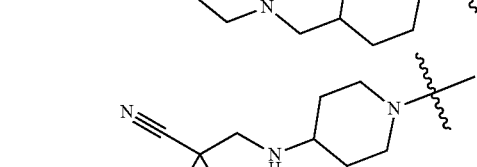
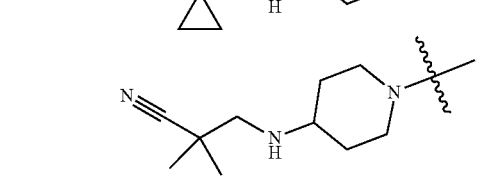
-continued
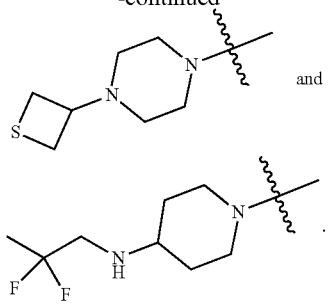
In one embodiment R¹ of a compound, salt or stereoisomer of Formula (I) is selected from the group consisting of:
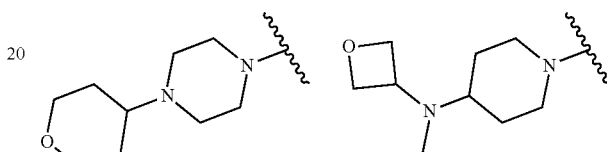
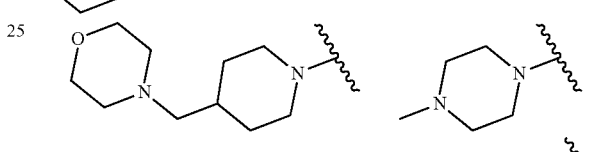
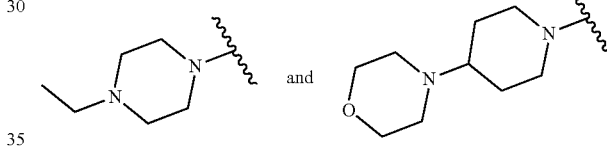
In one embodiment R² of a compound, salt or stereoisomer of Formula (I) is selected from the group consisting of:
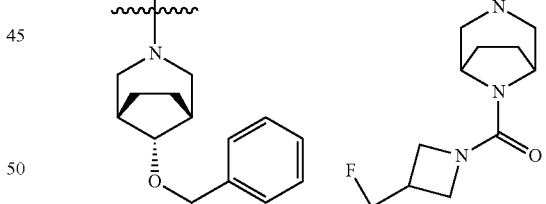
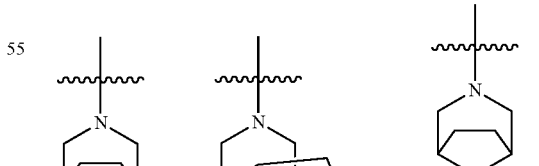
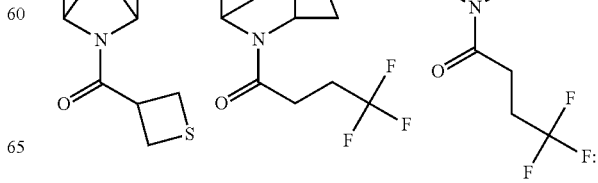

-continued
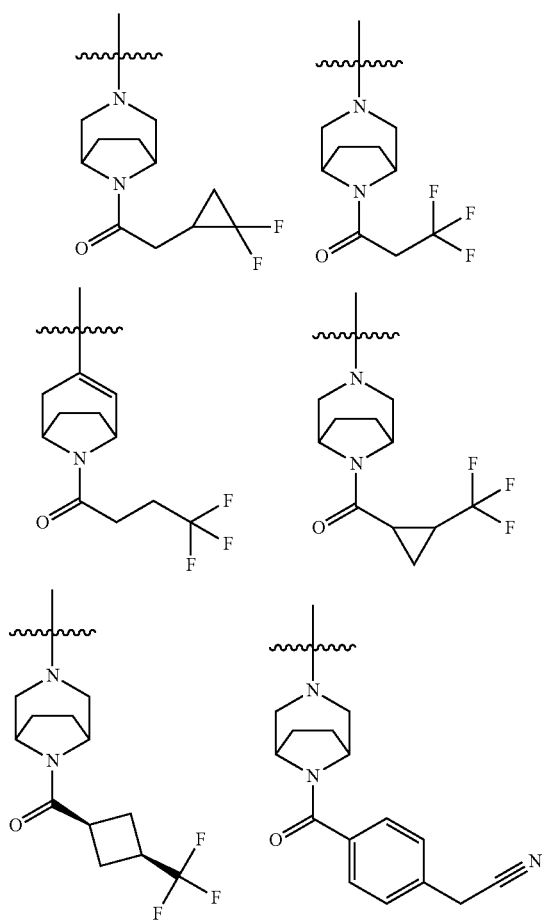
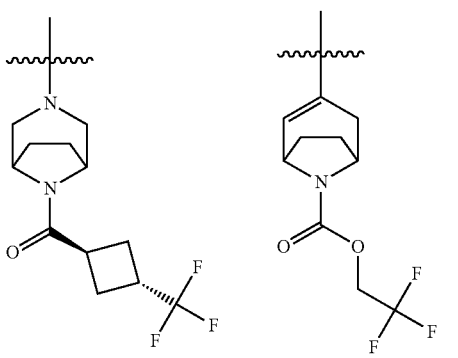
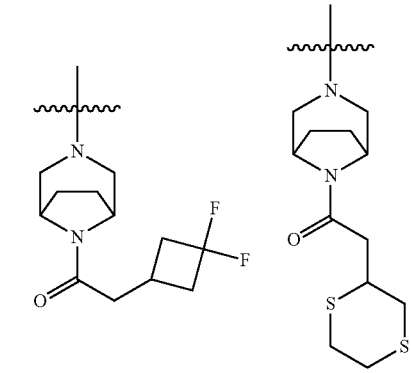
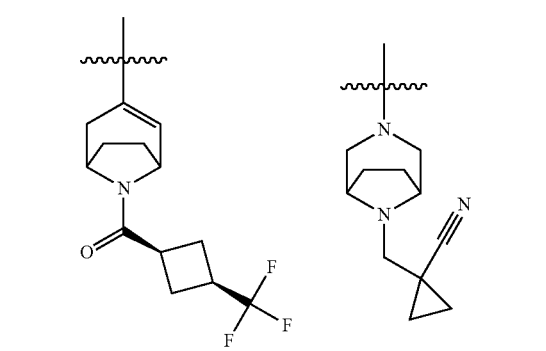
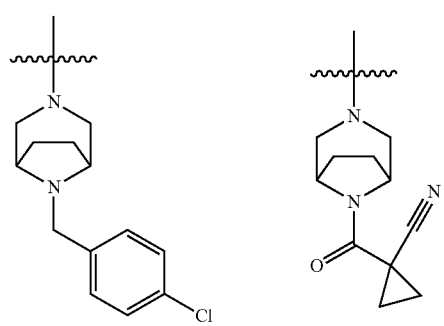

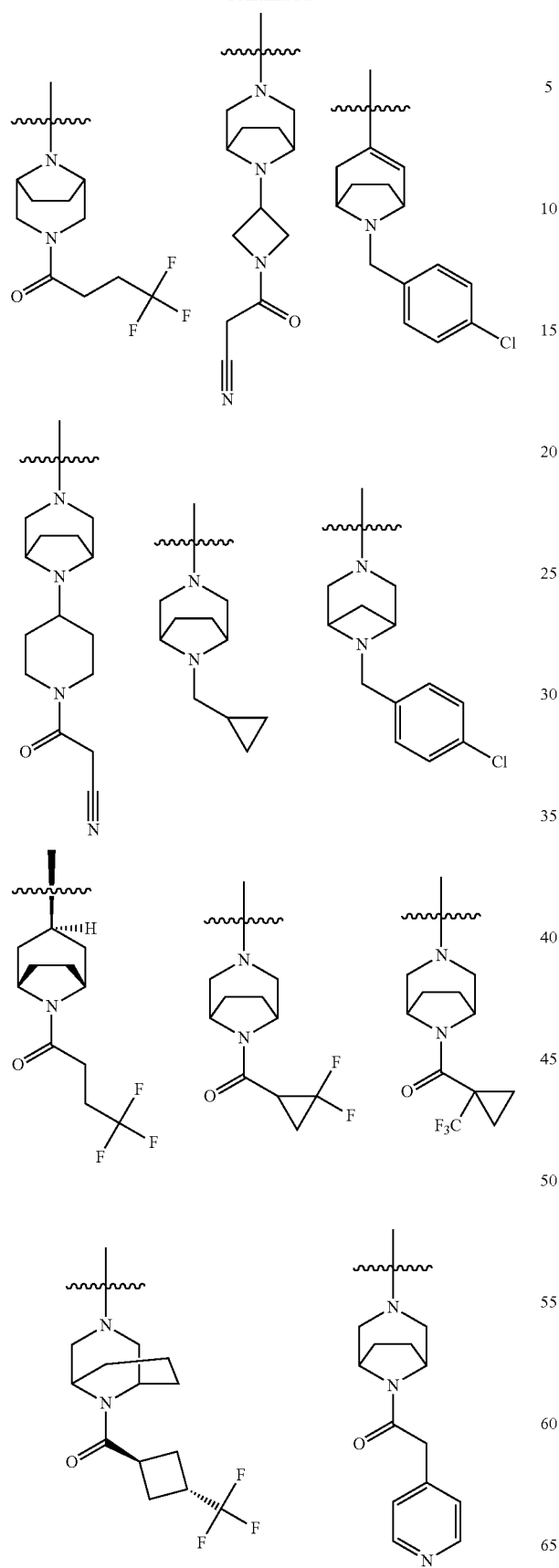
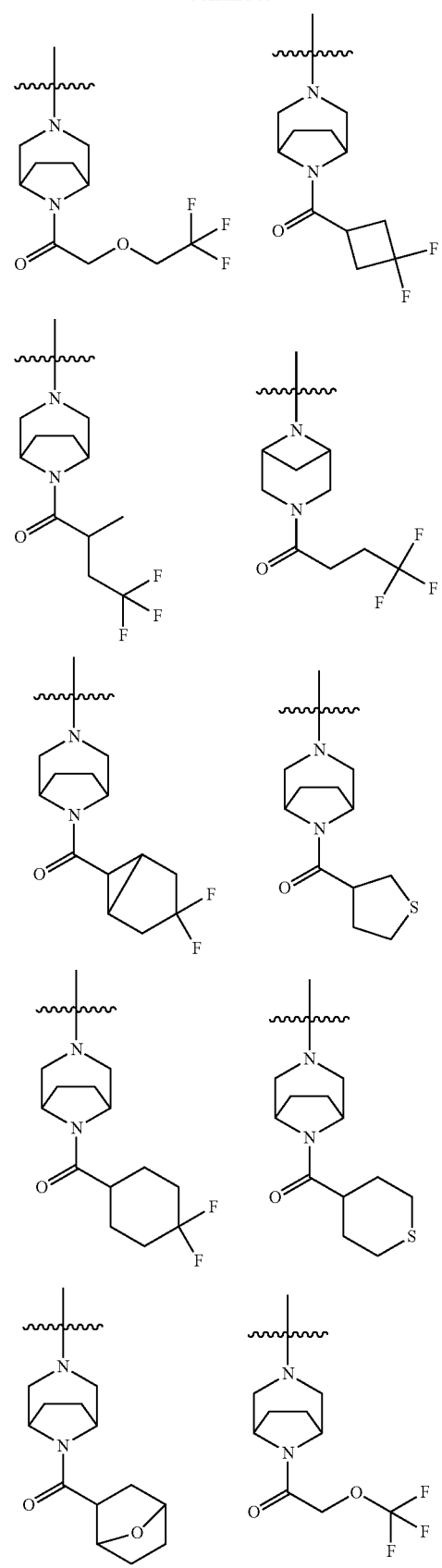

-continued
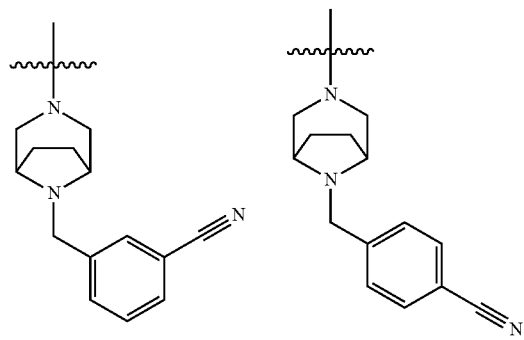
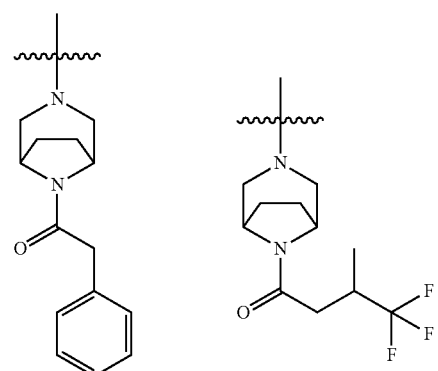
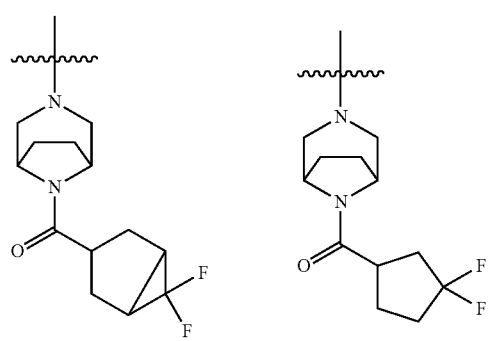
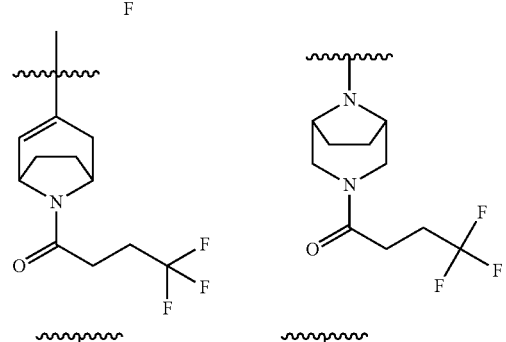
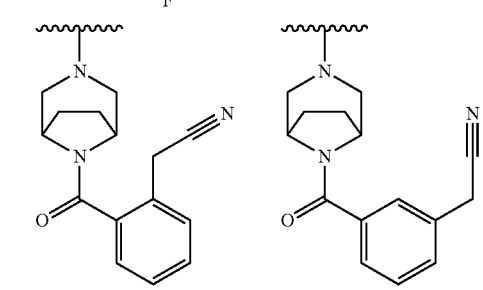
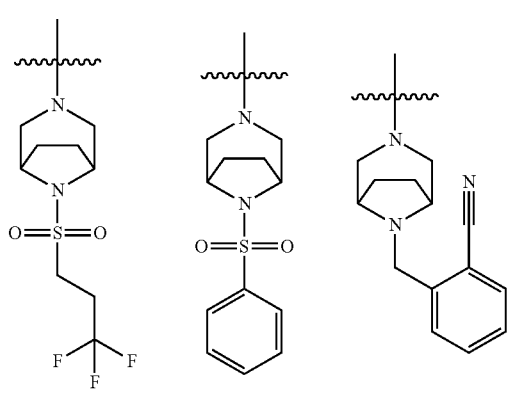
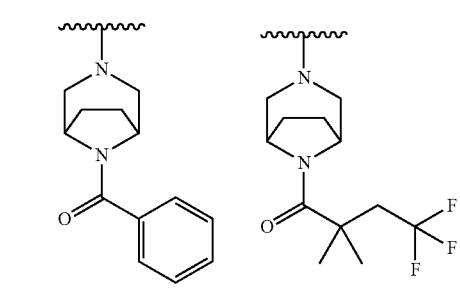
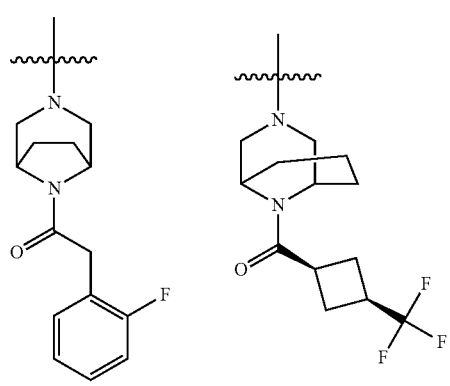
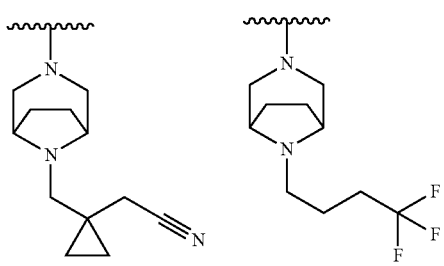

47
-continued
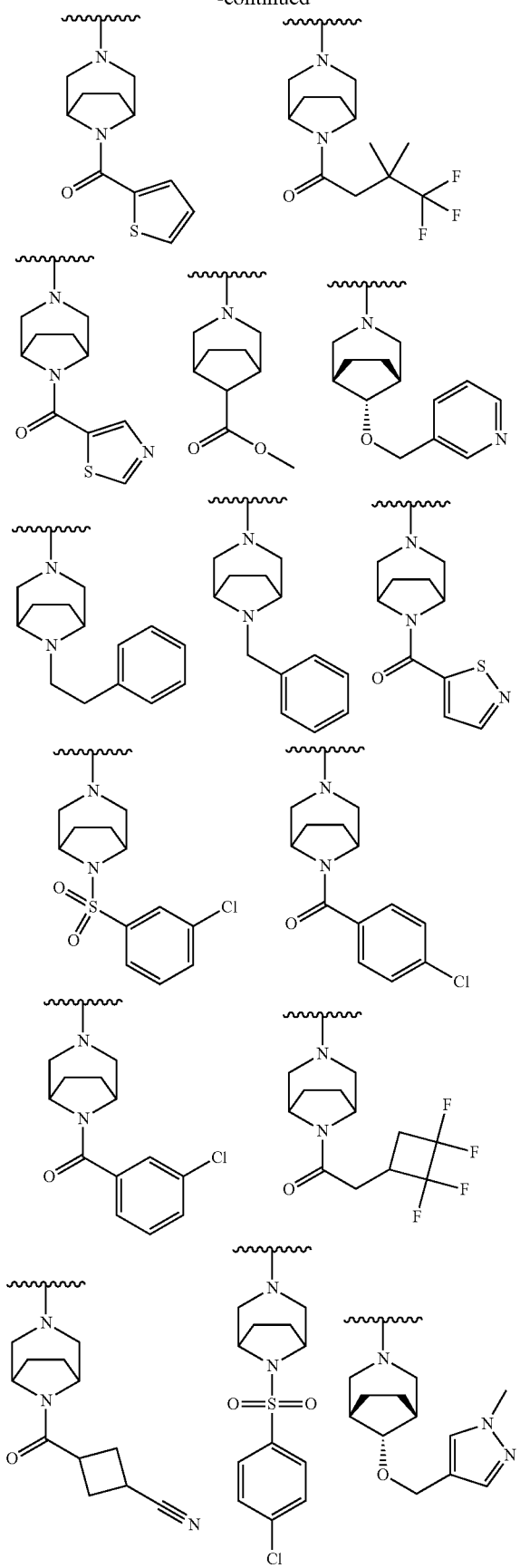
48
-continued
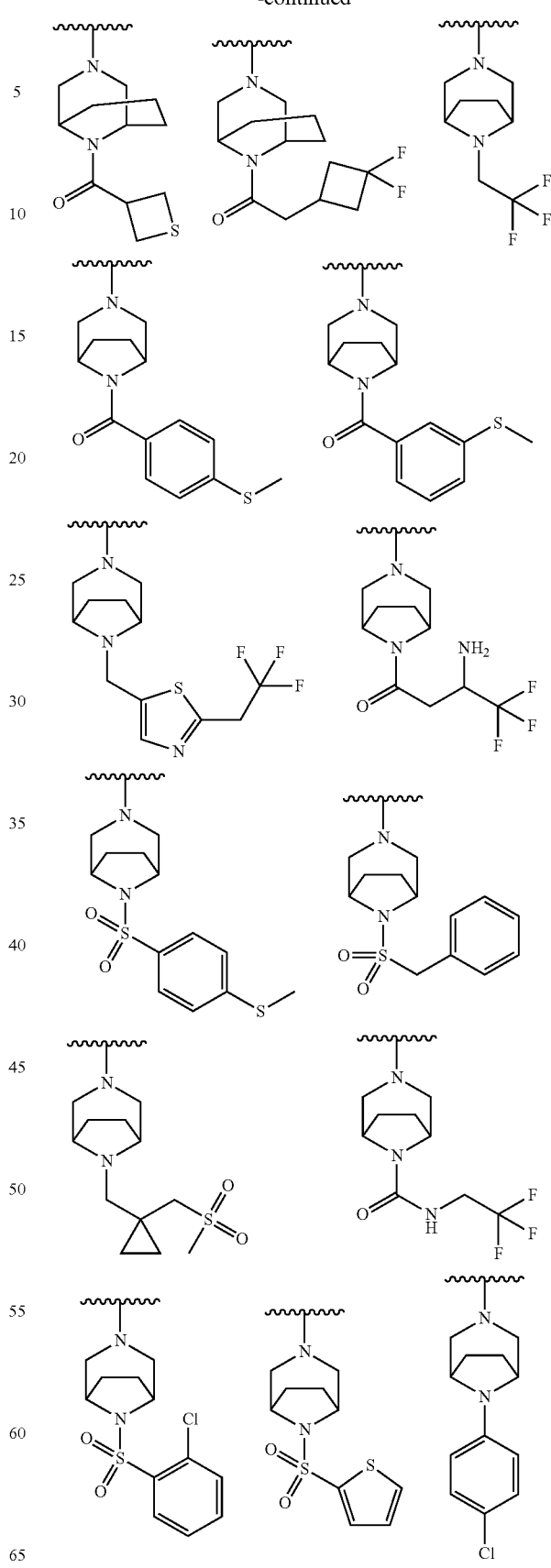

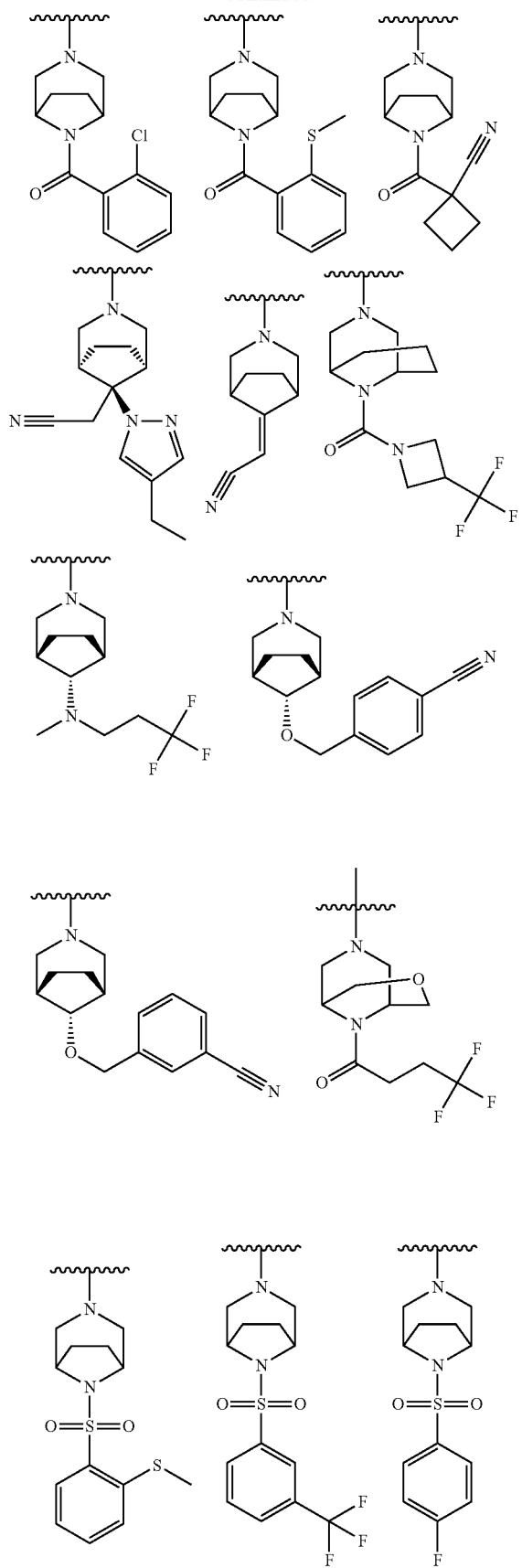
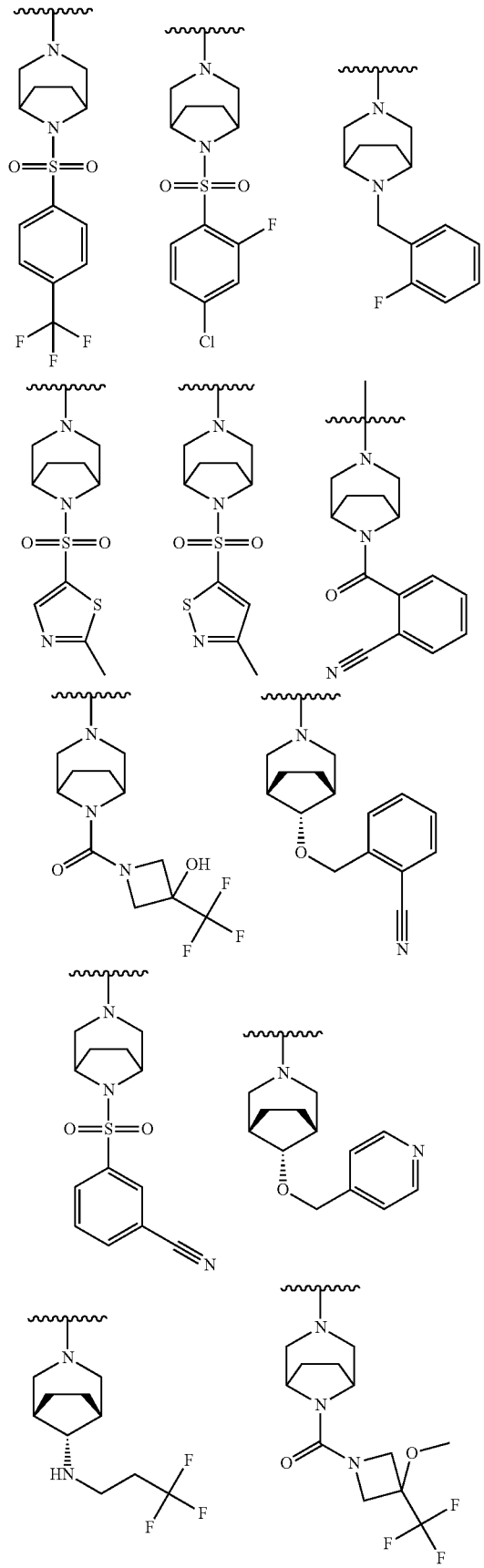

51
-continued
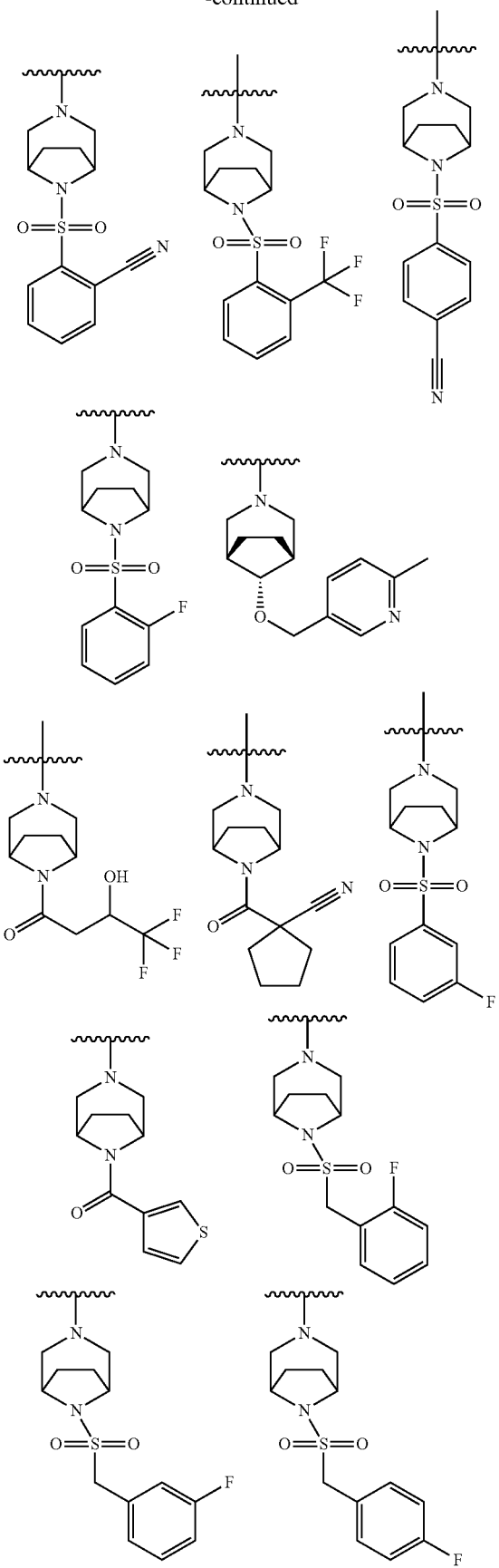
52
-continued
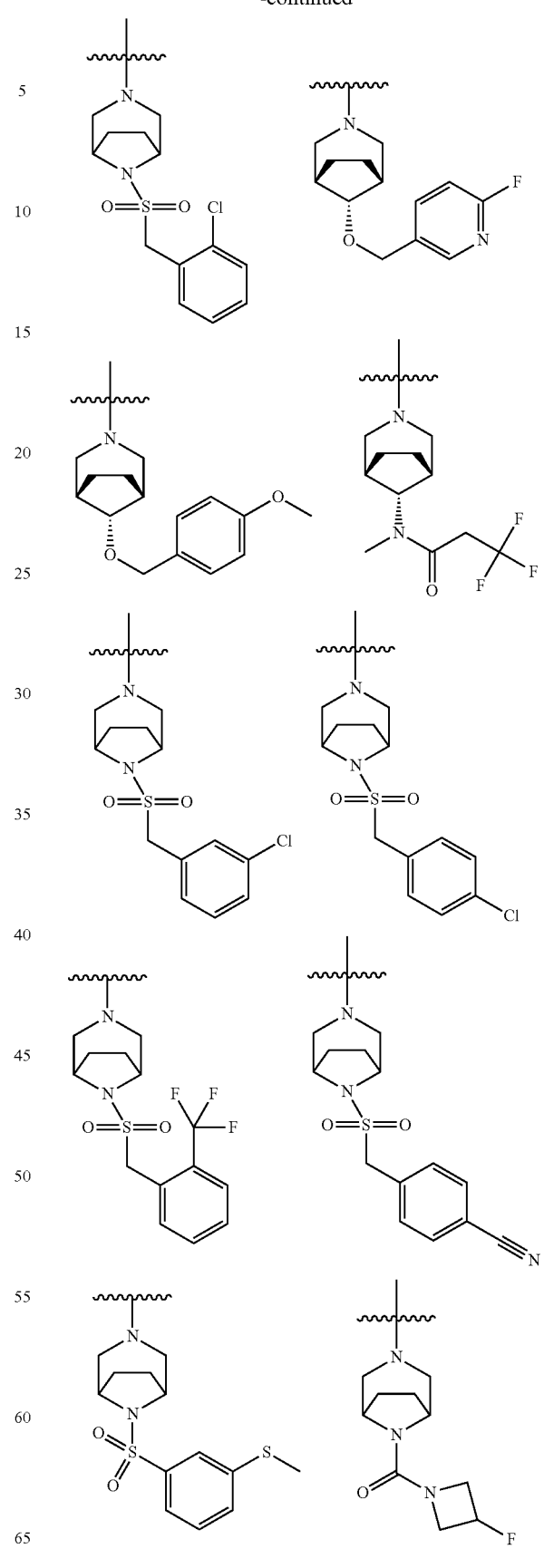

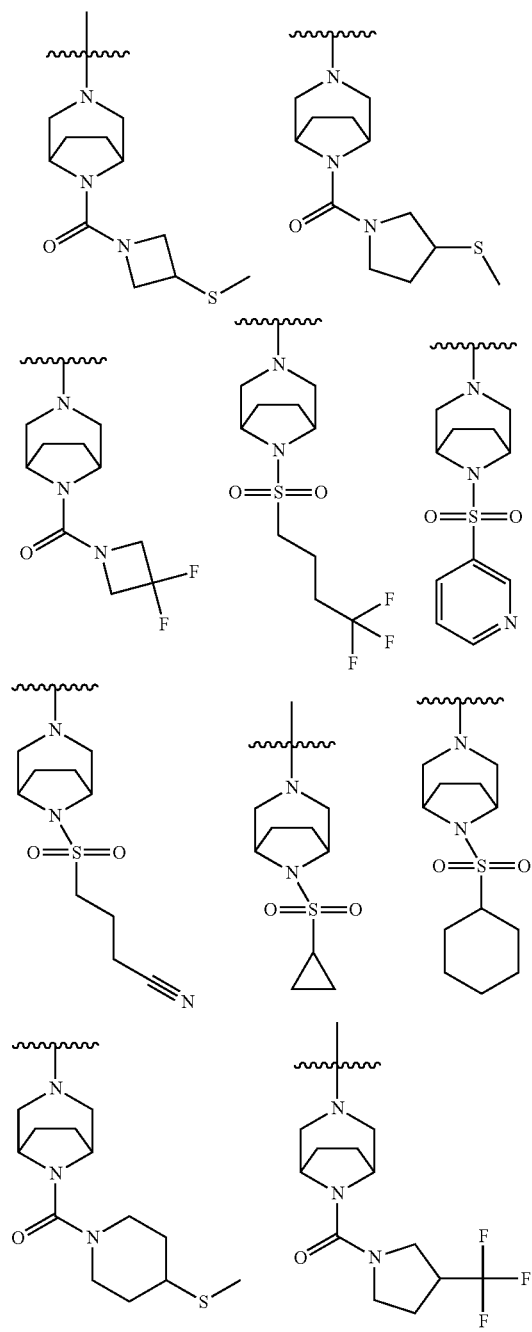
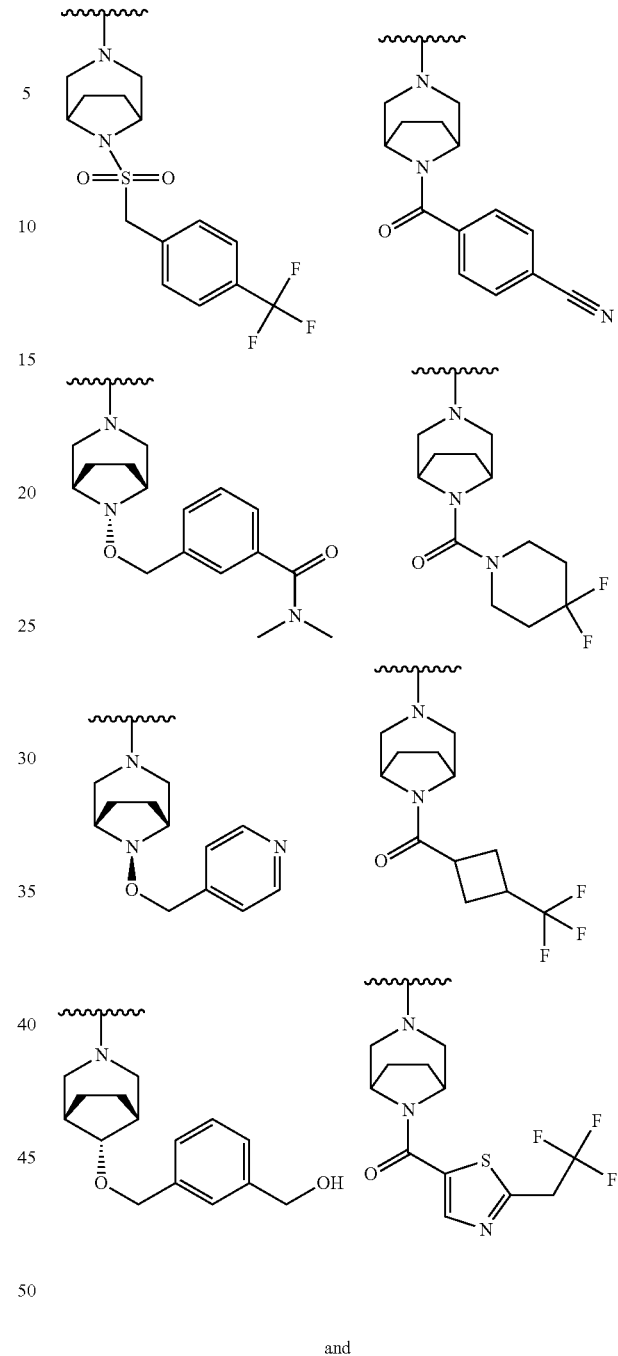
and
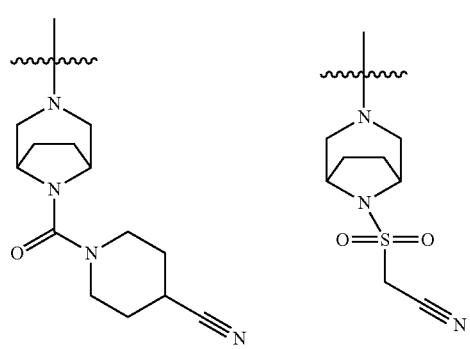
In one embodiment R² of a compound, salt or stereoisomer of Formula (I) is selected from the group consisting of:

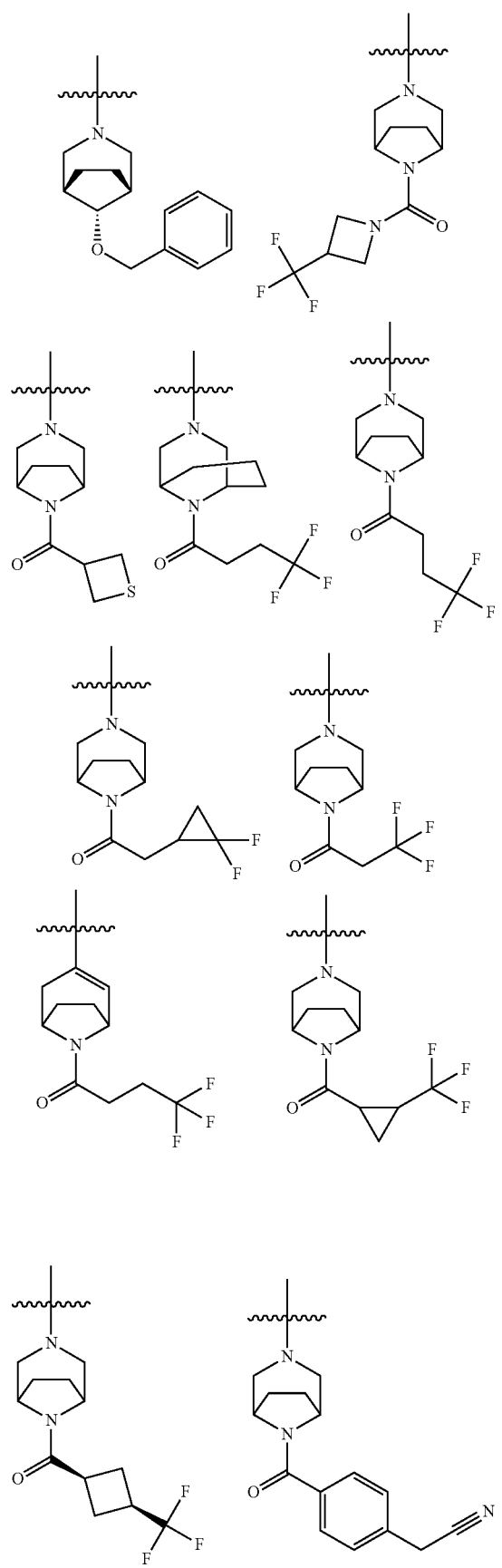

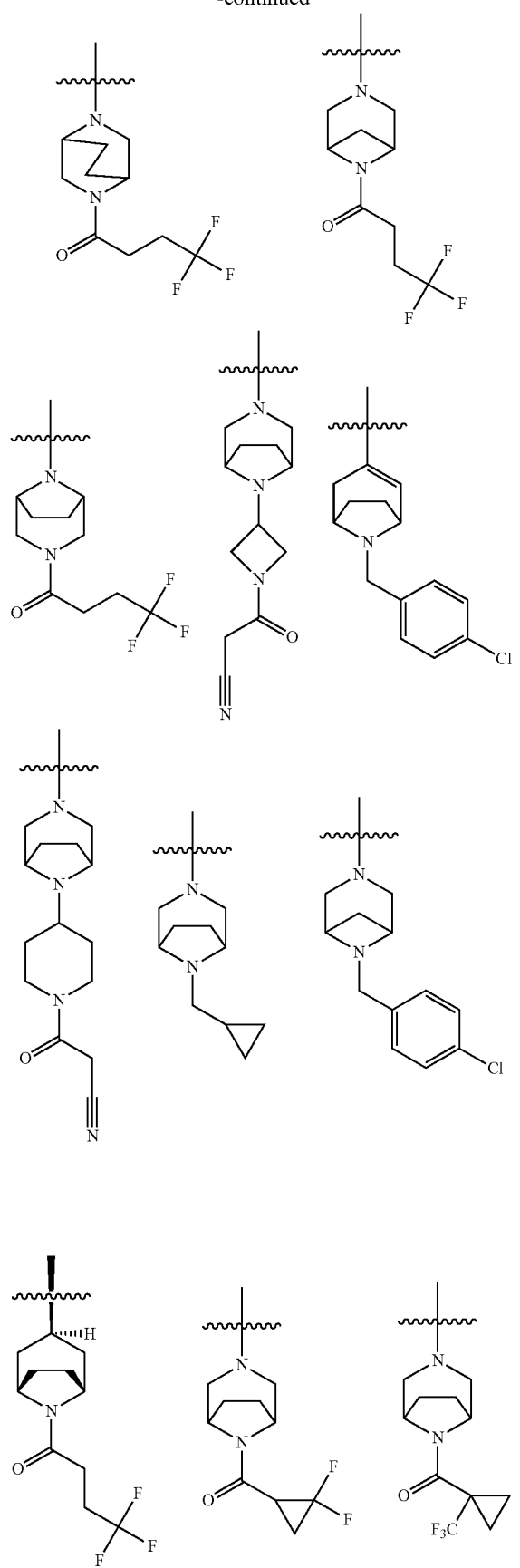
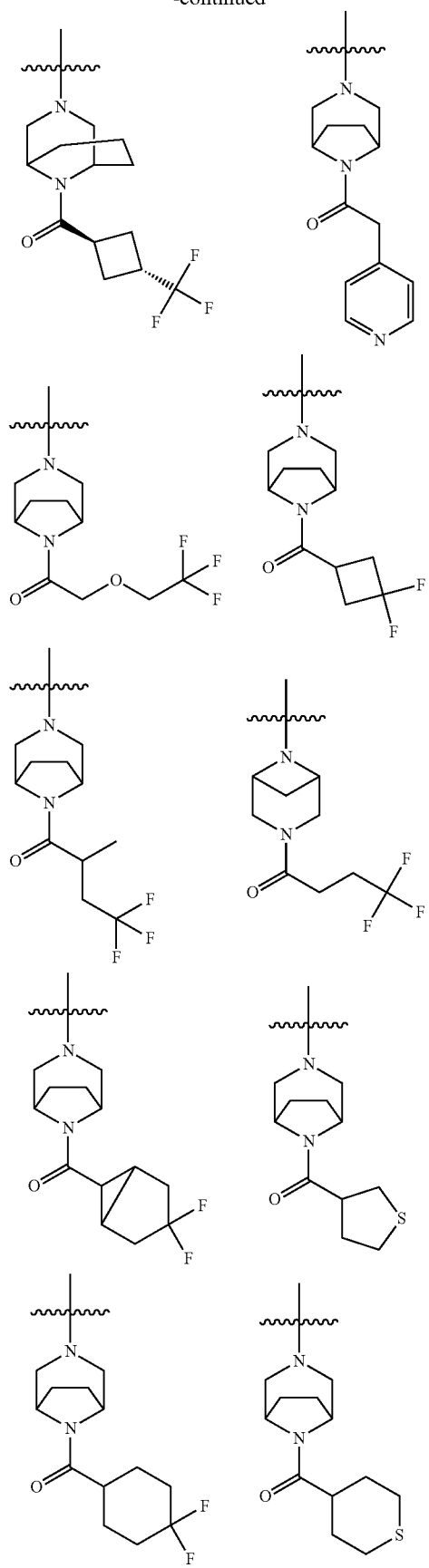

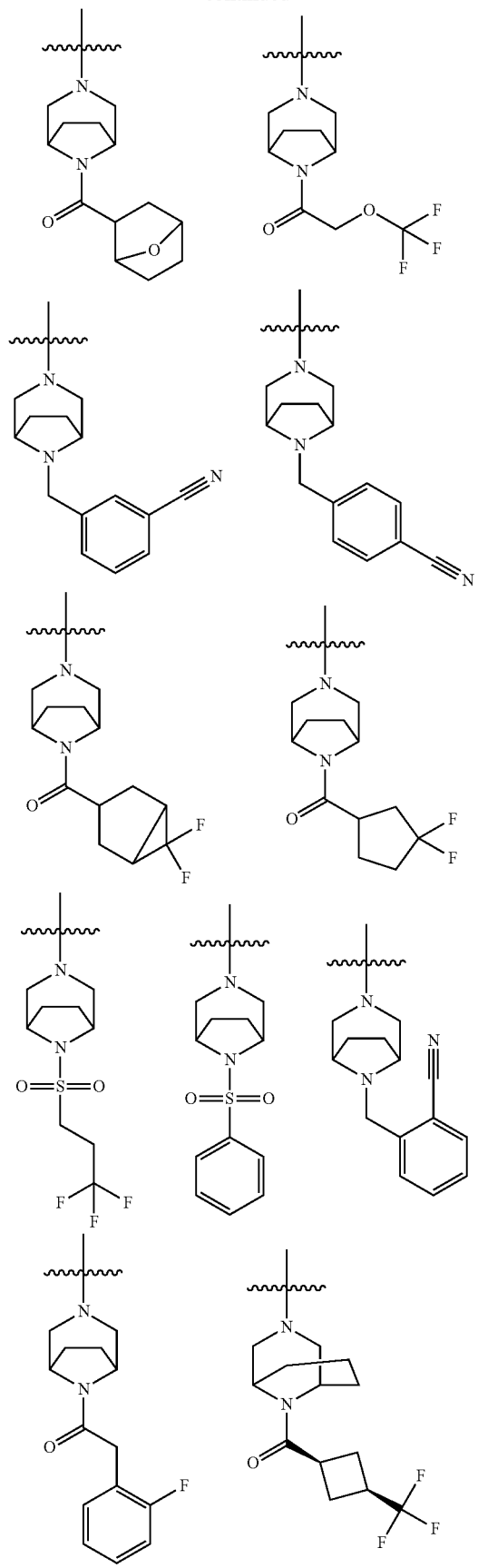
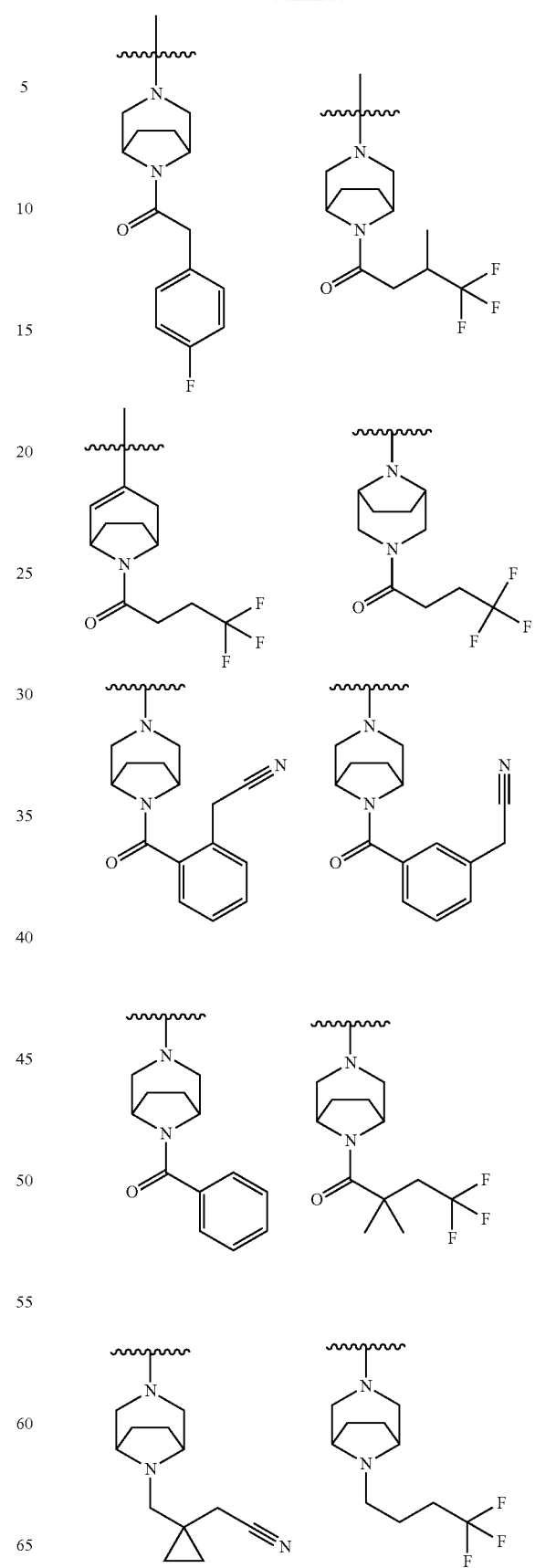

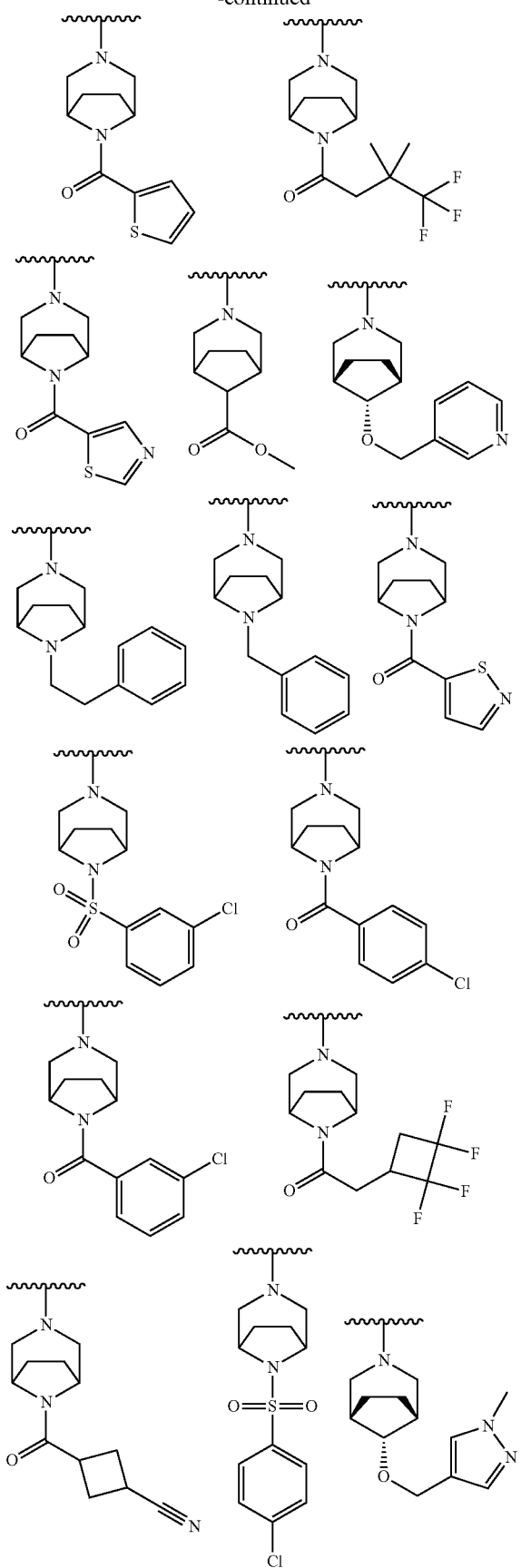
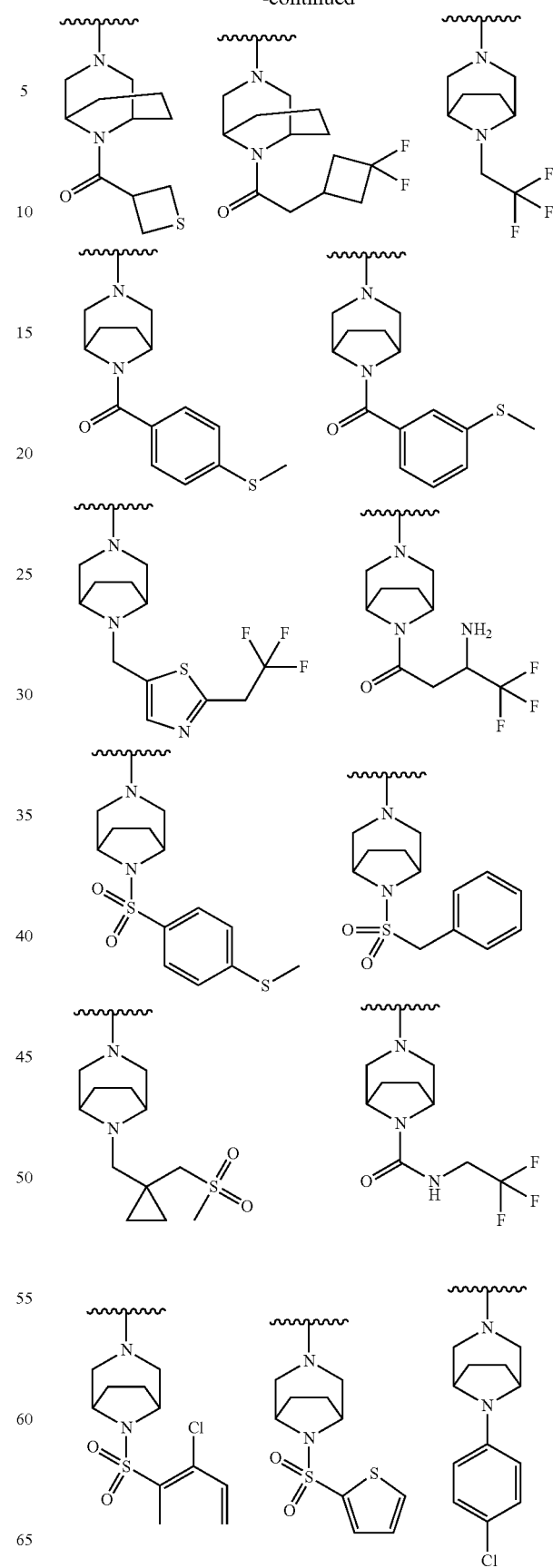

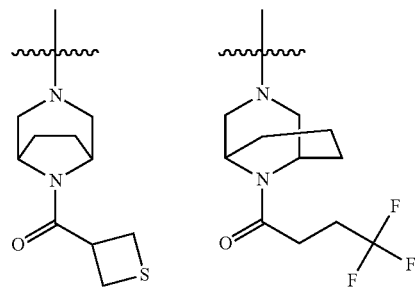
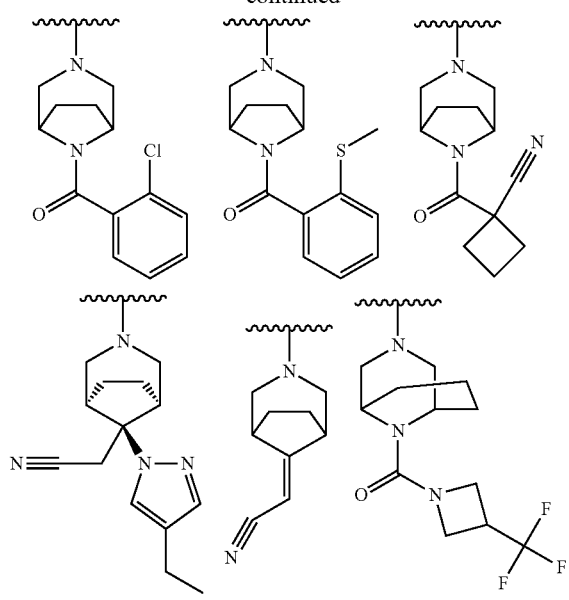
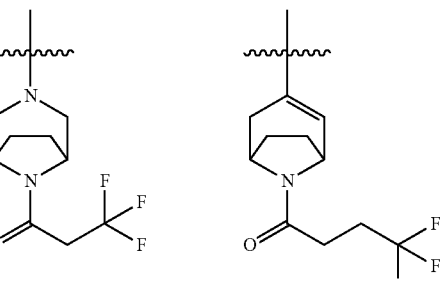
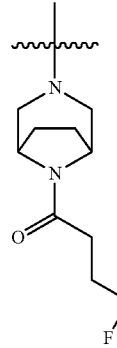
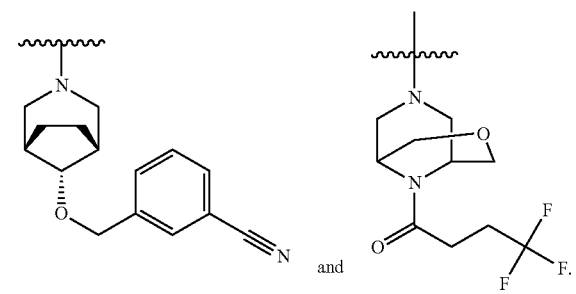
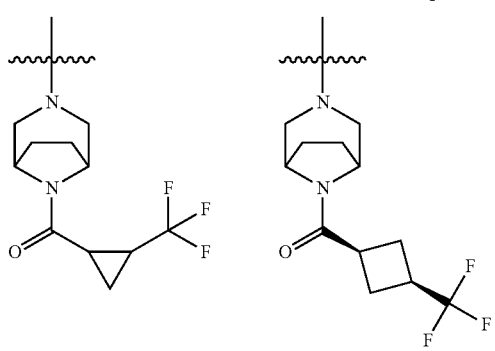
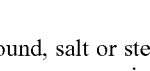
In one embodiment R² of a compound, salt or stereoisomer of Formula (I) is selected from the group consisting of:
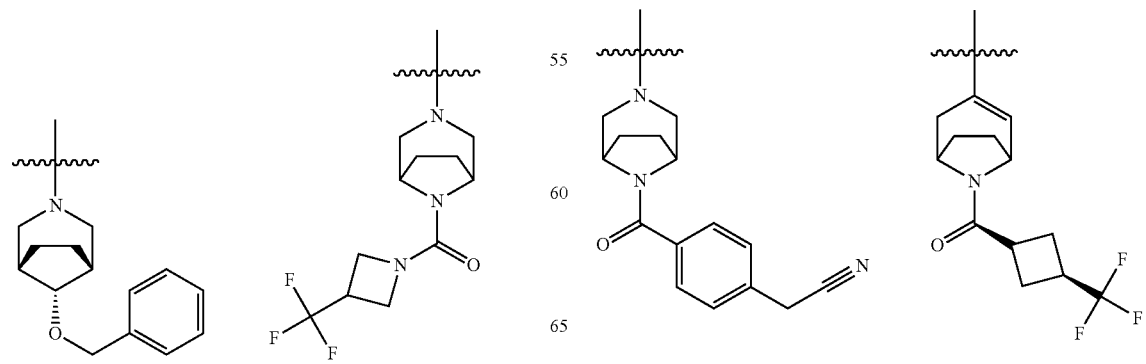

65
-continued
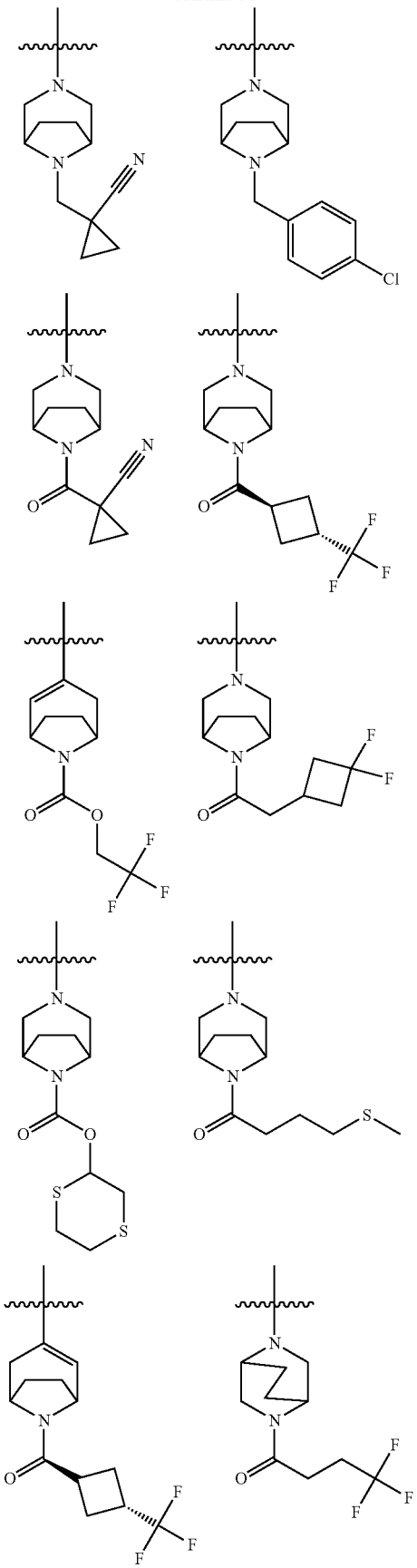
66
-continued
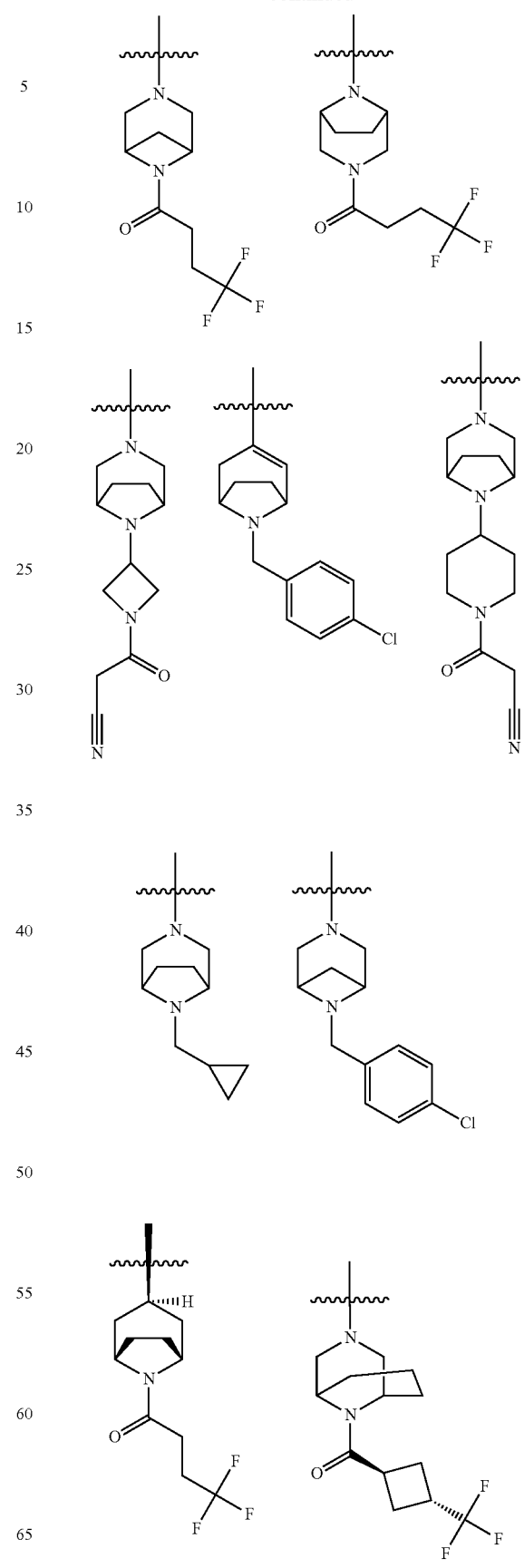

-continued
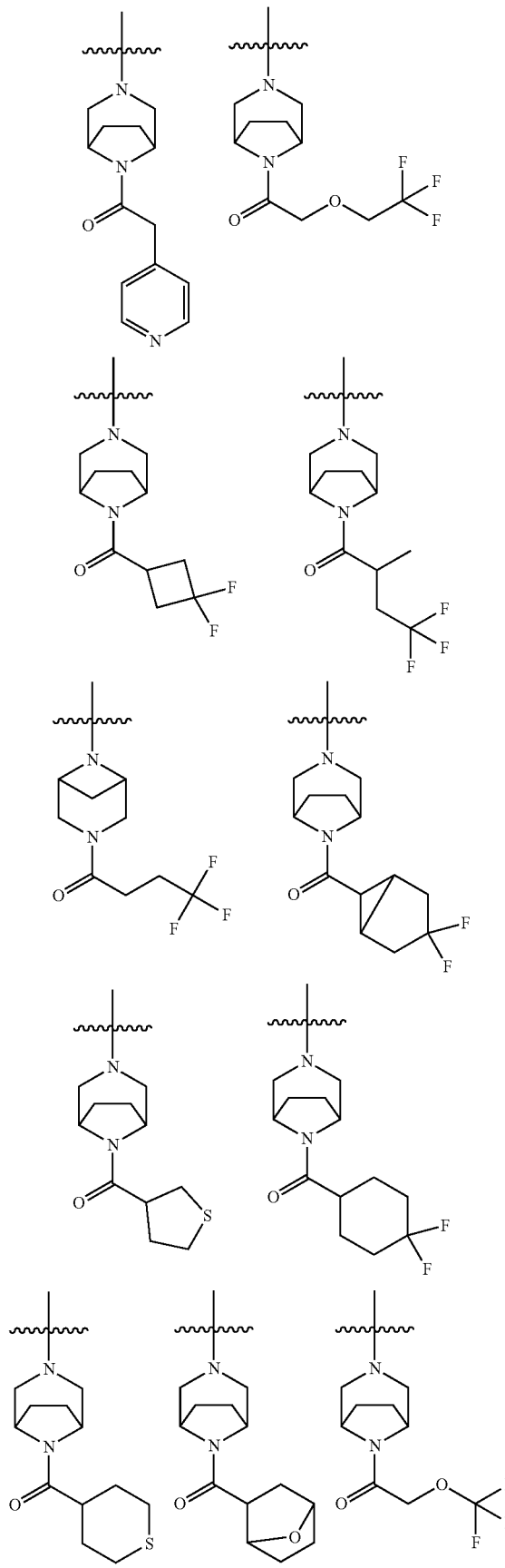
-continued
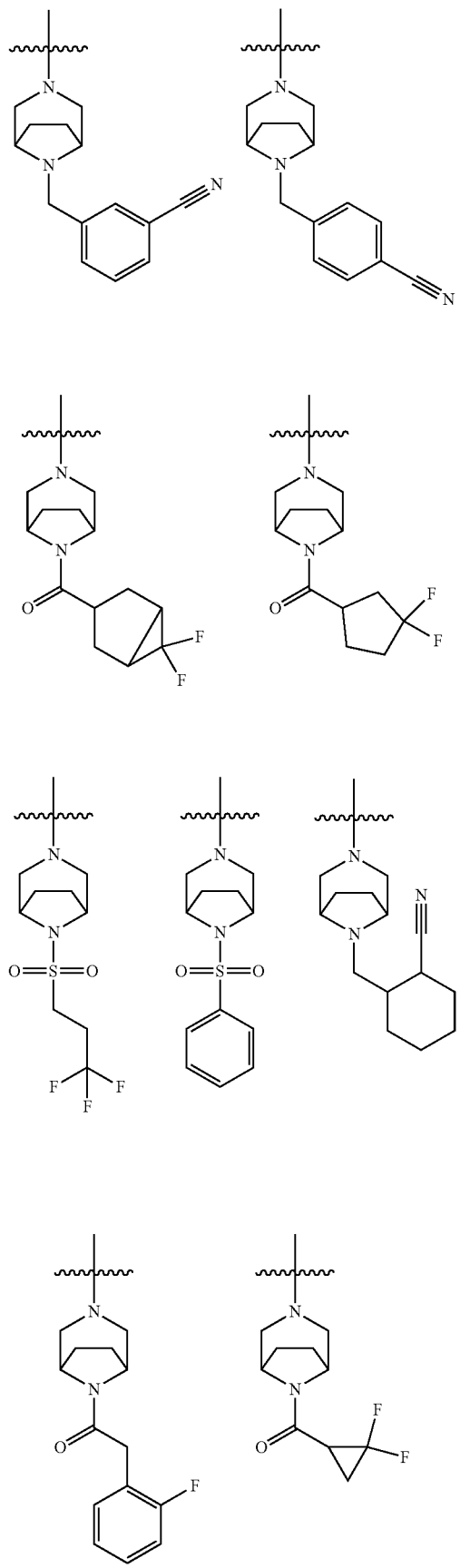

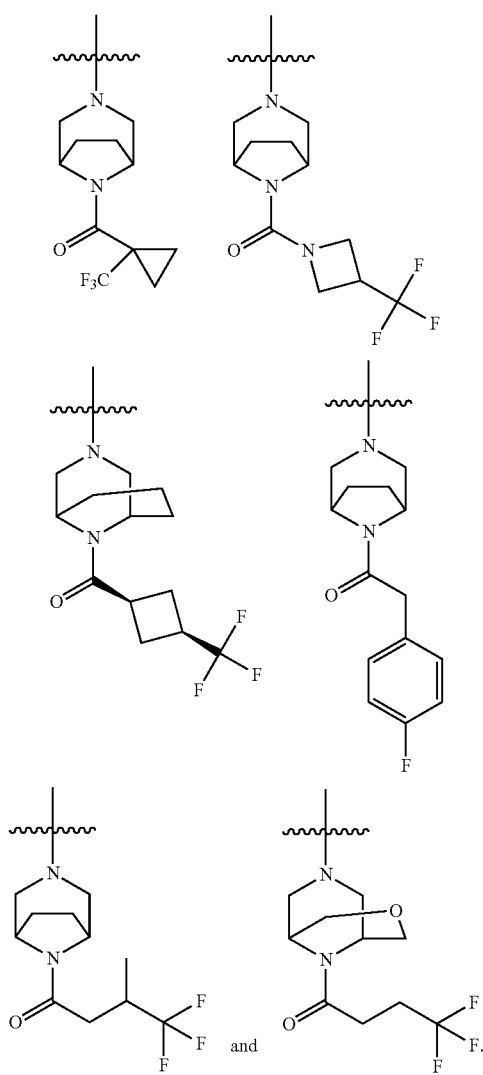
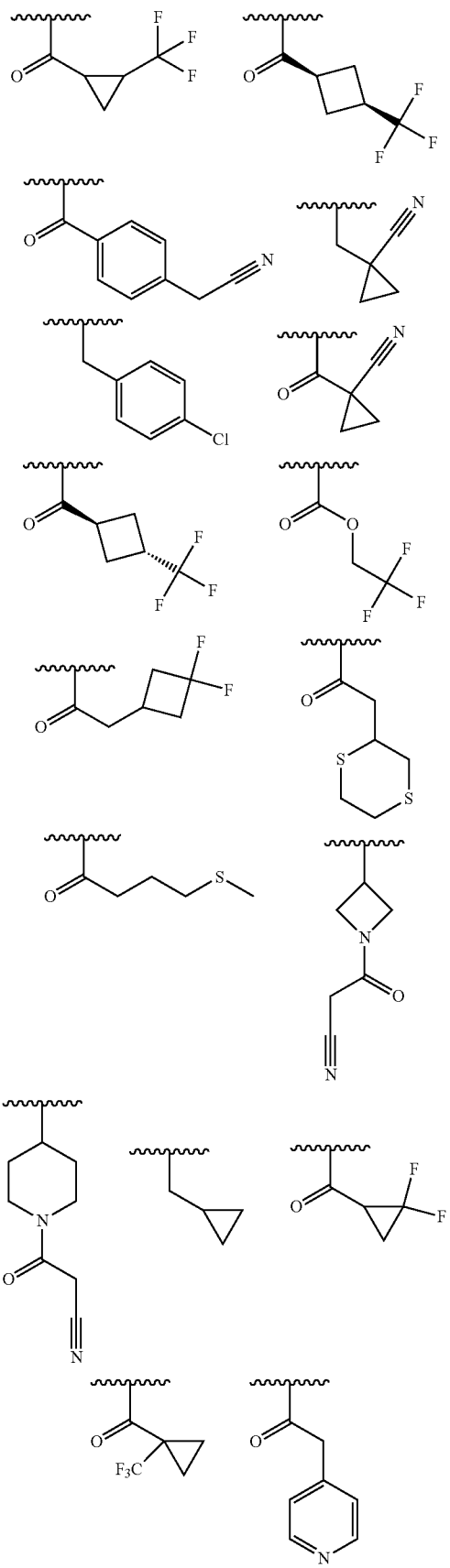
In one embodiment $R^b$ of a compound, salt or stereoisomer of Formula (I) is —C(O)NR$^f$R$^g$ or —C(O)R$^m$.
In one embodiment $R^b$ of a compound, salt or stereoisomer of Formula (I) is selected from the group consisting of:
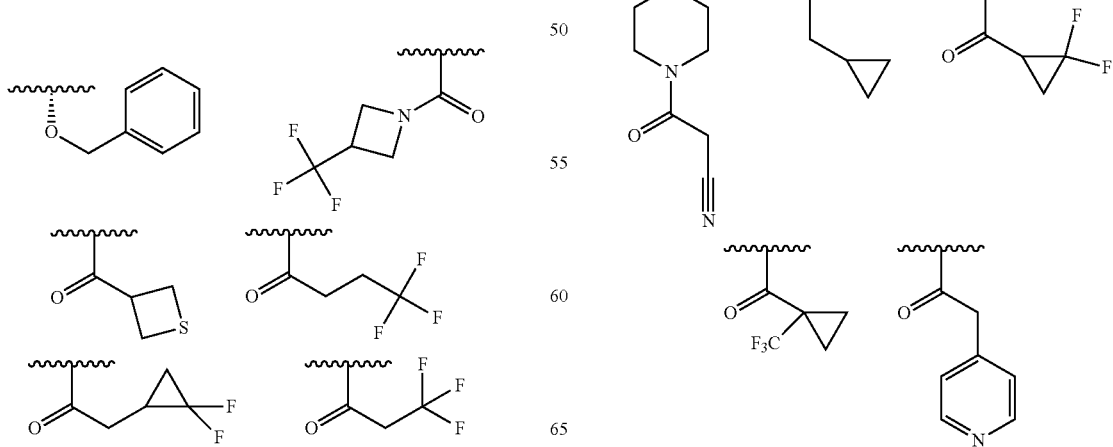

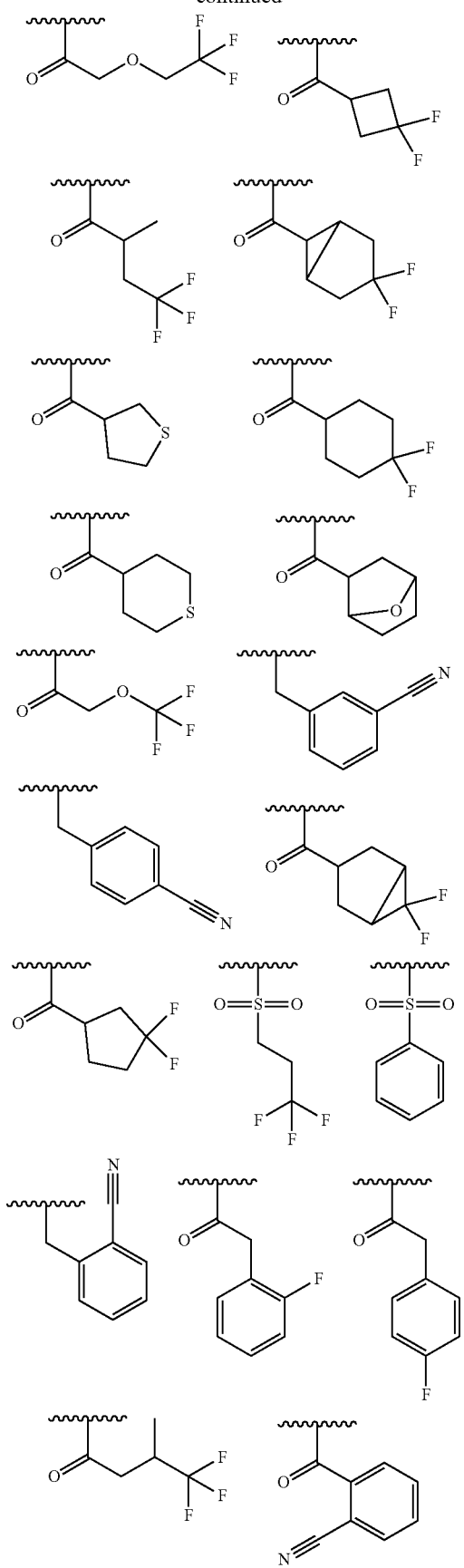
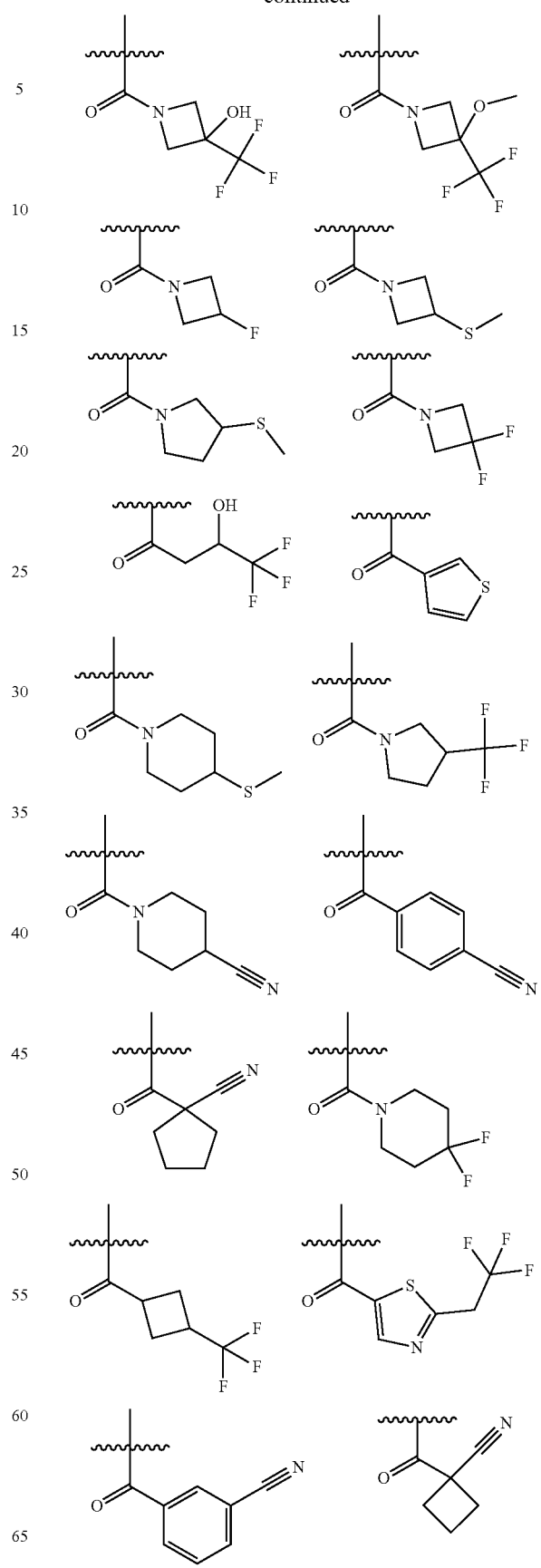

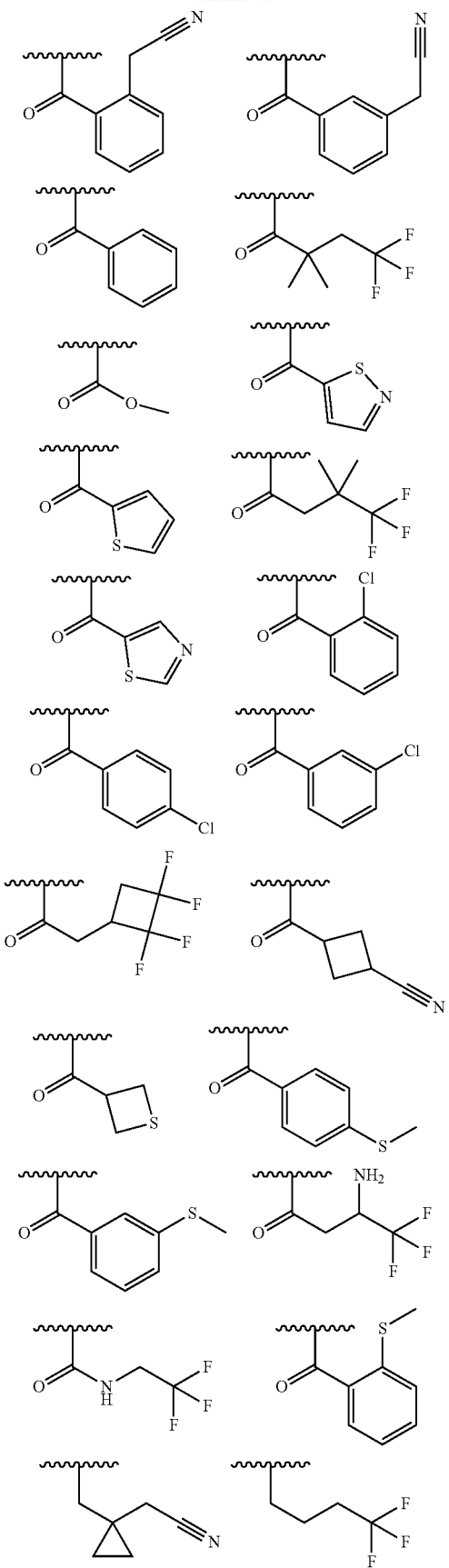
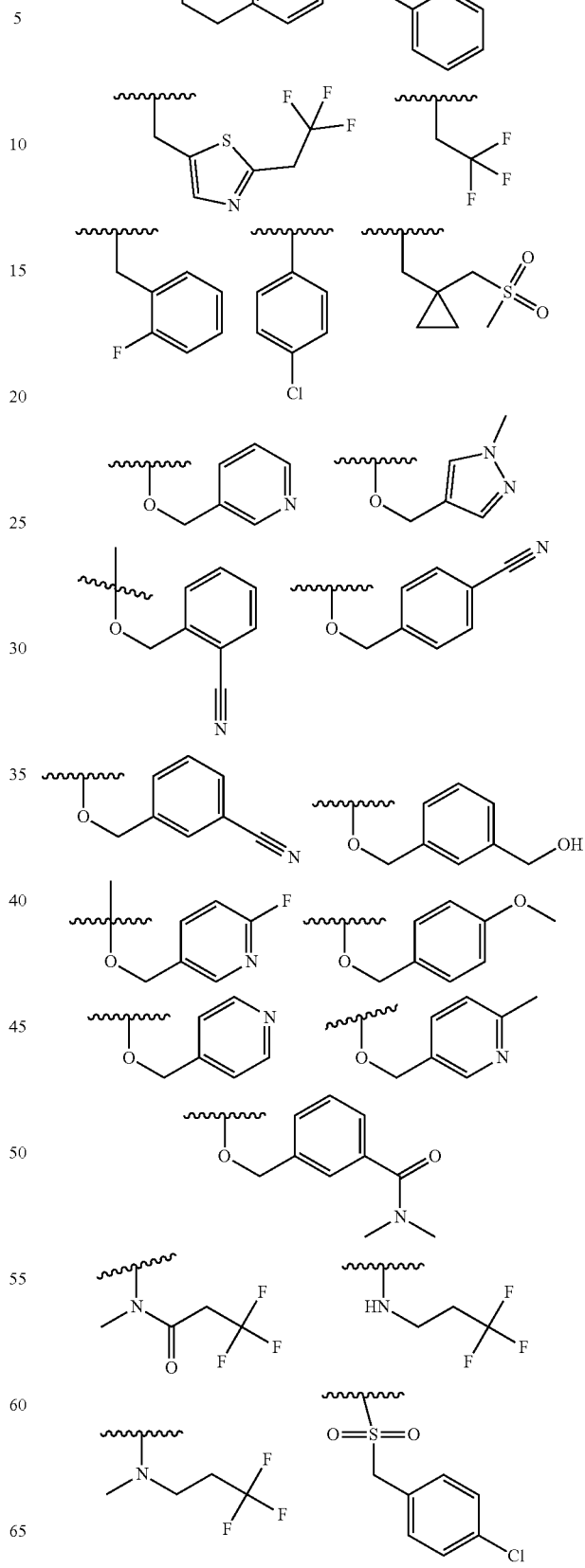

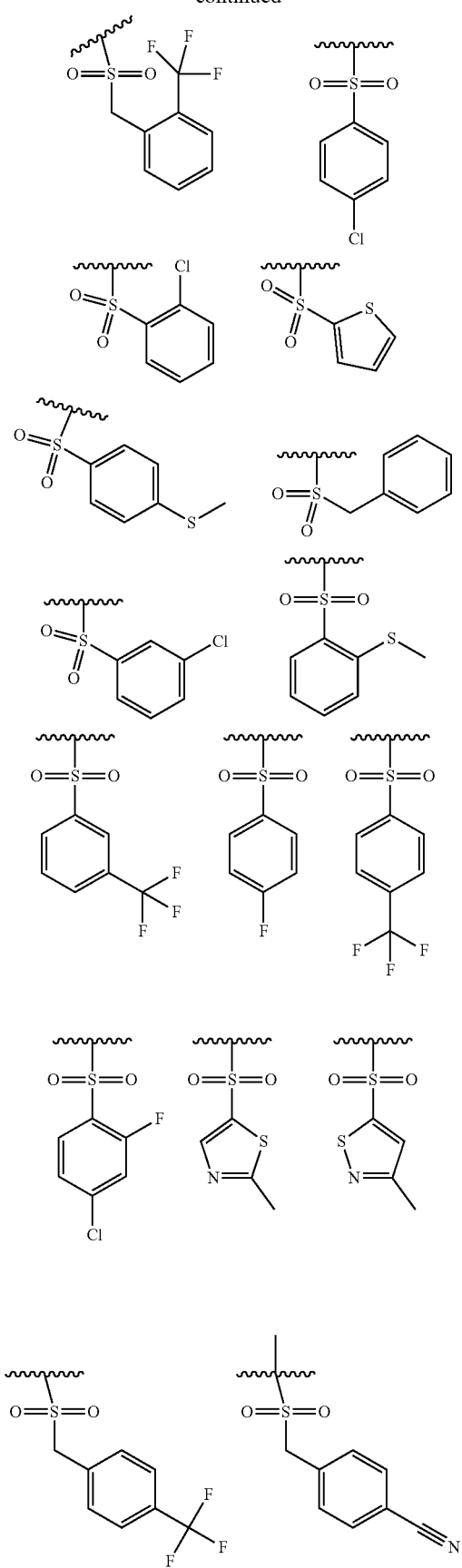
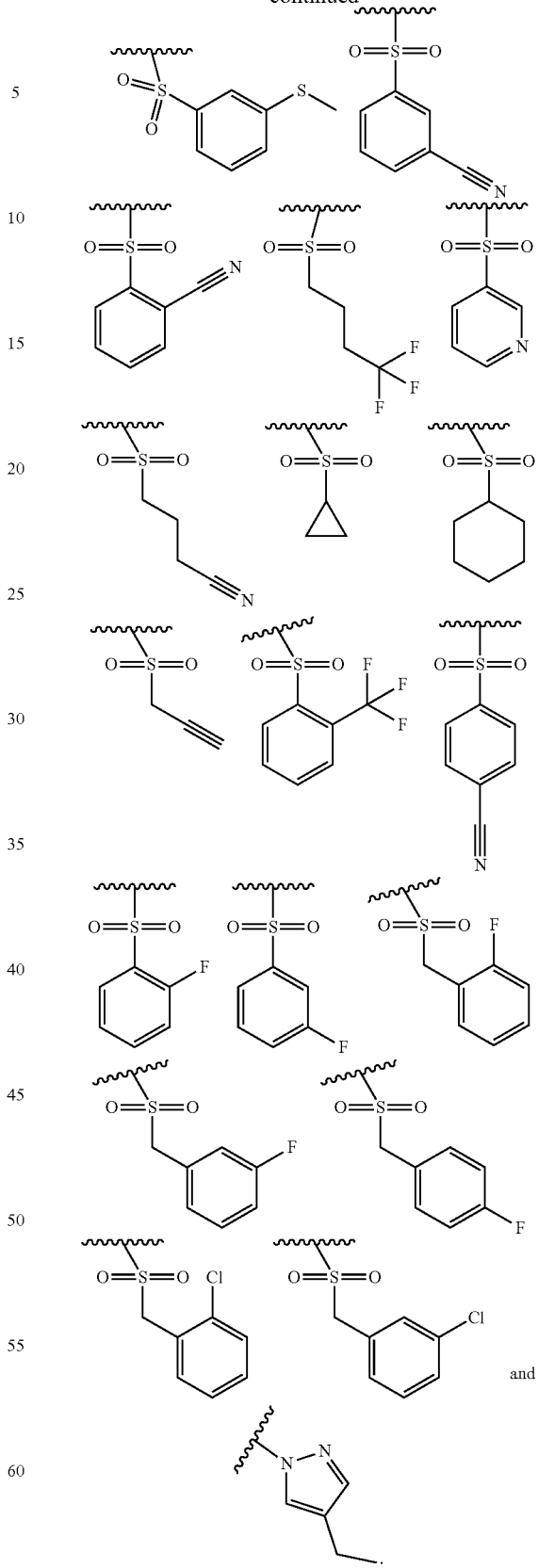
In one embodiment $R^b$ of a compound, salt or stereoisomer of Formula (I) is selected from the group consisting of:

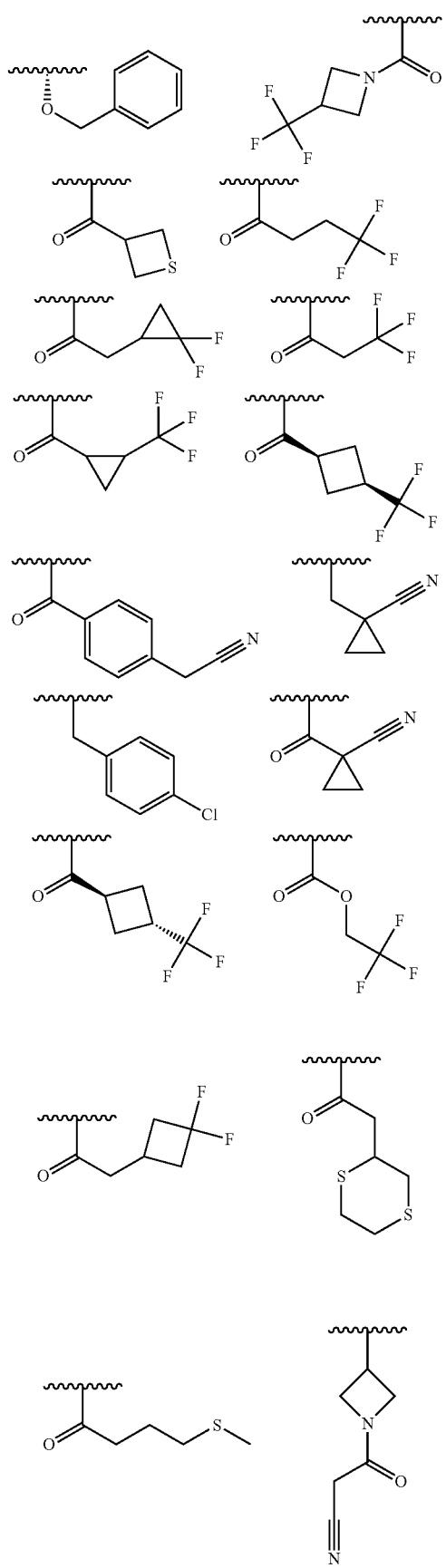
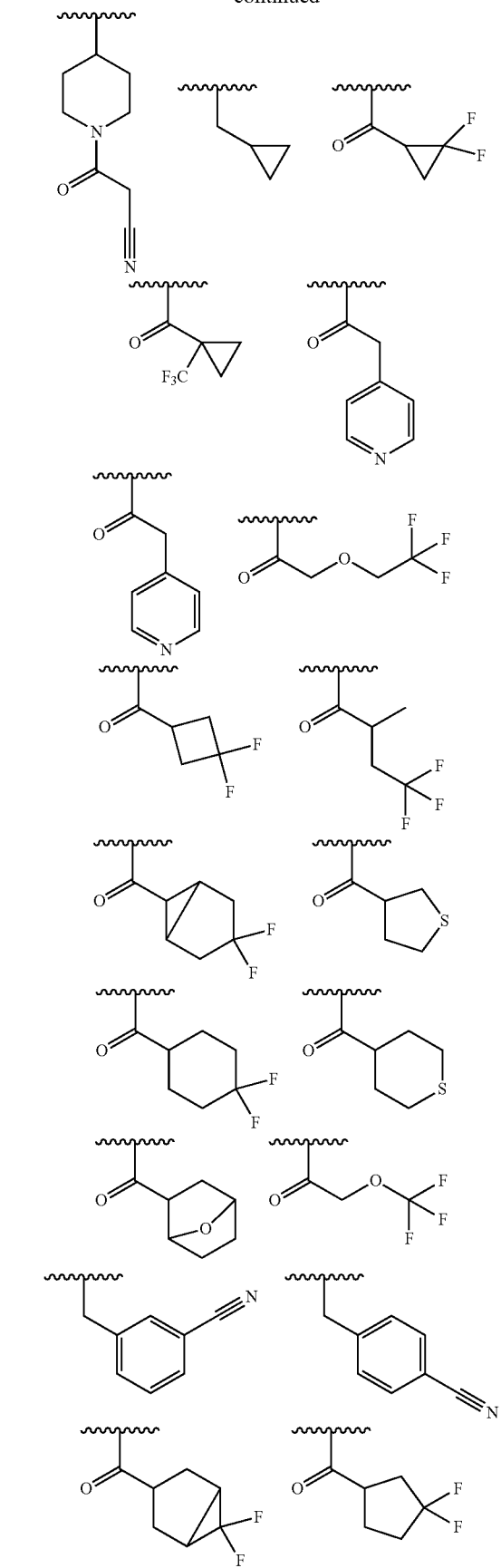

-continued
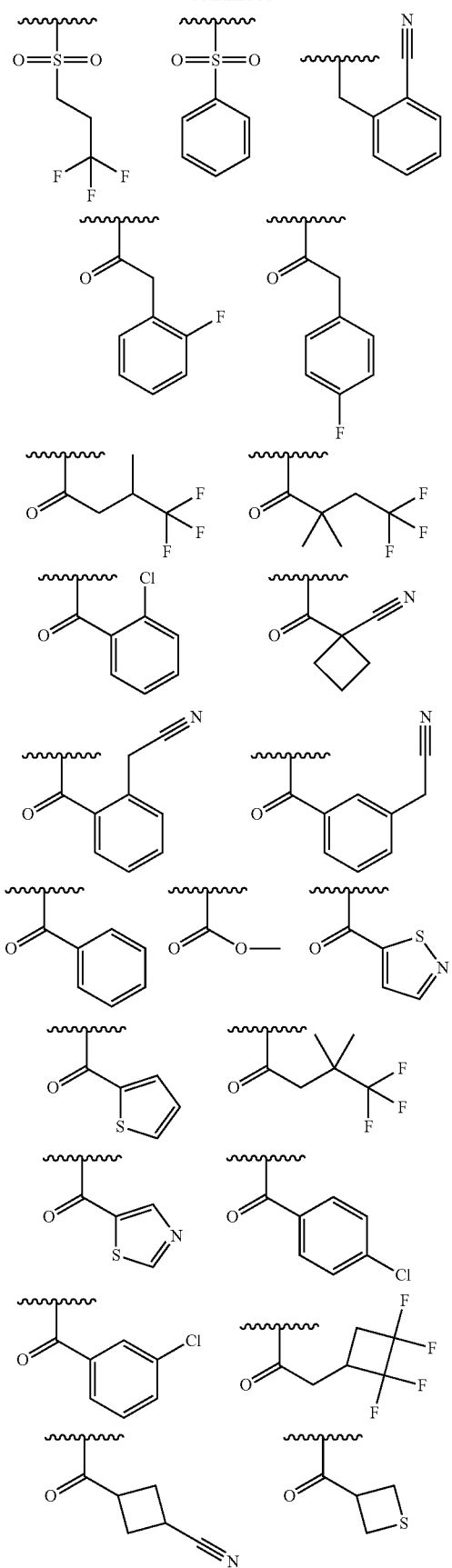
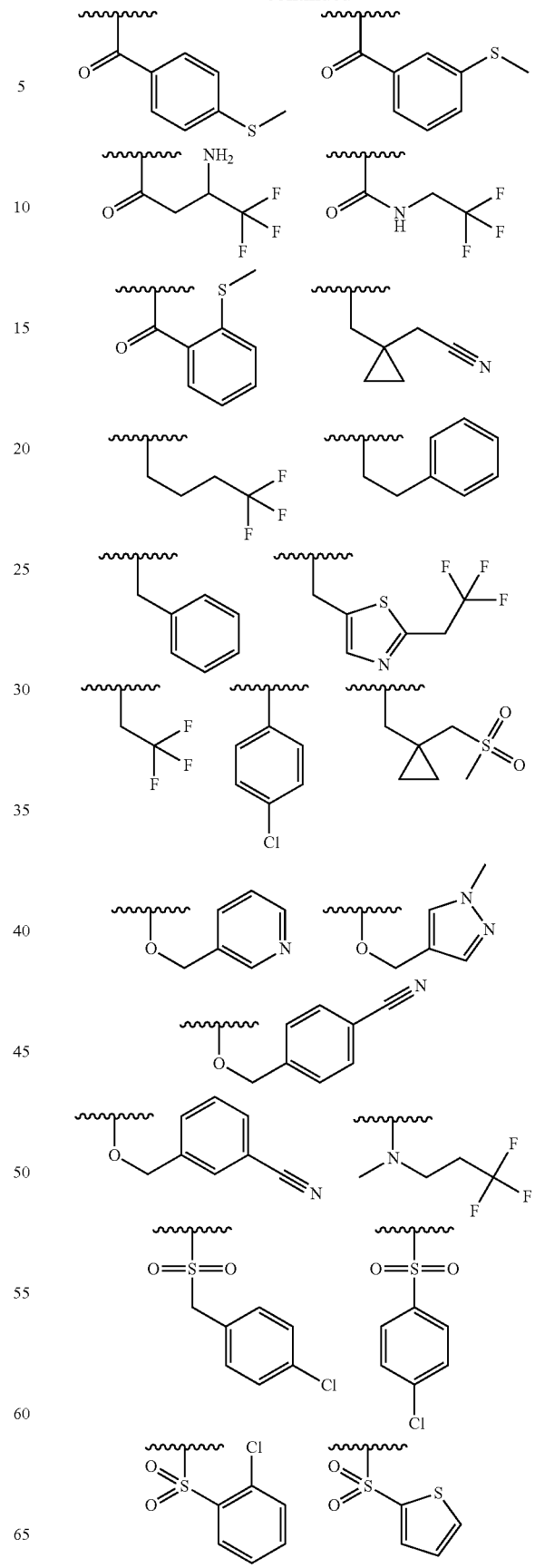

-continued
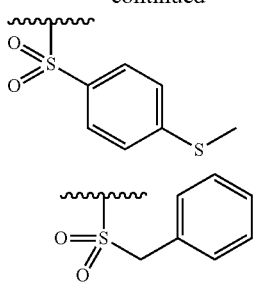
and
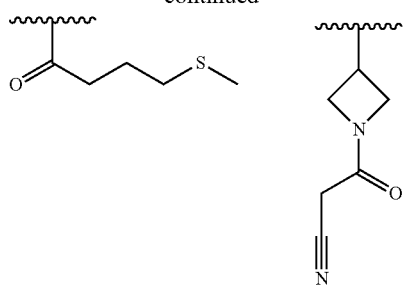
In one embodiment R$^b$ of a compound, salt or stereoisomer of Formula (I) is selected from the group consisting of:
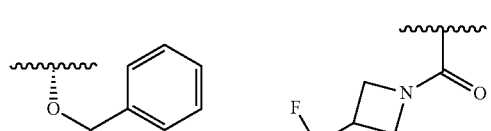
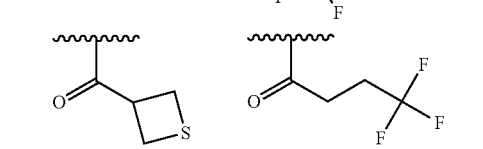
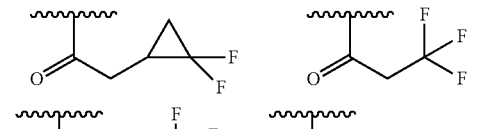
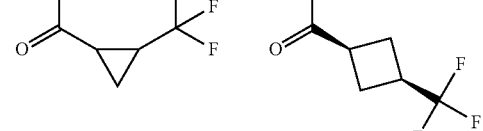
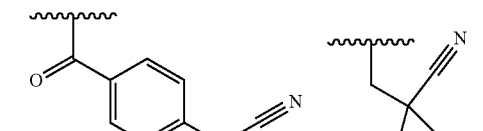
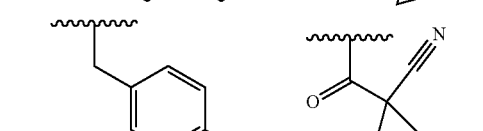
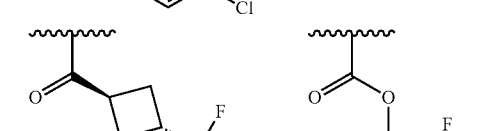
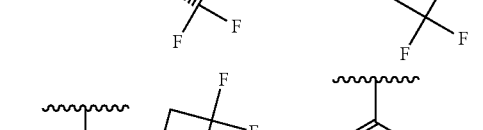
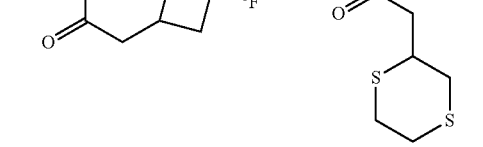
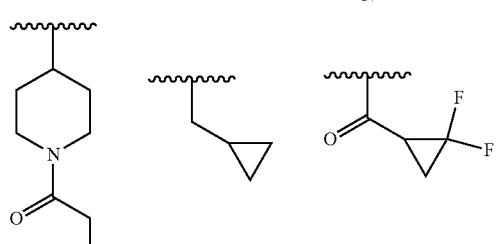
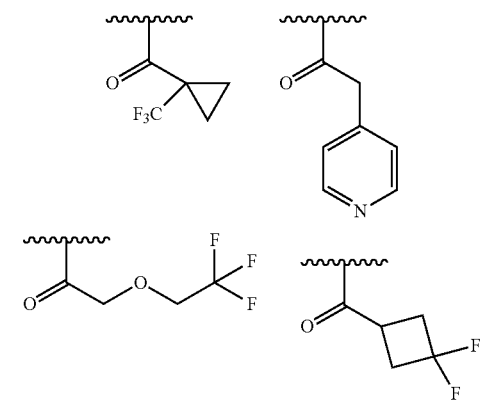
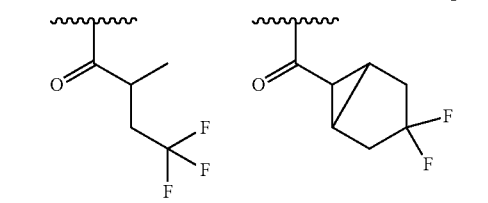
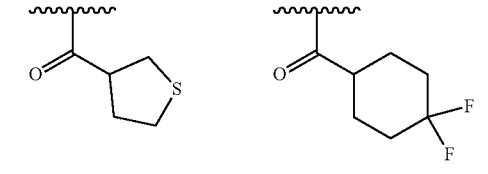
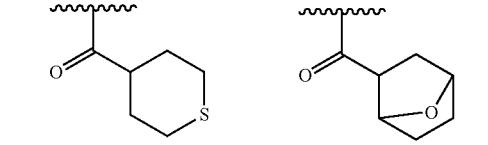
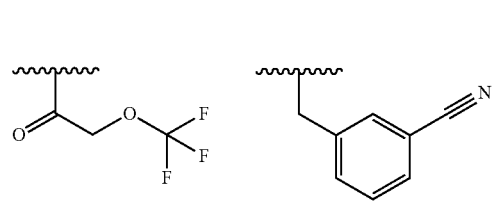

-continued

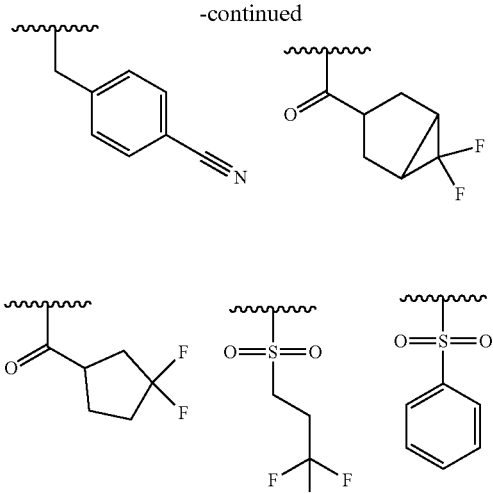

-continued

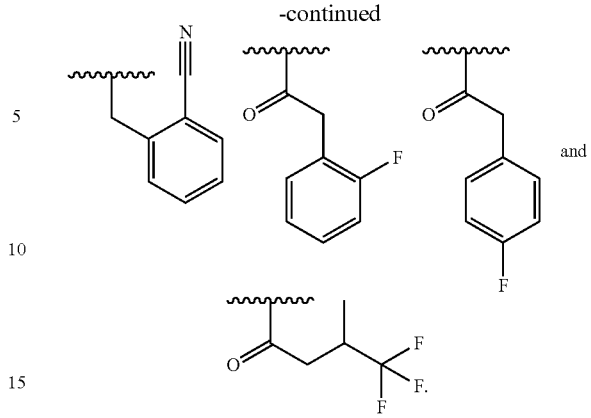

Exemplary compounds of the invention include compounds, salts and stereoisomers selected from Table 1. If a particular salt is depicted in Table 1, other salts are also contemplated:

TABLE 1

Representative Compounds

| Ex. | Structure | Name |
|---|---|---|
| 1 | 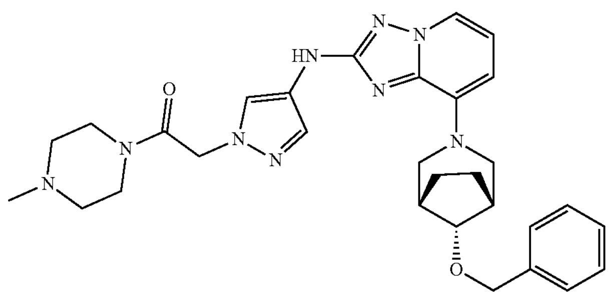 [SMILES: CN1CCN(C(=O)Cn2cc(Nc3nc4c(N5C[C@H]6CC[C@@H](C5)[C@H]6OCc5ccccc5)cccn4n3)cn2)CC1] | 2-[4-[[8-[(1S,5R)-8-benzyloxy-3-azabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 2 | 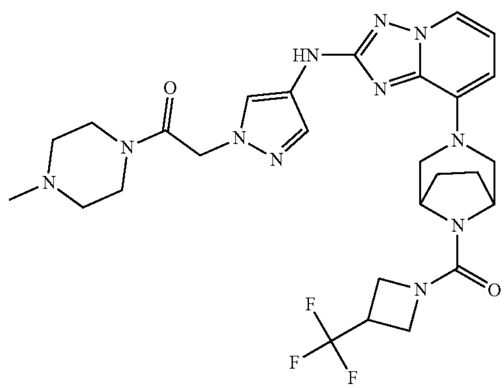 [SMILES: CN1CCN(C(=O)Cn2cc(Nc3nc4c(N5CC6CCC(C5)N6C(=O)N5CC(C(F)(F)F)C5)cccn4n3)cn2)CC1] | 1-(4-methylpiperazin-1-yl)-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 3 | 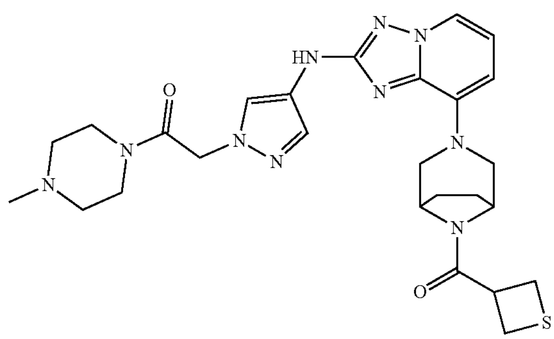 [SMILES: CN1CCN(C(=O)Cn2cc(Nc3nc4c(N5CC6CCC(C5)N6C(=O)C5CSC5)cccn4n3)cn2)CC1] | 1-(4-methylpiperazin-1-yl)-2-[4-[[8-[8-(thietane-3-carbonyl)-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 4 | 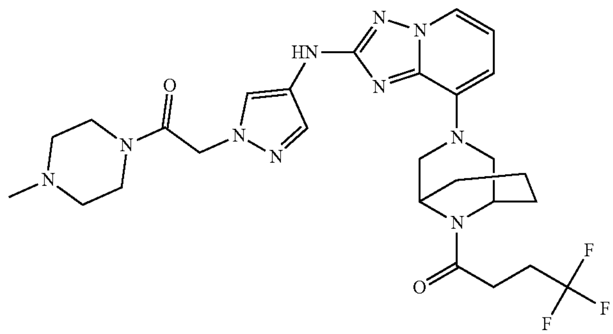 [SMILES: CN1CCN(C(=O)Cn2cc(Nc3nc4c(N5CC6CCCC(C5)N6C(=O)CCC(F)(F)F)cccn4n3)cn2)CC1] | 4,4,4-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,9-diazabicyclo[3.3.1]nonan-9-yl]butan-1-one |
| 5 | 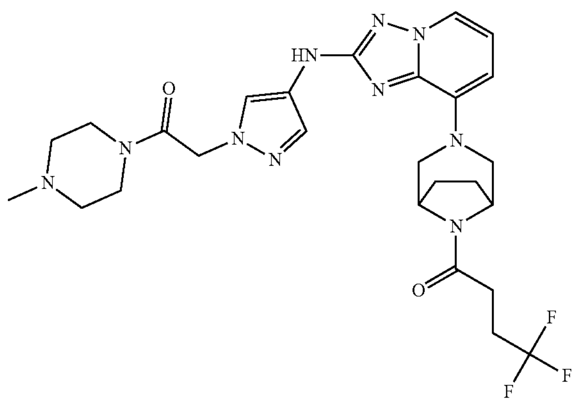 [SMILES: CN1CCN(C(=O)Cn2cc(Nc3nc4c(N5CC6CCC(C5)N6C(=O)CCC(F)(F)F)cccn4n3)cn2)CC1] | 4,4,4-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 6 | 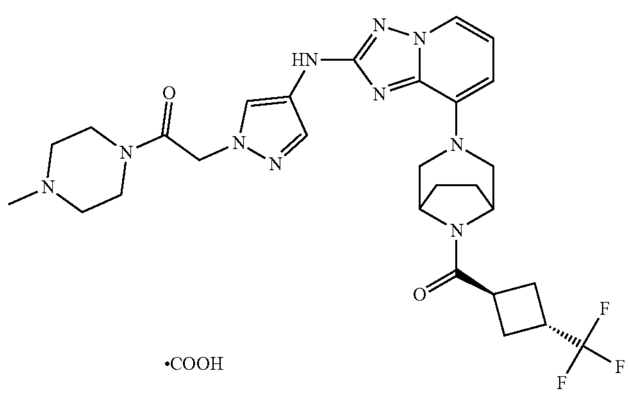 [SMILES: CN1CCN(C(=O)Cn2cc(Nc3nc4c(N5CC6CCC(C5)N6C(=O)[C@H]5C[C@H](C(F)(F)F)C5)cccn4n3)cn2)CC1 ; "·COOH"] | formic acid; 1-(4-methylpiperazin-1-yl)-2-[4-[[8-[8-[3-(trifluoromethyl)cyclobutanecarbonyl]-3,8-diazabicyclo[3.2.1]octan-3-yl]-[1,2,4]triazolo[1,5-a]pyridin-2-yl]amino]pyrazol-1-yl]ethanone |
| 7 | 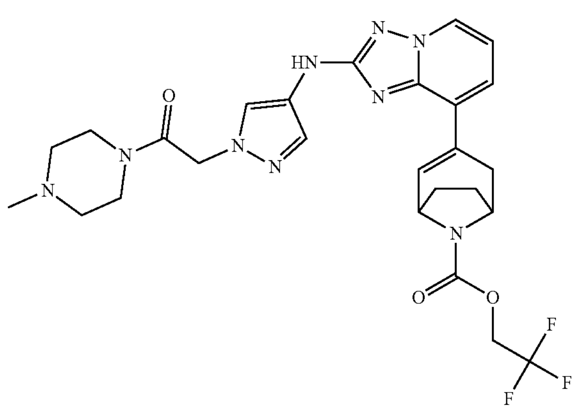 [SMILES: CN1CCN(C(=O)Cn2cc(Nc3nc4c(C5=CC6CCC(C5)N6C(=O)OCC(F)(F)F)cccn4n3)cn2)CC1] | 2,2,2-trifluoroethyl 3-[2-[[1-[2-(4-methylpiperazin-1-yl)-2-oxo-ethyl]pyrazol-4-yl]amino]-[1,2,4]triazolo[1,5-a]pyridin-8-yl]-8-azabicyclo[3.2.1]oct-3-ene-8-carboxylate |

TABLE 1-continued

Representative Compounds

| Ex. | Structure | Name |
|---|---|---|
| 8 | 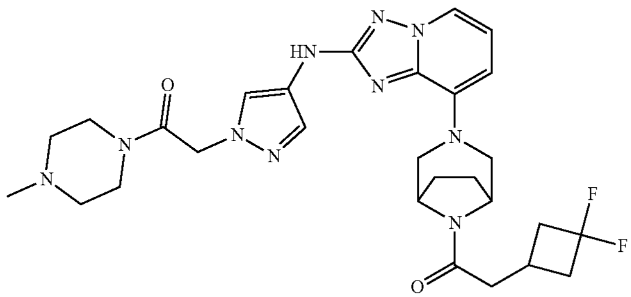 [SMILES: CN1CCN(C(=O)Cn2cc(Nc3nc4c(N5CC6CCC(C5)N6C(=O)CC5CC(F)(F)C5)cccn4n3)cn2)CC1] | 2-(3,3-difluorocyclobutyl)-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]ethanone |
| 9 | 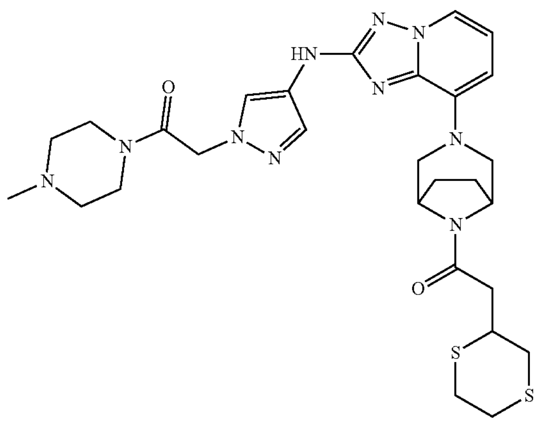 [SMILES: CN1CCN(C(=O)Cn2cc(Nc3nc4c(N5CC6CCC(C5)N6C(=O)CC5CSCCS5)cccn4n3)cn2)CC1] | 2-(1,4-dithian-2-yl)-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]ethanone |
| 10 | 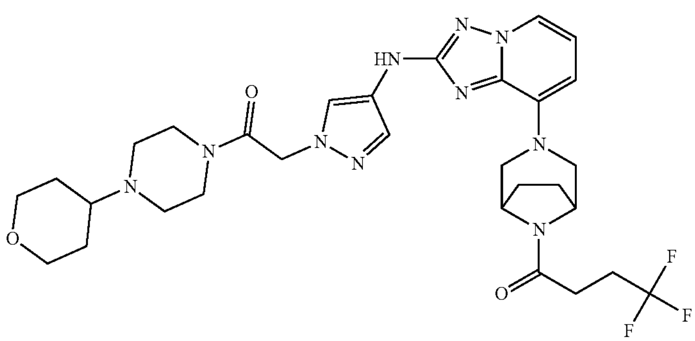 [SMILES: O=C(Cn1cc(Nc2nc3c(N4CC5CCC(C4)N5C(=O)CCC(F)(F)F)cccn3n2)cn1)N1CCN(C2CCOCC2)CC1] | 4,4,4-trifluoro-1-[3-[2-[[1-[2-oxo-2-(4-tetrahydropyran-4-ylpiperazin-1-yl)ethyl]pyrazol-4-yl]amino]-[1,2,4]triazolo[1,5-a]pyridin-8-yl]-3,8-diazabicyclo[3.2.1]octan-8-yl]butan-1-one |
| 11 | 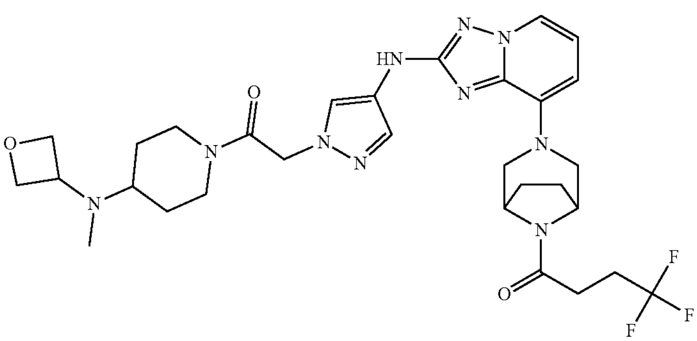 [SMILES: CN(C1CCN(C(=O)Cn2cc(Nc3nc4c(N5CC6CCC(C5)N6C(=O)CCC(F)(F)F)cccn4n3)cn2)CC1)C1COC1] | 4,4,4-trifluoro-1-[3-[2-[[1-[2-[4-[methyl(oxetan-3-yl)amino]-1-piperidyl]-2-oxo-ethyl]pyrazol-4-yl]amino]-[1,2,4]triazolo[1,5-a]pyridin-8-yl]-3,8-diazabicyclo[3.2.1]octan-8-yl]butan-1-one |

TABLE 1-continued

Representative Compounds

| Ex. | Structure | Name |
|---|---|---|
| 12 | 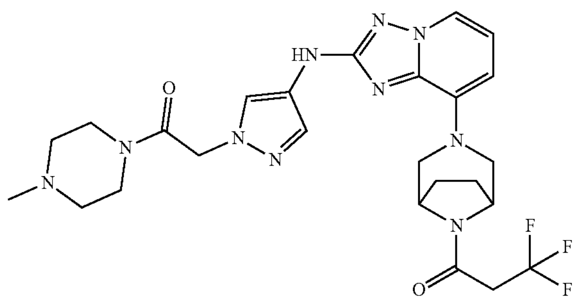 [SMILES: CN1CCN(C(=O)Cn2cc(Nc3nc4c(N5CC6CCC(C5)N6C(=O)CC(F)(F)F)cccn4n3)cn2)CC1] | 3,3,3-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]propan-1-one |
| 13 | 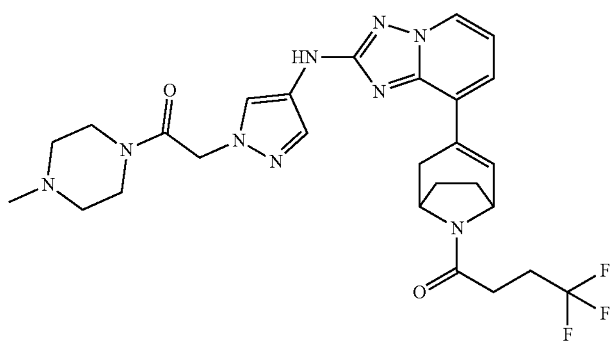 [SMILES: CN1CCN(C(=O)Cn2cc(Nc3nc4c(C5=CC6CCC(C5)N6C(=O)CCC(F)(F)F)cccn4n3)cn2)CC1] | 4,4,4-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-8-azabicyclo[3.2.1]oct-3-en-8-yl]butan-1-one |
| 14 | 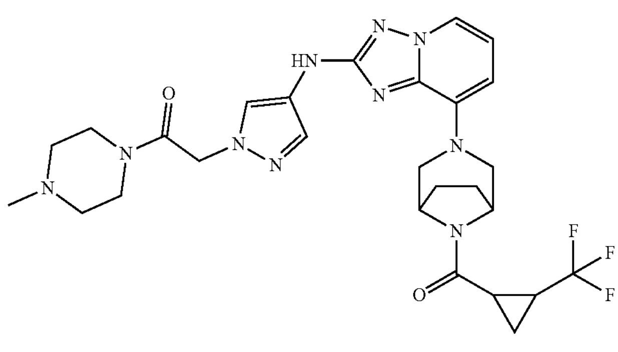 [SMILES: CN1CCN(C(=O)Cn2cc(Nc3nc4c(N5CC6CCC(C5)N6C(=O)C5CC5C(F)(F)F)cccn4n3)cn2)CC1] | 1-(4-methylpiperazin-1-yl)-2-[4-[[8-[8-[2-(trifluoromethyl)cyclopropanecarbonyl]-3,8-diazabicyclo[3.2.1]octan-3-yl]-[1,2,4]triazolo[1,5-a]pyridin-2-yl]amino]pyrazol-1-yl]ethanone |
| 15 | 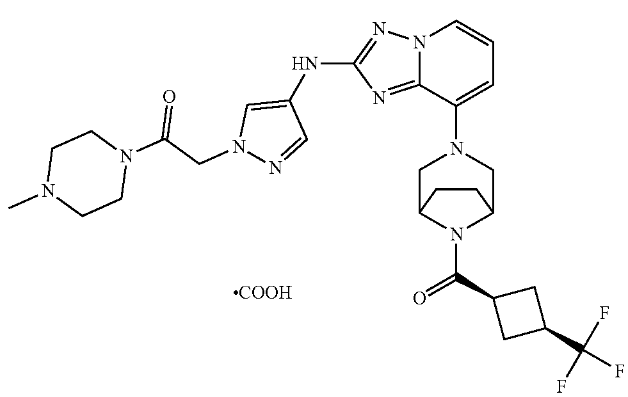 [SMILES: CN1CCN(C(=O)Cn2cc(Nc3nc4c(N5CC6CCC(C5)N6C(=O)[C@H]5C[C@@H](C(F)(F)F)C5)cccn4n3)cn2)CC1 ; "·COOH"] | formic acid; 1-(4-methylpiperazin-1-yl)-2-[4-[[8-[8-[3-(trifluoromethyl)cyclobutanecarbonyl]-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 16 | 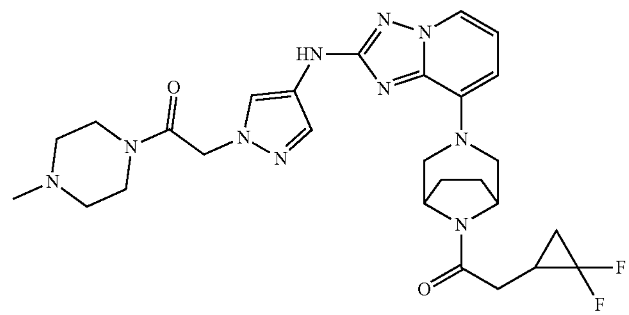 [SMILES: CN1CCN(C(=O)Cn2cc(Nc3nc4c(N5CC6CCC(C5)N6C(=O)CC5CC5(F)F)cccn4n3)cn2)CC1] | 2-(2,2-difluorocyclopropyl)-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]ethanone |
| 17 | 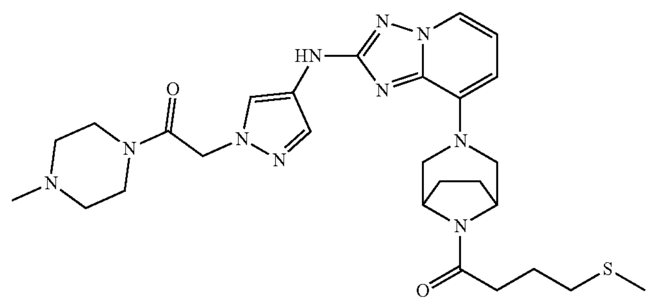 | 1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]-4-methylsulfanyl-butan-1-one |
| 18 | 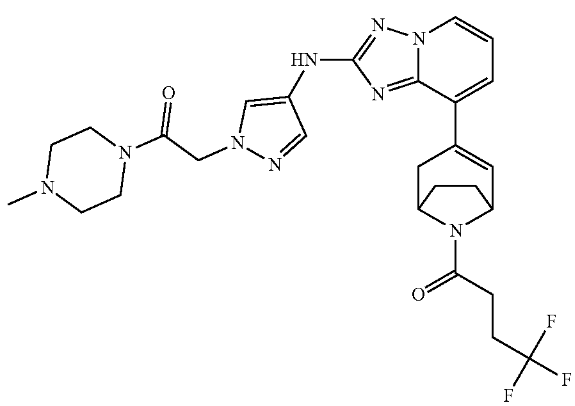 [SMILES: CN1CCN(C(=O)Cn2cc(Nc3nc4c(C5=CC6CCC(C5)N6C(=O)CCC(F)(F)F)cccn4n3)cn2)CC1] | 4,4,4-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-8-azabicyclo[3.2.1]oct-3-en-8-yl]butan-1-one |
| 19 | 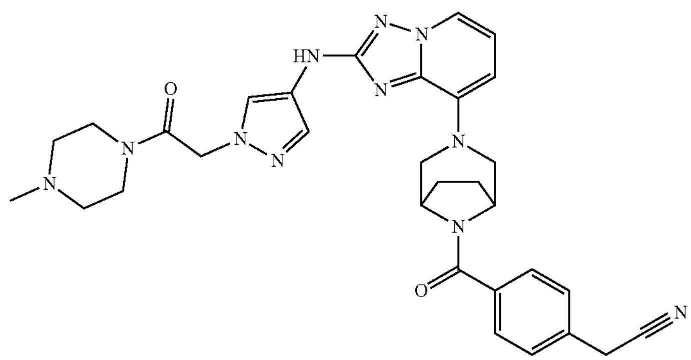 [SMILES: CN1CCN(C(=O)Cn2cc(Nc3nc4c(N5CC6CCC(C5)N6C(=O)c5ccc(CC#N)cc5)cccn4n3)cn2)CC1] | 2-[4-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]phenyl]acetonitrile |

TABLE 1-continued

Representative Compounds

| Ex. | Structure | Name |
|---|---|---|
| 20 | 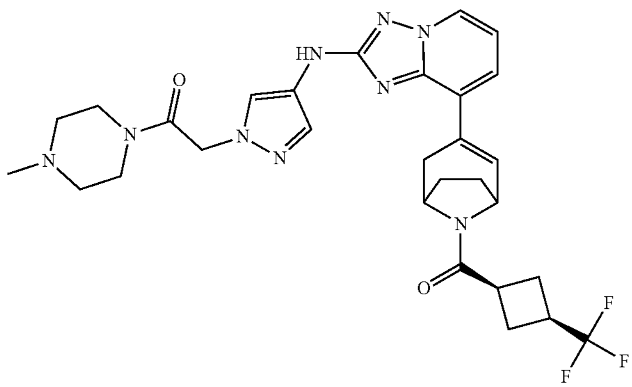 [SMILES: CN1CCN(C(=O)Cn2cc(Nc3nc4c(C5=CC6CCC(C5)N6C(=O)[C@H]5C[C@@H](C(F)(F)F)C5)cccn4n3)cn2)CC1] | 1-(4-methylpiperazin-1-yl)-2-[4-[[8-[8-[3-(trifluoromethyl)cyclobutanecarbonyl]-8-azabicyclo[3.2.1]oct-3-en-3-yl]-[1,2,4]triazolo[1,5-a]pyridin-2-yl]amino]pyrazol-1-yl]ethanone |
| 21 | 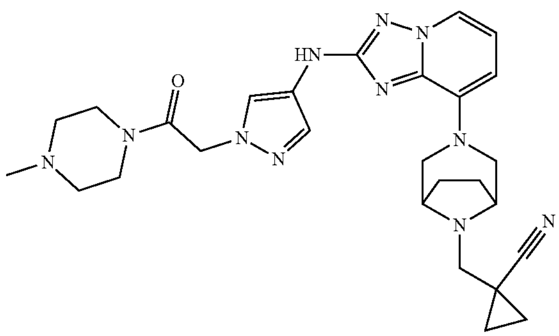 [SMILES: CN1CCN(C(=O)Cn2cc(Nc3nc4c(N5CC6CCC(C5)N6CC5(C#N)CC5)cccn4n3)cn2)CC1] | 1-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]methyl]cyclopropanecarbonitrile |
| 22 | 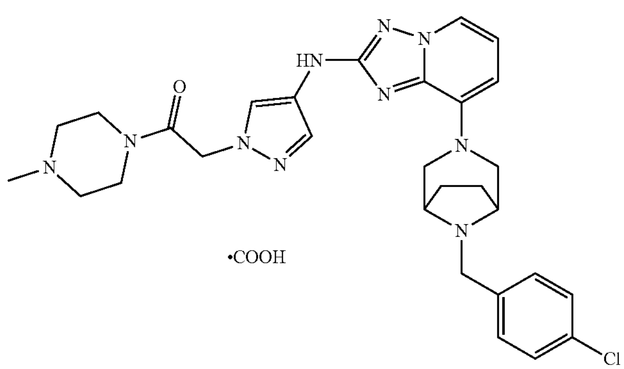 [SMILES: CN1CCN(C(=O)Cn2cc(Nc3nc4c(N5CC6CCC(C5)N6Cc5ccc(Cl)cc5)cccn4n3)cn2)CC1 ; "·COOH"] | 2-[4-[[8-[8-[(4-chlorophenyl)methyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone; formic acid |
| 23 | 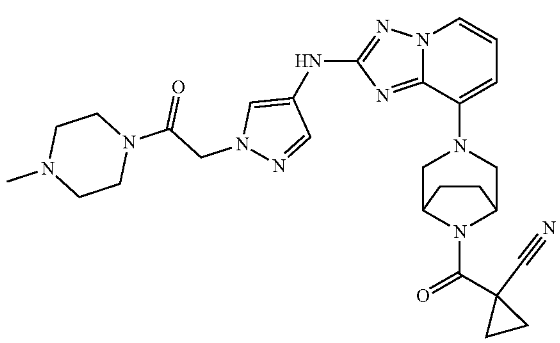 [SMILES: CN1CCN(C(=O)Cn2cc(Nc3nc4c(N5CC6CCC(C5)N6C(=O)C5(C#N)CC5)cccn4n3)cn2)CC1] | 1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]cyclopropanecarbonitrile |

TABLE 1-continued

Representative Compounds

| Ex. | Structure | Name |
|---|---|---|
| 24 | 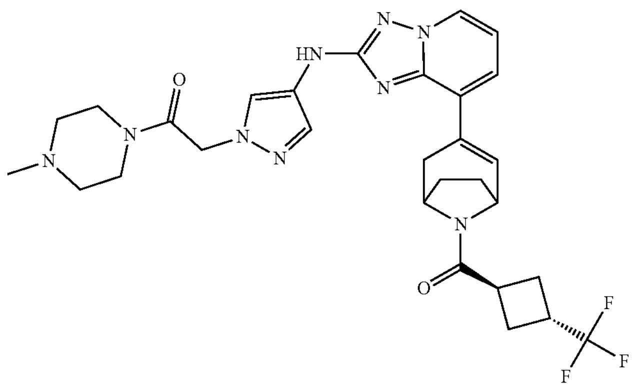 [SMILES: CN1CCN(C(=O)Cn2cc(Nc3nc4c(C5=CC6CCC(C5)N6C(=O)[C@H]5C[C@H](C(F)(F)F)C5)cccn4n3)cn2)CC1] | 1-(4-methylpiperazin-1-yl)-2-[4-[[8-[8-[3-(trifluoromethyl)cyclobutanecarbonyl]-8-azabicyclo[3.2.1]oct-3-en-3-yl]-[1,2,4]triazolo[1,5-a]pyridin-2-yl]amino]pyrazol-1-yl]ethanone |
| 25 | 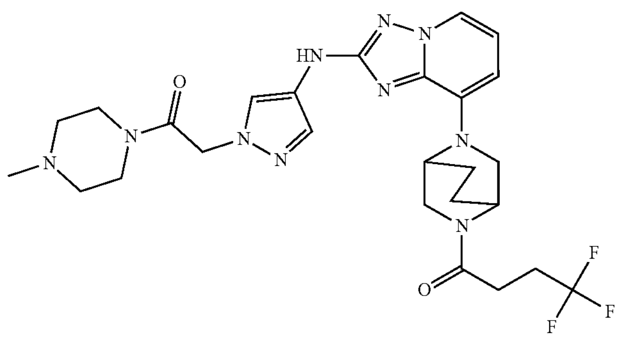 [SMILES: CN1CCN(C(=O)Cn2cc(Nc3nc4c(N5CC6CCC5CN6C(=O)CCC(F)(F)F)cccn4n3)cn2)CC1] | 4,4,4-trifluoro-1-[5-[2-[[1-[2-(4-methylpiperazin-1-yl)-2-oxo-ethyl]pyrazol-4-yl]amino]-[1,2,4]triazolo[1,5-a]pyridin-8-yl]-2,5-diazabicyclo[2.2.2]octan-2-yl]butan-1-one |
| 26 | 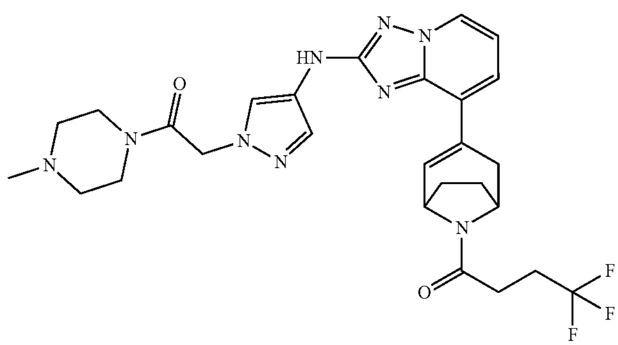 [SMILES: CN1CCN(C(=O)Cn2cc(Nc3nc4c(C5=CC6CCC(C5)N6C(=O)CCC(F)(F)F)cccn4n3)cn2)CC1] | 4,4,4-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-8-azabicyclo[3.2.1]oct-3-en-8-yl]butan-1-one |
| 27 | 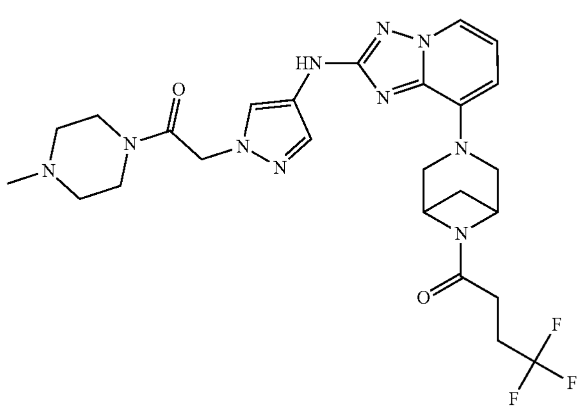 [SMILES: CN1CCN(C(=O)Cn2cc(Nc3nc4c(N5CC6CC(C5)N6C(=O)CCC(F)(F)F)cccn4n3)cn2)CC1] | 4,4,4-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,6-diazabicyclo[3.1.1]heptan-6-yl]butan-1-one |

TABLE 1-continued

Representative Compounds

| Ex. | Structure | Name |
|---|---|---|
| 28 | 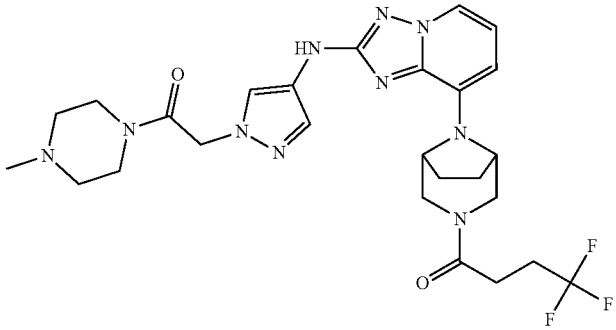 [SMILES: CN1CCN(C(=O)Cn2cc(Nc3nc4c(N5C6CCC5CN(C(=O)CCC(F)(F)F)C6)cccn4n3)cn2)CC1] | 4,4,4-trifluoro-1-[8-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-3-yl]butan-1-one |
| 29 | 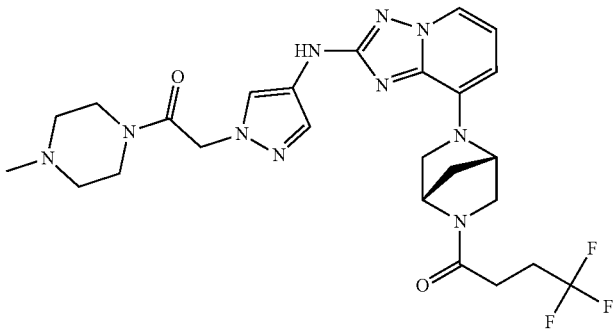 [SMILES: CN1CCN(C(=O)Cn2cc(Nc3nc4c(N5C[C@@H]6C[C@H]5CN6C(=O)CCC(F)(F)F)cccn4n3)cn2)CC1] | 4,4,4-trifluoro-1-[(1S,4S)-5-[2-[[1-[2-(4-methylpiperazin-1-yl)-2-oxo-ethyl]pyrazol-4-yl]amino]-[1,2,4]triazolo[1,5-a]pyridin-8-yl]-2,5-diazabicyclo[2.2.1]heptan-2-yl]butan-1-one |
| 30 | 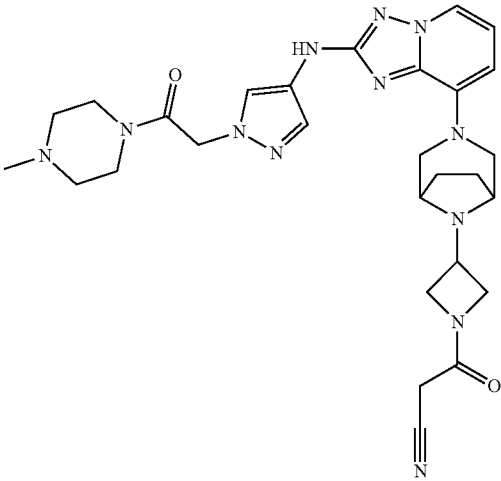 [SMILES: CN1CCN(C(=O)Cn2cc(Nc3nc4c(N5CC6CCC(C5)N6C5CN(C(=O)CC#N)C5)cccn4n3)cn2)CC1] | 3-[3-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]azetidin-1-yl]-3-oxo-propanenitrile |
| 31 | 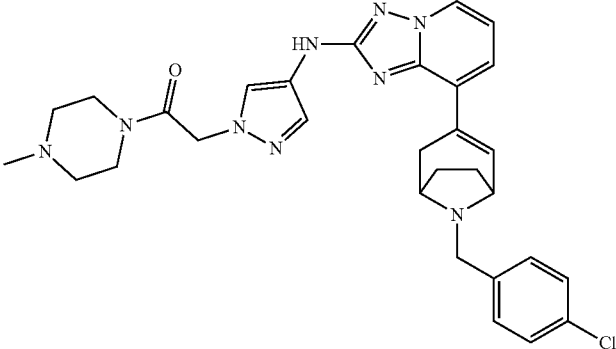 [SMILES: CN1CCN(C(=O)Cn2cc(Nc3nc4c(C5=CC6CCC(C5)N6Cc5ccc(Cl)cc5)cccn4n3)cn2)CC1] | 2-[4-[[8-[8-[(4-chlorophenyl)methyl]-8-azabicyclo[3.2.1]oct-3-en-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 32 | 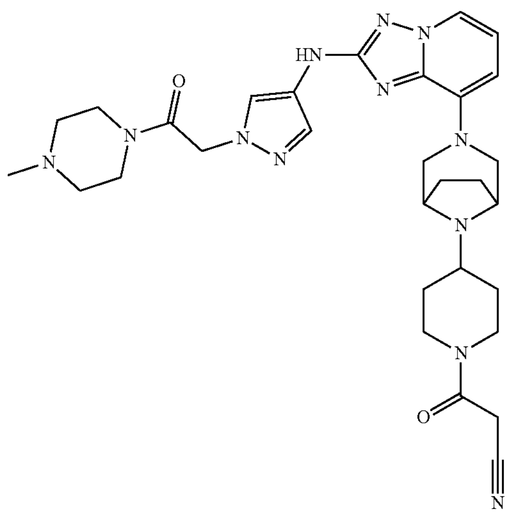 [SMILES: CN1CCN(C(=O)Cn2cc(Nc3nc4c(N5CC6CCC(C5)N6C5CCN(C(=O)CC#N)CC5)cccn4n3)cn2)CC1] | 3-[4-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]-1-piperidyl]-3-oxo-propanenitrile |
| 33 | 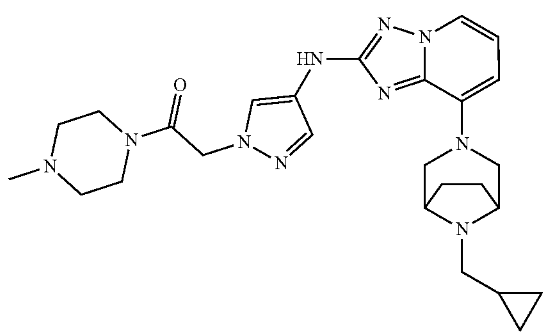 [SMILES: CN1CCN(C(=O)Cn2cc(Nc3nc4c(N5CC6CCC(C5)N6CC5CC5)cccn4n3)cn2)CC1] | 2-[4-[[8-[8-(cyclopropylmethyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 34 | 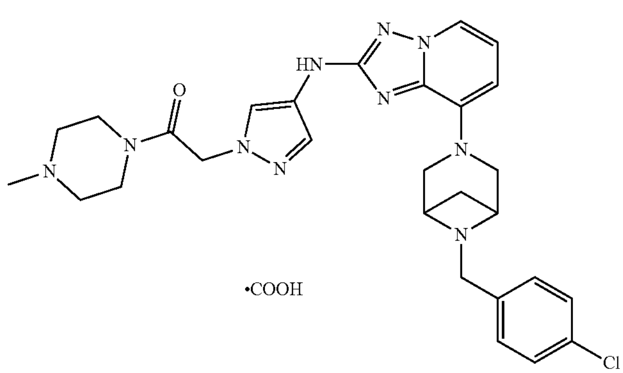 [SMILES: CN1CCN(C(=O)Cn2cc(Nc3nc4c(N5CC6CC(C5)N6Cc5ccc(Cl)cc5)cccn4n3)cn2)CC1 ; "·COOH"] | 2-[4-[[8-[6-[(4-chlorophenyl)methyl]-3,6-diazabicyclo[3.1.1]heptan-3-yl]-[1,2,4]triazolo[1,5-a]pyridin-2-yl]amino]pyrazol-1-yl]-1-(4-methylpiperazin-1-yl)ethanone; formic acid |

TABLE 1-continued

Representative Compounds

| Ex. | Structure | Name |
|---|---|---|
| 35 | 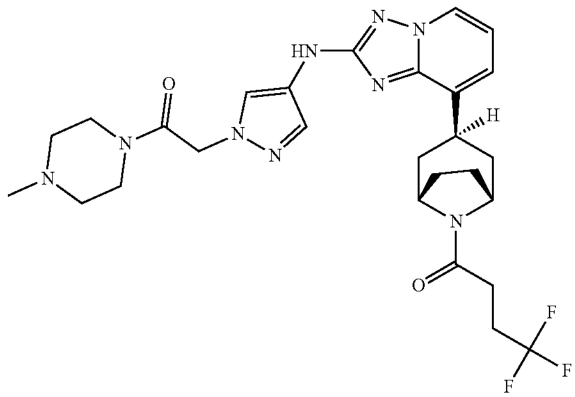 [SMILES: CN1CCN(C(=O)Cn2cc(Nc3nc4c([C@H]5C[C@H]6CC[C@@H](C5)N6C(=O)CCC(F)(F)F)cccn4n3)cn2)CC1] | 4,4,4-trifluoro-1-[(1S,5R)-3-[2-[[1-[2-(4-methylpiperazin-1-yl)-2-oxo-ethyl]pyrazol-4-yl]amino]-[1,2,4]triazolo[1,5-a]pyridin-8-yl]-8-azabicyclo[3.2.1]octan-8-yl]butan-1-one |
| 36 | 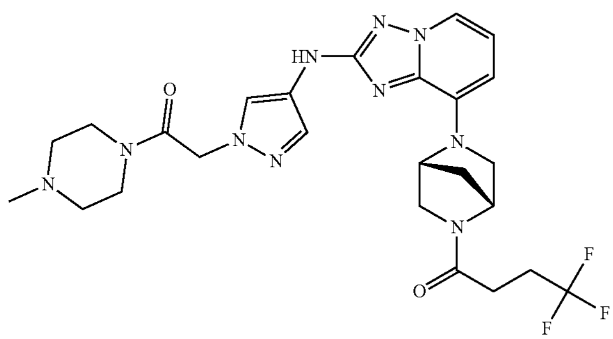 [SMILES: CN1CCN(C(=O)Cn2cc(Nc3nc4c(N5C[C@H]6C[C@@H]5CN6C(=O)CCC(F)(F)F)cccn4n3)cn2)CC1] | 4,4,4-trifluoro-1-[(1R,4R)-5-[2-[[1-[2-(4-methylpiperazin-1-yl)-2-oxo-ethyl]pyrazol-4-yl]amino]-[1,2,4]triazolo[1,5-a]pyridin-8-yl]-2,5-diazabicyclo[2.2.1]heptan-2-yl]butan-1-one |
| 37 | 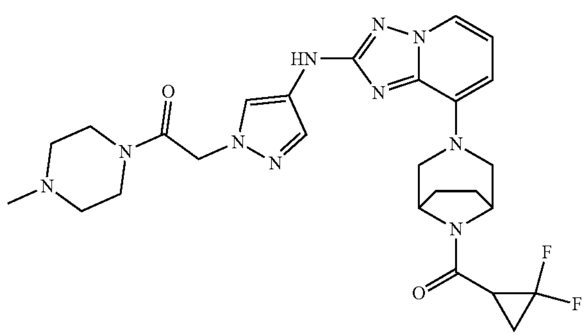 [SMILES: CN1CCN(C(=O)Cn2cc(Nc3nc4c(N5CC6CCC(C5)N6C(=O)C5CC5(F)F)cccn4n3)cn2)CC1] | 2-[4-[[8-[8-(2,2-difluorocyclopropanecarbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 38 | 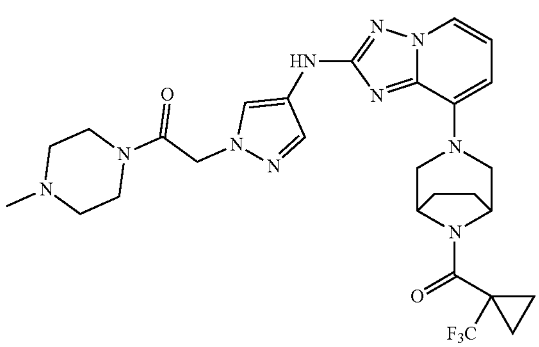 [SMILES: CN1CCN(C(=O)Cn2cc(Nc3nc4c(N5CC6CCC(C5)N6C(=O)C5(C(F)(F)F)CC5)cccn4n3)cn2)CC1] | 1-(4-methylpiperazin-1-yl)-2-[4-[[8-[8-[1-(trifluoromethyl)cyclopropanecarbonyl]-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|-----|-----------|------|
| 39 | 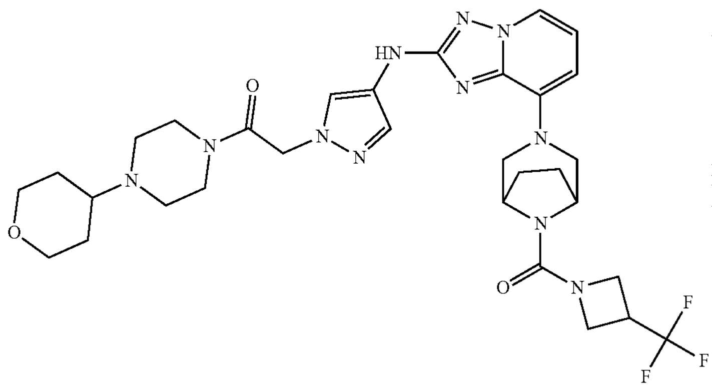 [SMILES: O=C(Cn1cc(Nc2nc3c(N4CC5CCC(C4)N5C(=O)N4CC(C(F)(F)F)C4)cccn3n2)cn1)N1CCN(C2CCOCC2)CC1] | 1-(4-tetrahydropyran-4-ylpiperazin-1-yl)-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 40 | 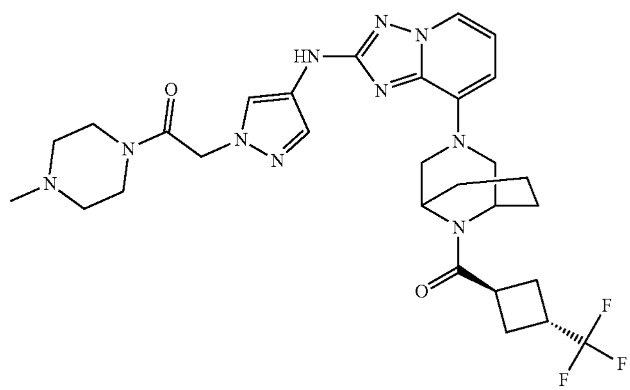 [SMILES: CN1CCN(C(=O)Cn2cc(Nc3nc4c(N5CC6CCCC(C5)N6C(=O)[C@H]5C[C@H](C(F)(F)F)C5)cccn4n3)cn2)CC1] | 1-(4-methylpiperazin-1-yl)-2-[4-[[8-[9-[3-(trifluoromethyl)cyclobutanecarbonyl]-3,9-diazabicyclo[3.3.1]nonan-3-yl]-[1,2,4]triazolo[1,5-a]pyridin-2-yl]amino]pyrazol-1-yl]ethanone |
| 41 | 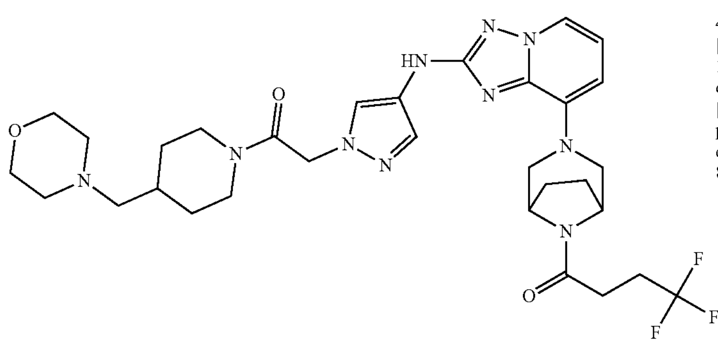 [SMILES: O=C(Cn1cc(Nc2nc3c(N4CC5CCC(C4)N5C(=O)CCC(F)(F)F)cccn3n2)cn1)N1CCC(CN2CCOCC2)CC1] | 4,4,4-trifluoro-1-[3-[2-[[1-[2-[4-(morpholinomethyl)-1-piperidyl]-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 42 | 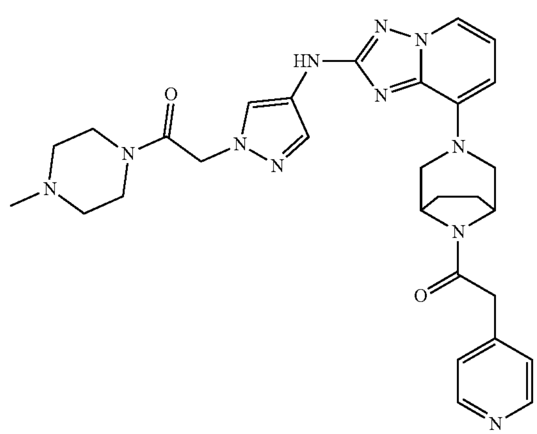 [SMILES: CN1CCN(C(=O)Cn2cc(Nc3nc4c(N5CC6CCC(C5)N6C(=O)Cc5ccncc5)cccn4n3)cn2)CC1] | 1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-pyridyl)ethanone |

TABLE 1-continued

Representative Compounds

| Ex. | Structure | Name |
|---|---|---|
| 43 | 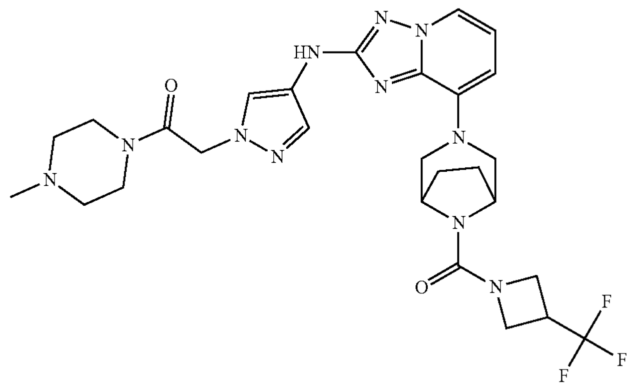 [SMILES: CN1CCN(C(=O)Cn2cc(Nc3nc4c(N5CC6CCC(C5)N6C(=O)N5CC(C(F)(F)F)C5)cccn4n3)cn2)CC1] | 1-(4-methylpiperazin-1-yl)-2-[4-[[8-[8-[3-(trifluoromethyl)azetidine-1-carbonyl]-3-azabicyclo[3.2.1]octan-3-yl]-[1,2,4]triazolo[1,5-a]pyridin-2-yl]amino]pyrazol-1-yl]ethanone |
| 44 | 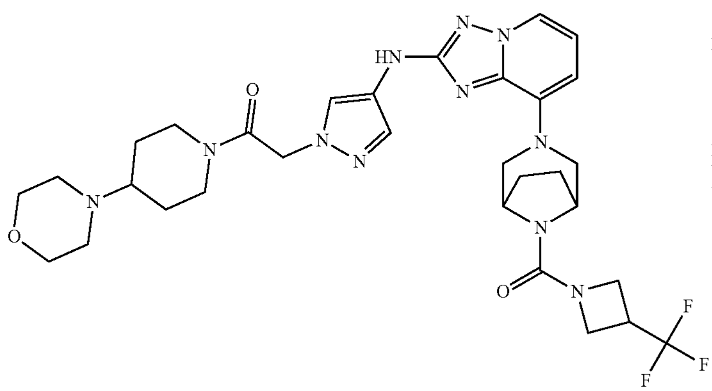 [SMILES: O=C(Cn1cc(Nc2nc3c(N4CC5CCC(C4)N5C(=O)N4CC(C(F)(F)F)C4)cccn3n2)cn1)N1CCC(N2CCOCC2)CC1] | 1-(4-morpholino-1-piperidyl)-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 45 | 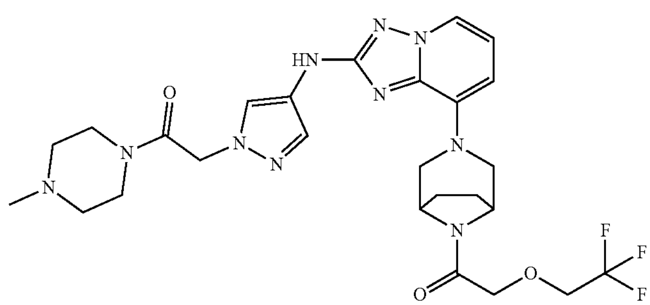 [SMILES: CN1CCN(C(=O)Cn2cc(Nc3nc4c(N5CC6CCC(C5)N6C(=O)COCC(F)(F)F)cccn4n3)cn2)CC1] | 1-(4-methylpiperazin-1-yl)-2-[4-[[8-[8-[2-(2,2,2-trifluoroethoxy)acetyl]-3,8-diazabicyclo[3.2.1]octan-3-yl]-[1,2,4]triazolo[1,5-a]pyridin-2-yl]amino]pyrazol-1-yl]ethanone |
| 46 | 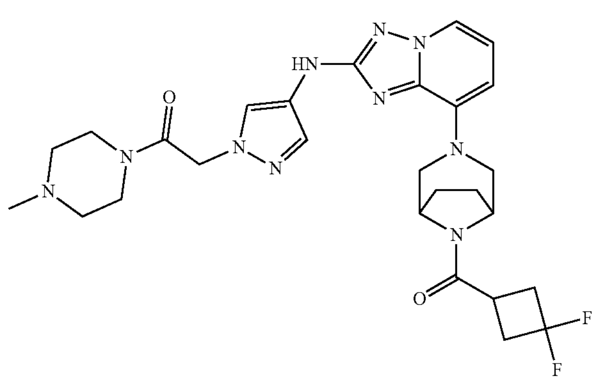 [SMILES: CN1CCN(C(=O)Cn2cc(Nc3nc4c(N5CC6CCC(C5)N6C(=O)C5CC(F)(F)C5)cccn4n3)cn2)CC1] | 2-[4-[[8-[8-(3,3-difluorocyclobutanecarbonyl)-3-yl]-3,8-diazabicyclo[3.2.1]octan-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 47 | 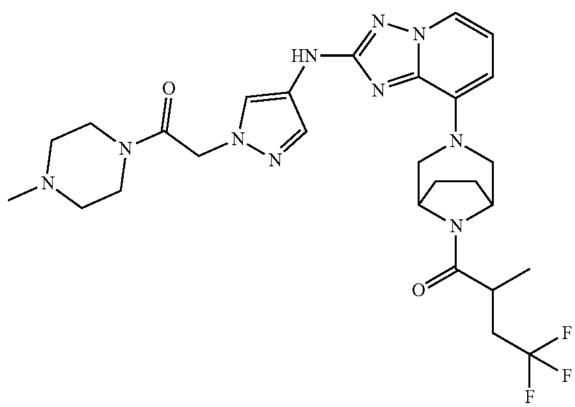 [SMILES: CC(CC(F)(F)F)C(=O)N1C2CCC1CN(c1cccn3nc(Nc4cnn(CC(=O)N5CCN(C)CC5)c4)nc13)C2] | 4,4,4-trifluoro-2-methyl-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 48 | 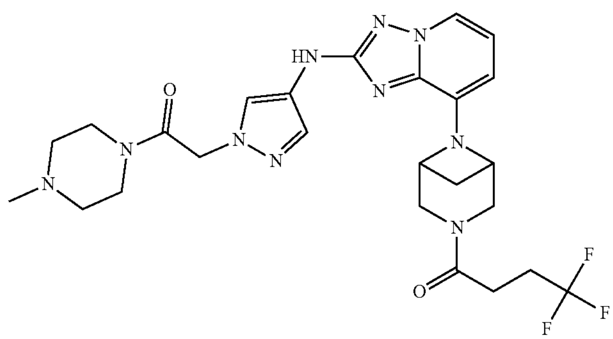 [SMILES: CN1CCN(C(=O)Cn2cc(Nc3nc4c(N5C6CC5CN(C(=O)CCC(F)(F)F)C6)cccn4n3)cn2)CC1] | 4,4,4-trifluoro-1-[6-[2-[[1-[2-(4-methylpiperazin-1-yl)-2-oxo-ethyl]pyrazol-4-yl]amino]-[1,2,4]triazolo[1,5-a]pyridin-8-yl]-3,6-diazabicyclo[3.1.1]heptan-3-yl]butan-1-one |
| 49 | 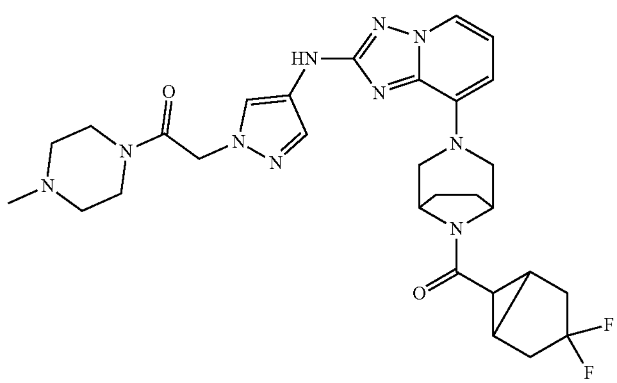 [SMILES: CN1CCN(C(=O)Cn2cc(Nc3nc4c(N5CC6CCC(C5)N6C(=O)C5C6CC(F)(F)CC65)cccn4n3)cn2)CC1] | 2-[4-[[8-[8-(3,3-difluorobicyclo[3.1.0]hexane-6-carbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 50 | 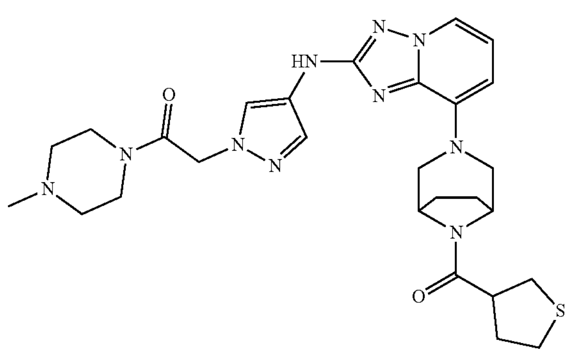 [SMILES: CN1CCN(C(=O)Cn2cc(Nc3nc4c(N5CC6CCC(C5)N6C(=O)C5CCSC5)cccn4n3)cn2)CC1] | 1-(4-methylpiperazin-1-yl)-2-[4-[[8-[8-(tetrahydrothiophene-3-carbonyl)-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 51 | 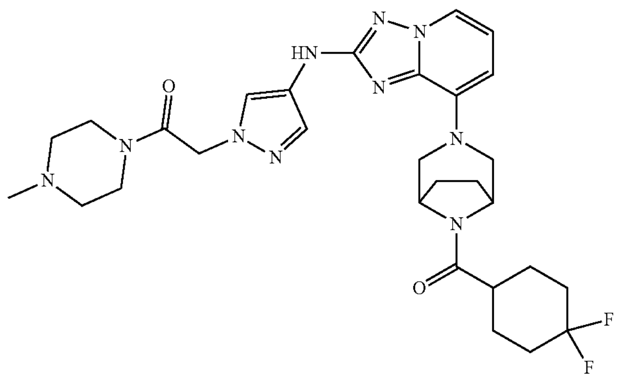 [SMILES: CN1CCN(C(=O)Cn2cc(Nc3nc4c(N5CC6CCC(C5)N6C(=O)C5CCC(F)(F)CC5)cccn4n3)cn2)CC1] | 2-[4-[[8-[8-(4,4-difluorocyclohexanecarbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 52 | 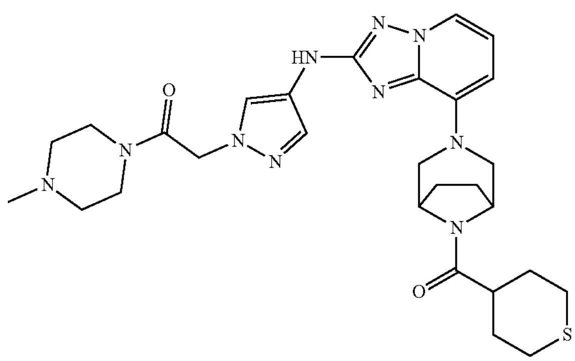 [SMILES: CN1CCN(C(=O)Cn2cc(Nc3nc4c(N5CC6CCC(C5)N6C(=O)C5CCSCC5)cccn4n3)cn2)CC1] | 1-(4-methylpiperazin-1-yl)-2-[4-[[8-[8-(tetrahydrothiopyran-4-carbonyl)-3,8-diazabicyclo[3.2.1]octan-3-yl]-[1,2,4]triazolo[1,5-a]pyridin-2-yl]amino]pyrazol-1-yl]ethanone |
| 53 | 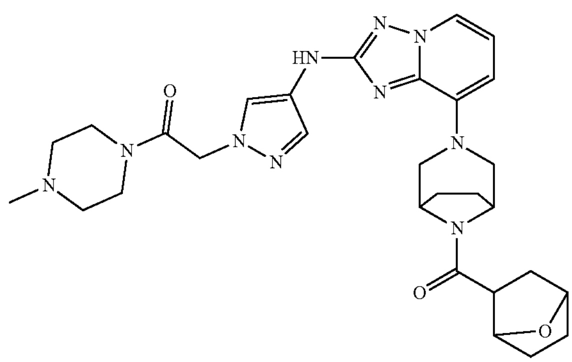 [SMILES: CN1CCN(C(=O)Cn2cc(Nc3nc4c(N5CC6CCC(C5)N6C(=O)C5CC6CCC5O6)cccn4n3)cn2)CC1] | 1-(4-methylpiperazin-1-yl)-2-[4-[[8-[8-(7-oxabicyclo[2.2.1]heptane-3-carbonyl)-3,8-diazabicyclo[3.2.1]octan-3-yl]-[1,2,4]triazolo[1,5-a]pyridin-2-yl]amino]pyrazol-1-yl]ethanone |
| 54 | 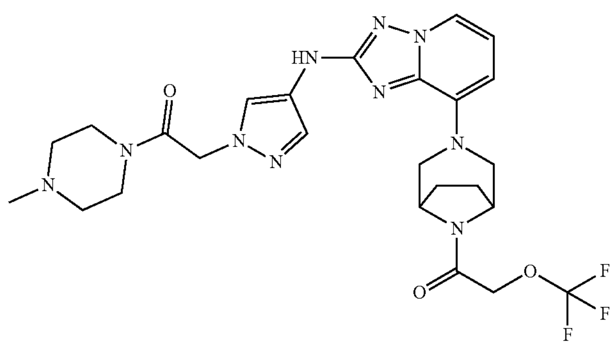 [SMILES: CN1CCN(C(=O)Cn2cc(Nc3nc4c(N5CC6CCC(C5)N6C(=O)COC(F)(F)F)cccn4n3)cn2)CC1] | 1-(4-methylpiperazin-1-yl)-2-[4-[[8-[8-[2-(trifluoromethoxy)acetyl]-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 55 | 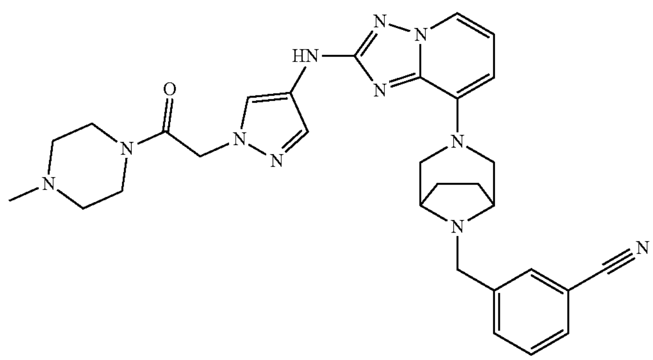 [SMILES: CN1CCN(C(=O)Cn2cc(Nc3nc4c(N5CC6CCC(C5)N6Cc5cccc(C#N)c5)cccn4n3)cn2)CC1] | 3-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]methyl]benzonitrile |
| 56 | 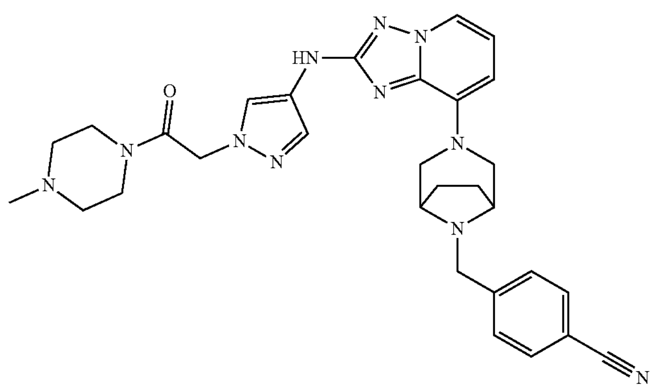 [SMILES: CN1CCN(C(=O)Cn2cc(Nc3nc4c(N5CC6CCC(C5)N6Cc5ccc(C#N)cc5)cccn4n3)cn2)CC1] | 4-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]methyl]benzonitrile |
| 57 | 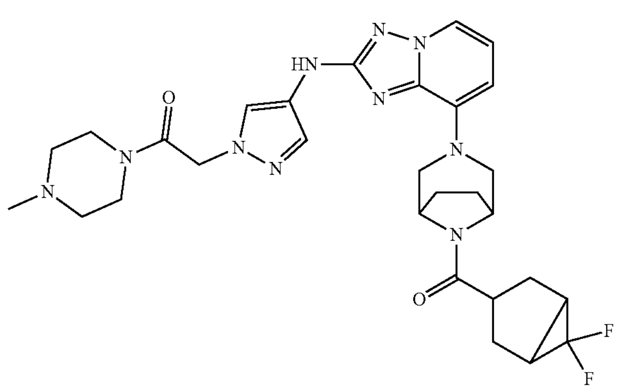 [SMILES: CN1CCN(C(=O)Cn2cc(Nc3nc4c(N5CC6CCC(C5)N6C(=O)C5CC6C(C5)C6(F)F)cccn4n3)cn2)CC1] | 2-[4-[[8-[8-(6,6-difluorobicyclo[3.1.0]hexane-3-carbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 58 | 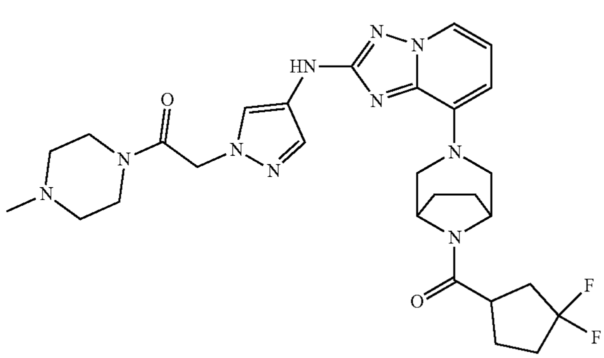 [SMILES: CN1CCN(C(=O)Cn2cc(Nc3nc4c(N5CC6CCC(C5)N6C(=O)C5CCC(F)(F)C5)cccn4n3)cn2)CC1] | 2-[4-[[8-[8-(3,3-difluorocyclopentanecarbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 59 | 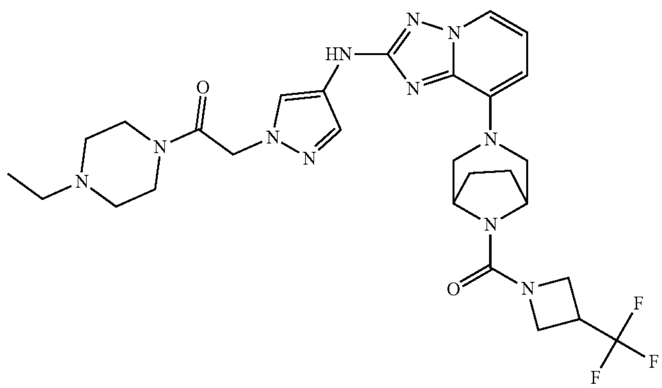 [SMILES: CCN1CCN(C(=O)Cn2cc(Nc3nc4c(N5CC6CCC(C5)N6C(=O)N5CC(C(F)(F)F)C5)cccn4n3)cn2)CC1] | 1-(4-ethylpiperazin-1-yl)-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 60 | 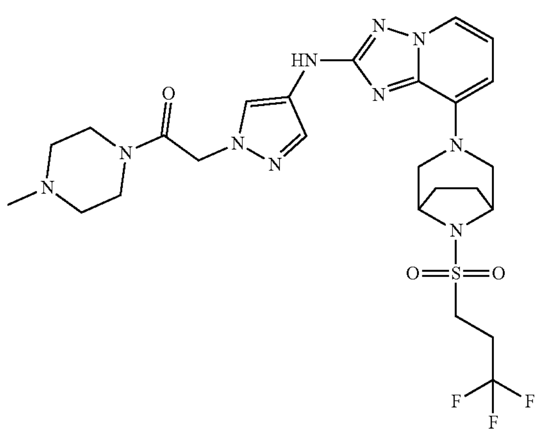 [SMILES: CN1CCN(C(=O)Cn2cc(Nc3nc4c(N5CC6CCC(C5)N6S(=O)(=O)CCC(F)(F)F)cccn4n3)cn2)CC1] | 1-(4-methylpiperazin-1-yl)-2-[4-[[8-[8-(3,3,3-trifluoropropylsulfonyl)-3,8-diazabicyclo[3.2.1]octan-3-yl]-[1,2,4]triazolo[1,5-a]pyridin-2-yl]amino]pyrazol-1-yl]ethanone |
| 61 | 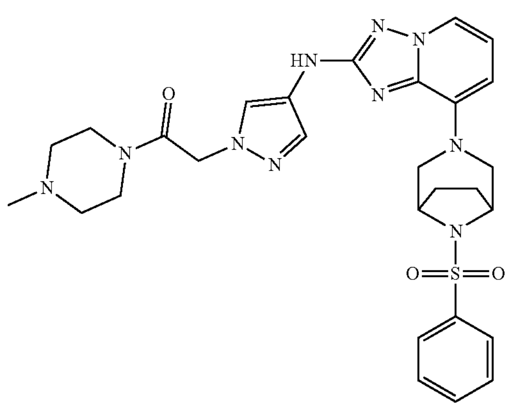 [SMILES: CN1CCN(C(=O)Cn2cc(Nc3nc4c(N5CC6CCC(C5)N6S(=O)(=O)c5ccccc5)cccn4n3)cn2)CC1] | 2-[4-[[8-[8-(benzenesulfonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 62 | 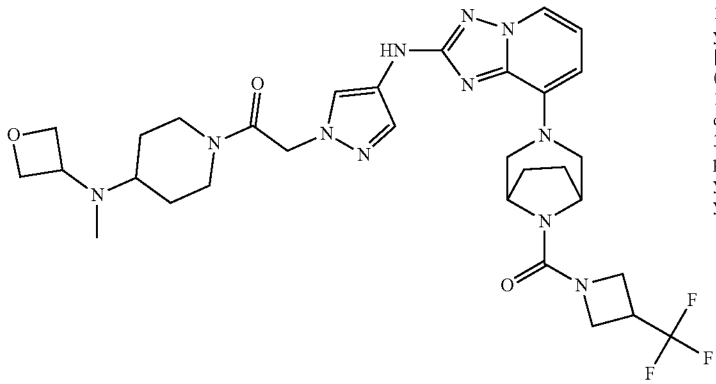 [SMILES: CN(C1CCN(C(=O)Cn2cc(Nc3nc4c(N5CC6CCC(C5)N6C(=O)N5CC(C(F)(F)F)C5)cccn4n3)cn2)CC1)C1COC1] | 1-[4-[methyl(oxetan-3-yl)amino]-1-piperidyl]-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 63 | 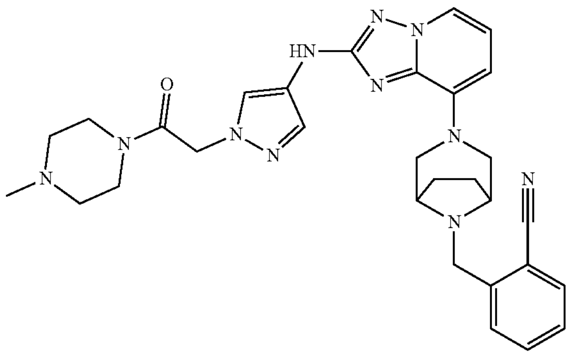 [SMILES: CN1CCN(C(=O)Cn2cc(Nc3nc4c(N5CC6CCC(C5)N6Cc5ccccc5C#N)cccn4n3)cn2)CC1] | 2-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]methyl]benzonitrile |
| 64 | 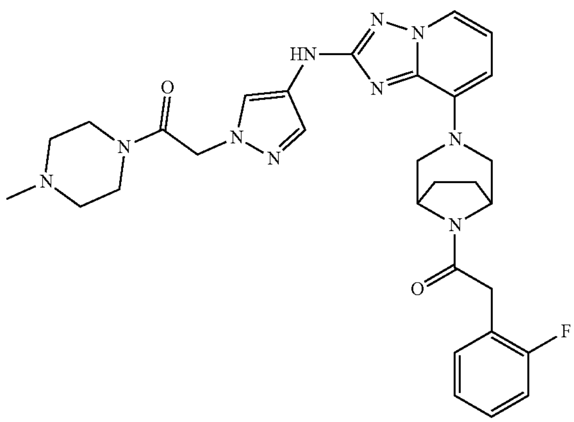 [SMILES: CN1CCN(C(=O)Cn2cc(Nc3nc4c(N5CC6CCC(C5)N6C(=O)Cc5ccccc5F)cccn4n3)cn2)CC1] | 2-(2-fluorophenyl)-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]ethanone |
| 65 | 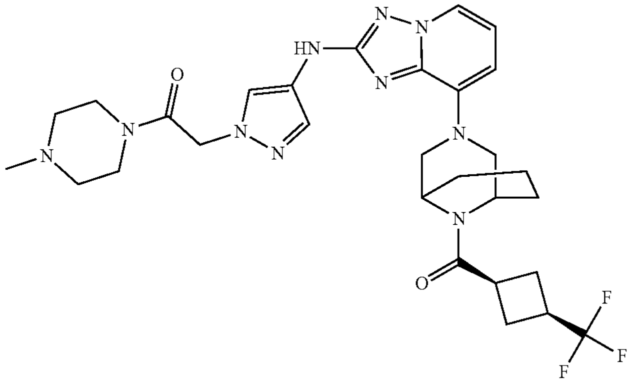 [SMILES: CN1CCN(C(=O)Cn2cc(Nc3nc4c(N5CC6CCCC(C5)N6C(=O)[C@H]5C[C@@H](C(F)(F)F)C5)cccn4n3)cn2)CC1] | 1-(4-methylpiperazin-1-yl)-2-[4-[[8-[9-[3-(trifluoromethyl)cyclobutanecarbonyl]-3,9-diazabicyclo[3.3.1]nonan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 66 | 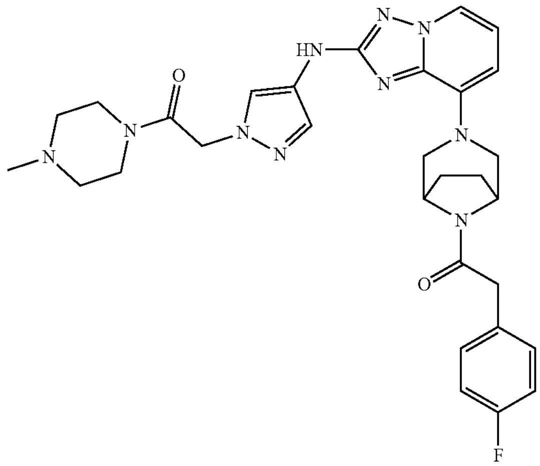 [SMILES: CN1CCN(C(=O)Cn2cc(Nc3nc4c(N5CC6CCC(C5)N6C(=O)Cc5ccc(F)cc5)cccn4n3)cn2)CC1] | 2-(4-fluorophenyl)-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]ethanone |
| 67 | 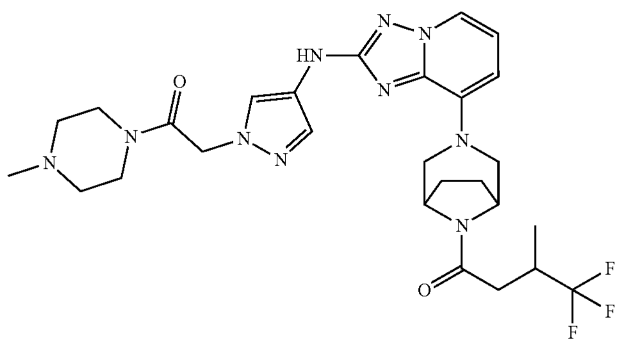 [SMILES: CC(CC(=O)N1C2CCC1CN(c1cccn3nc(Nc4cnn(CC(=O)N5CCN(C)CC5)c4)nc13)C2)C(F)(F)F] | 4,4,4-trifluoro-3-methyl-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 68 | 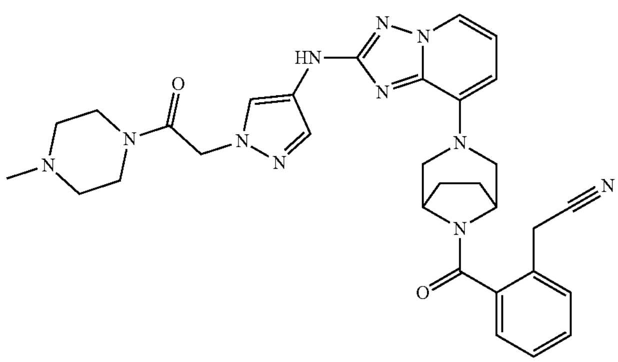 [SMILES: CN1CCN(C(=O)Cn2cc(Nc3nc4c(N5CC6CCC(C5)N6C(=O)c5ccccc5CC#N)cccn4n3)cn2)CC1] | 2-[2-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-carbonyl]phenyl]acetonitrile |
| 69 | 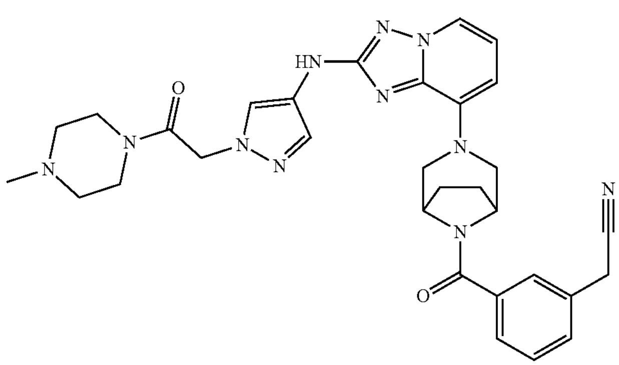 [SMILES: CN1CCN(C(=O)Cn2cc(Nc3nc4c(N5CC6CCC(C5)N6C(=O)c5cccc(CC#N)c5)cccn4n3)cn2)CC1] | 2-[3-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]phenyl]acetonitrile |

TABLE 1-continued

Representative Compounds

| Ex. | Structure | Name |
|---|---|---|
| 70 | 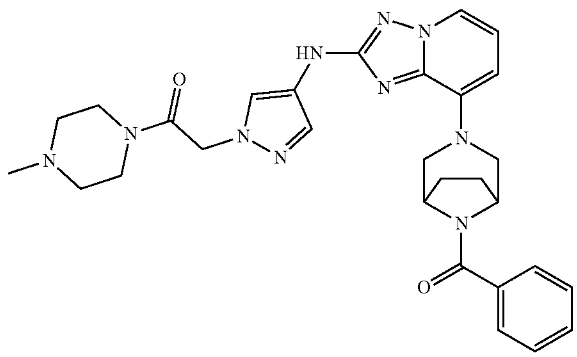 [SMILES: CN1CCN(C(=O)Cn2cc(Nc3nc4c(N5CC6CCC(C5)N6C(=O)c5ccccc5)cccn4n3)cn2)CC1] | 2-[4-[[8-(8-benzoyl-3,8-diazabicyclo[3.2.1]octan-3-yl)-[1,2,4]triazolo[1,5-a]pyridin-2-yl]amino]pyrazol-1-yl]-1-(4-methylpiperazin-1-yl)ethanone |
| 71 | 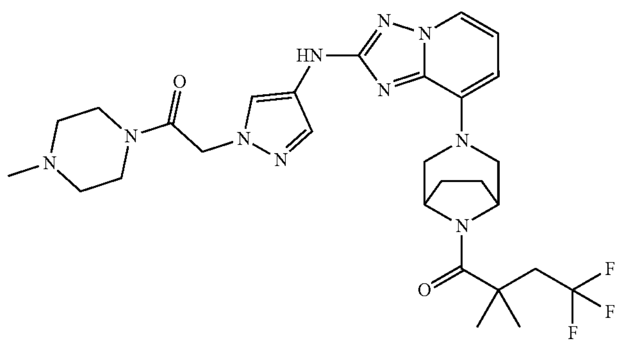 [SMILES: CN1CCN(C(=O)Cn2cc(Nc3nc4c(N5CC6CCC(C5)N6C(=O)C(C)(C)CC(F)(F)F)cccn4n3)cn2)CC1] | 4,4,4-trifluoro-2,2-dimethyl-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 72 | 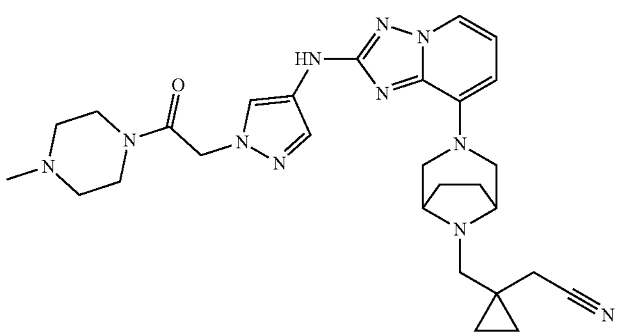 [SMILES: CN1CCN(C(=O)Cn2cc(Nc3nc4c(N5CC6CCC(C5)N6CC5(CC#N)CC5)cccn4n3)cn2)CC1] | 2-[1-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]methyl]cyclopropyl]acetonitrile |
| 73 | 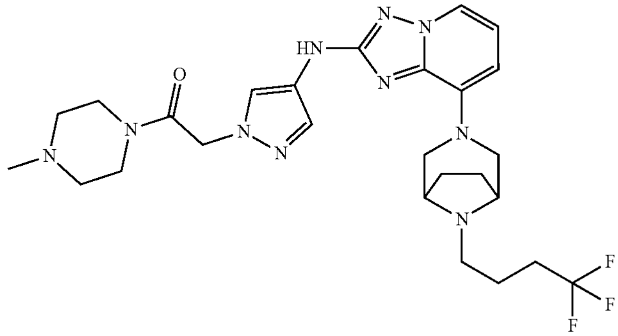 [SMILES: CN1CCN(C(=O)Cn2cc(Nc3nc4c(N5CC6CCC(C5)N6CCCC(F)(F)F)cccn4n3)cn2)CC1] | 1-(4-methylpiperazin-1-yl)-2-[4-[[8-[8-(4,4,4-trifluorobutyl)-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 74 | 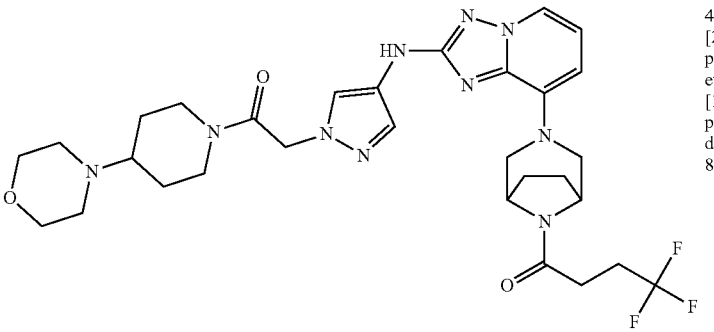 | 4,4,4-trifluoro-1-[3-[2-[[1-[2-(4-morpholino-1-piperidyl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 75 | 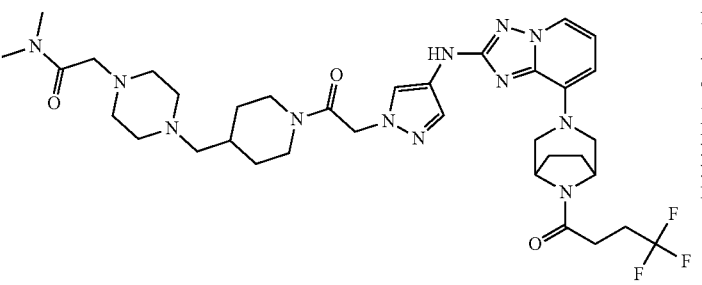 | N,N-dimethyl-2-[4-[[1-[2-[4-[[8-[8-(4,4,4-trifluorobutanoyl)-3,8-diazabicyclo[3.2.1]octan-3-yl]-[1,2,4]triazolo[1,5-a]pyridin-2-yl]amino]pyrazol-1-yl]acetyl]-4-piperidyl]methyl]piperazin-1-yl]acetamide |
| 76 | 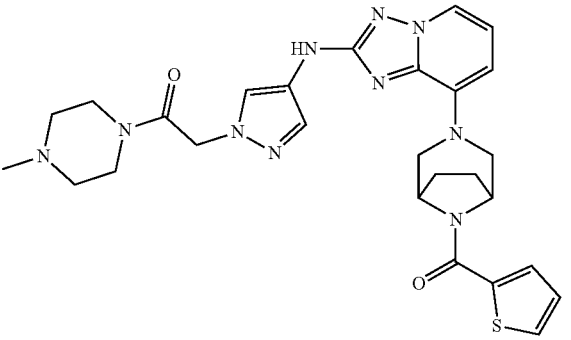 [SMILES: CN1CCN(C(=O)Cn2cc(Nc3nc4c(N5CC6CCC(C5)N6C(=O)c5cccs5)cccn4n3)cn2)CC1] | 1-(4-methylpiperazin-1-yl)-2-[4-[[8-[8-(thiophene-2-carbonyl)-3,8-diazabicyclo[3.2.1]octan-3-yl]-[1,2,4]triazolo[1,5-a]pyridin-2-yl]amino]pyrazol-1-yl]ethanone |
| 77 | 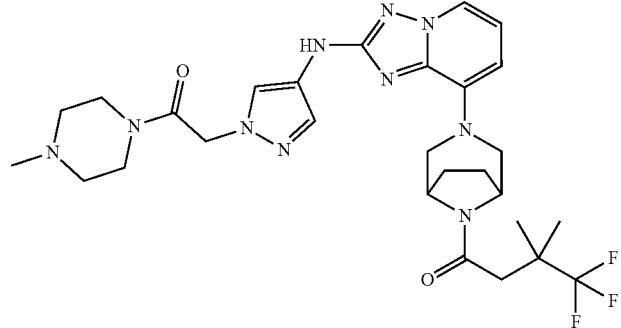 [SMILES: CN1CCN(C(=O)Cn2cc(Nc3nc4c(N5CC6CCC(C5)N6C(=O)CC(C)(C)C(F)(F)F)cccn4n3)cn2)CC1] | 4,4,4-trifluoro-3,3-dimethyl-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |

TABLE 1-continued

Representative Compounds

| Ex. | Structure | Name |
|---|---|---|
| 78 | 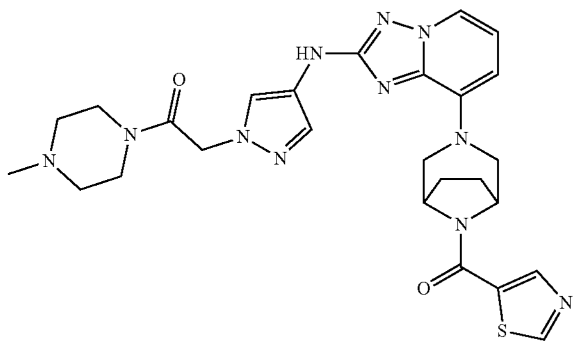 [SMILES: CN1CCN(C(=O)Cn2cc(Nc3nc4c(N5CC6CCC(C5)N6C(=O)c5cncs5)cccn4n3)cn2)CC1] | 1-(4-methylpiperazin-1-yl)-2-[4-[[8-[8-(thiazole-5-carbonyl)-3,8-diazabicyclo[3.2.1]octan-3-yl]-[1,2,4]triazolo[1,5-a]pyridin-2-yl]amino]pyrazol-1-yl]ethanone |
| 79 | 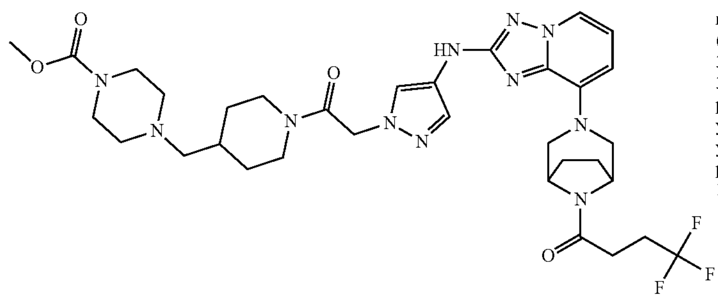 [SMILES: COC(=O)N1CCN(CC2CCN(C(=O)Cn3cc(Nc4nc5c(N6CC7CCC(C6)N7C(=O)CCC(F)(F)F)cccn5n4)cn3)CC2)CC1] | methyl 4-[[1-[2-[4-[[8-[8-(4,4,4-trifluorobutanoyl)-3,8-diazabicyclo[3.2.1]octan-3-yl]-[1,2,4]triazolo[1,5-a]pyridin-2-yl]amino]pyrazol-1-yl]acetyl]-4-piperidyl]methyl]piperazine-1-carboxylate |
| 80 | 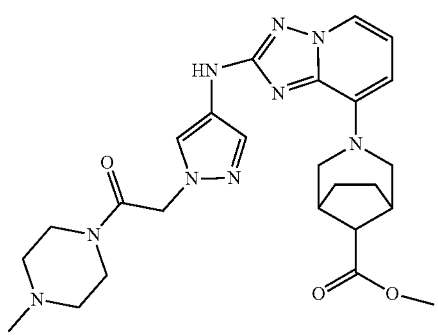 | methyl 3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octane-8-carboxylate |
| 81 | 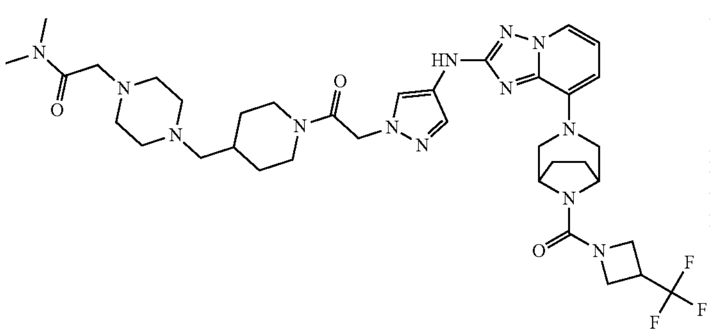 [SMILES: CN(C)C(=O)CN1CCN(CC2CCN(C(=O)Cn3cc(Nc4nc5c(N6CC7CCC(C6)N7C(=O)N6CC(C(F)(F)F)C6)cccn5n4)cn3)CC2)CC1] | N,N-dimethyl-2-[4-[[1-[2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]acetyl]-4-piperidyl]methyl]piperazin-1-yl]acetamide |

TABLE 1-continued

Representative Compounds

| Ex. | Structure | Name |
|---|---|---|
| 82 | 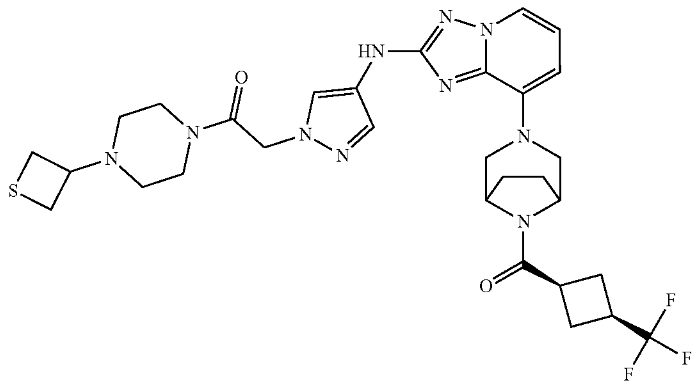 [SMILES: O=C(Cn1cc(Nc2nc3c(N4CC5CCC(C4)N5C(=O)[C@H]4C[C@@H](C(F)(F)F)C4)cccn3n2)cn1)N1CCN(C2CSC2)CC1] | 1-[4-(thietan-3-yl)piperazin-1-yl]-2-[4-[4[[8-[8-[3-(trifluoromethyl)cyclobutanecarbonyl]-3,8-diazabicyclo[3.2.1]octan-3-yl]-[1,2,4]triazolo[1,5-a]pyridin-2-yl]amino]pyrazol-1-yl]ethanone |
| 83 | 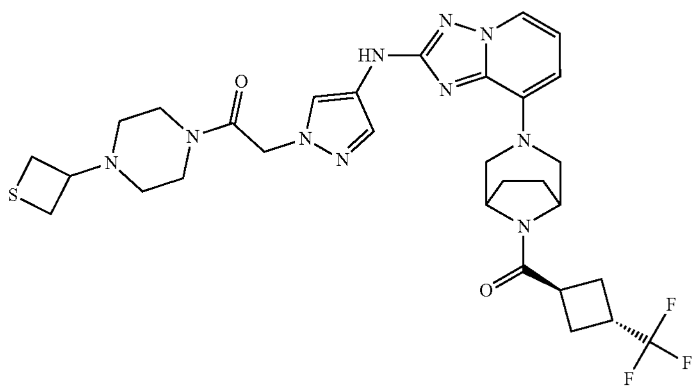 [SMILES: O=C(Cn1cc(Nc2nc3c(N4CC5CCC(C4)N5C(=O)[C@H]4C[C@H](C(F)(F)F)C4)cccn3n2)cn1)N1CCN(C2CSC2)CC1] | 1-[4-(thietan-3-yl)piperazin-1-yl]-2-[4-[[8-[8-[3-(trifluoromethyl)cyclobutanecarbonyl]-3,8-diazabicyclo[3.2.1]octan-3-yl]-[1,2,4]triazolo[1,5-a]pyridin-2-yl]amino]pyrazol-1-yl]ethanone |
| 84 | 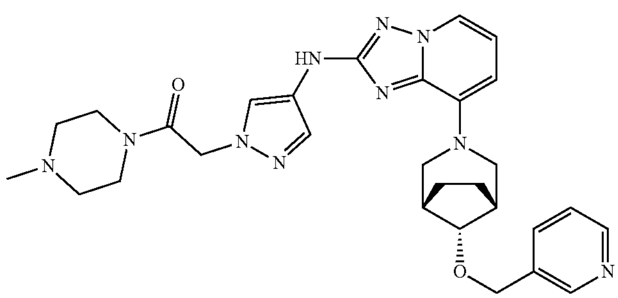 [SMILES: CN1CCN(C(=O)Cn2cc(Nc3nc4c(N5C[C@H]6CC[C@@H](C5)[C@H]6OCc5cccnc5)cccn4n3)cn2)CC1] | 1-(4-methylpiperazin-1-yl)-2-[4-[[8-[(1S,5R)-8-(3-pyridylmethoxy)-3-azabicyclo[3.2.1]octan-3-yl]-[1,2,4]triazolo[1,5-a]pyridin-2-yl]amino]pyrazol-1-yl]ethanone |
| 85 | 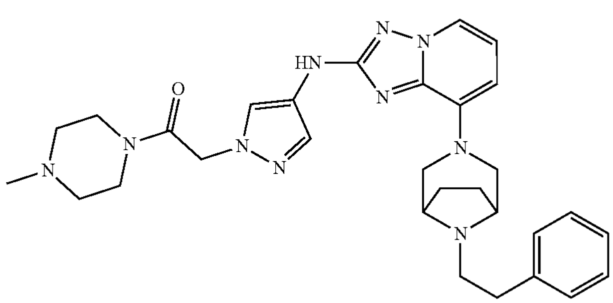 [SMILES: CN1CCN(C(=O)Cn2cc(Nc3nc4c(N5CC6CCC(C5)N6CCc5ccccc5)cccn4n3)cn2)CC1] | 1-(4-methylpiperazin-1-yl)-2-[4-[[8-[8-(2-phenylethyl)-3,8-diazabicyclo[3.2.1]octan-3-yl]-[1,2,4]triazolo[1,5-a]pyridin-2-yl]amino]pyrazol-1-pyridin-2-yl]ethanone |

TABLE 1-continued

Representative Compounds

| Ex. | Structure | Name |
|---|---|---|
| 86 | 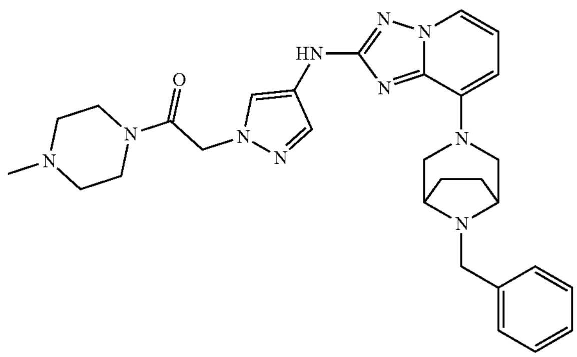 [SMILES: CN1CCN(C(=O)Cn2cc(Nc3nc4c(N5CC6CCC(C5)N6Cc5ccccc5)cccn4n3)cn2)CC1] | 2-[4-[[8-(8-benzyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 87 | 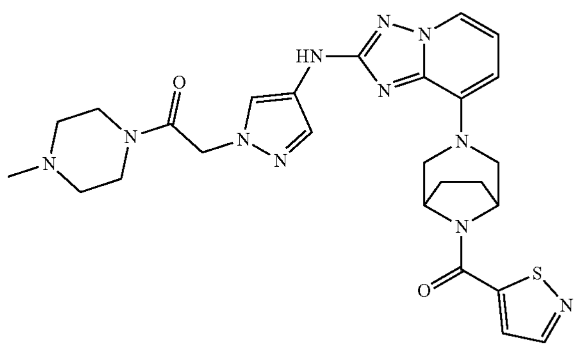 [SMILES: CN1CCN(C(=O)Cn2cc(Nc3nc4c(N5CC6CCC(C5)N6C(=O)c5ccns5)cccn4n3)cn2)CC1] | 2-[4-[[8-[8-(isothiazole-5-carbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 88 | 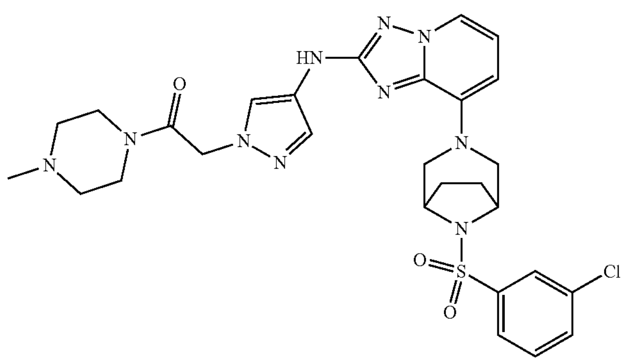 [SMILES: CN1CCN(C(=O)Cn2cc(Nc3nc4c(N5CC6CCC(C5)N6S(=O)(=O)c5cccc(Cl)c5)cccn4n3)cn2)CC1] | 2-[4-[[8-[8-(3-chlorophenyl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 89 | 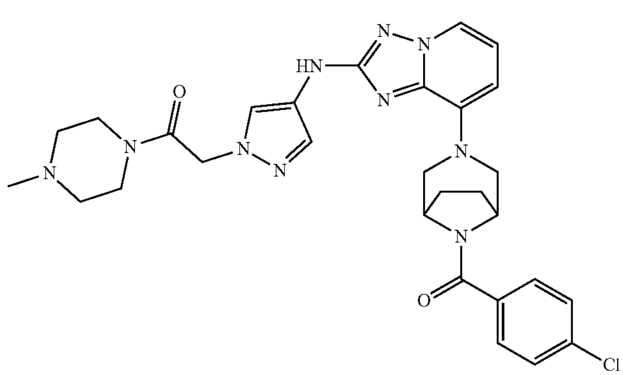 [SMILES: CN1CCN(C(=O)Cn2cc(Nc3nc4c(N5CC6CCC(C5)N6C(=O)c5ccc(Cl)cc5)cccn4n3)cn2)CC1] | chlorobenzoyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 90 | 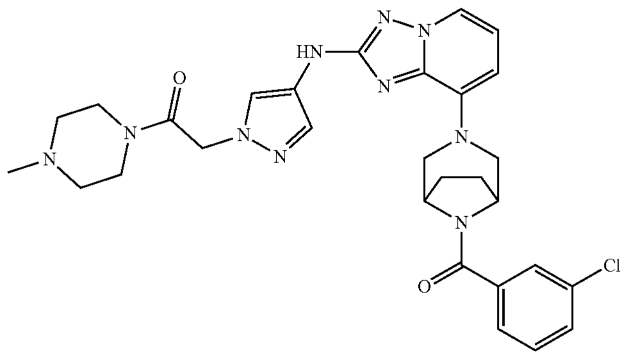 [SMILES: CN1CCN(C(=O)Cn2cc(Nc3nc4c(N5CC6CCC(C5)N6C(=O)c5cccc(Cl)c5)cccn4n3)cn2)CC1] | 2-[4-[[8-[8-(3-chlorobenzoyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 91 | 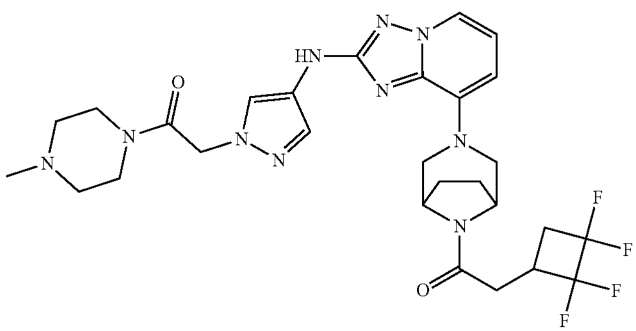 [SMILES: CN1CCN(C(=O)Cn2cc(Nc3nc4c(N5CC6CCC(C5)N6C(=O)CC5CC(F)(F)C5(F)F)cccn4n3)cn2)CC1] | 1-[3-[2-[[1-[2-(4-methylpiperazin-1-yl)-2-oxo-ethyl]pyrazol-4-yl]amino]-[1,2,4]triazolo[1,5-a]alpyridin-8-yl]-3,8-diazabicyclo[3.2.1]octan-8-yl]-2-(2,2,3,3-tetrafluorocyclobutyl)ethanone |
| 92 | 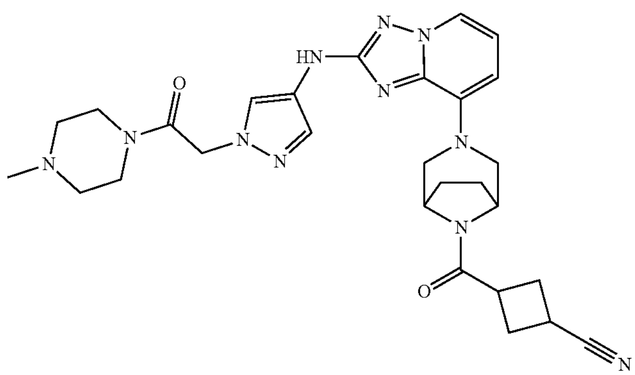 [SMILES: CN1CCN(C(=O)Cn2cc(Nc3nc4c(N5CC6CCC(C5)N6C(=O)C5CC(C#N)C5)cccn4n3)cn2)CC1] | 3-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]cyclobutanecarbonitrile |
| 93 | 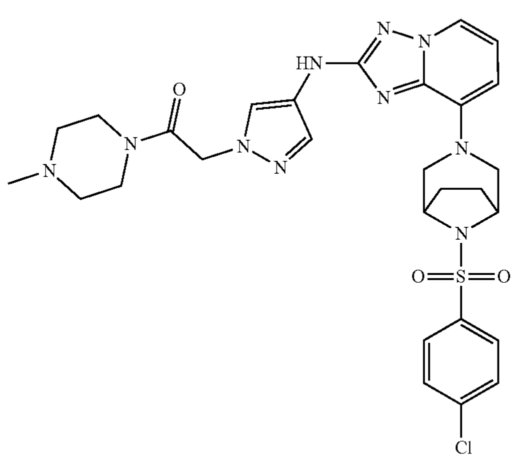 [SMILES: CN1CCN(C(=O)Cn2cc(Nc3nc4c(N5CC6CCC(C5)N6S(=O)(=O)c5ccc(Cl)cc5)cccn4n3)cn2)CC1] | 2-[4-[[8-[8-(4-chlorophenyl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 94 | 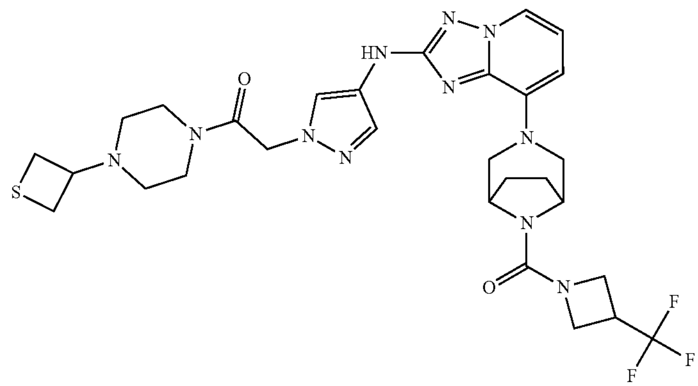 [SMILES: O=C(Cn1cc(Nc2nc3c(N4CC5CCC(C4)N5C(=O)N4CC(C(F)(F)F)C4)cccn3n2)cn1)N1CCN(C2CSC2)CC1] | 1-[4-(thietan-3-yl)piperazin-1-yl]-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 95 | 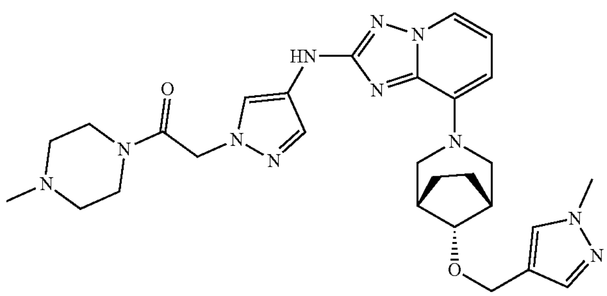 [SMILES: CN1CCN(C(=O)Cn2cc(Nc3nc4c(N5C[C@H]6CC[C@@H](C5)[C@H]6OCc5cnn(C)c5)cccn4n3)cn2)CC1] | 1-(4-methylpiperazin-1-yl)-2-[4-[[8-[[8-[(1S,5R)-8-[(1-methylpyrazol-4-yl)methoxy]-3-azabicyclo[3.2.1]octan-3-yl]-[1,2,4]triazolo[1,5-a]pyridin-2-yl]amino]pyrazol-1-yl]ethanone |
| 96 | 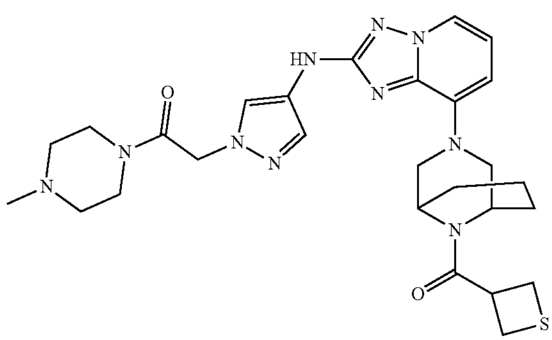 [SMILES: CN1CCN(C(=O)Cn2cc(Nc3nc4c(N5CC6CCCC(C5)N6C(=O)C5CSC5)cccn4n3)cn2)CC1] | 1-(4-methylpiperazin-1-yl)-2-[4-[[8-[9-(thietane-3-carbonyl)-3,9-diazabicyclo[3.3.1]nonan-3-yl]-[1,2,4]triazolo[1,5-a]pyridin-2-yl]amino]pyrazol-1-yl]ethanone |
| 97 | 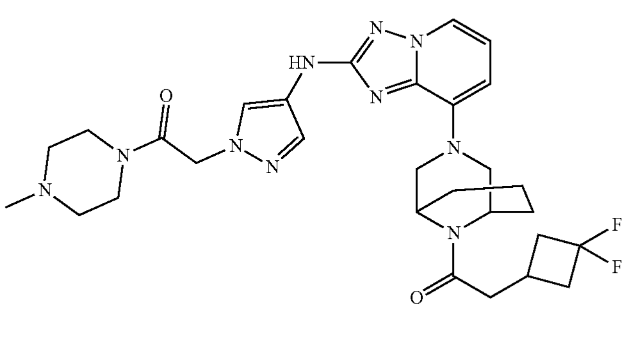 [SMILES: CN1CCN(C(=O)Cn2cc(Nc3nc4c(N5CC6CCCC(C5)N6C(=O)CC5CC(F)(F)C5)cccn4n3)cn2)CC1] | 2-(3,3-difluorocyclobutyl)-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,9-diazabicyclo[3.3.1]nonan-9-yl]ethanone |

TABLE 1-continued

Representative Compounds

| Ex. | Structure | Name |
|---|---|---|
| 98 | 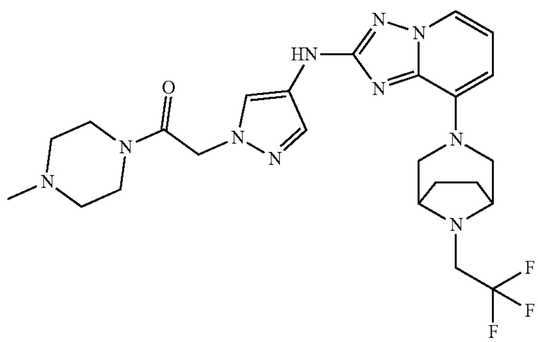 [SMILES: CN1CCN(C(=O)Cn2cc(Nc3nc4c(N5CC6CCC(C5)N6CC(F)(F)F)cccn4n3)cn2)CC1] | 1-(4-methylpiperazin-1-yl)-2-[4-[[8-[8-(2,2,2-trifluoroethyl)-3,8-diazabicyclo[3.2.1]octan-3-yl]-[1,2,4]triazolo[1,5-a]pyridin-2-yl]amino]pyrazol-1-yl]ethanone |
| 99 | 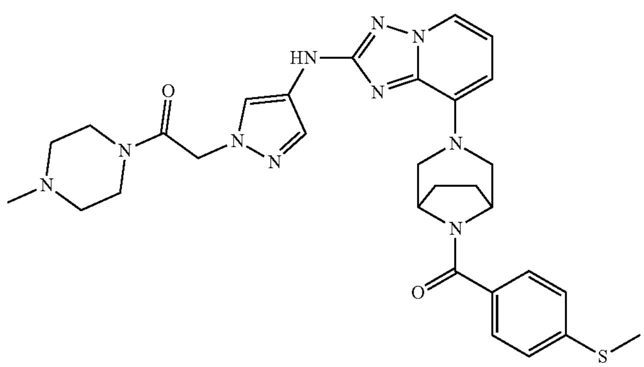 | 1-(4-methylpiperazin-1-yl)-2-[4-[[8-[8-(4-methylsulfanylbenzoyl)-3,8-diazabicyclo[3.2.1]octan-3-yl]-[1,2,4]triazolo[1,5-a]pyridin-2-yl]amino]pyrazol-1-yl]ethanone |
| 100 | 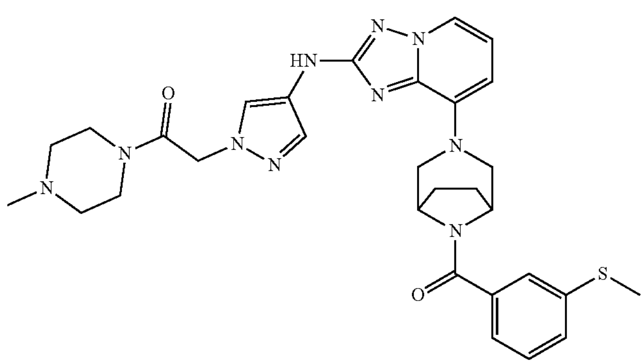 | 1-(4-methylpiperazin-1-yl)-2-[4-[[8-[8-(3-methylsulfanylbenzoyl)-3,8-diazabicyclo[3.2.1]octan-3-yl]-[1,2,4]triazolo[1,5-a]pyridin-2-yl]amino]pyrazol-1-yl]ethanone |
| 101 | 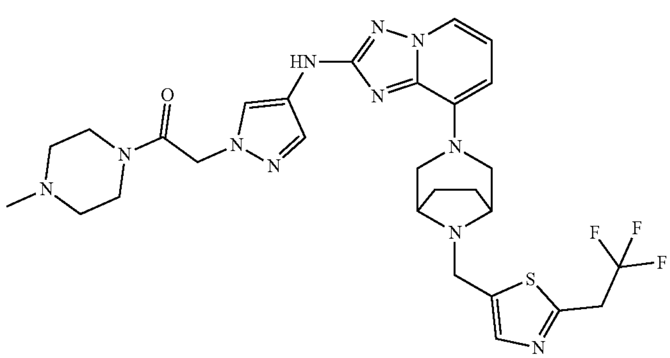 [SMILES: CN1CCN(C(=O)Cn2cc(Nc3nc4c(N5CC6CCC(C5)N6Cc5cnc(CC(F)(F)F)s5)cccn4n3)cn2)CC1] | 1-(4-methylpiperazin-1-yl)-2-[4-[[8-[8-[[2-(2,2,2-trifluoroethyl)thiazol-5-yl]methyl]-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 102 | 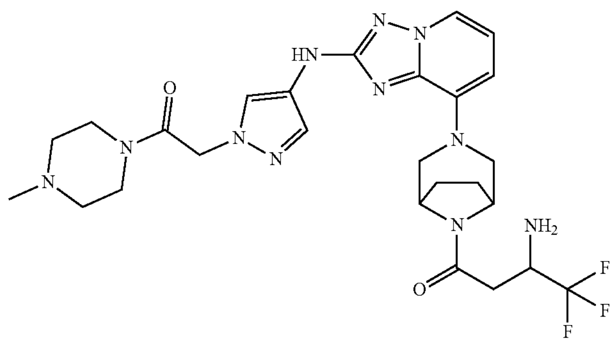 [SMILES: CN1CCN(C(=O)Cn2cc(Nc3nc4c(N5CC6CCC(C5)N6C(=O)CC(N)C(F)(F)F)cccn4n3)cn2)CC1] | 3-amino-4,4,4-trifluoro-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 103 | 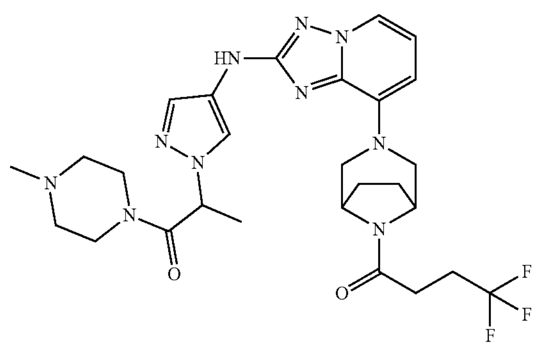 [SMILES: CC(C(=O)N1CCN(C)CC1)n1cc(Nc2nc3c(N4CC5CCC(C4)N5C(=O)CCC(F)(F)F)cccn3n2)cn1] | 4,4,4-trifluoro-1-[3-[2-[[1-[1-methyl-2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 104 | 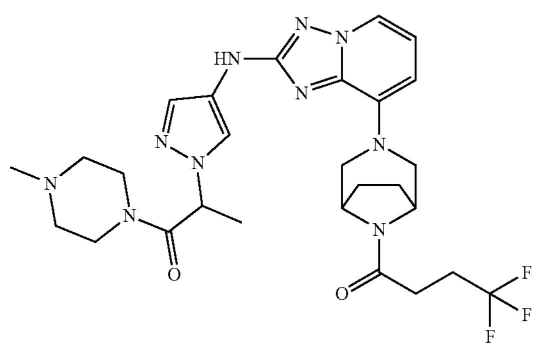 [SMILES: CC(C(=O)N1CCN(C)CC1)n1cc(Nc2nc3c(N4CC5CCC(C4)N5C(=O)CCC(F)(F)F)cccn3n2)cn1] | 4,4,4-trifluoro-1-[3-[2-[[1-[1-methyl-2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 105 | 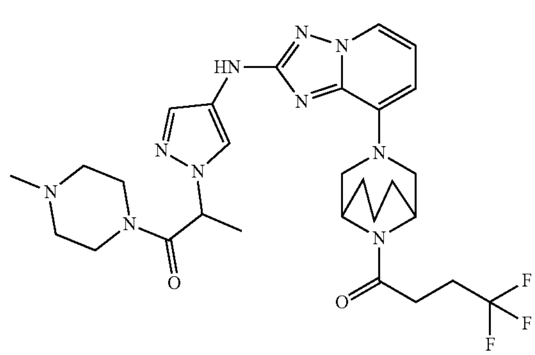 [SMILES: CC(C(=O)N1CCN(C)CC1)n1cc(Nc2nc3c(N4CC5CCCC(C4)N5C(=O)CCC(F)(F)F)cccn3n2)cn1] | 4,4,4-trifluoro-1-[3-[2-[[1-[1-methyl-2-(4-methylpiperazin-1-yl)-2-oxo-ethyl]pyrazol-4-yl]amino]-[1,2,4]triazolo[1,5-a]pyridin-8-yl]-3,9-diazabicyclo[3.3.1]nonan-9-yl]butan-1-one |

TABLE 1-continued

Representative Compounds

| Ex. | Structure | Name |
|---|---|---|
| 106 | 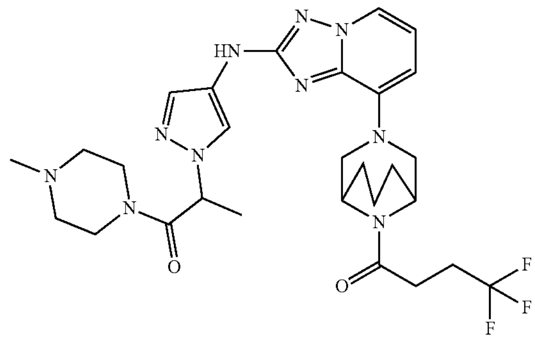 [SMILES: CC(C(=O)N1CCN(C)CC1)n1cc(Nc2nc3c(N4CC5CCCC(C4)N5C(=O)CCC(F)(F)F)cccn3n2)cn1] | 4,4,4-trifluoro-1-[3-[2-[[1-[1-methyl-2-(4-methylpiperazin-1-yl)-2-oxo-ethyl]pyrazol-4-yl]amino]-[1,2,4]triazolo[1,5-a]pyridin-8-yl]-3,9-diazabicyclo[3.3.1]nonan-9-yl]butan-1-one |
| 107 | 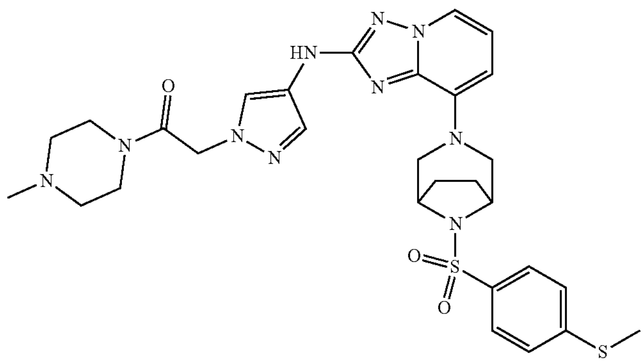 | 1-(4-methylpiperazin-1-yl)-2-[4-[[8-[8-(4-methylsulfanylphenyl)-sulfonyl-3,8-diazabicyclo[3.2.1]octan-3-yl]-[1,2,4]triazolo[1,5-a]pyridin-2-yl]amino]pyrazol-1-yl]ethanone |
| 108 | 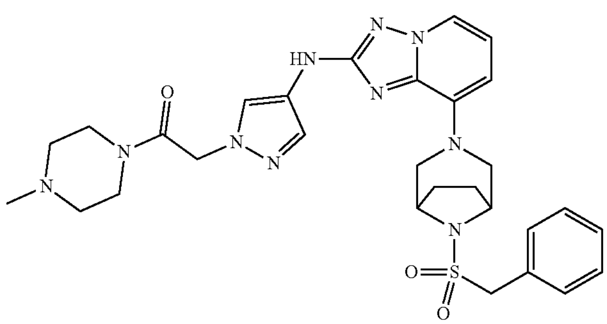 [SMILES: CN1CCN(C(=O)Cn2cc(Nc3nc4c(N5CC6CCC(C5)N6S(=O)(=O)Cc5ccccc5)cccn4n3)cn2)CC1] | 2-[4-[[8-(8-benzylsulfonyl-3,8-diazabicyclo[3.2.1]octan-3-yl)-[1,2,4]triazolo[1,5-a]pyridin-2-yl]amino]pyrazol-1-yl]-1-(4-methylpiperazin-1-yl)ethanone |
| 109 | 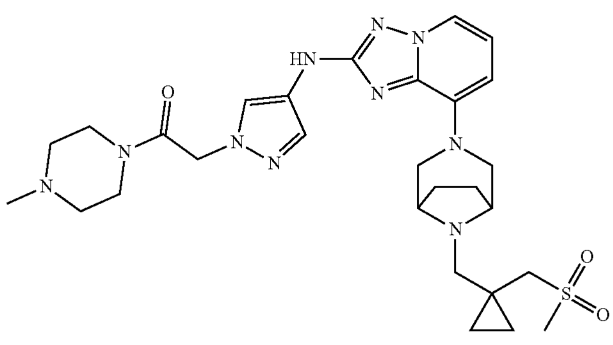 [SMILES: CN1CCN(C(=O)Cn2cc(Nc3nc4c(N5CC6CCC(C5)N6CC5(CS(C)(=O)=O)CC5)cccn4n3)cn2)CC1] | 1-(4-methylpiperazin-1-yl)-2-[4-[[8-[8-([1-(methylsulfonylmethyl)cyclopropyl]methyl]-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 110 | 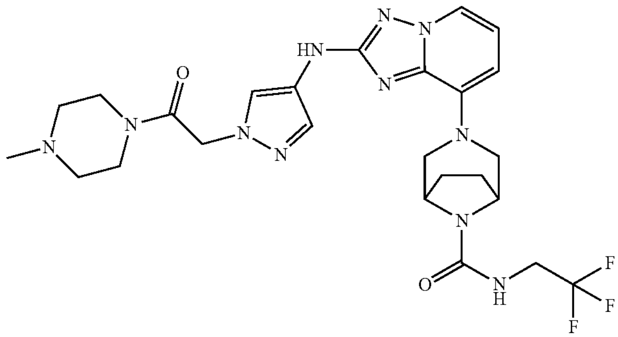 [SMILES: CN1CCN(C(=O)Cn2cc(Nc3nc4c(N5CC6CCC(C5)N6C(=O)NCC(F)(F)F)cccn4n3)cn2)CC1] | 3-[2-[[1-[2-(4-methylpiperazin-1-yl)-2-oxo-ethyl]pyrazol-4-yl]amino]-[1,2,4]triazolo[1,5-a]pyridin-8-yl]-N-(2,2,2-trifluoroethyl)-3,8-diazabicyclo[3.2.1]octane-8-carboxamide |
| 111 | 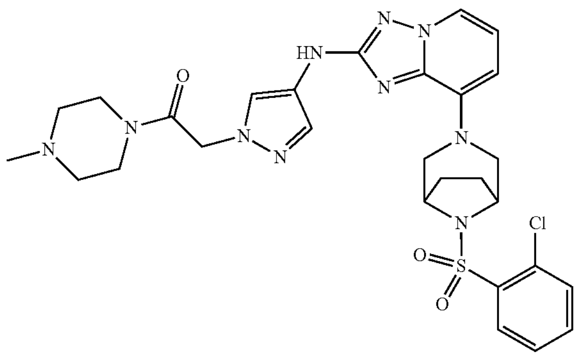 [SMILES: CN1CCN(C(=O)Cn2cc(Nc3nc4c(N5CC6CCC(C5)N6S(=O)(=O)c5ccccc5Cl)cccn4n3)cn2)CC1] | 2-[4-[[8-[8-(2-chlorophenyl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 112 | 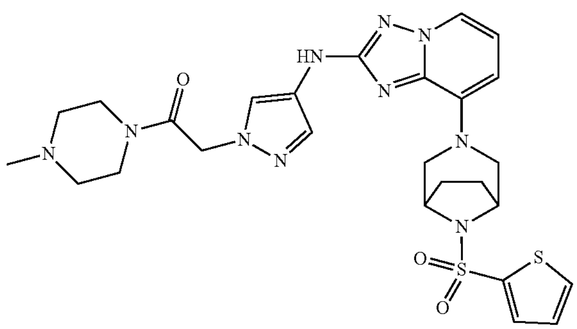 [SMILES: CN1CCN(C(=O)Cn2cc(Nc3nc4c(N5CC6CCC(C5)N6S(=O)(=O)c5cccs5)cccn4n3)cn2)CC1] | 1-(4-methylpiperazin-1-yl)-2-[4-[[8-[8-(2-thienylsulfonyl)-3,8-diazabicyclo[3.2.1]octan-3-yl]-[1,2,4]triazolo[1,5-a]pyridin-2-yl]amino]pyrazol-1-yl]ethanone |
| 113 | 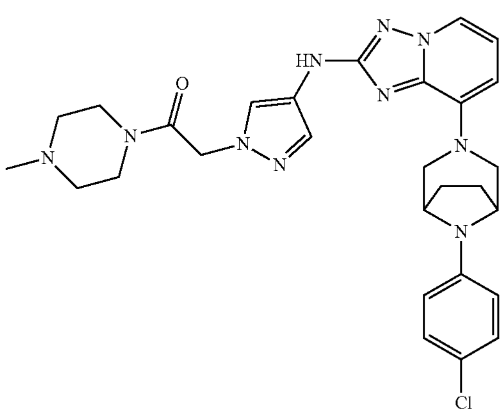 [SMILES: CN1CCN(C(=O)Cn2cc(Nc3nc4c(N5CC6CCC(C5)N6c5ccc(Cl)cc5)cccn4n3)cn2)CC1] | 2-[4-[[8-[8-(4-chlorophenyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 114 | 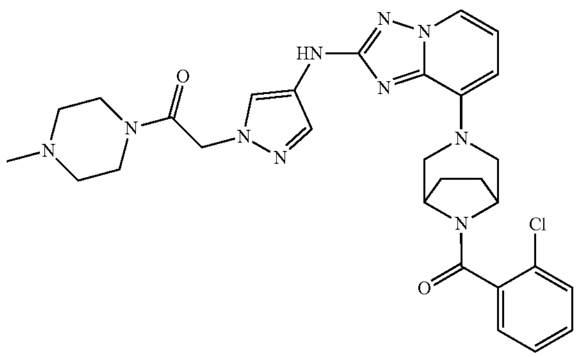 [SMILES: CN1CCN(C(=O)Cn2cc(Nc3nc4c(N5CC6CCC(C5)N6C(=O)c5ccccc5Cl)cccn4n3)cn2)CC1] | 2-[4-[[8-[8-(2-chlorobenzoyl)-3,8-diazabicyclo[3.2.1]octan-3-yl]-[1,2,4]triazolo[1,5-a]pyridin-2-yl]amino]pyrazol-1-yl]-1-yl)ethanone |
| 115 | 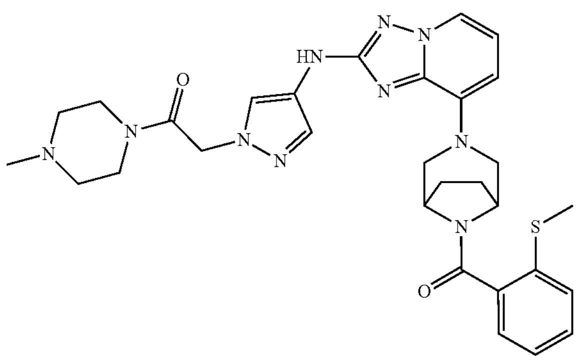 | 1-(4-methylpiperazin-1-1-(4-methylpiperazin-1-yl)-2-[4-[[8-[8-(2-methylsulfanylbenzoyl)-diazabicyclo[3.2.1]octan-3-yl]-[1,2,4]triazolo[1,5-a]pyridin-2-yl]amino]pyrazol-1-yl]ethanone |
| 116 | 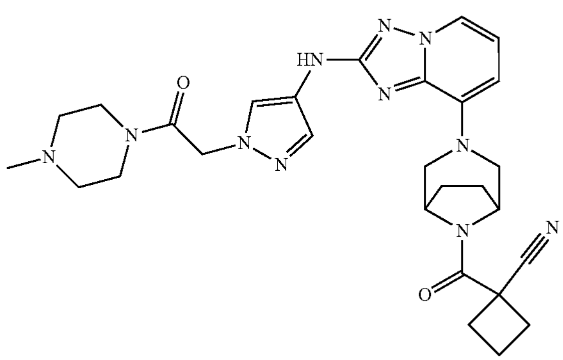 [SMILES: CN1CCN(C(=O)Cn2cc(Nc3nc4c(N5CC6CCC(C5)N6C(=O)C5(C#N)CCC5)cccn4n3)cn2)CC1] | 1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]cyclobutane-carbonitrile |
| 117 | 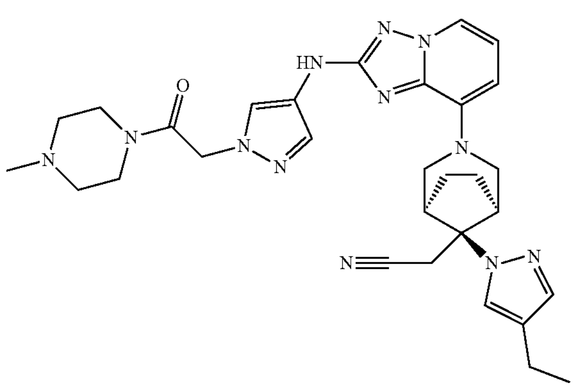 [SMILES: CCc1cnn([C@@]2(CC#N)[C@@H]3CC[C@H]2CN(c2cccn4nc(Nc5cnn(CC(=O)N6CCN(C)CC6)c5)nc24)C3)c1] | 2-[(1R,5S)-8-(4-ethylpyrazol-1-yl)-3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octan-8-yl]acetonitrile |

TABLE 1-continued

Representative Compounds

| Ex. | Structure | Name |
| --- | --- | --- |
| 118 | 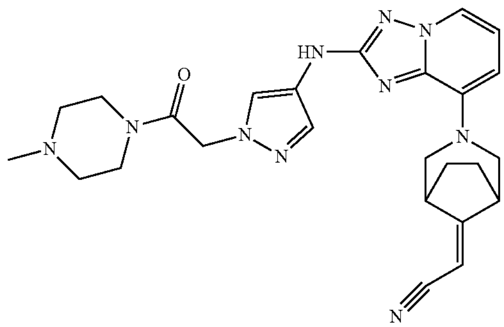 [SMILES: CN1CCN(C(=O)Cn2cc(Nc3nc4c(N5CC6CCC(C5)C6=CC#N)cccn4n3)cn2)CC1] | 2-[3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octan-8-ylidene]acetonitrile |
| 119 | 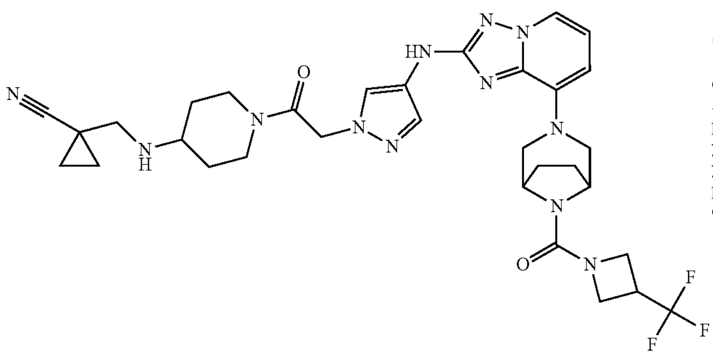 [SMILES: N#CC1(CNC2CCN(C(=O)Cn3cc(Nc4nc5c(N6CC7CCC(C6)N7C(=O)N6CC(C(F)(F)F)C6)cccn5n4)cn3)CC2)CC1] | 1-[[[1-[2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]acetyl]-4-piperidyl]amino]methyl]cyclopropanecarbonitrile |
| 120 | 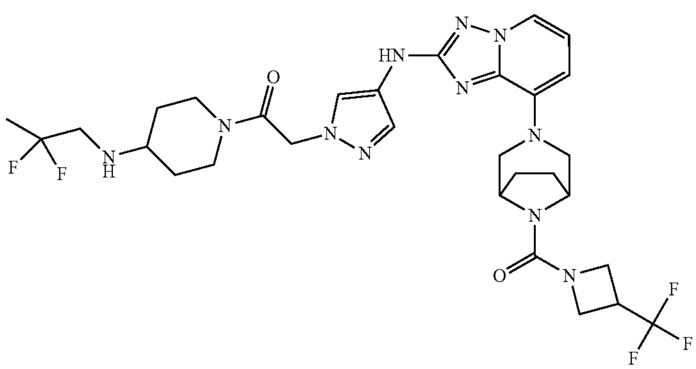 [SMILES: CC(F)(F)CNC1CCN(C(=O)Cn2cc(Nc3nc4c(N5CC6CCC(C5)N6C(=O)N5CC(C(F)(F)F)C5)cccn4n3)cn2)CC1] | 1-[4-(2,2-difluoropropylamino)-1-piperidyl]-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 121 | 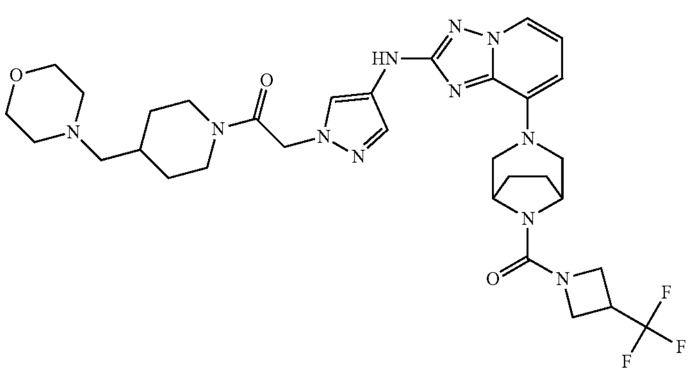 [SMILES: O=C(Cn1cc(Nc2nc3c(N4CC5CCC(C4)N5C(=O)N4CC(C(F)(F)F)C4)cccn3n2)cn1)N1CCC(CN2CCOCC2)CC1] | 1-[4-(morpholinomethyl)-1-piperidyl]-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 122 | 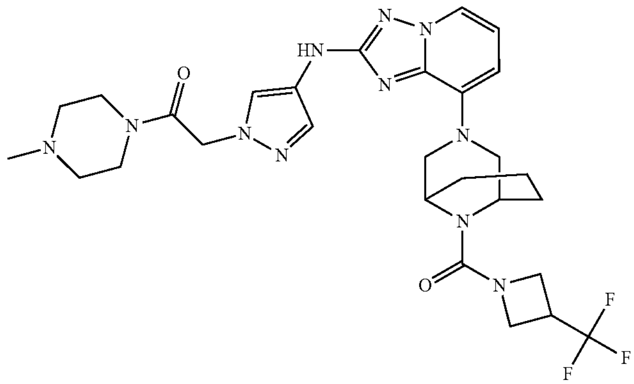 [SMILES: CN1CCN(C(=O)Cn2cc(Nc3nc4c(N5CC6CCCC(C5)N6C(=O)N5CC(C(F)(F)F)C5)cccn4n3)cn2)CC1] | 1-(4-methylpiperazin-1-yl)-2-[4-[[8-[9-[3-(trifluoromethyl)azetidine-1-carbonyl]-3,9-diazabicyclo[3.3.1]nonan-3-yl]-[1,2,4]triazolo[1,5-a]pyridin-2-yl]amino]pyrazol-1-yl]ethanone |
| 123 | 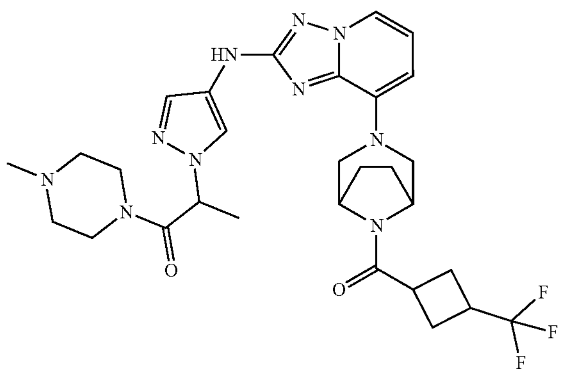 [SMILES: CC(C(=O)N1CCN(C)CC1)n1cc(Nc2nc3c(N4CC5CCC(C4)N5C(=O)C4CC(C(F)(F)F)C4)cccn3n2)cn1] | 1-(4-methylpiperazin-1-yl)-2-[4-[[8-[8-(3-(trifluoromethyl)-cyclobutanecarbonyl]-3,8-diazabicyclo[3.2.1]octan-3-yl]-[1,2,4]triazolo[1,5-a]pyridin-2-yl]amino]pyrazol-1-yl]propan-1-one |
| 124 | 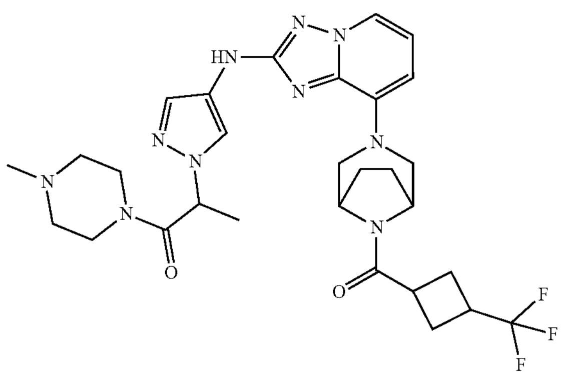 [SMILES: CC(C(=O)N1CCN(C)CC1)n1cc(Nc2nc3c(N4CC5CCC(C4)N5C(=O)C4CC(C(F)(F)F)C4)cccn3n2)cn1] | 1-(4-methylpiperazin-1-yl)-2-[4-[[8-[8-(3-(trifluoromethyl)-cyclobutanecarbonyl]-3,8-diazabicyclo[3.2.1]octan-3-yl]-[1,2,4]triazolo[1,5-a]pyridin-2-yl]amino]pyrazol-1-yl]propan-1-one |
| 125 | 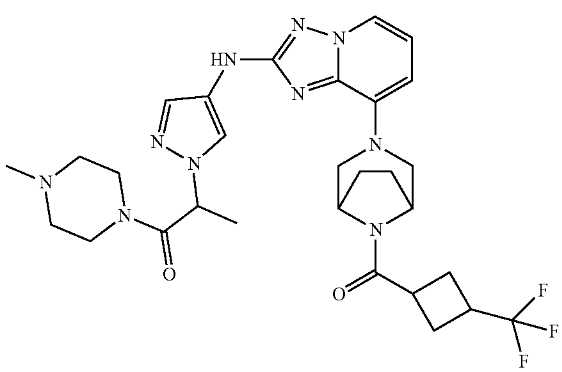 [SMILES: CC(C(=O)N1CCN(C)CC1)n1cc(Nc2nc3c(N4CC5CCC(C4)N5C(=O)C4CC(C(F)(F)F)C4)cccn3n2)cn1] | 1-(4-methylpiperazin-1-yl)-2-[4-[[8-[8-(3-(trifluoromethyl)-cyclobutanecarbonyl]-3,8-diazabicyclo[3.2.1]octan-3-yl]-[1,2,4]triazolo[1,5-a]pyridin-2-yl]amino]pyrazol-1-yl]propan-1-one |

TABLE 1-continued

Representative Compounds

| Ex. | Structure | Name |
|---|---|---|
| 126 | 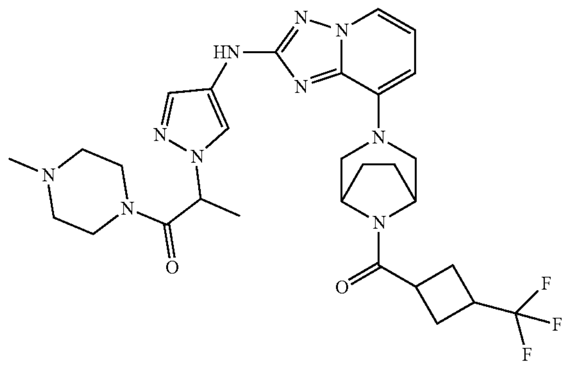 [SMILES: CC(C(=O)N1CCN(C)CC1)n1cc(Nc2nc3c(N4CC5CCC(C4)N5C(=O)C4CC(C(F)(F)F)C4)cccn3n2)cn1] | 1-(4-methylpiperazin-1-yl)-2-[4-[[8-[8-(3-(trifluoromethyl)-cyclobutanecarbonyl]-3,8-diazabicyclo[3.2.1]octan-3-yl]-[1,2,4]triazolo[1,5-a]pyridin-2-yl]amino]pyrazol-1-yl]propan-1-one |
| 127 | 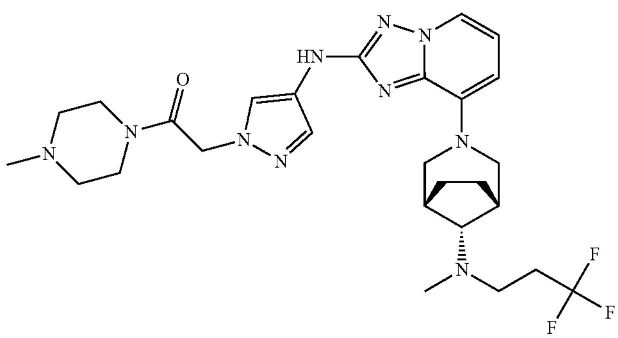 [SMILES: CN1CCN(C(=O)Cn2cc(Nc3nc4c(N5C[C@H]6CC[C@@H](C5)[C@H]6N(C)CCC(F)(F)F)cccn4n3)cn2)CC1] | 1-(4-methylpiperazin-1-yl)-2-[4-[[8-[(1S,5R)-8-[methyl(3,3,3-trifluoropropyl)amino]-3-azabicyclo[3.2.1]octan-3-yl]-[1,2,4]triazolo[1,5-a]pyridin-2-yl]amino]pyrazol-1-yl]ethanone |
| 128 | 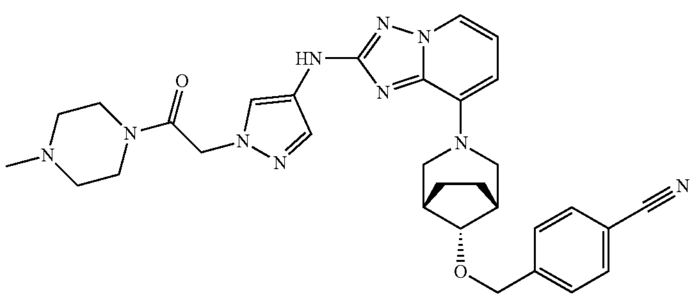 [SMILES: CN1CCN(C(=O)Cn2cc(Nc3nc4c(N5C[C@H]6CC[C@@H](C5)[C@H]6OCc5ccc(C#N)cc5)cccn4n3)cn2)CC1] | 4-[[(1S,5R)-3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octan-8-yl]oxymethyl]benzonitrile |
| 129 | 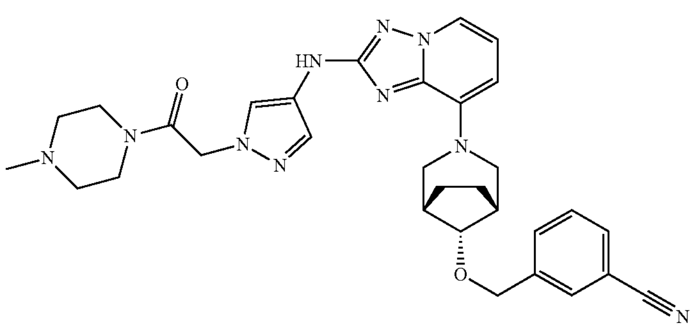 [SMILES: CN1CCN(C(=O)Cn2cc(Nc3nc4c(N5C[C@H]6CC[C@@H](C5)[C@H]6OCc5cccc(C#N)c5)cccn4n3)cn2)CC1] | 3-[[(1S,5R)-3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octan-8-yl]oxymethyl]benzonitrile |

TABLE 1-continued

Representative Compounds

| Ex. | Structure | Name |
|---|---|---|
| 130 | 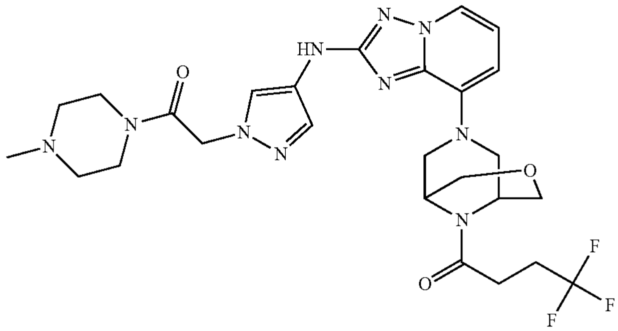 [SMILES: CN1CCN(C(=O)Cn2cc(Nc3nc4c(N5CC6COCC(C5)N6C(=O)CCC(F)(F)F)cccn4n3)cn2)CC1] | 4,4,4-trifluoro-1-[7-[2-[[1-[2-(4-methylpiperazin-1-yl)-2-oxo-ethyl]pyrazol-4-yl]amino]-[1,2,4]triazolo[1,5-a]pyridin-8-yl]-3-oxa-7,9-diazabicyclo[3.3.1]nonan-9-yl]butan-1-one |
| 131 | 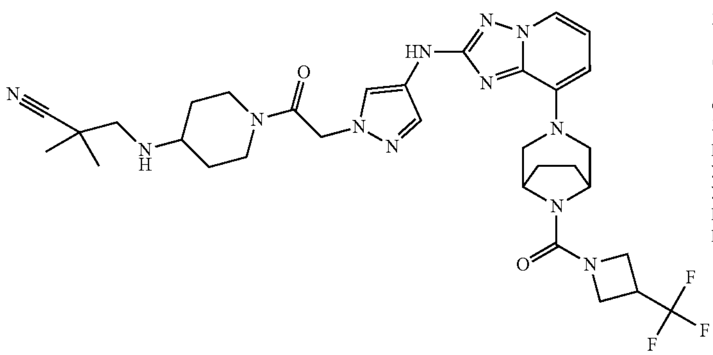 [SMILES: CC(C)(C#N)CNC1CCN(C(=O)Cn2cc(Nc3nc4c(N5CC6CCC(C5)N6C(=O)N5CC(C(F)(F)F)C5)cccn4n3)cn2)CC1] | 2,2-dimethyl-3-[[1-[2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]acetyl]-4-piperidyl]amino]-propanenitrile |
| 132 | 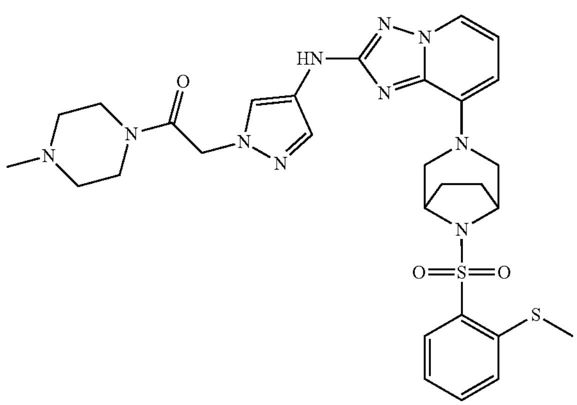 | 1-(4-methylpiperazin-1-yl)-2-[4-[[8-[8-(2-methylsulfanylphenyl)sulfonyl-3,8-diazabicyclo[3.2.1]octan-3-yl]-[1,2,4]triazolo[1,5-a]pyridin-2-yl]amino]pyrazol-1-yl]ethanone |
| 133 | 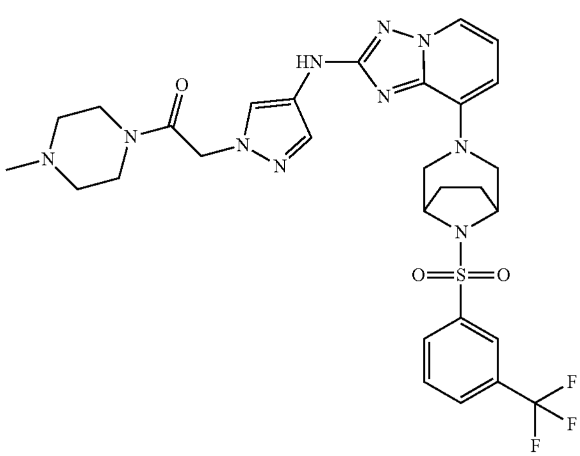 [SMILES: CN1CCN(C(=O)Cn2cc(Nc3nc4c(N5CC6CCC(C5)N6S(=O)(=O)c5cccc(C(F)(F)F)c5)cccn4n3)cn2)CC1] | 1-(4-methylpiperazin-1-yl)-2-[4-[[8-[8-[3-(trifluoromethyl)phenyl]sulfonyl-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 134 | 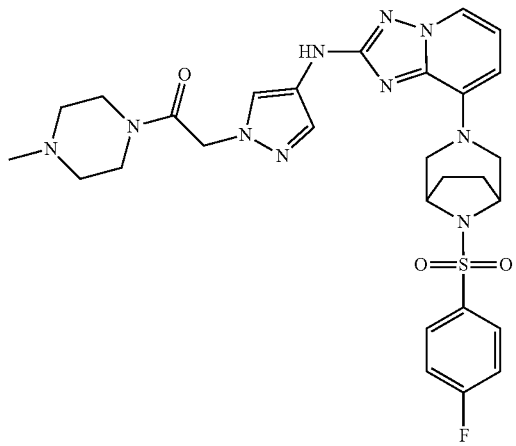 [SMILES: CN1CCN(C(=O)Cn2cc(Nc3nc4c(N5CC6CCC(C5)N6S(=O)(=O)c5ccc(F)cc5)cccn4n3)cn2)CC1] | 2-[4-[[8-[8-(4-fluorophenyl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 135 | 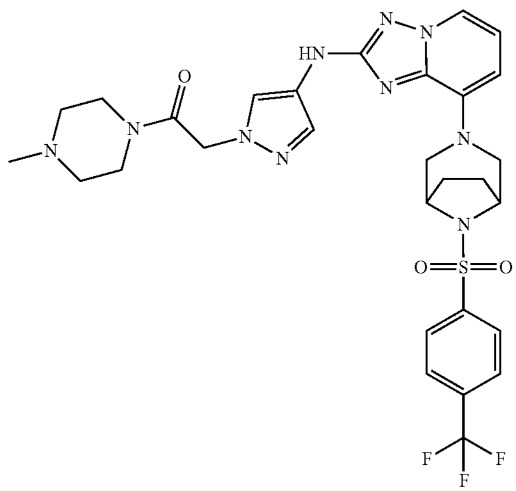 [SMILES: CN1CCN(C(=O)Cn2cc(Nc3nc4c(N5CC6CCC(C5)N6S(=O)(=O)c5ccc(C(F)(F)F)cc5)cccn4n3)cn2)CC1] | 1-(4-methylpiperazin-1-yl)-2-[4-[[8-[8-(4-(trifluoromethyl)phenyl]sulfonyl-3,8-diazabicyclo[3.2.1]octan-3-yl]-[1,2,4]triazolo[1,5-a]pyridin-2-yl]amino]pyrazol-1-yl]ethanone |
| 136 | 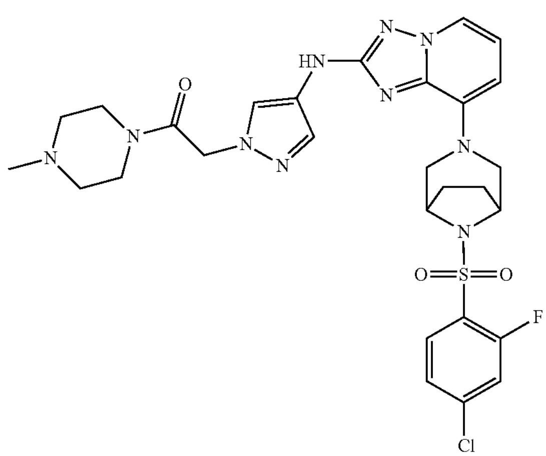 [SMILES: CN1CCN(C(=O)Cn2cc(Nc3nc4c(N5CC6CCC(C5)N6S(=O)(=O)c5ccc(Cl)cc5F)cccn4n3)cn2)CC1] | 2-[4-[[8-[8-(4-chloro-2-fluoro-phenyl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 137 | 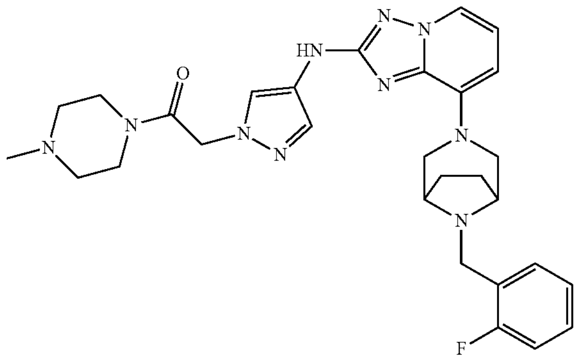 [SMILES: CN1CCN(C(=O)Cn2cc(Nc3nc4c(N5CC6CCC(C5)N6Cc5ccccc5F)cccn4n3)cn2)CC1] | 2-[4-[[8-[8-[(2-fluorophenyl)methyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 138 | 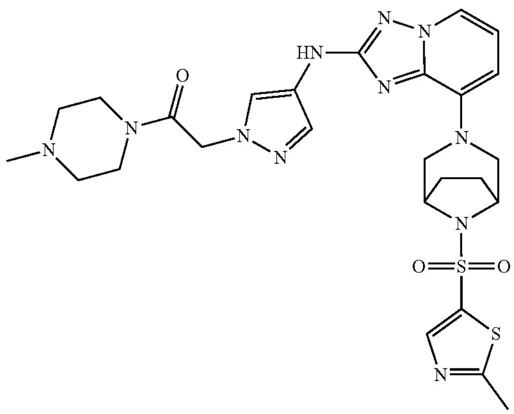 | 1-(4-methylpiperazin-1-yl)-2-[4-[[8-[8-(2-methylthiazol-5-yl)sulfonyl-3,8-diazabicyclo[3.2.1]octan-3-yl]-[1,2,4]triazolo[1,5-a]pyridin-2-yl]amino]pyrazol-1-yl]ethanone |
| 139 | 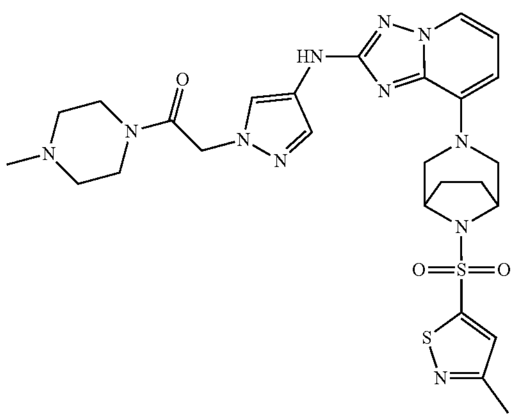 | 2-[4-[[8-[8-(3-yl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 140 | 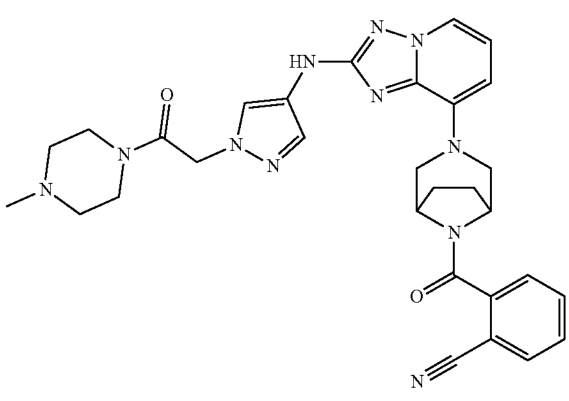 [SMILES: CN1CCN(C(=O)Cn2cc(Nc3nc4c(N5CC6CCC(C5)N6C(=O)c5ccccc5C#N)cccn4n3)cn2)CC1] | 2-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]benzonitrile |

TABLE 1-continued

Representative Compounds

| Ex. | Structure | Name |
|---|---|---|
| 141 | 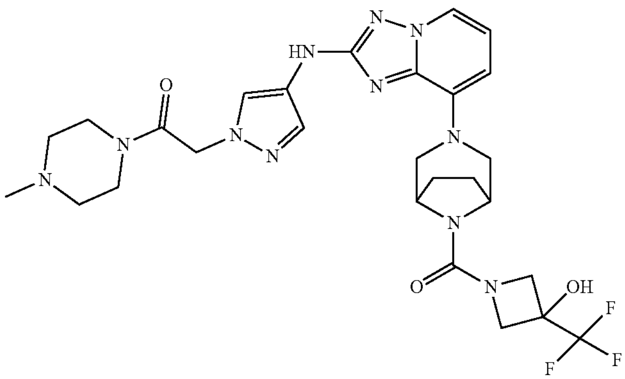 [SMILES: CN1CCN(C(=O)Cn2cc(Nc3nc4c(N5CC6CCC(C5)N6C(=O)N5CC(O)(C(F)(F)F)C5)cccn4n3)cn2)CC1] | 2-[4-[[8-[8-[3-hydroxy-3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 142 | 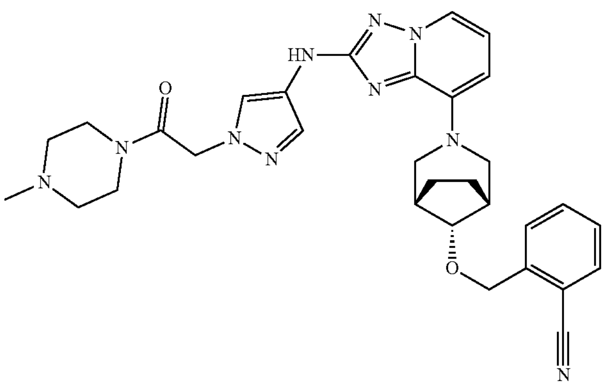 [SMILES: CN1CCN(C(=O)Cn2cc(Nc3nc4c(N5C[C@H]6CC[C@@H](C5)[C@H]6OCc5ccccc5C#N)cccn4n3)cn2)CC1] | 2-[[rac-(1S,5R)-3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octan-8-yl]oxymethyl]benzonitrile |
| 143 | 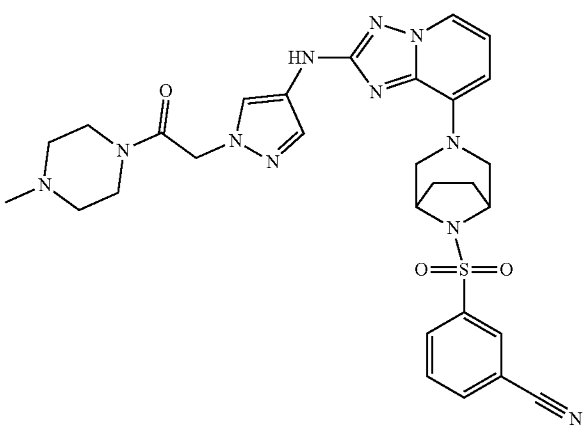 [SMILES: CN1CCN(C(=O)Cn2cc(Nc3nc4c(N5CC6CCC(C5)N6S(=O)(=O)c5cccc(C#N)c5)cccn4n3)cn2)CC1] | 3-[[3-[2-[[1-[2-(4-methylpiperazin-1-yl)-2-oxo-ethyl]pyraol-4-yl]amino]-[1,2,4]triazolo[1,5-a]pyridin-8-yl]-3,8-diazabicyclo[3.2.1]octan-8-yl]sulfonyl]benzonitrile |
| 144 | 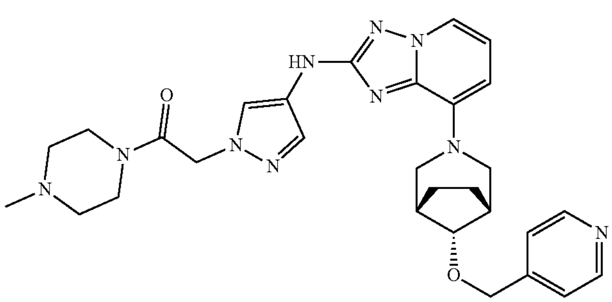 [SMILES: CN1CCN(C(=O)Cn2cc(Nc3nc4c(N5C[C@H]6CC[C@@H](C5)[C@H]6OCc5ccncc5)cccn4n3)cn2)CC1] | 1-(4-methylpiperazin-1-yl)-2-[4-[[8-[rac-(1S,5R)-8-(4-pyridylmethoxy)-3-azabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 145 | 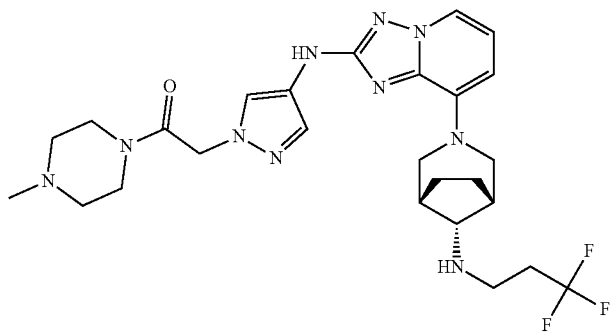 [SMILES: CN1CCN(C(=O)Cn2cc(Nc3nc4c(N5C[C@H]6CC[C@@H](C5)[C@H]6NCCC(F)(F)F)cccn4n3)cn2)CC1] | 1-(4-methylpiperazin-1-yl)-2-[4-[[8-[rac-(1S,5R)-8-(3,3,3-trifluoropropylamino)-3-azabicyclo[3.2.1]octan-3-yl]-[1,2,4]triazolo[1,5-a]pyridin-2-yl]amino]pyrazol-1-yl]ethanone |
| 146 | 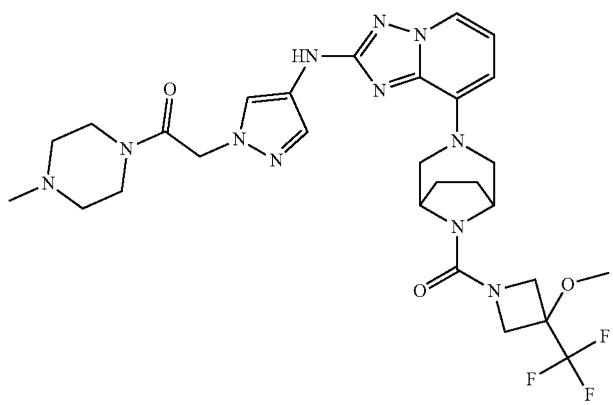 | 2-[4-[[8-[8-[3-methoxy-3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 147 | 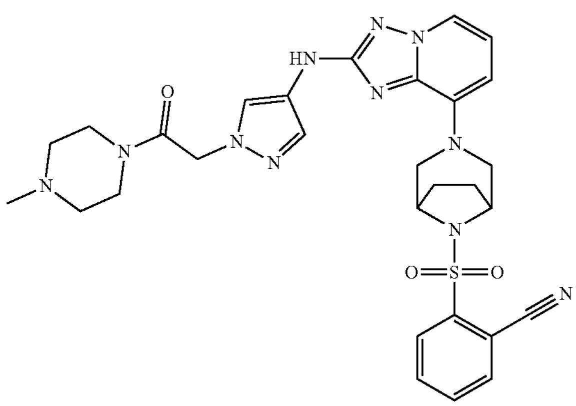 [SMILES: CN1CCN(C(=O)Cn2cc(Nc3nc4c(N5CC6CCC(C5)N6S(=O)(=O)c5ccccc5C#N)cccn4n3)cn2)CC1] | 2-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]sulfonyl]benzonitrile |
| 148 | 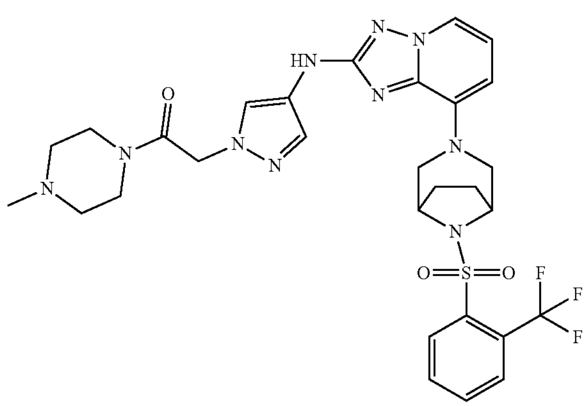 [SMILES: CN1CCN(C(=O)Cn2cc(Nc3nc4c(N5CC6CCC(C5)N6S(=O)(=O)c5ccccc5C(F)(F)F)cccn4n3)cn2)CC1] | 1-(4-methylpiperazin-1-yl)-2-[4-[[8-[8-[2-(trifluoromethyl)phenyl]sulfonyl-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 149 | 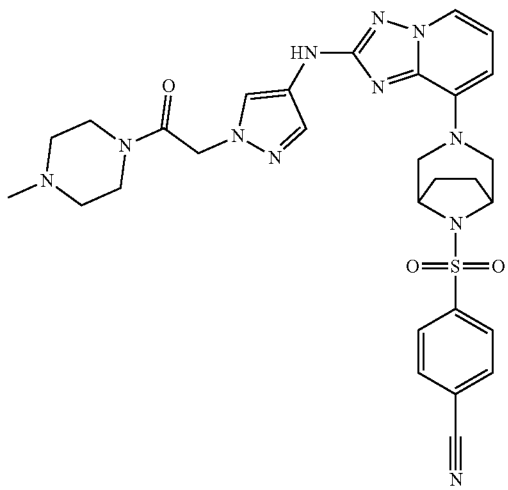 [SMILES: CN1CCN(C(=O)Cn2cc(Nc3nc4c(N5CC6CCC(C5)N6S(=O)(=O)c5ccc(C#N)cc5)cccn4n3)cn2)CC1] | 4-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]sulfonyl]benzonitrile |
| 150 | 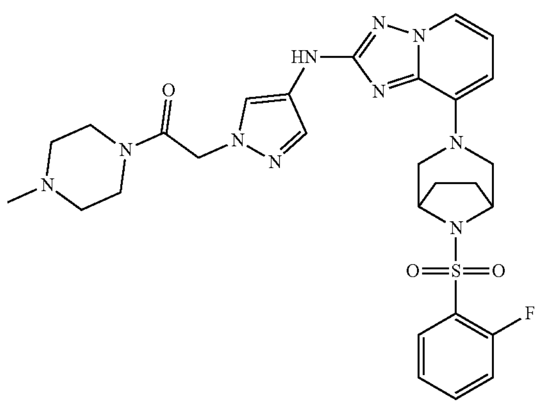 [SMILES: CN1CCN(C(=O)Cn2cc(Nc3nc4c(N5CC6CCC(C5)N6S(=O)(=O)c5ccccc5F)cccn4n3)cn2)CC1] | 2-[4-[[8-[8-(2-fluorophenyl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 151 | 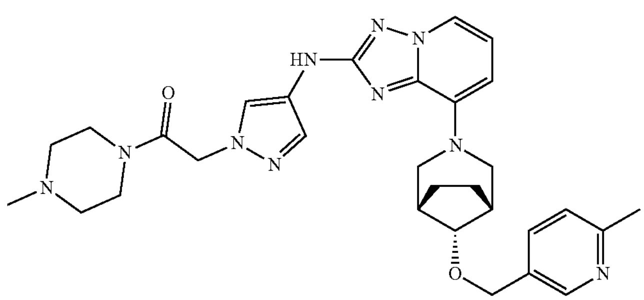 | 1-(4-methylpiperazin-1-yl)-2-[4-[[8-[[rac-(1S,5R)-8-[(6-methyl-3-pyridyl)methoxy]-3-azabicyclo[3.2.1]octan-3-yl]-[1,2,4]triazolo[1,5-a]pyridin-2-yl]amino]pyrazol-1-yl]ethanone |
| 152 | 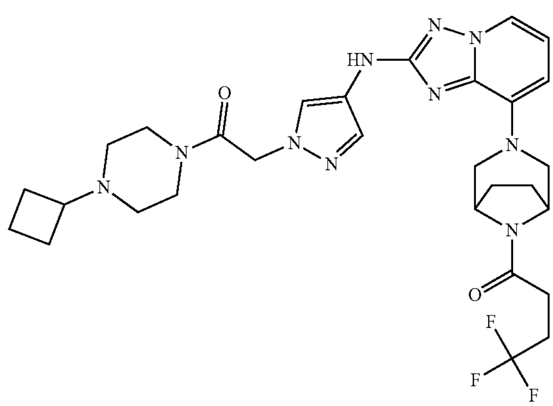 [SMILES: O=C(Cn1cc(Nc2nc3c(N4CC5CCC(C4)N5C(=O)CCC(F)(F)F)cccn3n2)cn1)N1CCN(C2CCC2)CC1] | 1-[3-[2-[[1-[2-(4-cyclobutylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]-4,4,4-trifluoro-butan-1-one |

TABLE 1-continued

Representative Compounds

| Ex. | Structure | Name |
|---|---|---|
| 153 | 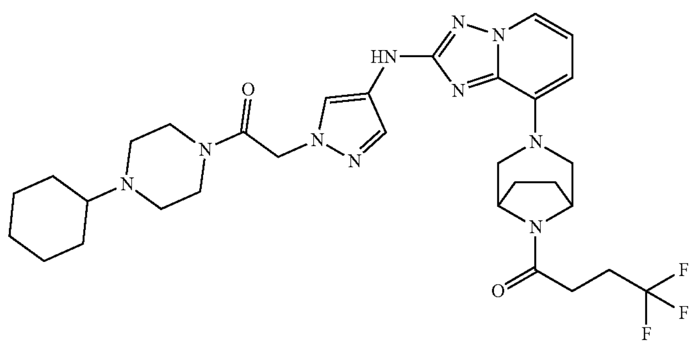 [SMILES: O=C(Cn1cc(Nc2nc3c(N4CC5CCC(C4)N5C(=O)CCC(F)(F)F)cccn3n2)cn1)N1CCN(C2CCCCC2)CC1] | 1-[3-[2-[[1-[2-(4-cyclohexylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]-4,4,4-trifluoro-butan-1-one |
| 154 | 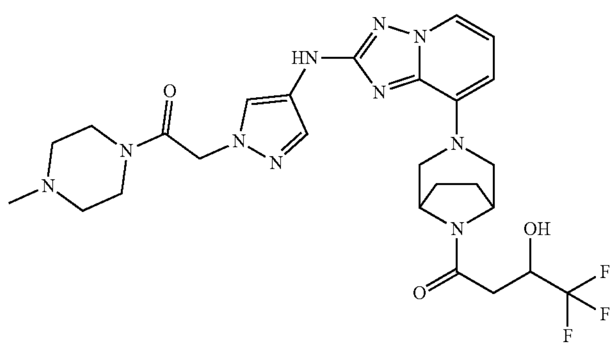 [SMILES: CN1CCN(C(=O)Cn2cc(Nc3nc4c(N5CC6CCC(C5)N6C(=O)CC(O)C(F)(F)F)cccn4n3)cn2)CC1] | 4,4,4-trifluoro-3-hydroxy-1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]butan-1-one |
| 155 | 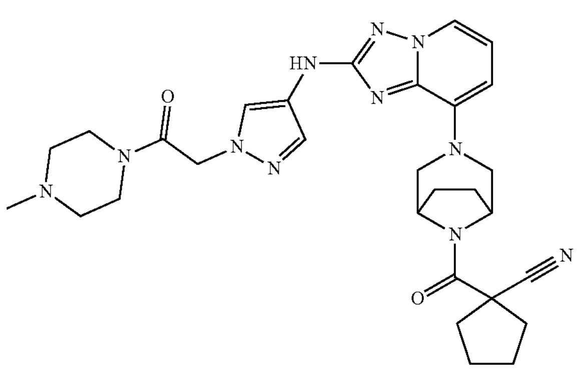 [SMILES: CN1CCN(C(=O)Cn2cc(Nc3nc4c(N5CC6CCC(C5)N6C(=O)C5(C#N)CCCC5)cccn4n3)cn2)CC1] | 1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]cyclopentane-carbonitrile |
| 156 | 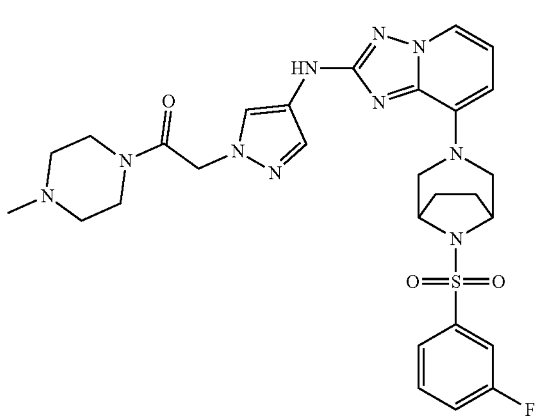 [SMILES: CN1CCN(C(=O)Cn2cc(Nc3nc4c(N5CC6CCC(C5)N6S(=O)(=O)c5cccc(F)c5)cccn4n3)cn2)CC1] | 2-[4-[[8-[8-(3-fluorophenyl)sulfonyl-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 157 | 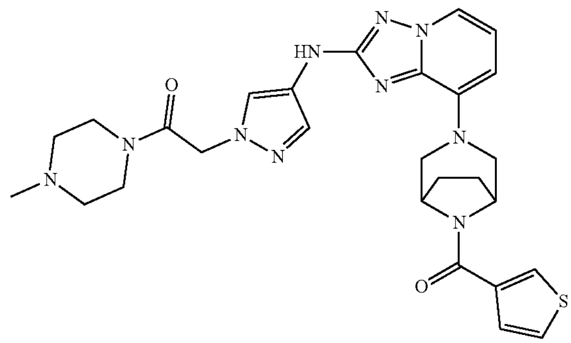 [SMILES: CN1CCN(C(=O)Cn2cc(Nc3nc4c(N5CC6CCC(C5)N6C(=O)c5ccsc5)cccn4n3)cn2)CC1] | 1-(4-methylpiperazin-1-yl)-2-[4-[[8-[8-(thiophene-3-carbonyl)-3,8-diazabicyclo[3.2.1]octan-3-yl]-[1,2,4]triazolo[1,5-a]pyridin-2-yl]amino]pyrazol-1-yl]ethanone |
| 158 | 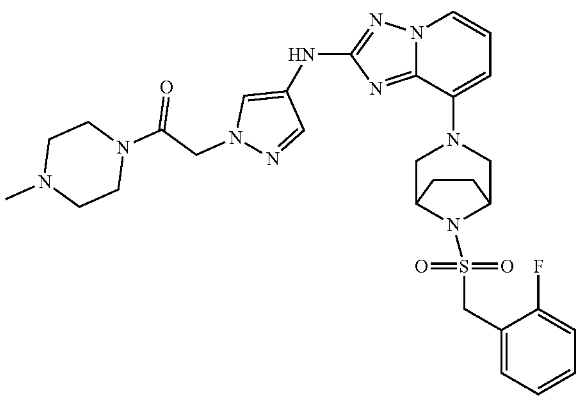 [SMILES: CN1CCN(C(=O)Cn2cc(Nc3nc4c(N5CC6CCC(C5)N6S(=O)(=O)Cc5ccccc5F)cccn4n3)cn2)CC1] | 2-[4-[[8-[8-[(2-fluorophenyl)methylsulfonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 159 | 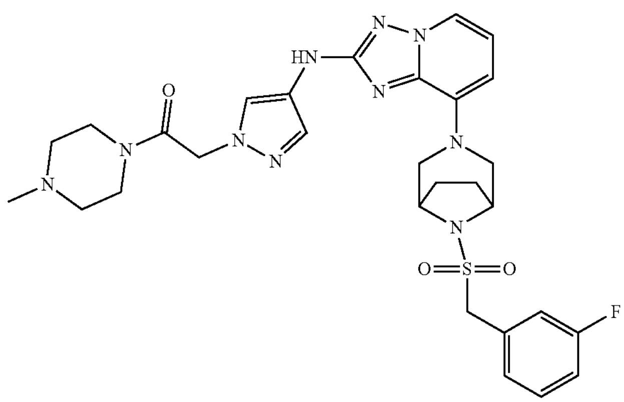 [SMILES: CN1CCN(C(=O)Cn2cc(Nc3nc4c(N5CC6CCC(C5)N6S(=O)(=O)Cc5cccc(F)c5)cccn4n3)cn2)CC1] | 2-[4-[[8-[8-[(3-fluorophenyl)methylsulfonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 160 | 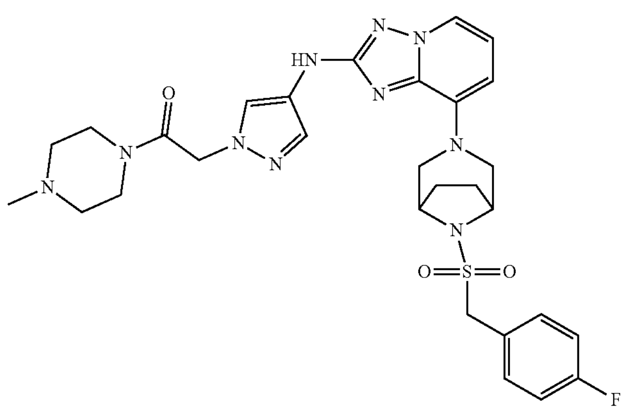 [SMILES: CN1CCN(C(=O)Cn2cc(Nc3nc4c(N5CC6CCC(C5)N6S(=O)(=O)Cc5ccc(F)cc5)cccn4n3)cn2)CC1] | 2-[4-[[8-[8-[(4-fluorophenyl)methylsulfonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |

TABLE 1-continued

Representative Compounds

| Ex. | Structure | Name |
|---|---|---|
| 161 | 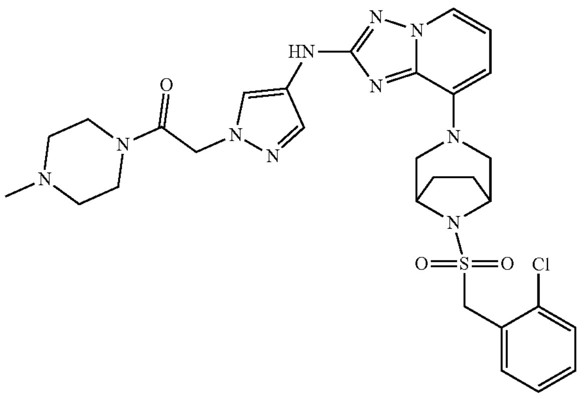 | 2-[4-[[8-[8-[(2-chlorophenyl)methylsulfonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 162 | 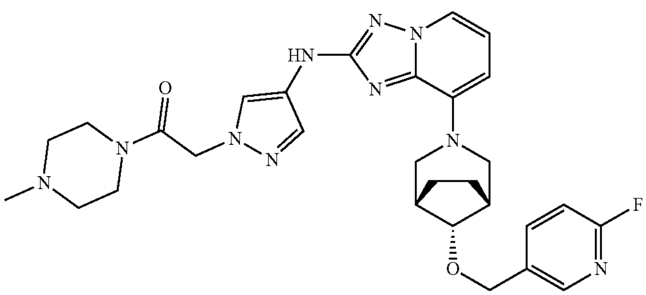 [SMILES: CN1CCN(C(=O)Cn2cc(Nc3nc4c(N5C[C@H]6CC[C@@H](C5)[C@H]6OCc5ccc(F)nc5)cccn4n3)cn2)CC1] | 1-(4-methylpiperazin-1-yl)-2-[4-[[8-[rac-(1S,5R)-8-[(6-fluoro-3-pyridyl)methoxy]-3-azabicyclo[3.2.1]octan-3-yl]-[1,2,4]triazolo[1,5-a]pyridin-2-yl]amino]pyrazol-1-yl]ethanone |
| 163 | 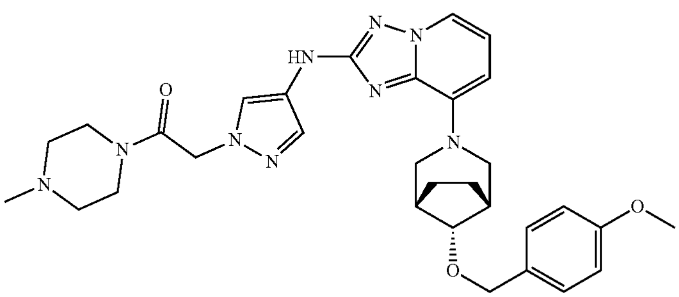 | 1-(4-methylpiperazin-1-yl)-2-[4-[[8-[rac-(1S,5R)-8-[(4-methoxyphenyl)methoxy]-3-azabicyclo[3.2.1]octan-3-yl]-[1,2,4]triazolo[1,5-a]pyridin-2-yl]amino]pyrazol-1-yl]ethanone |
| 164 | 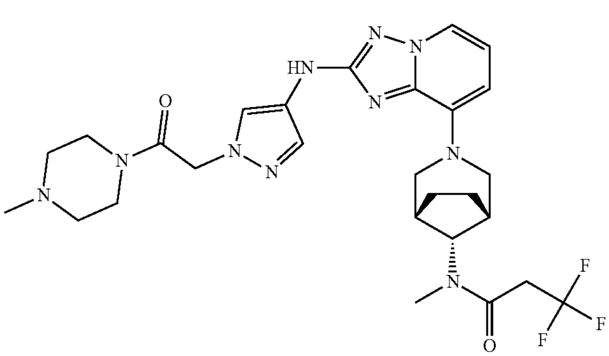 [SMILES: CN1CCN(C(=O)Cn2cc(Nc3nc4c(N5C[C@H]6CC[C@@H](C5)[C@H]6N(C)C(=O)CC(F)(F)F)cccn4n3)cn2)CC1] | 3,3,3-trifluoro-N-methyl-N-[rac-(1S,5R)-3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octan-8-yl]propanamide |

TABLE 1-continued

Representative Compounds

| Ex. | Structure | Name |
|---|---|---|
| 165 | 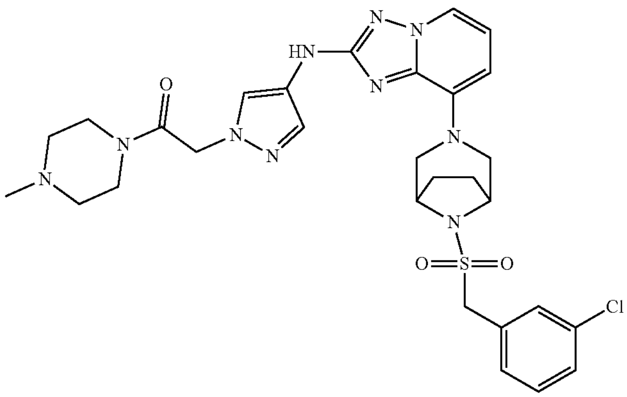 [SMILES: CN1CCN(C(=O)Cn2cc(Nc3nc4c(N5CC6CCC(C5)N6S(=O)(=O)Cc5cccc(Cl)c5)cccn4n3)cn2)CC1] | 2-[4-[[8-[8-[(3-chlorophenyl)methylsulfonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 166 | 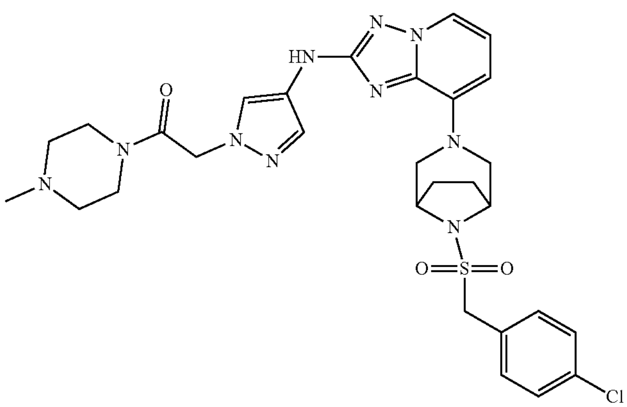 [SMILES: CN1CCN(C(=O)Cn2cc(Nc3nc4c(N5CC6CCC(C5)N6S(=O)(=O)Cc5ccc(Cl)cc5)cccn4n3)cn2)CC1] | 2-[4-[[8-[8-[(4-chlorophenyl)methylsulfonyl]-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 167 | 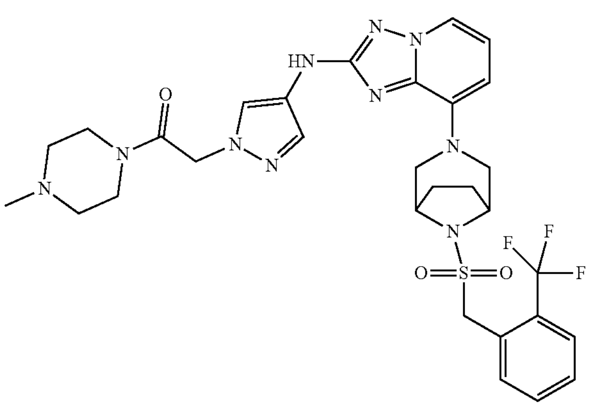 [SMILES: CN1CCN(C(=O)Cn2cc(Nc3nc4c(N5CC6CCC(C5)N6S(=O)(=O)Cc5ccccc5C(F)(F)F)cccn4n3)cn2)CC1] | 1-(4-methylpiperazin-1-yl)-2-[4-[[8-[8-([2-(trifluoromethyl)phenyl]methylsulfonyl]-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 168 | 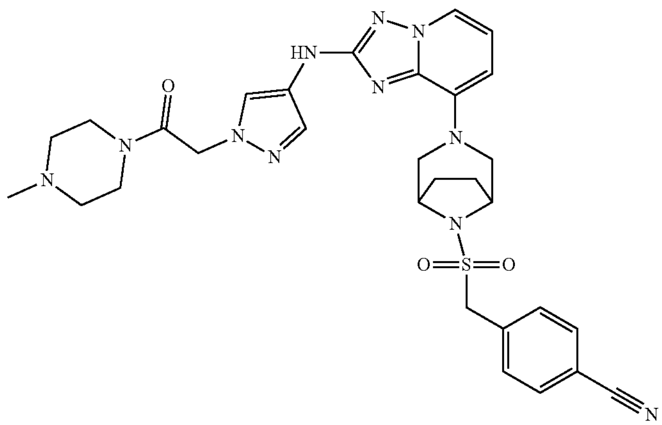 [SMILES: CN1CCN(C(=O)Cn2cc(Nc3nc4c(N5CC6CCC(C5)N6S(=O)(=O)Cc5ccc(C#N)cc5)cccn4n3)cn2)CC1] | 4-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]sulfonylmethyl]-benzonitrile |
| 169 | 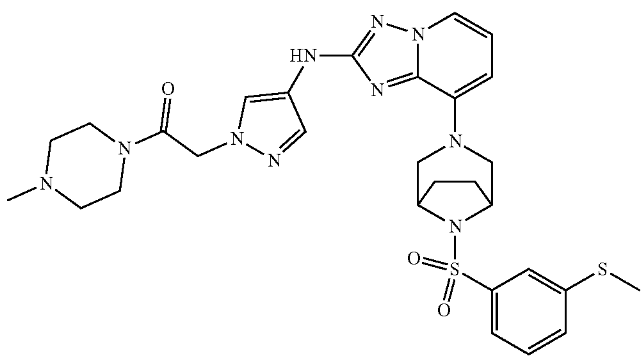 | 1-(4-methylpiperazin-1-yl)-2-[4-[[8-[8-(3-methylsulfanylphenyl)sulfonyl-3,8-diazabicyclo[3.2.1]octan-3-yl]-[1,2,4]triazolo[1,5-a]pyridin-2-yl]amino]pyrazol-1-yl]ethanone |
| 170 | 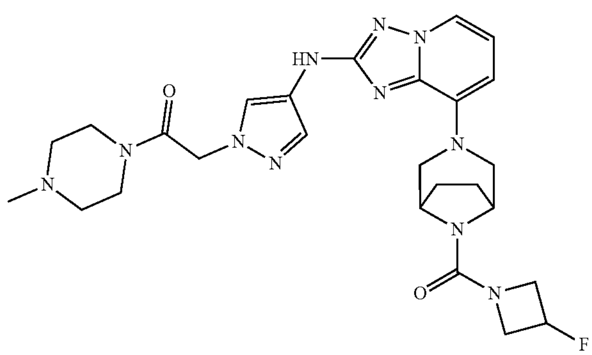 [SMILES: CN1CCN(C(=O)Cn2cc(Nc3nc4c(N5CC6CCC(C5)N6C(=O)N5CC(F)C5)cccn4n3)cn2)CC1] | 2-[4-[[8-[8-(3-fluoroazetidine-1-carbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 171 | 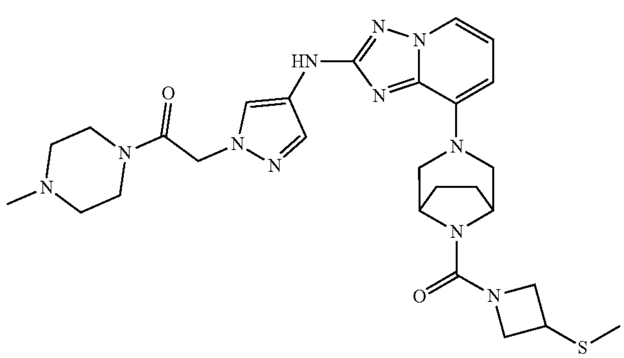 | 1-(4-methylpiperazin-1-yl)-2-[4-[[8-[8-(3-methylsulfanylazetidine-1-carbonyl)-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 172 | 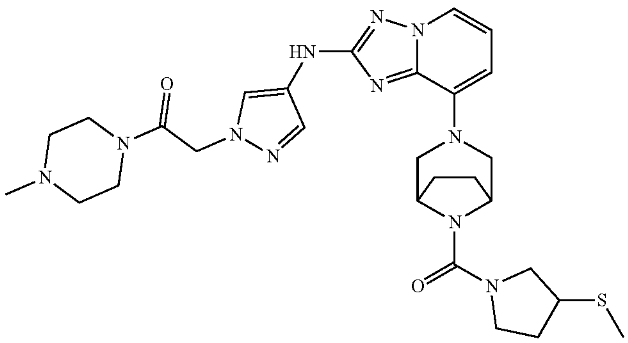 | 1-(4-methylpiperazin-1-yl)-2-[4-[[8-[8-(3-methylsulfanylpyrrolidine-1-carbonyl)-3,8-diazabicyclo[3.2.1]octan-3-yl]-[1,2,4]triazolo[1,5-a]pyridin-2-yl]amino]pyrazol-1-yl]ethanone |
| 173 | 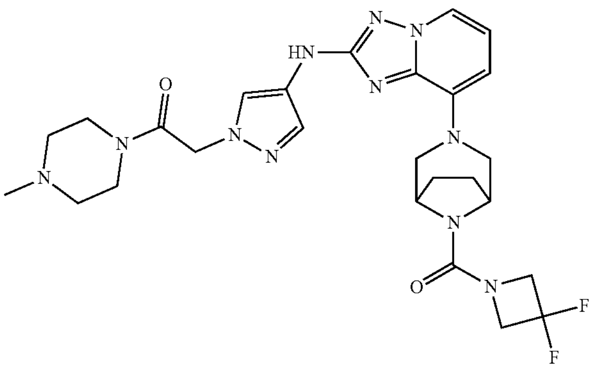 [SMILES: CN1CCN(C(=O)Cn2cc(Nc3nc4c(N5CC6CCC(C5)N6C(=O)N5CC(F)(F)C5)cccn4n3)cn2)CC1] | 2-[4-[[8-[8-(3,3-difluoroazetidine-1-carbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 174 | 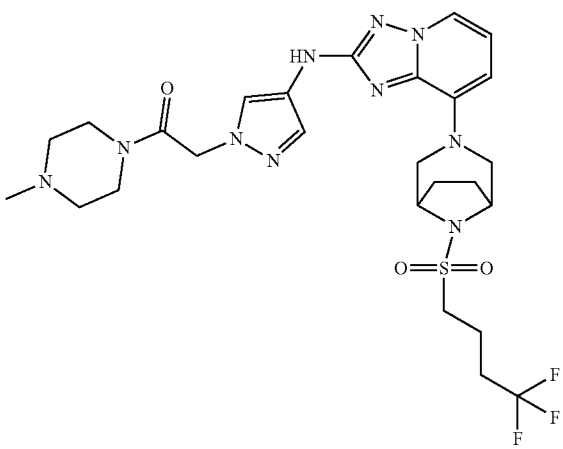 [SMILES: CN1CCN(C(=O)Cn2cc(Nc3nc4c(N5CC6CCC(C5)N6S(=O)(=O)CCCC(F)(F)F)cccn4n3)cn2)CC1] | 1-(4-methylpiperazin-1-yl)-2-[4-[[8-[8-(4,4,4-trifluorobutylsulfonyl)-3,8-diazabicyclo[3.2.1]octan-3-yl]-[1,2,4]triazolo[1,5-a]pyridin-2-yl]amino]pyrazol-1-yl]ethanone |
| 175 | 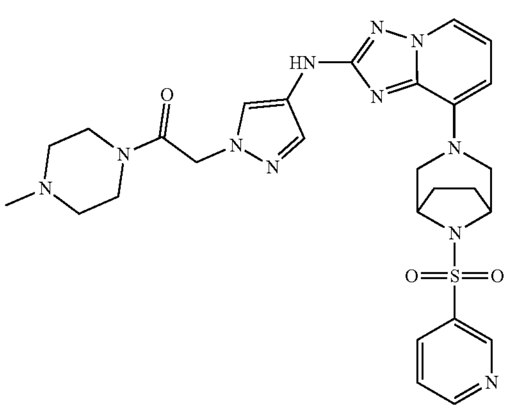 [SMILES: CN1CCN(C(=O)Cn2cc(Nc3nc4c(N5CC6CCC(C5)N6S(=O)(=O)c5cccnc5)cccn4n3)cn2)CC1] | 1-(4-methylpiperazin-1-yl)-2-[4-[[8-[8-(3-pyridylsulfonyl)-3,8-diazabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 176 | 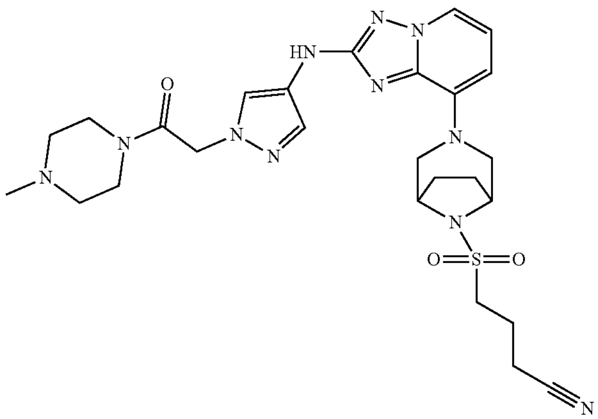 [SMILES: CN1CCN(C(=O)Cn2cc(Nc3nc4c(N5CC6CCC(C5)N6S(=O)(=O)CCCC#N)cccn4n3)cn2)CC1] | 4-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]sulfonyl]butanenitrile |
| 177 | 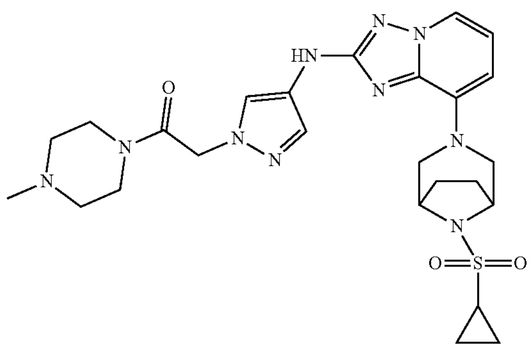 [SMILES: CN1CCN(C(=O)Cn2cc(Nc3nc4c(N5CC6CCC(C5)N6S(=O)(=O)C5CC5)cccn4n3)cn2)CC1] | 2-[4-[[8-(8-cyclopropylsulfonyl-3,8-diazabicyclo[3.2.1]octan-3-yl)-[1,2,4]triazolo[1,5-a]pyridin-2-yl]amino]pyrazol-1-yl]-1-(4-methylpiperazin-1-yl)ethanone |
| 178 | 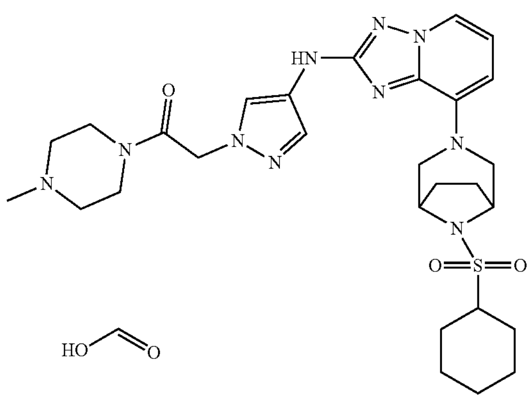 [SMILES: CN1CCN(C(=O)Cn2cc(Nc3nc4c(N5CC6CCC(C5)N6S(=O)(=O)C5CCCCC5)cccn4n3)cn2)CC1 ; O=CO] | 2-[4-[[8-(8-cyclohexylsulfonyl-3,8-diazabicyclo[3.2.1]octan-3-yl)-[1,2,4]triazolo[1,5-a]pyridin-2-yl]amino]pyrazol-1-yl]-1-(4-methylpiperazin-1-yl)ethanone; formic acid |
| 179 | 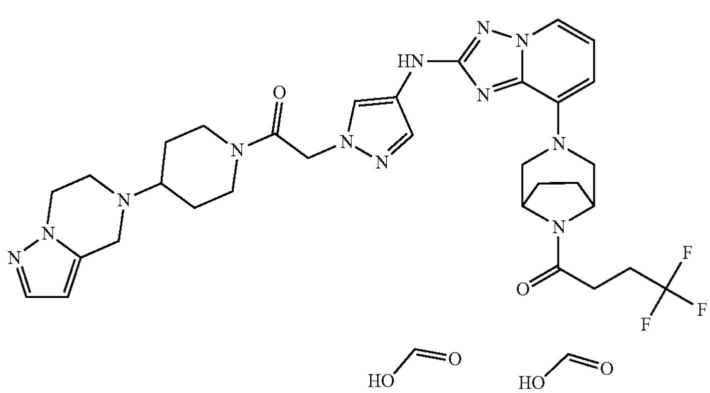 | 1-[3-[2-[[1-[2-[4-(6,7-dihydro-4H-pyrazolo[1,5-a]pyrazin-5-yl)-1-piperidyl]-2-oxo-ethyl]pyrazol-4-yl]amino]-[1,2,4]triazolo[1,5-a]pyridin-8-yl]-3,8-diazabicyclo[3.2.1]octan-8-yl]-4,4,4-trifluoro-butan-1-one; formic acid |

TABLE 1-continued

Representative Compounds

| Ex. | Structure | Name |
|---|---|---|
| 180 | 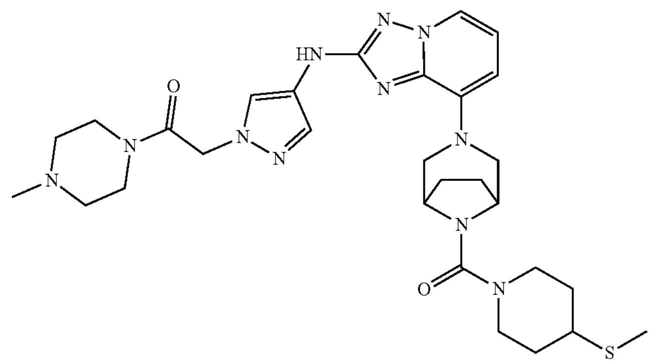 | 1-(4-methylpiperazin-1-yl)-2-[4-[[8-[8-(4-methylsulfanylpiperidine-1-carbonyl)-3,8-diazabicyclo[3.2.1]octan-3-yl]-[1,2,4]triazolo[1,5-a]pyridin-2-yl]amino]pyrazol-1-yl]ethanone |
| 181 | 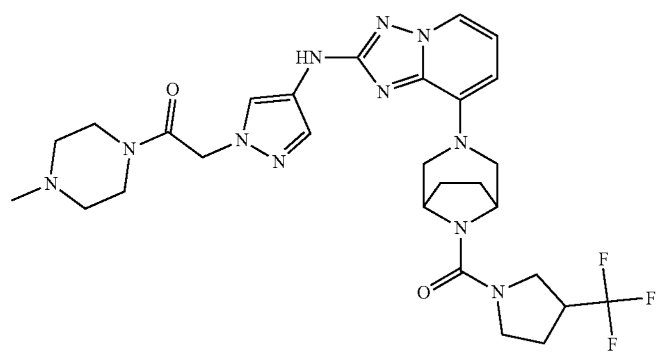 [SMILES: CN1CCN(C(=O)Cn2cc(Nc3nc4c(N5CC6CCC(C5)N6C(=O)N5CCC(C(F)(F)F)C5)cccn4n3)cn2)CC1] | 1-(4-methylpiperazin-1-yl)-2-[4-[[8-[8-(3-(trifluoromethyl)pyrrolidine-1-carbonyl]-3,8-diazabicyclo[3.2.1]octan-3-yl]-[1,2,4]triazolo[1,5-a]pyridin-2-yl]amino]pyrazol-1-yl]ethanone |
| 182 | 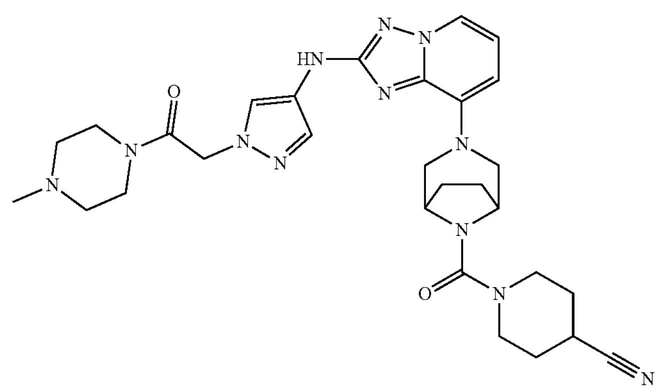 [SMILES: CN1CCN(C(=O)Cn2cc(Nc3nc4c(N5CC6CCC(C5)N6C(=O)N5CCC(C#N)CC5)cccn4n3)cn2)CC1] | 1-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]piperidine-4-carbonitrile |
| 183 | 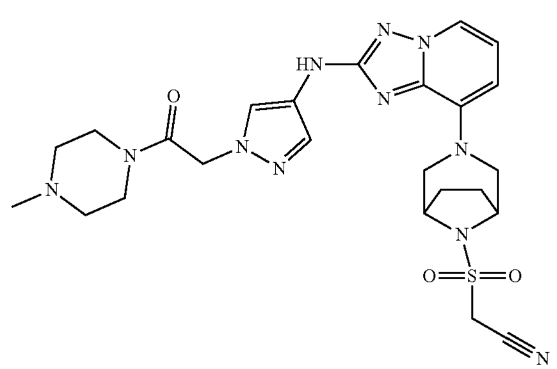 | 2-[[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octan-8-yl]sulfonyl]acetonitrile |

TABLE 1-continued

Representative Compounds

| Ex. | Structure | Name |
|---|---|---|
| 184 | 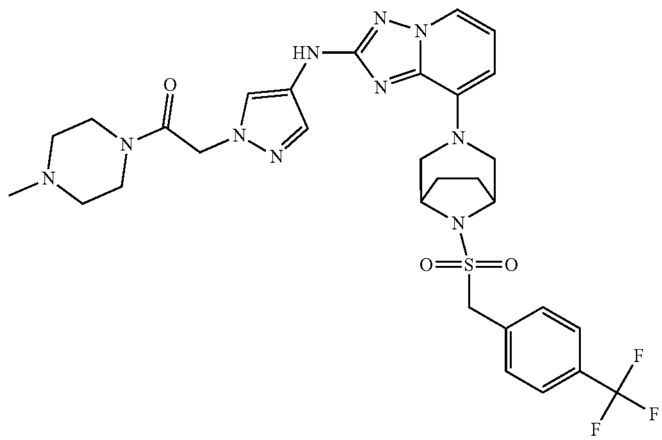 [SMILES: CN1CCN(C(=O)Cn2cc(Nc3nc4c(N5CC6CCC(C5)N6S(=O)(=O)Cc5ccc(C(F)(F)F)cc5)cccn4n3)cn2)CC1] | 1-(4-methylpiperazin-1-yl)-2-[4-[[8-[8-([4-(trifluoromethyl)phenyl]methylsulfonyl]-3,8-diazabicyclo[3.2.1]octan-3-yl]-[1,2,4]triazolo[1,5-a]pyridin-2-yl]amino]pyrazol-1-yl]ethanone |
| 185 | 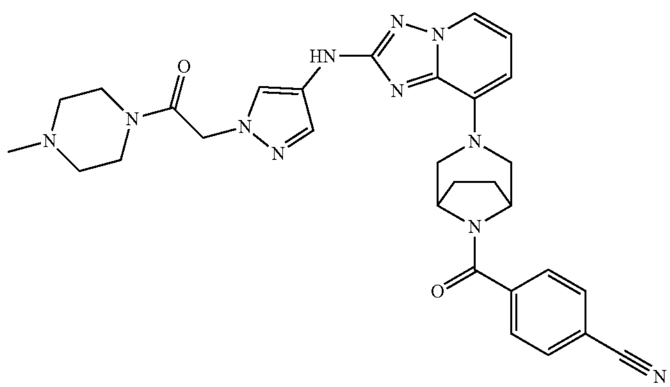 [SMILES: CN1CCN(C(=O)Cn2cc(Nc3nc4c(N5CC6CCC(C5)N6C(=O)c5ccc(C#N)cc5)cccn4n3)cn2)CC1] | 4-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-carbonyl]benzonitrile |
| 186 | 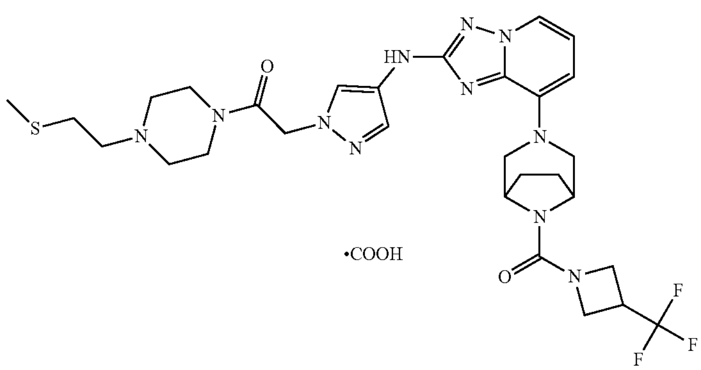 [SMILES: CSCCN1CCN(C(=O)Cn2cc(Nc3nc4c(N5CC6CCC(C5)N6C(=O)N5CC(C(F)(F)F)C5)cccn4n3)cn2)CC1 ; "·COOH"] | 1-[4-(2-methylsulfanylethyl)piperazin-1-yl]-2-[4-[[8-[8-(3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone; formic acid |
| 187 | 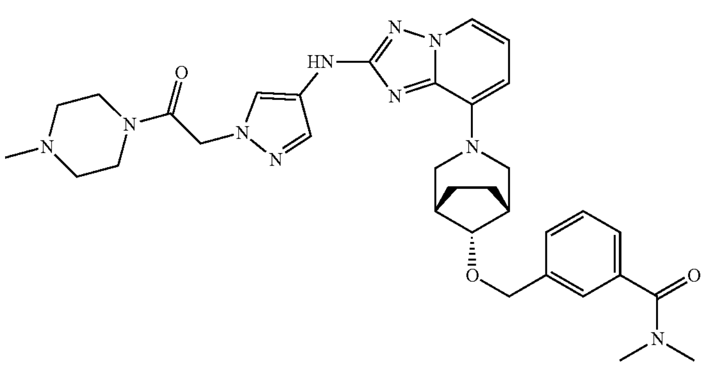 | N,N-dimethyl-3-[[rac-(1S,5R)-3-[2-[[1-[2-(4-methylpiperazin-1-yl)-2-oxo-ethyl]pyrazol-4-yl]amino]-[1,2,4]triazolo[1,5-a]pyridin-8-yl]-3-azabicyclo[3.2.1]octan-8-yl]oxymethyl]benzamide |

TABLE 1-continued

Representative Compounds

| Ex. | Structure | Name |
|---|---|---|
| 188 | 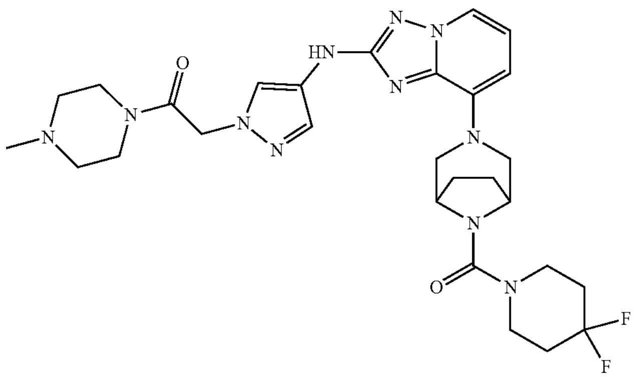 [SMILES: CN1CCN(C(=O)Cn2cc(Nc3nc4c(N5CC6CCC(C5)N6C(=O)N5CCC(F)(F)CC5)cccn4n3)cn2)CC1] | 2-[4-[[8-[8-(4,4-difluoropiperidine-1-carbonyl)-3,8-diazabicyclo[3.2.1]octan-3-yl]-[1,2,4]triazolo[1,5-a]pyridin-2-yl]amino]pyrazol-1-yl]-1-(4-methylpiperazin-1-yl)ethanone |
| 189 | 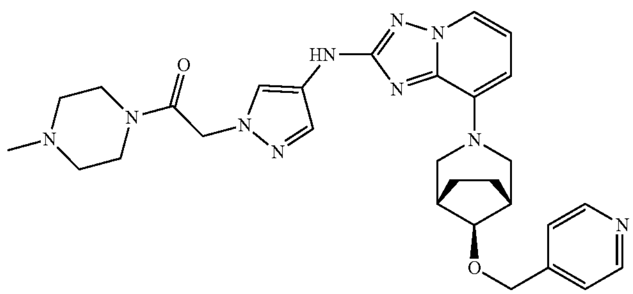 [SMILES: CN1CCN(C(=O)Cn2cc(Nc3nc4c(N5C[C@H]6CC[C@@H](C5)[C@@H]6OCc5ccncc5)cccn4n3)cn2)CC1] | 1-(4-methylpiperazin-1-yl)-2-[4-[[8-[rac-(1S,5R)-8-(4-pyridylmethoxy)-3-azabicyclo[3.2.1]octan-3-yl]-[1,2,4]triazolo[1,5-a]pyridin-2-yl]amino]pyrazol-1-yl]ethanone |
| 190 | 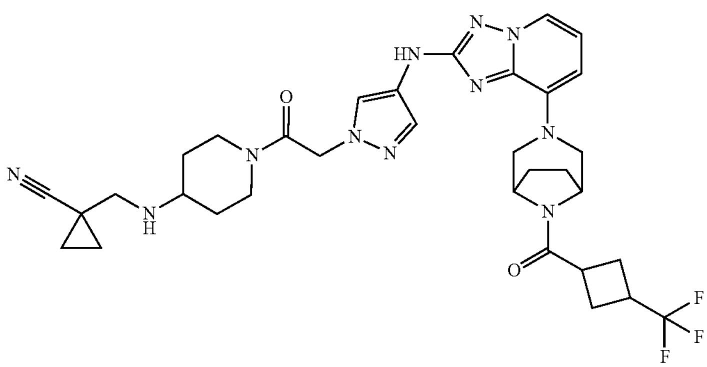 [SMILES: N#CC1(CNC2CCN(C(=O)Cn3cc(Nc4nc5c(N6CC7CCC(C6)N7C(=O)C6CC(C(F)(F)F)C6)cccn5n4)cn3)CC2)CC1] | 1-[[[1-[2-[4-[[8-[8-[3-(trifluoromethyl)cyclobutanecarbonyl]-3,8-diazabicyclo[3.2.1]octan-3-yl]-[1,2,4]triazolo[1,5-a]pyridin-2-yl]amino]pyrazol-1-yl]acetyl]-4-piperidyl]amino]methyl]-cyclopropanecarbonitrile |
| 191 | 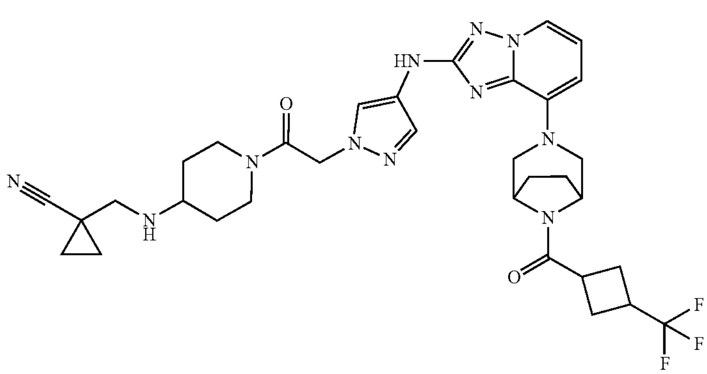 [SMILES: N#CC1(CNC2CCN(C(=O)Cn3cc(Nc4nc5c(N6CC7CCC(C6)N7C(=O)C6CC(C(F)(F)F)C6)cccn5n4)cn3)CC2)CC1] | 1-[[[1-[2-[4-[[8-[8-[3-(trifluoromethyl)cyclobutanecarbonyl]-3,8-diazabicyclo[3.2.1]octan-3-yl]-[1,2,4]triazolo[1,5-a]pyridin-2-yl]amino]pyrazol-1-yl]acetyl]-4-piperidyl]amino]methyl]-cyclopropanecarbonitrile |

TABLE 1-continued

Representative Compounds

| Ex. | Structure | Name |
|---|---|---|
| 192 | 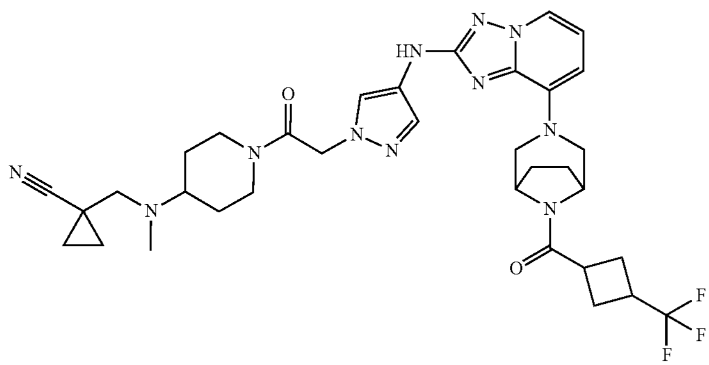 [SMILES: CN(CC1(C#N)CC1)C1CCN(C(=O)Cn2cc(Nc3nc4c(N5CC6CCC(C5)N6C(=O)C5CC(C(F)(F)F)C5)cccn4n3)cn2)CC1] | 1-[[methyl-[1-[2-[4-[[8-[8-[3-(trifluoromethyl)cyclo-butanecarbonyl]-3,8-diazabicyclo[3.2.1]octan-3-yl]-[1,2,4]triazolo[1,5-a]alpyridin-2-yl]amino]pyrazol-1-yl]acetyl]-4-piperidyl]amino]methyl]-cyclopropanecarbonitrile |
| 193 | 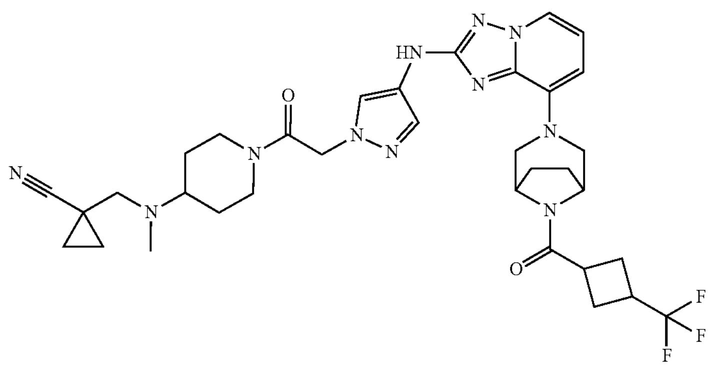 [SMILES: CN(CC1(C#N)CC1)C1CCN(C(=O)Cn2cc(Nc3nc4c(N5CC6CCC(C5)N6C(=O)C5CC(C(F)(F)F)C5)cccn4n3)cn2)CC1] | 1-[[methyl-[1-[2-[4-[[8-[8-[3-(trifluoromethyl)cyclobutanecarbonyl]-3,8-diazabicyclo[3.2.1]octan-3-yl]-[1,2,4]triazolo[1,5-a]pyridin-2-yl]amino]pyrazol-1-yl]acetyl]-4-piperidyl]amino]methyl]-cyclopropanecarbonitrile |
| 194 | 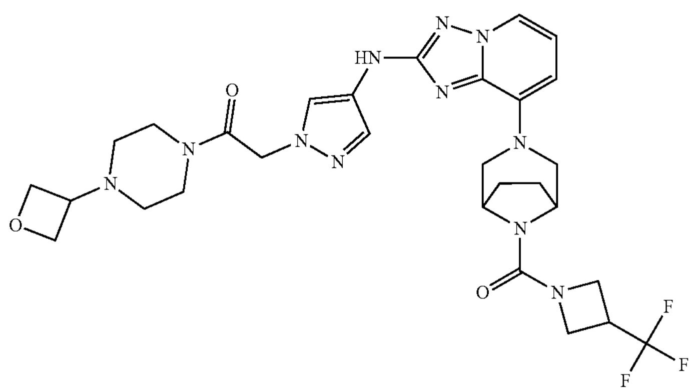 [SMILES: O=C(Cn1cc(Nc2nc3c(N4CC5CCC(C4)N5C(=O)N4CC(C(F)(F)F)C4)cccn3n2)cn1)N1CCN(C2COC2)CC1] | 1-[4-(oxetan-3-yl)piperazin-1-yl]-2-[4-[[8-[8-[3-(trifluoromethyl)azetidine-1-carbonyl]-3,8-diazabicyclo[3.2.1]octan-3-yl]-[1,2,4]triazolo[1,5-a]pyridin-2-yl]amino]pyrazol-1-yl]ethanone |
| 195 | 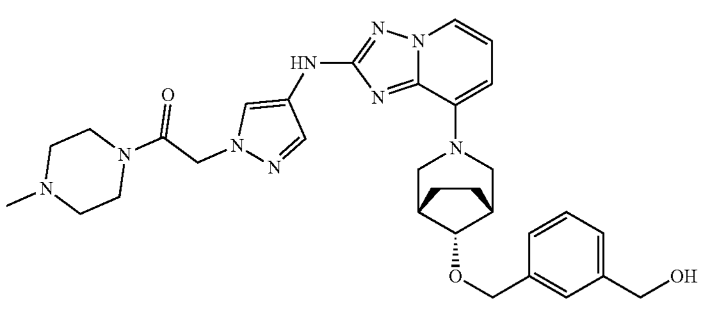 [SMILES: CN1CCN(C(=O)Cn2cc(Nc3nc4c(N5C[C@H]6CC[C@@H](C5)[C@H]6OCc5cccc(CO)c5)cccn4n3)cn2)CC1] | 1-(4-methylpiperazin-1-yl)-2-[4-[[8-[rac-(1S,5R)-8-[[3-(hydroxymethyl)phenyl]methoxy]-3-azabicyclo[3.2.1]octan-3-yl]-[1,2,4]triazolo[1,5-a]pyridin-2-yl]amino]pyrazol-1-yl]ethanone |

TABLE 1-continued

Representative Compounds

| Ex. | Structure | Name |
|---|---|---|
| 196 | 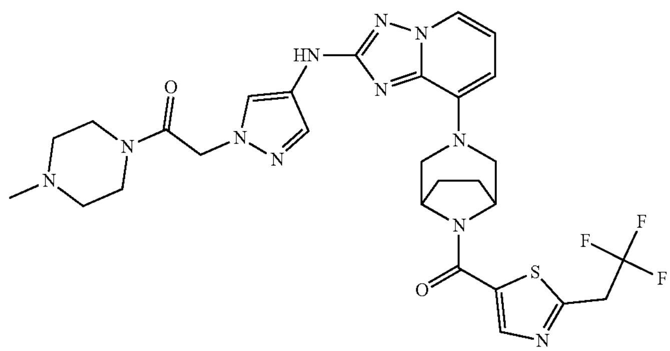 [SMILES: CN1CCN(C(=O)Cn2cc(Nc3nc4c(N5CC6CCC(C5)N6C(=O)c5cnc(CC(F)(F)F)s5)cccn4n3)cn2)CC1] | 1-(4-methylpiperazin-1-yl)-2-[4-[[8-[8-(2-(2,2,2-trifluoroethypthiazole-5-carbonyl]-3,8-diazabicyclo[3.2.1]octan-3-yl]-[1,2,4]triazolo[1,5-a]pyridin-2-yl]amino]pyrazol-1-yl]ethanone |
| 197 | 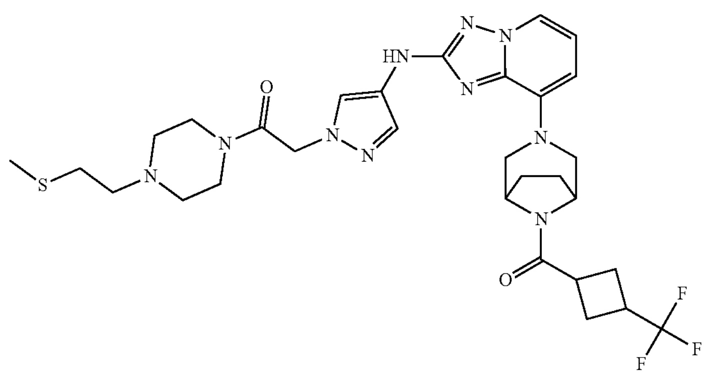 [SMILES: CSCCN1CCN(C(=O)Cn2cc(Nc3nc4c(N5CC6CCC(C5)N6C(=O)C5CC(C(F)(F)F)C5)cccn4n3)cn2)CC1] | 1-[4-(2-methylsulfanylethyl)-piperazin-1-yl]-2-[4-[[8-[8-[3-(trifluoromethyl)-cyclobutanecarbonyl]-3,8-diazabicyclo[3.2.1]octan-3-yl]-[1,2,4]triazolo[1,5-a]pyridin-2-yl]amino]pyrazol-1-yl]ethanone |
| 198 | 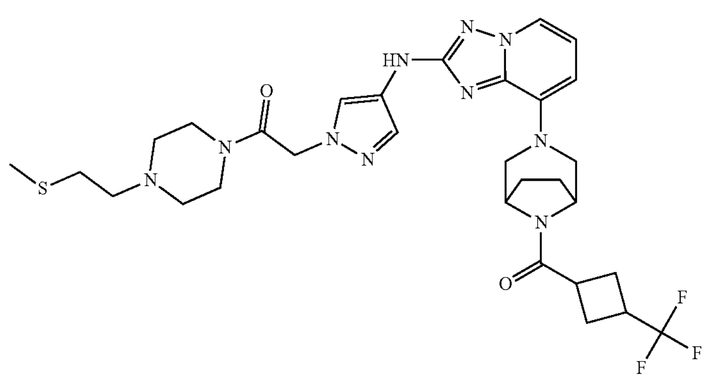 [SMILES: CSCCN1CCN(C(=O)Cn2cc(Nc3nc4c(N5CC6CCC(C5)N6C(=O)C5CC(C(F)(F)F)C5)cccn4n3)cn2)CC1] | 1-[4-(2-methylsulfanylethyl)-piperazin-1-yl]-2-[4-[[8-[8-[3-(trifluoromethyl)-cyclobutanecarbonyl]-3,8-diazabicyclo[3.2.1]octan-3-yl]-[1,2,4]triazolo[1,5-a]pyridin-2-yl]amino]pyrazol-1-yl]ethanone |
| 199 | 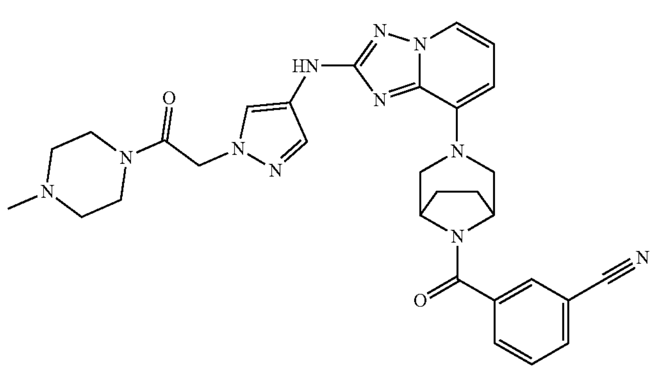 [SMILES: CN1CCN(C(=O)Cn2cc(Nc3nc4c(N5CC6CCC(C5)N6C(=O)c5cccc(C#N)c5)cccn4n3)cn2)CC1] | 3-[3-[2-[[1-[2-(4-methylpiperazin-1-yl)-2-oxo-ethyl]pyrazol-4-yl]amino]-[1,2,4]triazolo[1,5-a]pyridin-8-yl]-3,8-diazabicyclo[3.2.1]octane-8-carbonyl]benzonitrile |

In one embodiment, a compound of Formula (I-II):

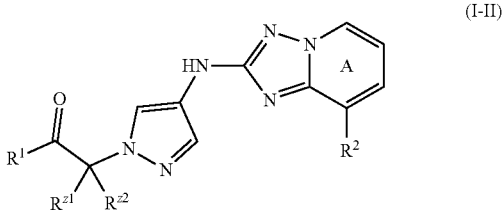

(I-II)

or a salt or stereoisomer thereof is provided, wherein:
$R^{z1}$ and $R^{z2}$ are each independently selected from hydrogen and $C_1$-$C_6$alkyl;
$R^1$ is a 3-11 membered heterocyclyl that is optionally substituted with one or more $R^a$;
$R^2$ is selected from the group consisting of:

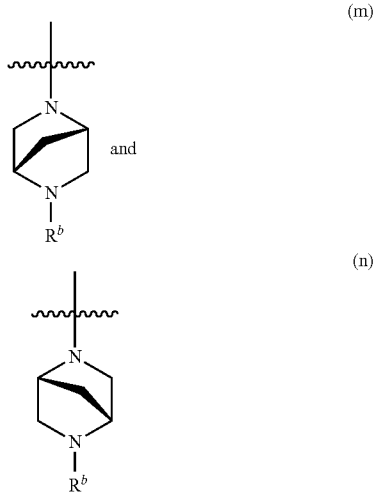

(m)

and (n)

each $R^a$ is independently selected from the group consisting of OH, halo, $C_1$-$C_6$alkyl, $C_3$-$C_8$cycloalkyl, 6-10 membered aryl, 3-11 membered heterocyclyl, C(O)NR$^c$R$^d$, NR$^c$R$^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, $C_3$-$C_8$cycloalkyl, 3-11 membered heterocyclyl, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —OR$^k$, —CN, $C_1$-$C_6$alkyl, $C_3$-$C_8$cycloalkyl, 6-10 membered aryl, 3-11 membered heterocyclyl, —C(O)NR$^f$R$^g$, —S(O)$_n$R$^e$, —S(O)$_2$NR$^f$R$^g$, and —C(O)R$^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from R$^h$;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively R$^c$ and R$^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, $C_1$-$C_6$alkoxy, $C_3$-$C_8$cycloalkyl, and $C_1$-$C_6$alkyl that is optionally substituted with one or more groups independently selected from the group consisting of halo, $C_1$-$C_6$alkoxy, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively R$^f$ and R$^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, and 6-10 membered aryl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl is optionally substituted with one or more groups R$^n$;

each $R^n$ is independently selected from the group consisting of halo, cyano, $C_1$-$C_6$alkyl, $C_1$-$C_6$alkoxy, $C_3$-$C_8$cycloalkyl, —SH, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano; and n is 0, 1, or 2; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl. In some embodiments, ring A is not optionally substituted.

In some embodiments regarding a compound of Formula (I-I):

$R^{z1}$ and $R^{z2}$ are each independently selected from hydrogen and $C_1$-$C_6$alkyl;

$R^1$ is a 3-11 membered heterocyclyl that is optionally substituted with one or more $R^a$;

$R^2$ is selected from the group consisting of:

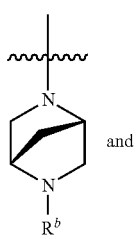 (m)

and

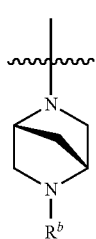 (n)

each $R^a$ is independently selected from the group consisting of OH, halo, $C_1$-$C_6$alkyl, $C_3$-$C_8$cycloalkyl, 6-10 membered aryl, 3-11 membered heterocyclyl, C(O)NR$^c$R$^d$, NR$^c$R$^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, $C_3$-$C_8$cycloalkyl, 3-11 membered heterocyclyl that is optionally substituted with —($C_1$-$C_6$alkyl)-C(O)—NR$^c$R$^d$ or —($C_1$-$C_6$alkyl)-C(O)—OR$^k$, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —OR$^k$, —CN, $C_1$-$C_6$alkyl, $C_3$-$C_8$cycloalkyl, 6-10 membered aryl, 3-11 membered heterocyclyl, NR$^c$R$^d$, —C(O) NR$^f$R$^g$, —S(O)$_n$R$^e$, —S(O)$_2$NR$^f$R$^g$, and —C(O)R$^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from R$^h$;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl; or alternatively R$^c$ and R$^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, $C_1$-$C_6$alkoxy, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively R$^f$ and R$^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, cyano, S(O)$_2$NR$^f$R$^g$, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, 6-10 membered aryl and 3-11 membered heterocyclyl, wherein any said 6-10 aryl and 3-11 membered heterocyclyl is optionally substituted with halo, cyano, or $C_1$-$C_6$alkyl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl is optionally substituted with one or more groups R$^n$;

each $R^n$ is independently selected from the group consisting of halo, cyano, $C_1$-$C_6$alkyl, $C_1$-$C_6$alkoxy, $C_3$-$C_8$cycloalkyl, —SH, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano;

n is 0, 1, or 2;

$R^{z1}$ and $R^{z2}$ are each independently selected from hydrogen and $C_1$-$C_6$alkyl; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl. In some embodiments, ring A is not optionally substituted.

In one embodiment a compound of Formula (Im):

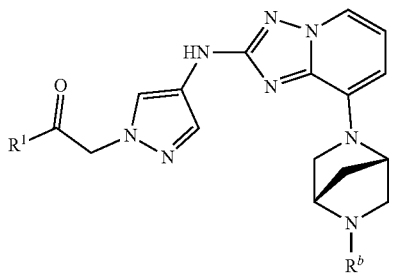

(Im)

or a salt or stereoisomer thereof is provided.

In one embodiment a compound of Formula (In):

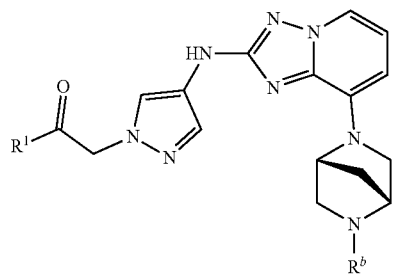

(In)

or a salt or stereoisomer thereof is provided.

In one embodiment $R^2$ is selected from the group consisting of:

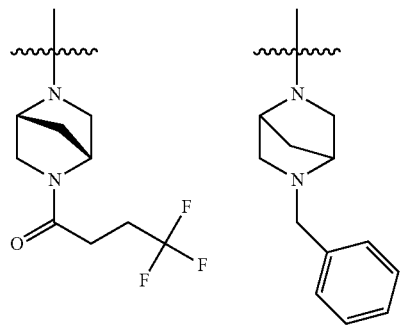

and

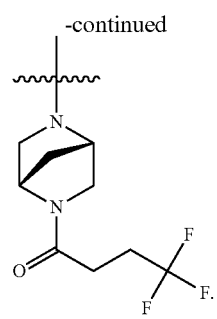

In one embodiment $R^b$ is benzyl.

In one embodiment the compound is selected from:

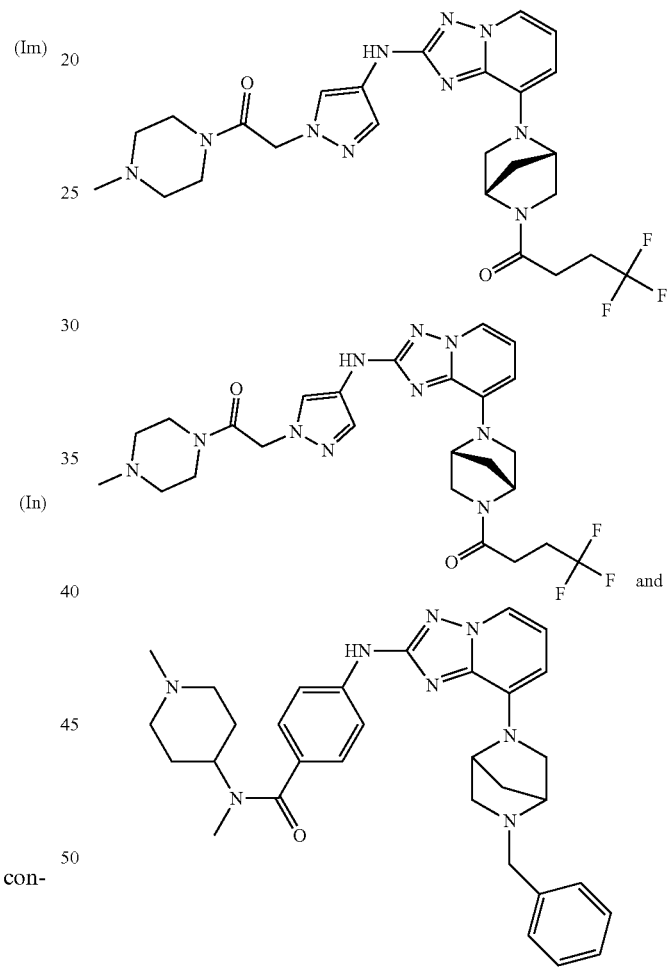

or a salt or stereoisomer thereof.

In one embodiment the disease or condition is cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions.

In one embodiment the use of a compound of Formula (I) or a pharmaceutically acceptable salt thereof, for the treatment of cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions is provided.

In one embodiment a composition that is formulated for administration by inhalation is provided.

In one embodiment a metered dose inhaler that comprises a compound of Formula (I) or a pharmaceutically acceptable salt thereof is provided. In one embodiment a dry powder inhaler that comprises a compound of Formula (I) or a pharmaceutically acceptable salt thereof is provided.

In one embodiment the compound of Formula (I) or the pharmaceutically acceptable salt thereof is at least five-times more potent as an inhibitor of JAK1 than as an inhibitor of JAK2.

In one embodiment the compound of Formula (I) or the pharmaceutically acceptable salt thereof is at least ten-times more potent as an inhibitor of JAK1 than as an inhibitor of JAK2.

In one embodiment the compound of Formula (I) or the pharmaceutically acceptable salt thereof is at least five-times more potent as an inhibitor of JAK1 than as an inhibitor of JAK3.

In one embodiment the compound of Formula (I) or the pharmaceutically acceptable salt thereof is at least ten-times more potent as an inhibitor of JAK1 than as an inhibitor of JAK3.

In one embodiment a method for treating hair loss in a mammal comprising administering a compound of Formula (I) or a pharmaceutically acceptable salt thereof to the mammal is provided.

In one embodiment the use of a compound of Formula (I) or a pharmaceutically acceptable salt thereof for the treatment of hair loss is provided.

In one embodiment the use of a compound of Formula (I) or a pharmaceutically acceptable salt thereof to prepare a medicament for treating hair loss in a mammal is provided.

Synthesis of Janus Kinase Inhibitor Compounds

Compounds of the invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the invention, such as a compound of Formula (I), (I-I), (Ia), (Ib), (Ic), (Id), (Ie), (If), (Ig), (Ih), (Ii), (Ij), (Im), (In), (Io), (Ip), or (Iq), or a compound of Table 1 or 2.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the invention, and which can be carried out using a variety of reagents and conditions, include the following:

(1) Reaction of a carboxylic acid with an amine to form an amide. Such a transformation can be achieved using various reagents known to those skilled in the art but a comprehensive review can be found in Tetrahedron, 2005, 61, 10827-10852.

(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in Comprehensive Organic Name Reactions and Reagents, 2010, 575-581.

(3) A palladium cross-coupling reaction between an aryl halide and a vinyl boronic acid or boronate ester. This transformation is a type of "Suzuki-Miyaura cross-coupling," a class of reaction that has been thoroughly reviewed in Chemical Reviews, 1995, 95(7), 2457-2483.

(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).

Reaction Scheme 1

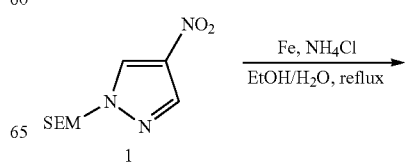

1

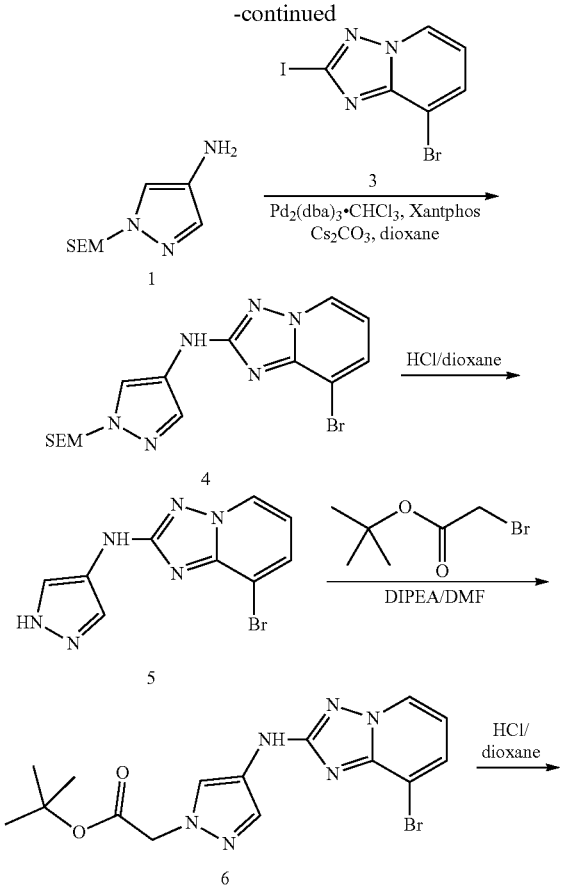
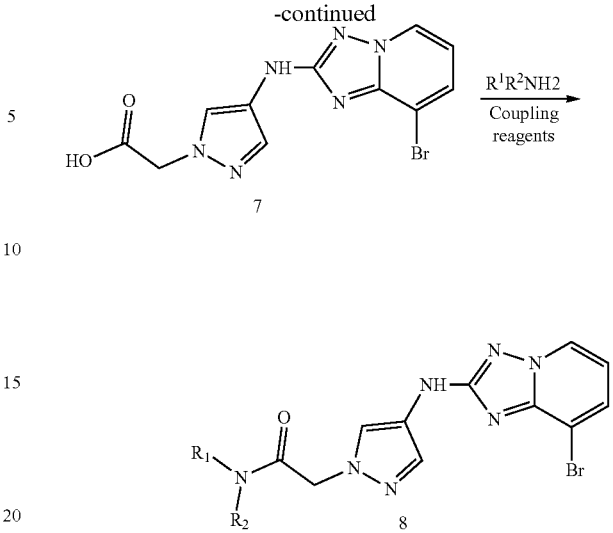

As shown in Scheme 1, compounds of type 8 may be accessed starting with compounds of type 1. Reduction of the nitro group present in 1 produces compound 2. Compound 2 may be reacted under appropriate conditions such as Buchwald-Hartwig type conditions with an aryl halide or aryl halide equivalent such as 3 to produce compounds of type 4. Compound 4 may be deprotected under acidic conditions to produce compounds of type 5, which may then be reacted with appropriate electrophiles such as tert-butyl 2-bromoacetate to provide compounds of type 6. Treatment of 6 with acidic conditions liberates the free acid 7, which may then be coupled with amines under standard conditions to provide amide compounds of type 8.

Reaction Scheme 2

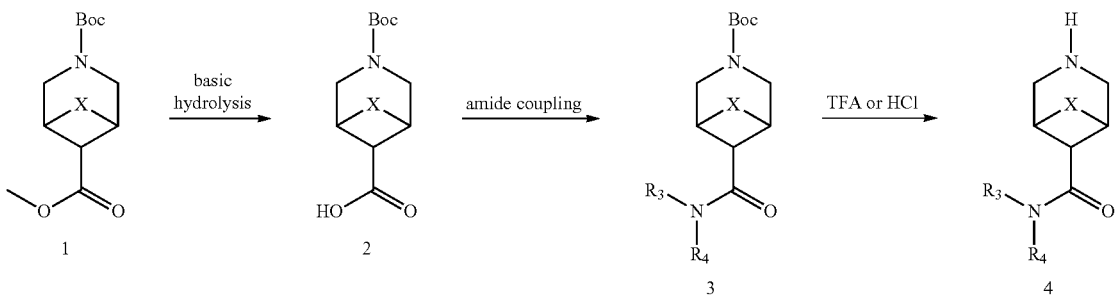

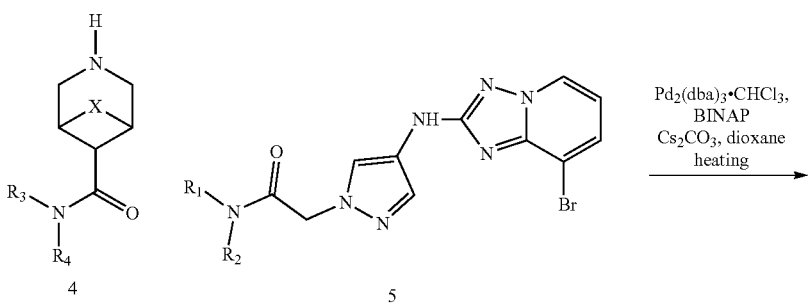

-continued

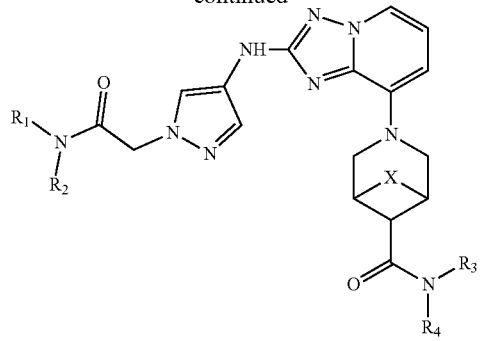

6

X = —CH$_2$—, —CH$_2$CH$_2$—, —CH$_2$CH$_2$CH$_2$—, —CH$_2$OCH$_2$—, —CH$_2$SCH$_2$—

As shown in Scheme 2, compounds of type 6 may be accessed by starting with compounds of type 1. The X group may be comprised of the moieties listed at the bottom of Scheme 2. Hydrolysis of 1 can provide compounds of type 2, which may then be coupled with appropriate amines under standard conditions to provide amide compounds of type 3. Deprotection of 3 under acidic conditions provides compounds of type 4, which can then be reacted under appropriate conditions such as Buchwald-Hartwig type conditions with an aryl halide or aryl halide equivalent such as 5 to produce compounds of type 6.

Reaction Scheme 3

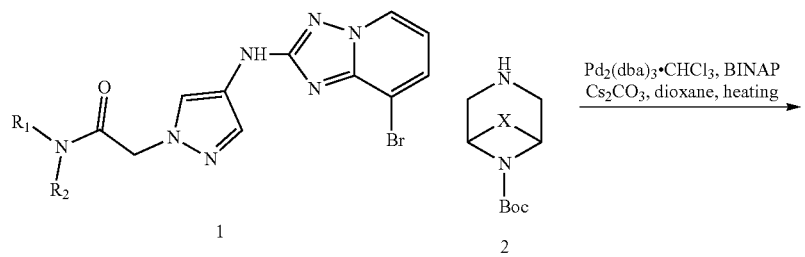

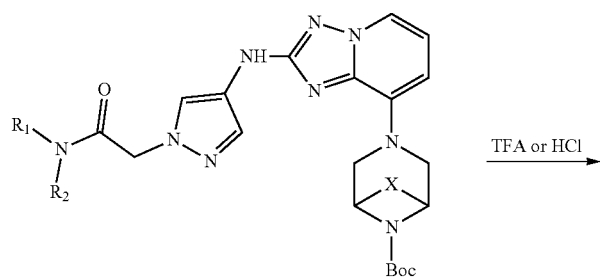

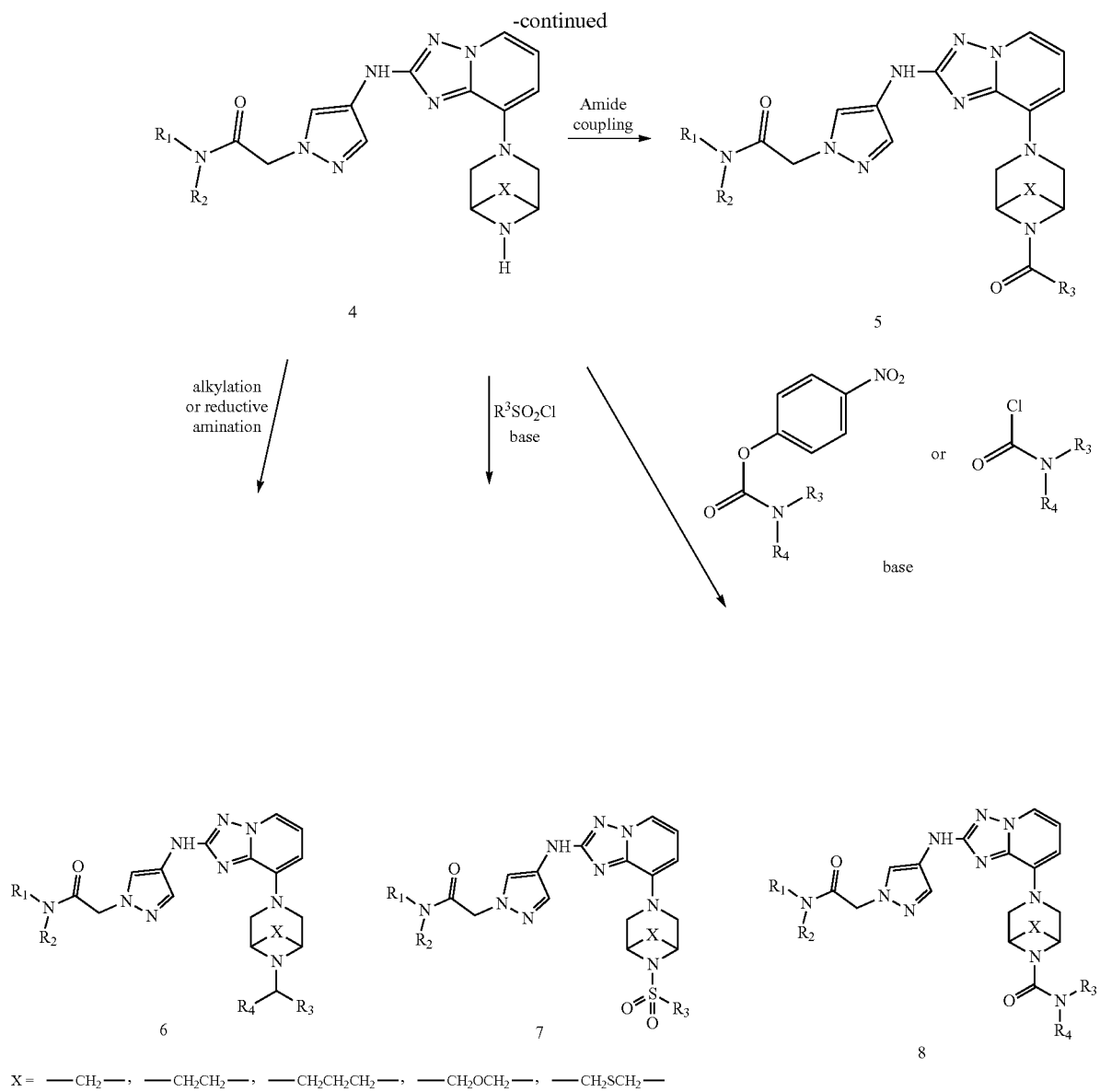

As shown in Scheme 3, compounds of type 5, 6, 7, and 8 may be accessed by starting with compounds of type 1 and 2. The X group may be comprised of the moieties listed at the bottom of Scheme 3. Reaction of compounds of type 2 under appropriate conditions such as Buchwald-Hartwig type conditions with an aryl halide or aryl halide equivalent such as 1 can produce compounds of type 3. Treatment of 3 with acidic conditions liberates the free amine present in compound 4. Reaction of amine 4 under various electrophilic conditions (with a subsequent reduction step in the case of reductive amination) produces compounds of type 5, 6, 7, and 8.

Reaction Scheme 4

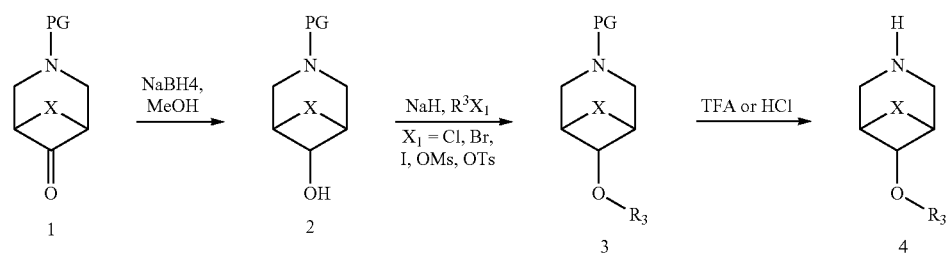

-continued

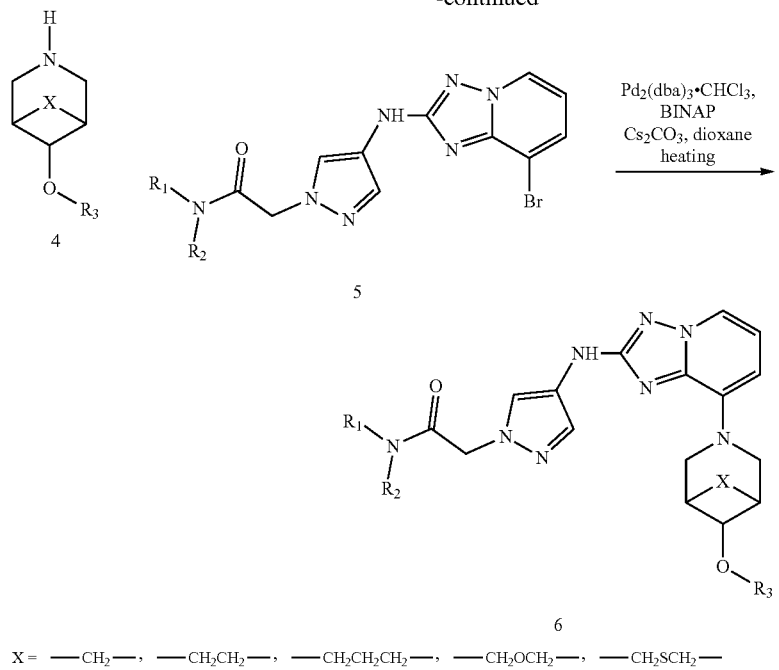

X = —CH₂—, —CH₂CH₂—, —CH₂CH₂CH₂—, —CH₂OCH₂—, —CH₂SCH₂—

As shown in Scheme 4, compounds of type 6 may be accessed by starting with compounds of type 1. The X group may be comprised of the moieties listed at the bottom of Scheme 4. Reduction of ketones of type 1 produces alcohols of type 2. Alkylation of 2 produces compounds of type 3. Treatment of 3 with acidic conditions liberates free amines of type 4. Reaction of compounds of type 4 under appropriate conditions such as Buchwald-Hartwig type conditions with an aryl halide or aryl halide equivalent such as 5 can produce compounds of type 6.

Reaction Scheme 5

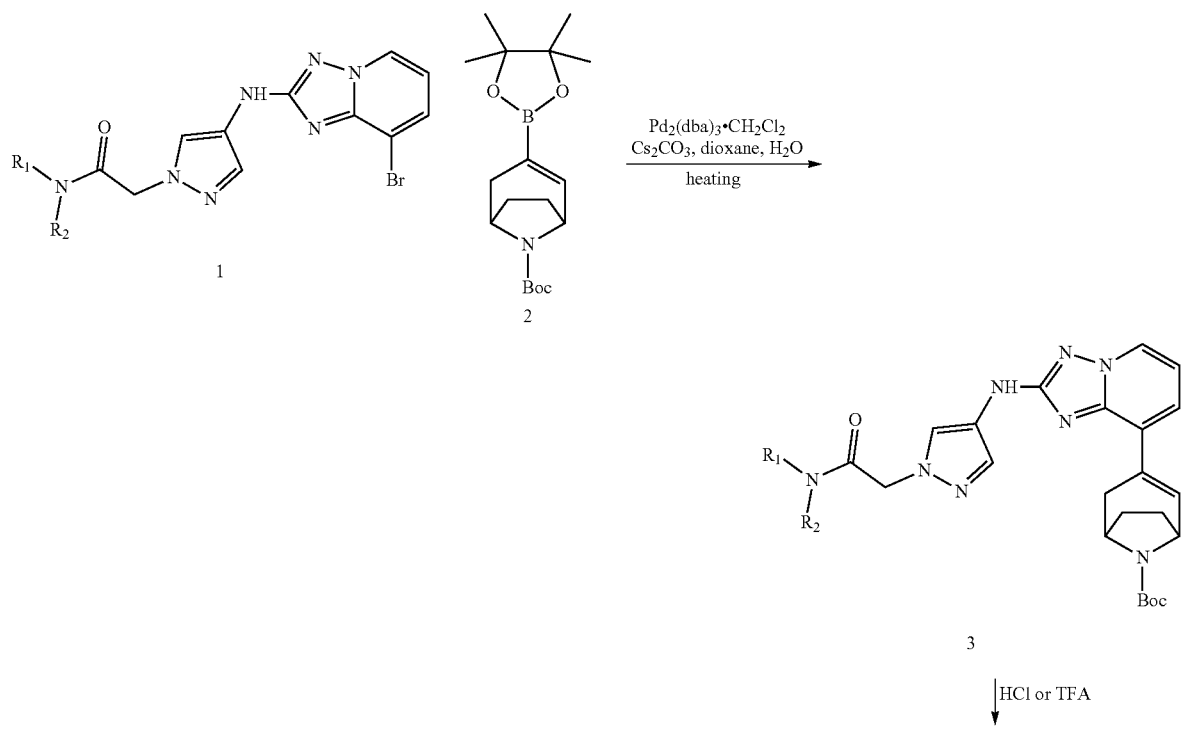

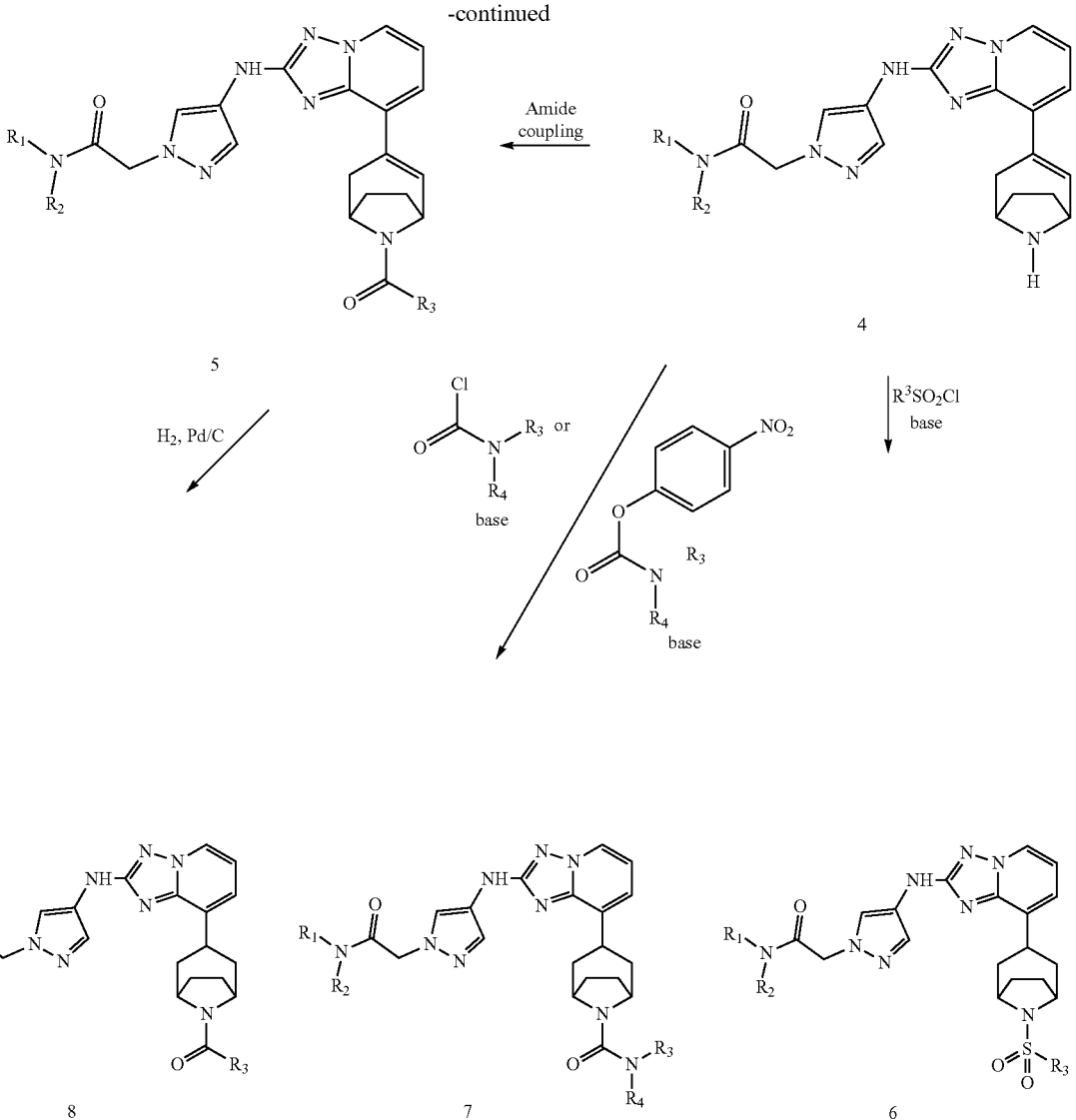

As shown in Scheme 5, compounds of type 5, 6, 7, and 8 may be accessed by starting with compounds of type 2. Reaction of compounds of type 2 under appropriate conditions such as Suzuki type conditions with an aryl halide or aryl halide equivalent such as 1 can produce compounds of type 3. Treatment of 3 with acidic conditions can liberate amine compounds of type 4, which can then be reacted under various electrophilic conditions to produce compounds of type 5, 6, and 7. Compounds of type 5 may further be treated with hydrogenation conditions such as hydrogen gas in the presence of palladium on activated carbon to produce compounds of type 8.

Substitution on ring A of Formula (I) may be accomplished using techniques known in the art. See, e.g., WO 2015/032286 and references cited therein.

Reaction Scheme 6

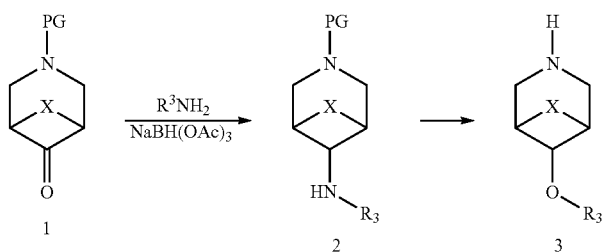

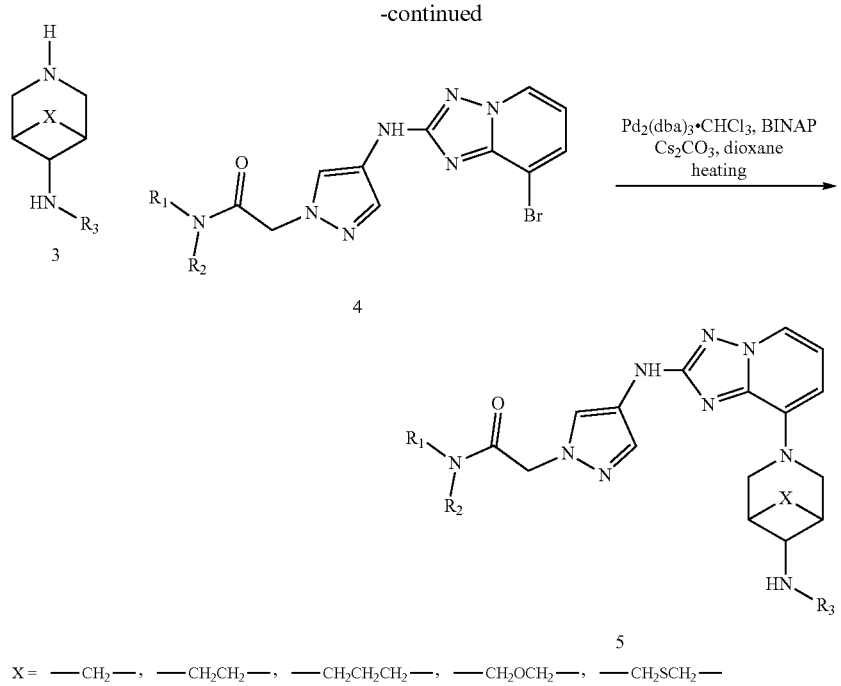

X = —CH₂—, —CH₂CH₂—, —CH₂CH₂CH₂—, —CH₂OCH₂—, —CH₂SCH₂—

As shown in Scheme 6, compounds of type 5 may be accessed by starting with compounds of type 1. The X group may be comprised of the moieties listed at the bottom of Scheme 6. Reductive amination of ketones of type 1 with $R^3NH_2$ produce amines of type 2. Treatment of 3 under acidic conditions liberates free amines of type 3. Reaction of compounds of type 3 under appropriate conditions such as Buchwald-Hartwig type conditions with an aryl halide or aryl halide equivalent such as 4 can produce compounds of type 5.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

| Abbreviations | |
|---|---|
| AcOH | Acetic acid |
| BINAP | (rac)-(1,1'-Binaphthalene-2,2'-diyl)bis(diphenylphosphine) |
| Boc₂O | Di-tert butyl dicarbonate |
| Cs₂CO₃ | Cesium carbonate |
| DIPEA | Diisopropylethylamine |
| DMAP | 4-Dimethylaminopyridine |
| DMF | N,N-Dimethylformamide |
| DMSO | Dimethylsulfoxide |
| DMSO-d6 | Deuterated dimethylsulfoxide |
| EDC•HCl | Ethyl carbodiimide hydrochloride salt |
| EtOAc | Ethyl acetate |
| EtOH | Ethanol |
| g | Gram |
| HATU | (O-(7-azabenzotriazol-1-yl)-N,N,N',N'-tetramethyluronium hexafluorophosphate) |
| HCl | Hydrochloric acid |
| HM-N | Isolute HM-N is a modified form of diatomaceous earth |
| HOBt | Hydroxybenzotriazole |
| KOH | Potassium hydroxide |
| L | Liter |
| MeCN | Acetonitrile |
| MeOH | Methanol |
| mg | Milligram |
| mL | Milliliter |
| NaBH₃CN | Sodium cyanoborohydride |
| NaBH(OAc)₃ | Sodium triacetoxyborohydride |
| NaOH | Sodium hydroxide |
| Na₂SO₄ | Sodium sulfate |
| Pd₂(dba)₃•CHCl₃ | Tris(dibenzylidineacetone)palladium•chloroform complex |
| Pd(dppf)Cl₂ | [1,1'-Bis(diphenylphosphino)ferrocene]-dichloropalladium-(II), complex with dichloromethane |
| Pd(OAc)₂ | Palladium (II) acetate |
| Pd(PPh₃)₄ | Tetrakis(triphenylphosphine)palladium(0) |
| RT | Ambient temperature |
| THF | Tetrahydrofuran |
| TFA | Trifluoroacetic acid |
| TLC | Thin layer chromatography |
| XantPhos | 4,5-Bis(diphenylphosphino)-9,9-dimethylxanthene |

NMR Analytical Methods

1H NMR spectra were recorded at ambient temperature using a Bruker Avance III 300 (300 MHz) spectrometer with a 5 mm Broadband liquid probe BBFO with ATM+Z and a Bruker Avance III HD (400 MHz) spectrometer with a 5 mm Broadband liquid probe BBFO with ATM+Z. Chemical shifts are expressed in ppm relative to tetramethylsilane. The following abbreviations have been used: br=broad signal, s=singlet, d=doublet, dd=double doublet, t=triplet, q=quartet, m=multiplet.

Method A

Experiments were performed on a SHIMADZU 20A HPLC with Shim-Pack XR-ODS column (50×3 mm, 2.2 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 2.00 | 1.0 | 0 | 100 |
| 3.20 | 1.0 | 0 | 100 |
| 3.30 | 1.0 | 95 | 5 |

Detection—UV (220 and 254 nm) and ELSD

Method B

Experiments were performed on a SHIMADZU 20A HPLC with a C18-reverse-phase column (50×3 mm Xtimate TM—C18, 2.2 m particle size), mobile phases: Solvent A: water+0.1% formic acid; Solvent B: acetonitrile+0.05% formic acid. Gradient:

| Gradient - Time | flow ml/min | % A | % B |
| --- | --- | --- | --- |
| 0.00 | 1.0 | 95 | 5 |
| 2.00 | 1.0 | 0 | 100 |
| 3.10 | 1.0 | 0 | 100 |
| 3.20 | 1.0 | 95 | 5 |

Detection—UV (220 and 254 nm) and ELSD

Method C

Experiments were performed on a SHIMADZU 20A HPLC with a C18-reverse-phase column (50×3 mm, Gemini-NX 3μ-C18 110A, 3.0 m particle size), mobile phases: Solvent A: water/5 mM NH$_4$HCO$_3$; Solvent B: acetonitrile. Gradient:

| Gradient - Time | flow ml/min | % A | % B |
| --- | --- | --- | --- |
| 0.00 | 1.2 | 90 | 10 |
| 2.20 | 1.2 | 5 | 95 |
| 3.20 | 1.2 | 5 | 95 |
| 3.30 | 1.2 | 90 | 10 |

Detection—UV (220 and 254 nm) and ELSD

Method D

Experiments were performed on a SHIMADZU 20A HPLC with a C18-reverse-phase column (50×2.1 mm Ascentis Express C18, 2.7 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 2.00 | 1.0 | 0 | 100 |
| 2.70 | 1.0 | 0 | 100 |
| 2.80 | 1.0 | 95 | 5 |

Detection—UV (220 and 254 nm) and ELSD

Method E

Experiments were performed on a SHIMADZU 20A HPLC with a C18-reverse-phase column (50×2.1 mm Xtimate TM—C18, 2.6 m particle size), mobile phases: Solvent A: Water+0.05% TFA; Solvent B: Acetonitrile+0.05% TFA:

| Gradient - Time | flow ml/min | % A | % B |
| --- | --- | --- | --- |
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection—UV (220 and 254 nm) and ELSD

Method F

Experiments were performed on a SHIMADZU 20A HPLC with a Shim-pack XR-ODS column (50×3 mm Xtimate TM—C18, 2.2 m particle size), mobile phases: Solvent A: water+0.05% TFA; Solvent B: acetonitrile+0.05% TFA. Gradient:

| Gradient - Time | flow ml/min | % A | % B |
| --- | --- | --- | --- |
| 0.00 | 1.0 | 95 | 5 |
| 1.20 | 1.0 | 0 | 100 |
| 2.20 | 1.0 | 0 | 100 |
| 2.30 | 1.0 | 95 | 5 |

Detection—UV (220 and 254 nm) and ELSD

Method G

Experiments were performed on a SHIMADZU 20A HPLC with a C18-reverse-phase column (50×2.1 mm Xtimate TM—C18, 2.7 m particle size), mobile phases: Solvent A: water+0.05% trifluoroacetic acid; Solvent B: acetonitrile+0.05% trifluoroacetic acid.

Gradient:

| Gradient - Time | flow ml/min | % A | % B |
| --- | --- | --- | --- |
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection—UV (220 and 254 nm) and ELSD

Method H

Experiments were performed on a SHIMADZU 20A HPLC with Shim-Pack XR-ODS column (50×3 mm, 2.2 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 3.50 | 1.0 | 30 | 70 |
| 3.80 | 1.0 | 0 | 100 |
| 4.60 | 1.0 | 0 | 100 |
| 4.75 | 1.0 | 95 | 5 |

Detection—UV (220 and 254 nm) and ELSD

Method I

Experiments were performed on a SHIMADZU 20A HPLC with Shim-Pack XR-ODS column (50×3 mm, 2.2 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 3.10 | 1.0 | 50 | 50 |
| 3.80 | 1.0 | 0 | 100 |
| 4.60 | 1.0 | 0 | 100 |
| 4.75 | 1.0 | 95 | 5 |

Detection—UV (220 and 254 nm) and ELSD
Method J
Experiments were performed on a SHIMADZU 20A HPLC with a C18-reverse-phase column (50×3 mm, Gemini-NX 3 t-C18 110A, 3.0 m particle size), mobile phases: Solvent A: water/5 mM $NH_4HCO_3$; Solvent B: acetonitrile. Gradient:

| Gradient - Time | flow ml/min | % A | % B |
| --- | --- | --- | --- |
| 0.00 | 1.2 | 70 | 30 |
| 3.50 | 1.2 | 20 | 80 |
| 4.30 | 1.2 | 20 | 80 |
| 4.40 | 1.2 | 95 | 5 |

Detection—UV (220 and 254 nm) and ELSD
Method K
Experiments were performed on a SHIMADZU 20A HPLC with a C18-reverse-phase column (50×3 mm, Gemini-NX 3μ-C18 110A, 3.0 m particle size), mobile phases: Solvent A: water/5 mM $NH_4HCO_3$; Solvent B: acetonitrile. Gradient:

| Gradient - Time | flow ml/min | % A | % B |
| --- | --- | --- | --- |
| 0.00 | 1.2 | 90 | 10 |
| 1.20 | 1.2 | 5 | 95 |
| 2.20 | 1.2 | 5 | 95 |
| 2.30 | 1.2 | 90 | 10 |

Detection—UV (220 and 254 nm) and ELSD
Method L
Experiments performed on an Agilent 1290 UHPLC coupled with Agilent MSD (6140) mass spectrometer using ESI as ionization source. The LC separation was using a Phenomenex XB-C18, 1.7 μm, 50×2.1 mm column with a 0.4 mL/minute flow rate. Solvent A is water with 0.1% formic acid and solvent B is acetonitrile with 0.1% formic acid. The gradient consisted of 2-98% solvent B over 7 min and hold 98% B for 1.5 min following equilibration for 1.5 min. LC column temperature is 40 OC. UV absorbance was collected at 220 nm and 254 nm and mass spec full scan was applied to all experiments.
Method M
Experiments were performed on a SHIMADZU 20A HPLC with Shim-Pack XR-ODS column (50×3 mm, 2.2 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 3.20 | 1.0 | 40 | 60 |
| 3.80 | 1.0 | 0 | 100 |
| 4.60 | 1.0 | 0 | 100 |
| 4.75 | 1.0 | 95 | 5 |

Detection—UV (220 and 254 nm) and ELSD
Method N
Experiments were performed on a SHIMADZU 20A HPLC with a C18-reverse-phase column (50×2.1 mm Ascentis Express C18, 2.7 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 2.00 | 1.0 | 5 | 95 |
| 2.70 | 1.0 | 5 | 95 |
| 2.80 | 1.0 | 95 | 5 |

Detection—UV (220 and 254 nm) and ELSD
Method O
Experiments were performed on a SHIMADZU 20A HPLC with Shim-Pack XR-ODS column (50×3 mm, 2.2 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.2 | 95 | 5 |
| 2.00 | 1.2 | 5 | 95 |
| 2.70 | 1.2 | 5 | 95 |
| 2.75 | 1.2 | 95 | 5 |

Detection—UV (220 and 254 nm) and ELSD
Method P
Experiments were performed on a SHIMADZU 20A HPLC with Shim-Pack XR-ODS column (50×3 mm, 2.2 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 2.20 | 1.0 | 0 | 100 |
| 3.20 | 1.0 | 0 | 100 |
| 3.30 | 1.0 | 95 | 5 |

Detection—UV (220 and 254 nm) and ELSD
Method Q
Experiments were performed on a SHIMADZU 20A HPLC with a C18-reverse-phase column (50×2.1 mm Ascentis Express C18, 2.7 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 4.00 | 1.0 | 40 | 60 |
| 4.50 | 1.0 | 5 | 95 |
| 5.00 | 1.0 | 5 | 95 |
| 5.10 | 1.0 | 95 | 5 |

Detection—UV (220 and 254 nm) and ELSD
Method R
Experiments were performed on a SHIMADZU 20A HPLC with a C18-reverse-phase column (50×2.1 mm Ascentis Express C18, 2.7 m particle size), mobile phases:

Solvent A: water+0.05% trifluoroacetic acid; Solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 4.00 | 1.0 | 50 | 50 |
| 4.50 | 1.0 | 5 | 95 |
| 5.00 | 1.0 | 5 | 95 |
| 5.10 | 1.0 | 95 | 5 |

Detection—UV (220 and 254 nm) and ELSD
Method S
Experiments were performed on a SHIMADZU 20A HPLC with a C18-reverse-phase column (50×3 mm, Gemini-NX 3 t-C18 110A, 3.0 m particle size), mobile phases: Solvent A: water/5 mM $NH_4HCO_3$; Solvent B: acetonitrile. Gradient:

| Gradient - Time | flow ml/min | % A | % B |
|---|---|---|---|
| 0.00 | 1.2 | 90 | 10 |
| 3.20 | 1.2 | 30 | 70 |
| 4.30 | 1.2 | 30 | 70 |
| 4.40 | 1.2 | 90 | 10 |

Detection—UV (220 and 254 nm) and ELSD
Method T
Experiments were performed on a SHIMADZU 20A HPLC with a C18-reverse-phase column (50×2.1 mm Ascentis Express C18, 2.7 m particle size), mobile phases: Solvent A: water+0.05% trifluoroacetic acid; Solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 4.20 | 1.0 | 50 | 70 |
| 4.50 | 1.0 | 5 | 95 |
| 5.00 | 1.0 | 5 | 95 |
| 5.10 | 1.0 | 95 | 5 |

Detection—UV (220 and 254 nm) and ELSD
Method U
Experiments were performed on a Waters Acquity UPLC with a Shim-pack XR-ODS column (100×2.1 mm Acquity BEH C18, 1.7 μm particle size), elution with solvent A: Water/0.05% TFA; solvent B: Acetonitrile/0.05% TFA at 40° C. Gradient:

| Gradient - Time | flow ml/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—UV (220 and 254 nm) and PDA
MS ionisation method—ESI+
Method V
Experiments were performed on an Agilent 1290 UHPLC coupled with Agilent MSD (6140) mass spectrometer using ESI as ionization source (Phenomenex XB-C18, 1.7 uμm, 50×2.1 mm, 1.7 μm particle size), elution with solvent A: water+0.1% formic acid; solvent B: acetonitrile+0.1% formic acid. Gradient:

| Gradient - Time (min) | flow ml/min | % A | % B |
|---|---|---|---|
| 0 | 0.4 | 98 | 2 |
| 1.5 | 0.4 | 2 | 98 |
| 8.5 | 0.4 | 2 | 98 |
| 10 | 0.4 | 2 | 98 |
| 11.5 | 0.4 | 98 | 2 |

Detection—UV (200 nm, 254 nm)

Example 1

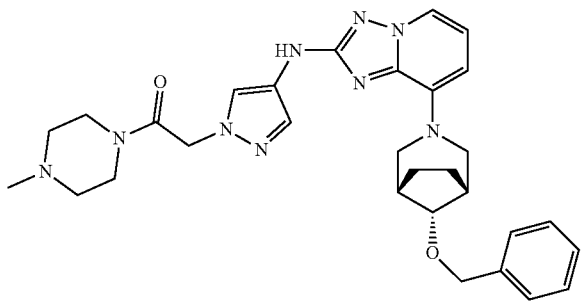 [SMILES: CN1CCN(C(=O)Cn2cc(Nc3nc4c(N5C[C@H]6CC[C@@H](C5)[C@H]6OCc5ccccc5)cccn4n3)cn2)CC1]

2-[4-([8-[(1R,5 S,8R)-8-(benzyloxy)-3-azabicyclo[3.2.1]octan-3-yl]-[1,2,4]triazolo[1,5-a]pyridin-2-yl]amino)-1H-pyrazol-1-yl]-1-(4-methylpiperazin-1-yl)ethan-1-one A solution of tert-butyl 8-oxo-3-azabicyclo[3.2.1]octane-3-carboxylate (1.00 g, 4.44 mmol) in methanol (30 mL) was cooled to 0° C. under ice bath, and $NaBH_4$ (173 mg, 4.57 mmol) was added in small portions at the rate to keep reaction temperature at 0° C. The resulting solution was stirred for another 5 min at 0° C. The resulting mixture was concentrated under vacuum. The residue was purified by flash chromatography on silica gel eluting with ethyl acetate/petroleum ether (4/1) to give 992 mg (98%) of (1R, 5S, 8r)-tert-butyl 8-hydroxy-3-azabicyclo[3.2.1]octane-3-carboxylate as colorless oil. TLC: petroleum ether/ethyl acetate=1/1, $R_f$=0.4.

To a suspension of sodium hydride (63.1 mg, 2.63 mmol) in DMF (10 mL) was added tert-butyl 8-hydroxy-3-azabicyclo[3.2.1]octane-3-carboxylate (300 mg, 1.32 mmol). The resulting solution was stirred for 20 min at 0° C. Then (bromomethyl)benzene (339 mg, 1.98 mmol) was added. The resulting solution was stirred for 4 h at room temperature. The reaction was then quenched by the addition of 10 mL of water. The resulting solution was extracted with 3×50 mL of ethyl acetate and the organic layers combined and concentrated under vacuum. The residue was purified by flash chromatography on silica gel eluting with ethyl acetate/petroleum ether (4/1). The appropriate fractions were combined and concentrated under vacuum to afford 457 mg (73%) of tert-butyl 8-(benzyloxy)-3-azabicyclo[3.2.1]octane-3-carboxylate as a white solid. LC/MS (Method K, ESI): [M+H]⁺=262.2, $R_T$=1.64 min.

tert-Butyl 8-(benzyloxy)-3-azabicyclo[3.2.1]octane-3-carboxylate (200 mg, 0.630 mmol) was added into HCl/dioxane (4M, 10 mL) in small portions. The resulting solution was stirred at room temperature overnight and concentrated under vacuum. The residue was dissolved in 20 mL of $H_2O$. The pH value of the solution was adjusted to 8-9 with potassium carbonate (3 mol/L). The resulting mixture was concentrated under vacuum. The residue was dissolved in 20 mL of DCM/MeOH=5/1. The solids were filtered out. The filtrate was concentrated under vacuum to give 117 mg (85%) of 8-(benzyloxy)-3-azabicyclo[3.2.1]octane as a light yellow solid. LC/MS (Method K, ESI): [M+H]$^+$=218.2, $R_T$=1.22 min.

To a solution of 2-[4-([8-bromo-[1,2,4]triazolo[1,5-a]pyridin-2-yl]amino)-1H-pyrazol-1-yl]-1-(4-methylpiperazin-1-yl)ethan-1-one (128 mg, 0.305 mmol) in dioxane (10 mL) was added 8-(benzyloxy)-3-azabicyclo[3.2.1]octane (200 mg, 0.920 mmol), Pd$_2$(dba)$_3$CHCl$_3$ (63 mg, 0.061 mmol), BINAP (76 mg, 0.122 mmol) and Cs$_2$CO$_3$ (199 mg, 0.611 mmol) under nitrogen. The resulting solution was stirred overnight at 100° C. The resulting mixture was concentrated under vacuum. The residue was passed through a short pad of silica gel eluting with DCM/MeOH (10/1). The appropriate fractions were combined and concentrated. The crude product (87 mg) was further purified by Prep-HPLC with the following conditions: Column, Gemini-NX C18 AXAI Packed 21.2*150 mm, 5 um; mobile phase A, 10 mmol/L NH$_4$HCO$_3$ in water; mobile phase B, MeCN; (35.0% B up to 60% B in 6 min); Detector, UV 254 nm to give 8.21 mg of 2-[4-([8-[(1R,5S,8R)-8-(benzyloxy)-3-azabicyclo[3.2.1]octan-3-yl]-[1,2,4]triazolo[1,5-a]pyridin-2-yl]amino)-1H-pyrazol-1-yl]-1-(4-methylpiperazin-1-yl)ethan-1-one as a light yellow solid. LC/MS (Method J, ESI): [M+H]$^+$=556.4, $R_T$=2.06 min. $^1$H NMR (300 MHz, CD$_3$OD-d$_4$): δ (ppm) 8.01 (dd, J=6.6, 0.9 Hz, 1H), 7.90 (d, J=0.6 Hz, 1H), 7.63 (d, J=0.6 Hz, 1H), 7.42-7.27 (m, 5H), 6.81 (dd, J=7.8, 6.6 Hz, 1H), 6.71 (d, J=6.9 Hz, 1H), 5.10 (s, 2H), 4.65 (s, 2H), 3.93-3.84 (m, 3H), 3.62 (t, J=5.1 Hz, 4H), 3.39-3.35 (m, 2H), 2.46 (m, t, J=5.1 Hz, 4H), 2.36-2.33 (m, 2H), 2.32 (s, 3H), 2.00-1.96 (m, 2H), 1.82-1.78 (m, 2H).

Example 2

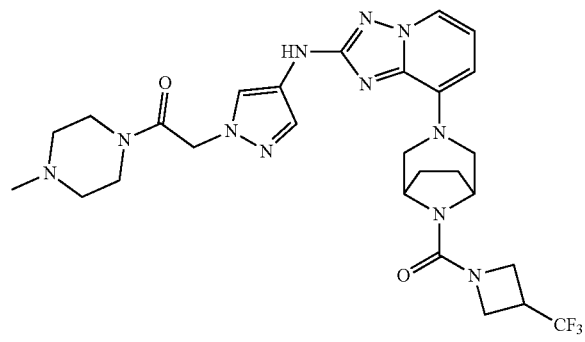 [SMILES: CN1CCN(C(=O)Cn2cc(Nc3nc4c(N5CC6CCC(C5)N6C(=O)N5CC(C(F)(F)F)C5)cccn4n3)cn2)CC1]

1-(4-methylpiperazin-1-yl)-2-(4-[[8-(8-[[3-(trifluoromethyl)azetidin-1-yl]carbonyl]-3,8-diazabicyclo[3.2.1]octan-3-yl)-[1,2,4]triazolo[1,5-a]pyridin-2-yl]amino]-1H-pyrazol-1-yl)ethan-1-one To a solution of 3-(trifluoromethyl)azetidine hydrochloride (500 mg, 3.10 mmol) in toluene (10 mL) was 4-nitrophenyl chloroformate (624 mg, 3.10 mmol). The resulting solution was stirred for 2 h at 110° C. in an oil bath. The reaction mixture was cooled. The resulting mixture was concentrated under vacuum. The residue was purified by flash chromatography on silica gel eluting with ethyl acetate/petroleum ether (1/4). The appropriate fractions were combined and concentrated under vacuum. This resulted in 790 mg (88%) of 4-nitrophenyl 3-(trifluoromethyl)azetidine-1-carboxylate as light yellow oil. TLC: $R_f$=0.4; ethyl acetate/hexane=1/2.

To a solution of tert-butyl 3,8-diazabicyclo[3.2.1]octane-8-carboxylate (600 mg, 2.83 mmol) and 2-[4-([8-bromo-[1,2,4]triazolo[1,5-a]pyridin-2-yl]amino)-1H-pyrazol-1-yl]-1-(4-methylpiperazin-1-yl)ethan-1-one (592 mg, 1.41 mmol) in dioxane (12 mL) was added Pd$_2$(dba)$_3$CHCl$_3$ (293 mg, 0.283 mmol), BINAP (352 mg, 0.566 mmol) and Cs$_2$CO$_3$ (923 mg, 2.83 mmol) under nitrogen. The resulting solution was stirred overnight at 100° C. The reaction mixture was cooled to room temperature and concentrated under vacuum. The residue was purified by flash chromatography on silica gel eluting with dichloromethane/methanol (91/9) to give 730 mg (94%) of tert-butyl 3-[2-([1-[2-(4-methylpiperazin-1-yl)-2-oxoethyl]-1H-pyrazol-4-yl]amino)-[1,2,4]triazolo[1,5-a]pyridin-8-yl]-3,8-diazabicyclo[3.2.1]octane-8-carboxylate as yellow oil. LC/MS (Method E, ESI): [M+H]$^+$=551.3, $R_T$=1.01 min; To a solution of tert-butyl 3-[2-([1-[2-(4-methylpiperazin-1-yl)-2-oxoethyl]-1H-pyrazol-4-yl]amino)-[1,2,4]triazolo[1,5-a]pyridin-8-yl]-3,8-diazabicyclo[3.2.1]octane-8-carboxylate (730 mg, 1.33 mmol) in dichloromethane (10 mL) was added trifluoroacetic acid (5.0 mL). The resulting solution was stirred for 60 min at room temperature. The resulting mixture was concentrated under vacuum. The residue was dissolved in of DCM. The pH value of the solution was adjusted to 8 with DIPEA. The resulting mixture was concentrated under vacuum. This resulted in 2.50 g (crude) of 2-[4-[(8-[3,8-diazabicyclo[3.2.1]octan-3-yl]-[1,2,4]triazolo[1,5-a]pyridin-2-yl)amino]-1H-pyrazol-1-yl]-1-(4-methylpiperazin-1-yl)ethan-1-one and DIPEA TFA salt. LC/MS (Method K, ESI): [M+H]$^+$=451.3, $R_T$=0.58 min.

To a solution of 2-[4-[(8-[3,8-diazabicyclo[3.2.1]octan-3-yl]-[1,2,4]triazolo[1,5-a]pyridin-2-yl)amino]-1H-pyrazol-1-yl]-1-(4-methylpiperazin-1-yl)ethan-1-one and DIPEA TFA salt (100 mg, ~0.05 mmol) from previous step was added 4-nitrophenyl 3-(trifluoromethyl)azetidine-1-carboxylate (130 mg, 0.448 mmol) and DIPEA (86.1 mg, 0.665 mmol). The resulting solution was stirred for 3 days at 85° C. The resulting mixture was concentrated under vacuum. The residue was purified by flash chromatography on silica gel eluting with dichloromethane/methanol (70/30). The crude product (80 mg) was further purified by Prep-HPLC with the following conditions: Column, XBridge Shield RP18 OBD Column, 19*150 mm, 5 um; mobile phase A, 10 mmol/L NH$_4$HCO$_3$ in water; mobile phase B, MeCN; (22.0% MeCN B up to 46.0% B in 7 min); Detector, UV 254 nm.

This resulted in 12.1 mg of 1-(4-methylpiperazin-1-yl)-2-(4-[[8-(8-[[3-(trifluoromethyl)azetidin-1-yl]carbonyl]-3,8-diazabicyclo[3.2.1]octan-3-yl)-[1,2,4]triazolo[1,5-a]pyridin-2-yl]amino]-1H-pyrazol-1-yl)ethan-1-one as a white solid. LC/MS (Method H, ESI): [M+H]$^+$=602.4, $R_T$=2.20 min; $^1$H NMR (300 MHz, CD$_3$OD-d$_4$): δ (ppm) 7.97 (d, J=6.3 Hz, 1H), 7.82 (s, 1H), 7.51 (s, 1H), 6.73 (t, J=7.2 Hz, 1H), 6.61 (d, J=7.5 Hz, 1H), 5.13 (s, 2H), 4.24-4.17 (m, 4H), 4.05-3.97 (m, 4H), 3.56-3.50 (m, 4H), 3.44-3.35 (m, 1H), 2.94-2.86 (m, 2H), 2.41-2.33 (m, 4H), 2.22 (s, 3H), 2.08-2.02 (m, 2H), 1.89-1.84 (m, 2H).

Examples 6 and 15

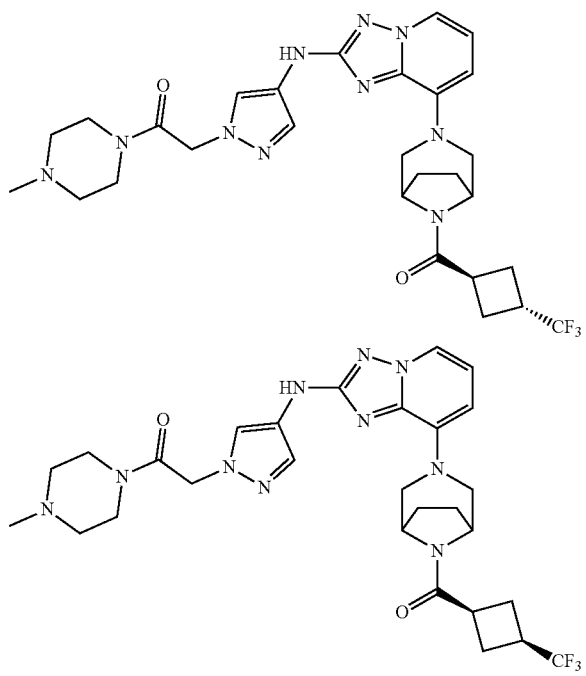

1-(4-methylpiperazin-1-yl)-2-(4-[[8-(8-[[(1 r,3r)-3-(trifluoromethyl)cyclobutyl]carbonyl]-3,8-diazabicyclo[3.2.1]octan-3-yl)-[1,2,4]triazolo[1,5-a]pyridin-2-yl]amino]-1H-pyrazol-1-yl)ethan-1-one (Trans isomer) and 1-(4-methylpiperazin-1-yl)-2-(4-[[8-(8-[[(1s,3s)-3-(trifluoromethyl)cyclobutyl]carbonyl]-3,8-diazabicyclo[3.2.1]octan-3-yl)-[1,2,4]triazolo[1,5-a]pyridin-2-yl]amino]-1H-pyrazol-1-yl)ethan-1-one (Cis isomer)

To a solution of crude 2-[4-[(8-[3,8-diazabicyclo[3.2.1]octan-3-yl]-[1,2,4]triazolo[1,5-a]pyridin-2-yl)amino]-1H-pyrazol-1-yl]-1-(4-methylpiperazin-1-yl)ethan-1-one containing some DIPEA TFA salt (100 mg, ~0.05 mmol) in DMF (10 mL) was added a cis/trans mixture of 3-(trifluoromethyl)cyclobutane-1-carboxylic acid (38 mg, 0.226 mmol), EDC.HCl (86.1 mg, 0.449 mmol), HOBt (60.2 mg, 0.444 mmol) and DIPEA (115 mg, 0.890 mmol). The resulting solution was stirred overnight at room temperature. The resulting mixture was concentrated under vacuum. The residue was purified by flash chromatography on silica gel eluting with dichloromethane/methanol (85/15) to afford the cis/trans amide mixture, which was separated by Prep-HPLC with the following conditions: Column, Gemini-NX C18 AXAI Packed 21.2*150 mm 5 um; mobile phase, 0.1% formic acid in water and MeCN (32.0% MeCN up to 58.0% in 6 min); Detector, UV 254 nm to give two isomers:

The first fraction: 8.21 mg as its formic acid salt. LC/MS (Method C, ESI): [M+H]$^+$=601.4, $R_T$=1.47 min; $^1$H NMR (300 MHz, CD$_3$OD-d$_4$): δ (ppm) 8.08 (d, J=6.3 Hz, 1H), 7.90 (s, 1H), 7.61 (s, 1H), 6.81 (t, J=7.2 Hz, 1H), 6.70 (d, J=7.2 Hz, 1H), 5.11 (s, 2H), 4.41-4.37 (m, 1H), 4.20 (d, J=11.1 Hz, 1H), 4.09 (d, J=11.1 Hz, 1H), 3.67 (t, J=5.4 Hz, 4H), 3.46-3.40 (m, 1H), 3.11-3.02 (m, 1H), 2.99-2.84 (m, 2H), 2.62 (t, J=5.1 Hz, 4H), 2.47-2.39 (m, 8H), 2.23-2.11 (m, 2H), 2.00-1.93 (m, 2H).

The second fraction: 4.7 mg, formic acid salt as a white solid. LC/MS (Method K, ESI): [M+H]$^+$=601.4, $R_T$=1.14 min; $^1$H NMR (300 MHz, CD$_3$OD-d$_4$): δ (ppm) 8.07 (d, J=6.3 Hz, 1H), 7.90 (s, 1H), 7.61 (s, 1H), 6.81 (t, J=6.6 Hz, 1H), 6.71 (d, J=7.2 Hz, 1H), 5.11 (s, 2H), 4.37-4.32 (m, 1H), 4.18 (d, J=11.1 Hz, 1H), 4.11 (d, J=11.1 Hz, 1H), 3.65 (t, J=5.4 Hz, 4H), 3.68-3.50 (m, 1H), 3.11-3.00 (m, 1H), 2.98-2.84 (m, 2H), 2.66-2.50 (m, 9H), 2.40 (s, 3H), 2.24-2.11 (m, 2H), 2.05-1.88 (m, 2H).

Example 18

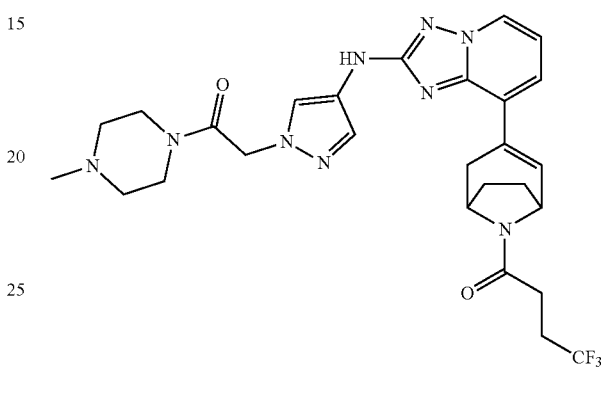

4,4,4-trifluoro-1-[3-[2-([1-[2-(4-methylpiperazin-1-yl)-2-oxoethyl]-1H-pyrazol-4-yl]amino)-[1,2,4]triazolo[1,5-a]pyridin-8-yl]-8-azabicyclo[3.2.1]oct-2-en-8-yl]butan-1-one To a solution of 2-[4-([8-bromo-[1,2,4]triazolo[1,5-a]pyridin-2-yl]amino)-1H-pyrazol-1-yl]-1-(4-methylpiperazin-1-yl)ethan-1-one (500 mg, 1.19 mmol) in 1,4-dioxane (10 mL) and water (2.0 mL) was added successively tert-butyl 3-(tetramethyl-1,3,2-dioxaborolan-2-yl)-8-azabicyclo[3.2.1]oct-2-ene-8-carboxylate (605 mg, 1.81 mmol), Pd(dppf)Cl$_2$·CH$_2$Cl$_2$ (98.0 mg, 0.120 mmol) and Cs$_2$CO$_3$ (780 mg, 2.39 mmol) under nitrogen at room temperature. The resulting solution was stirred overnight at 80° C. under nitrogen, and allowed to cool to room temperature. The resulting mixture was concentrated under vacuum. The residue was purified by flash chromatography on silica gel eluting with dichloromethane/methanol (96/4-92/8) to afford 517 mg (79%) of tert-butyl 3-[2-([1-[2-(4-methylpiperazin-1-yl)-2-oxoethyl]-1H-pyrazol-4-yl]amino)-[1,2,4]triazolo[1,5-a]pyridin-8-yl]-8-azabicyclo[3.2.1]oct-2-ene-8-carboxylate as an oil. LC/MS (Method A, ESI): [M+H]$^+$=548.4, $R_T$=1.69 min.

To a solution of tert-butyl 3-[2-([1-[2-(4-methylpiperazin-1-yl)-2-oxoethyl]-1H-pyrazol-4-yl]amino)-[1,2,4]triazolo[1,5-a]pyridin-8-yl]-8-azabicyclo[3.2.1]oct-2-ene-8-carboxylate (500 mg, 0.913 mmol) in dichloromethane (5.0 mL) was added trifluoroacetic acid (5.0 mL). The resulting solution was stirred for 3 h at room temperature and concentrated under vacuum. This resulted in 950 mg of 2-[4-[(8-[8-azabicyclo[3.2.1]oct-2-en-3-yl]-[1,2,4]triazolo[1,5-a]pyridin-2-yl)amino]-1H-pyrazol-1-yl]-1-(4-methylpiperazin-1-yl)ethan-1-one as its TFA salt. LC/MS (Method A, ESI): [M+H]$^+$=448.3, $R_T$=1.36 min.

To a solution of 2-[4-[(8-[8-azabicyclo[3.2.1]oct-2-en-3-yl]-[1,2,4]triazolo [1,5-a]pyridin-2-yl)amino]-1H-pyrazol-1-yl]-1-(4-methylpiperazin-1-yl)ethan-1-one (200 mg, TFA salt) in DMF (10 mL) was added 4,4,4-trifluorobutanoic acid (127 mg, 0.894 mmol), HATU (255 mg, 0.671 mmol), DIPEA (173 mg, 1.34 mmol). The resulting solution was stirred overnight at room temperature. The resulting mixture was concentrated under vacuum. The residue was passed through a short pad of silica gel eluting with dichloromethane/methanol (80/20). The appropriate fractions were combined and concentrated under vacuum. The crude product was further purified by Prep-HPLC with the following conditions: Column, XBridge Shield RP18 OBD Column, 19*150 mm, 5 um; mobile phase A, 10 mmol/L $NH_4HCO_3$ in water; mobile phase B, MeCN; (25.0% B up to 50.0% B in 9 min); Detector, UV 254 nm to obtain 53.1 mg of 4,4,4-trifluoro-1-[3-[2-([1-[2-(4-methylpiperazin-1-yl)-2-oxoethyl]-1H-pyrazol-4-yl]amino)-[1,2,4]triazolo[1,5-a]pyridin-8-yl]-8-azabicyclo[3.2.1]oct-2-en-8-yl]butan-1-one as an off-white solid. LC/MS (Method I, ESI): [M+H]$^+$ =572.4, $R_T$=2.53 min; $^1$H NMR (300 MHz, $CD_3OD$-$d_4$): δ (ppm) 8.40 (d, J=6.9 Hz, 1H), 7.96 (d, J=3.0 Hz, 1H), 7.65-7.59 (m, 1H), 7.62 (s, 1H), 7.44 (d, J=7.8 Hz, 1H), 6.94 (t, J=7.2 Hz, 1H), 5.13 (s, 2H), 5.05-5.03 (m, 1H), 4.75-4.62 (m, 2H), 3.64 (t, J=5.4 Hz, 4H), 3.23-3.10 (m, 1H), 2.73-2.60 (m, 4H), 2.51-2.40 (m, 5H), 2.33 (s, 3H), 2.23-2.11 (m, 2H), 2.06-1.82 (m, 1H).

Example 34

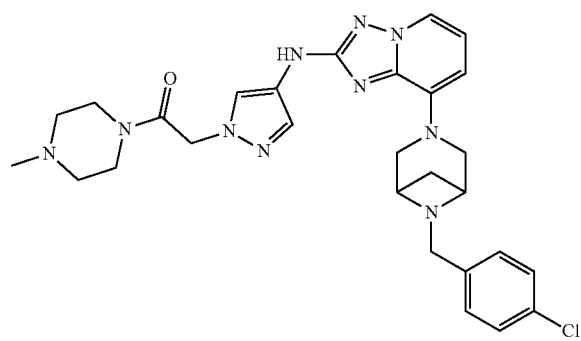 [SMILES: CN1CCN(C(=O)Cn2cc(Nc3nc4c(N5CC6CC(C5)N6Cc5ccc(Cl)cc5)cccn4n3)cn2)CC1]

2-[4-[(8-[6-[(4-chlorophenyl)methyl]-3,6-diazabicyclo[3.1.1]heptan-3-yl]-[1,2,4]triazolo[1,5-a]pyridin-2-yl)amino]-1H-pyrazol-1-yl]-1-(4-methylpiperazin-1-yl)ethan-1-one To a solution of 2-[4-([8-bromo-[1,2,4]triazolo[1,5-a]pyridin-2-yl]amino)-1H-pyrazol-1-yl]acetic acid (10.3 g, 30.6 mmol) in DMF (50 ml) was added HATU (23.5 g, 61.8 mmol), DIPEA (16 g, 124 mmol) and 1-methylpiperazine (6.20 g, 61.9 mmol). The resulting solution was stirred for 4 h at room temperature. The resulting mixture was concentrated under vacuum. The residue was partitioned between 1 N NaOH (200 mL) and dichloromethane (500 mL). Phases were separated, and the aqueous phase was extracted with 2×500 mL of dichloromethane. The organic layers were combined and washed with brine, dried, and concentrated under vacuum. The crude product was re-crystallized from methanol to give 9.80 g (77%) of 2-[4-([8-bromo-[1,2,4]triazolo [1,5-a]pyridin-2-yl]amino)-1H-pyrazol-1-yl]-1-(4-methylpiperazin-1-yl)ethan-1-one as a yellow solid. LC/MS (Method G, ESI): [M+H]$^+$=419.0, $R_T$=0.72 min.

To a solution of 2-[4-([8-bromo-[1,2,4]triazolo[1,5-a]pyridin-2-yl]amino)-1H-pyrazol-1-yl]-1-(4-methylpiperazin-1-yl)ethan-1-one (1.00 g, 2.39 mmol) in dioxane (20 mL) was added tert-butyl 3,6-diazabicyclo[3.1.1]heptane-6-carboxylate (474 mg, 2.39 mmol), $Pd_2(dba)_3$·$CHCl_3$ (248 mg, 0.240 mmol), BINAP (298 mg, 0.479 mmol) and $Cs_2CO_3$ (1.56 g, 4.79 mmol) under nitrogen. The resulting solution was stirred overnight at 100° C. under nitrogen. The reaction mixture was cooled to room temperature and concentrated under vacuum. The residue was purified by flash chromatography on silica gel eluting with dichloromethane/methanol (80/20) to give 801 mg (63%) of tert-butyl 3-[2-([1-[2-(4-methylpiperazin-1-yl)-2-oxoethyl]-1H-pyrazol-4-yl]amino)-[1,2,4]triazolo[1,5-a]pyridin-8-yl]-3,6-diazabicyclo[3.1.1]heptane-6-carboxylate as a yellow solid. LC/MS (Method G, ESI): [M+H]$^+$=537.3, $R_T$=0.72 min.

To a solution of tert-butyl 3-[2-([1-[2-(4-methylpiperazin-1-yl)-2-oxoethyl]-1H-pyrazol-4-yl]amino)-[1,2,4]triazolo[1,5-a]pyridin-8-yl]-3,6-diazabicyclo[3.1.1]heptane-6-carboxylate (800 mg, 1.49 mmol) in dichloromethane (15 mL) was added trifluoroacetic acid (7.0 mL). The reaction mixture was stirred for 3 h at room temperature and concentrated under vacuum. DIPEA was added to the residue until pH of the resulting solution >7. The resulting mixture was concentrated under vacuum. The residue was purified by flash chromatography on silica gel eluting with dichloromethane/methanol (80/20-50/50) to give 602 mg (92%) of 2-[4-[(8-[3,6-diazabicyclo[3.1.1]heptan-3-yl]-[1,2,4]triazolo[1,5-a]pyridin-2-yl)amino]-1H-pyrazol-1-yl]-1-(4-methylpiperazin-1-yl)ethan-1-one as light yellow oil. LC/MS (Method G, ESI): [M+H]$^+$=437.2, $R_T$=0.48 min.

To a solution of 2-[4-[(8-[3,6-diazabicyclo[3.1.1]heptan-3-yl]-[1,2,4]triazolo[1,5-a]pyridin-2-yl)amino]-1H-pyrazol-1-yl]-1-(4-methylpiperazin-1-yl)ethan-1-one (150 mg, 0.344 mmol) in ethanol (10 mL) was added Ti(Oi-Pr)$_4$ (200 mg, 0.704 mmol) and 4-chlorobenzaldehyde (193 mg, 1.37 mmol). The resulting solution was stirred overnight at 60° C. AcOH (0.1 mL, 1.745 mmol) and $NaBH_3CN$ (22 mg, 0.350 mmol) were added. The resulting solution was allowed to react with stirring for an additional 3 h at 60° C. The resulting mixture was concentrated under vacuum. The residue was filtered through a short pad of silica gel eluting with dichloromethane/methanol (70/30). Concentration of appropriate fractions gave the crude product (200 mg), which was further purified by Prep-HPLC with the following conditions: Column, XBridge Shield RP18 OBD Column, 19*150 mm, 5 um; mobile phase, 0.1% formic acid in water and MeCN (10.0% MeCN up to 35.0% in 8 min); Detector, UV 254 nm to obtain 15.8 mg of 2-[4-[(8-[6-[(4-chlorophenyl)methyl]-3,6-diazabicyclo[3.1.1]heptan-3-yl]-[1,2,4]triazolo[1,5-a]pyridin-2-yl)amino]-1H-pyrazol-1-yl]-1-(4-methylpiperazin-1-yl)ethan-1-one as a formic acid salt (with two equivalents of formic acid judging by 1HNMR). LC/MS (Method A, ESI): [M+H]$^+$=561.4, $R_T$=1.21 min; $^1$H NMR (300 MHz, DMSO-d$_6$): δ (ppm) 9.07 (s, 1H, H of formic acid), 8.14 (s, 1H, H of formic acid), 8.08 (d, J=6.6 Hz, 1H), 7.72 (s, 1H), 7.55-7.44 (m, 5H), 6.84 (t, J=7.8 Hz, 1H), 6.58 (d, J=7.8 Hz, 1H), 5.09 (s, 2H), 4.25-3.97 (m, 9H), 3.63-3.20 (m, 4H), 2.72-2.67 (m, 5H), 2.46 (s, 3H), 1.95-1.86 (m, 1H).

Example 43

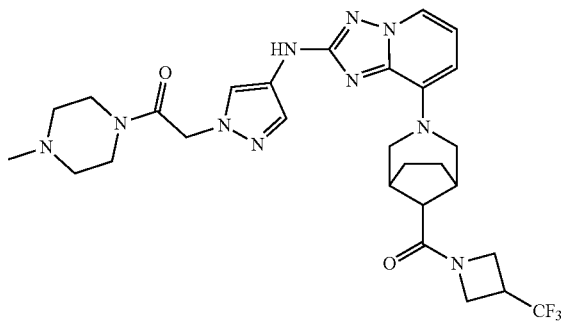 [SMILES: CN1CCN(C(=O)Cn2cc(Nc3nc4c(N5CC6CCC(C5)C6C(=O)N5CC(C(F)(F)F)C5)cccn4n3)cn2)CC1]

1-(4-methylpiperazin-1-yl)-2-(4-[[8-(8-[[3-(trifluoromethyl)azetidin-1-yl]carbonyl]-3-azabicyclo[3.2.1]octan-3-yl)-[1,2,4]triazolo[1,5-a]pyridin-2-yl]amino]-1H-pyrazol-1-yl)ethan-1-one (~1:1 mixture of endo/exo isomers)

To a solution of methyl 3-azabicyclo[3.2.1]octane-8-carboxylate hydrochloride (200 mg, 0.972 mmol) in dichloromethane (20 mL) was added Boc$_2$O (436 mg, 2.00 mmol), DMAP (25.0 mg, 0.205 mmol) and DIPEA (516 mg, 3.99 mmol). The resulting solution was stirred overnight at room temperature. The resulting mixture was concentrated under vacuum. The residue was purified by flash chromatography on silica gel eluting with ethyl acetate/petroleum ether (20/80) to afford 270 mg of 3-tert-butyl 8-methyl 3-azabicyclo[3.2.1]octane-3,8-dicarboxylate as colorless oil. LC/MS (Method F, ESI): [M+H]$^+$=255.0, R$_T$=1.53 min.

To a solution of 3-tert-butyl 8-methyl 3-azabicyclo[3.2.1]octane-3,8-dicarboxylate (270 mg, 1.00 mmol) in water (3.0 mL) and ethanol (6.0 mL) was added KOH (280 mg, 4.99 mmol). The resulting solution was stirred for 5 h at room temperature. The pH value of the solution was adjusted to 6 with hydrogen chloride (1 mol/L). The resulting mixture was concentrated under vacuum to dryness. The residue was diluted with MeOH/DCM (50/50). The solids were filtered out. The filtrate was concentrated under vacuum. This resulted in 300 mg (crude) of 3-[(tert-butoxy)carbonyl]-3-azabicyclo[3.2.1]octane-8-carboxylic acid as a white solid.

To a solution of 3-[(tert-butoxy)carbonyl]-3-azabicyclo[3.2.1]octane-8-carboxylic acid (300 mg, 1.18 mmol) in DMF (10 mL) was added HATU (668 mg, 1.76 mmol), 3-(trifluoromethyl)azetidine hydrochloride (350 mg, 2.17 mmol) and DIPEA (454 mg, 3.51 mmol). The resulting solution was stirred for 4 h at room temperature. The resulting mixture was concentrated under vacuum. The residue was purified by flash chromatography on silica gel eluting with dichloromethane/petroleum ether (40/60). The appropriate fractions were combined and concentrated under vacuum to afford 300 mg (82% over two steps) of tert-butyl 8-[[3-(trifluoromethyl)azetidin-1-yl]carbonyl]-3-azabicyclo[3.2.1]octane-3-carboxylate as a white solid. LC/MS (Method F, ESI): [M+Na]$^+$=385.0, R$_T$=1.53 min.

The product from previous step tert-butyl 8-[[3-(trifluoromethyl)azetidin-1-yl]carbonyl]-3-azabicyclo[3.2.1]octane-3-carboxylate (300 mg, 0.828 mmol) was added to HCl/dioxane (4M, 20 mL). The resulting solution was stirred for 1 h at room temperature. The resulting mixture was concentrated under vacuum. The pH value of the solution was adjusted to 8 with potassium carbonate. The resulting mixture was concentrated under vacuum. The resulted mixture was diluted with 100 ml of DCM/MeOH=5/1. The solid was filtered out. The filtrate was concentrated under vacuum. This resulted in 300 mg (crude) of 8-[[3-(trifluoromethyl)azetidin-1-yl]carbonyl]-3-azabicyclo[3.2.1]octane as brown oil.

To a solution of 2-[4-([8-bromo-[1,2,4]triazolo[1,5-a]pyridin-2-yl]amino)-1H-pyrazol-1-yl]-1-(4-methylpiperazin-1-yl)ethan-1-one (75.0 mg, 0.179 mmol) in dioxane (10 mL) was added successively 8-[3-(trifluoromethyl)azetidin-1-yl]carbonyl-3-azabicyclo[3.2.1]octane (70.0 mg, 0.267 mmol), Pd$_2$(dba)$_3$·CHCl$_3$ (37.0 mg, 0.0361 mmol), BINAP (45.0 mg, 0.0723 mmol) and Cs$_2$CO$_3$ (220 mg, 0.675 mmol) under nitrogen. The resulting solution was stirred overnight at 100° C. and cooled to room temperature. The resulting mixture was concentrated under vacuum. The residue was passed through a short pad of silica gel eluting with dichloromethane/methanol (86/14). The appropriate fractions were combined and concentrated under vacuum. The crude product was further purified by Prep-HPLC with the following conditions: Column, SunFire Prep C$_{18}$ OBD Column 19×150 mm 5 um; mobile phase A, 10 mmol/L NH$_4$HCO$_3$ in water; mobile phase B, MeCN; (23.0% B up to 45.0% B in 8 min); Detector, UV 254 nm to give 15.7 mg of 1-(4-methylpiperazin-1-yl)-2-(4-[[8-(8-[[3-(trifluoromethyl)-azetidin-1-yl]carbonyl]-3-azabicyclo[3.2.1]octan-3-yl)-[1,2,4]triazolo[1,5-a]pyridin-2-yl]amino]-1H-pyrazol-1-yl)ethan-1-one (~1:1 mixture of endo/exo isomer) as a white solid. LC/MS (Method H, ESI): [M+H]$^+$=601.4, R$_T$=2.30 min & 2.33; $^1$H NMR (300 MHz, CD$_3$OD-d$_4$): δ (ppm) 8.03-8.00 (m, 1H), 7.92 (7.90) (s, 1H), 7.63 (7.62) (s, 1H), 6.83-6.77 (m, 1H), 6.69-6.64 (m, 1H), 5.11 (s, 2H), 4.56-4.54 (m, 1H), 4.39-4.35 (m, 1H), 4.22-4.18 (m, 2H), 4.03-3.97 (m, 2H), 3.64-3.62 (m, 4H), 3.55-3.52 (m, 1H), 3.36-3.32 (m, 1H), 2.92-2.86 (m, 1H), 2.64-2.45 (m, 7H), 2.33 (2.32) (s, 3H), 2.03-1.86 (m, 4H).

Example 62

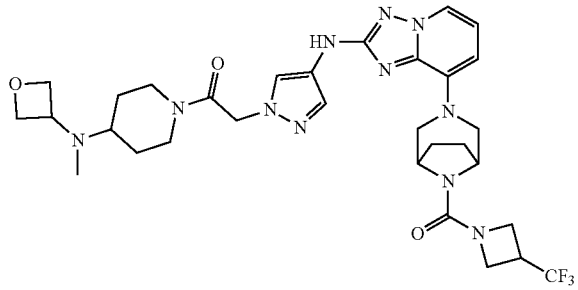 [SMILES: CN(C1CCN(C(=O)Cn2cc(Nc3nc4c(N5CC6CCC(C5)N6C(=O)N5CC(C(F)(F)F)C5)cccn4n3)cn2)CC1)C1COC1]

1-[4-[methyl(oxetan-3-yl)amino]piperidin-1-yl]-2-(4-[[8-(8-[[3-(trifluoromethyl)azetidin-1-yl]carbonyl]-3,8-diazabicyclo[3.2.1]octan-3-yl)-[1,2,4]triazolo[1,5-a]pyridin-2-yl]amino]-1H-pyrazol-1-yl)ethan-1-one To a solution of 2-[4-([8-bromo-[1,2,4]triazolo[1,5-a]pyridin-2-yl]amino)-1H-pyrazol-1-yl]acetic acid (1.00 g, 2.97 mmol) in DMF (15 mL) was added N-methyl-N-(oxetan-3-yl)piperidin-4-amine (506 mg, 2.97 mmol), EDC·HCl (1.14 g, 5.95 mmol), HOBt (800 mg, 5.92 mmol), DIPEA (1.54 g, 11.9 mmol). The resulting solution was stirred overnight at room temperature. The resulting mixture was concentrated under vacuum. The residue was partitioned between dichloromethane and water. The aqueous phase was extracted with dichloromethane (2×), and the combined organic phase were washed with brine and dried over Na$_2$SO$_4$, filtered and concentrated under reduced pressure. The residue was purified by flash chromatography on silica gel eluting with dichloromethane/methanol (4/1) to give 1.01 g (69%) of 2-[4-([8-bromo-[1,2,4]triazolo[1,5-a]pyridin-2-yl]amino)-1H-pyrazol-1-yl]-1-[4-[methyl(oxetan-3-yl)amino]piperidin-1-yl]ethan-1-one as a light yellow solid. LC/MS (Method G, ESI): [M+H]$^+$=491.2, R$_T$=0.54 min.

To a solution of 2-[4-([8-bromo-[1,2,4]triazolo[1,5-a]pyridin-2-yl]amino)-1H-pyrazol-1-yl]-1-[4-[methyl(oxetan-3-yl)amino]piperidin-1-yl]ethan-1-one (200 mg, 0.409 mmol) in dioxane (10 mL) was added tert-butyl 3,8-diazabicyclo[3.2.1]octane-8-carboxylate (96.0 mg, 0.452 mmol), Pd$_2$(dba)$_3$·CHCl$_3$ (43.0 mg, 0.042 mmol), BINAP (51.0 mg, 0.082 mmol) and Cs$_2$CO$_3$ (268 mg, 0.823 mmol) under nitrogen. The resulting solution was stirred overnight at 100° C. The resulting mixture was concentrated under vacuum. The residue was purified by flash chromatography on silica gel eluting with dichloromethane/methanol (4/1) to afford 200 mg (79%) of tert-butyl 3-(2-[[1-(2-[4-[methyl(oxetan-3-yl)amino]piperidin-1-yl]-2-oxoethyl)-1H-pyrazol-4-yl]amino]-[1,2,4]triazolo[1,5-a]pyridin-8-yl)-3,8-diazabicyclo[3.2.1]octane-8-carboxylate as a yellow solid. LC/MS (Method G, ESI): [M+H]$^+$=621.4, R$_T$=0.93 min.

To a solution of tert-butyl 3-(2-[[1-(2-[4-[methyl(oxetan-3-yl)amino]piperidin-1-yl]-2-oxoethyl)-1H-pyrazol-4-yl]amino]-[1,2,4]triazolo[1,5-a]pyridin-8-yl)-3,8-diazabicyclo[3.2.1]octane-8-carboxylate (200 mg, 0.322 mmol) in dichloromethane (10 mL) was added trifluoroacetic acid (8 mL). The resulting solution was stirred for 3 h at room temperature. The resulting mixture was concentrated under vacuum. The pH value of the solution was adjusted to >7 with DIPEA. The resulting mixture was concentrated under vacuum. This resulted in 180 mg (crude) of 2-[4-[(8-[3,8-diazabicyclo[3.2.1]octan-3-yl]-[1,2,4]triazolo[1,5-a]pyridin-2-yl)amino]-1H-pyrazol-1-yl]-1-[4-[methyl(oxetan-3-yl)amino]piperidin-1-yl]ethan-1-one containing DIPEA/TFA salt. LC/MS (Method G, ESI): [M+H]$^+$=521.4, R$_T$=0.47 min.

To a solution of above crude product (90 mg, ~0.16 mmol) in ethanol (5.0 mL) was added 4-nitrophenyl 3-(trifluoromethyl)azetidine-1-carboxylate (100 mg, 0.345 mmol) and DIPEA (67.0 mg, 0.518 mmol). The resulting solution was stirred for 3 days at 85° C. The resulting mixture was concentrated under vacuum. The residue was first purified by flash chromatography on silica gel eluting with dichloromethane/methanol (9/1). The crude product (50 mg) was further purified by Prep-HPLC with the following conditions: Column, XBridge Shield RP18 OBD Column, 19*150 mm, 5 um; mobile phase A, 10 mmol/L NH$_4$HCO$_3$ in water; mobile phase B, MeCN; (23.0% B up to 45.0% B in 8 min); Detector, UV 254 nm. This resulted in 2.30 mg of 1-[4-[methyl(oxetan-3-yl)amino]piperidin-1-yl]-2-(4-[[8-(8-[[3-(trifluoromethyl)azetidin-1-yl]carbonyl]-3,8-diazabicyclo[3.2.1]octan-3-yl)-[1,2,4]triazolo[1,5-a]pyridin-2-yl]amino]-1H-pyrazol-1-yl)ethan-1-one as a white solid. LC/MS (Method C, ESI): [M+H]$^+$=672.5, R$_T$=1.35 min; $^1$H NMR (300 MHz, CD$_3$OD-d$_4$): δ (ppm) 8.07 (d, J=6.3 Hz, 1H), 7.94 (s, 1H), 7.60 (s, 1H), 6.83 (t, J=7.2 Hz, 1H), 6.72 (d, J=7.5 Hz, 1H), 5.22-4.99 (m, 4H), 4.63-4.61 (m, 3H), 4.33-4.30 (m, 4H), 4.13-4.03 (m, 4H), 4.02-3.98 (m, 2H), 3.50-3.48 (m, 1H), 3.14-3.12 (m, 1H), 3.00 (d, J=11.1 Hz, 2H), 2.69-2.61 (m, 2H), 2.19 (s, 3H), 2.17-2.12 (m, 2H), 1.98-1.95 (m, 2H), 1.74-1.71 (m, 2H), 1.44-1.38 (m, 2H).

Intermediate 1

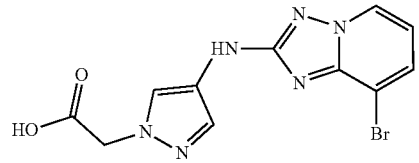

2-[4-([8-bromo-[1,2,4]triazolo[1,5-a]pyridin-2-yl]amino)-1H-pyrazol-1-yl]acetic acid

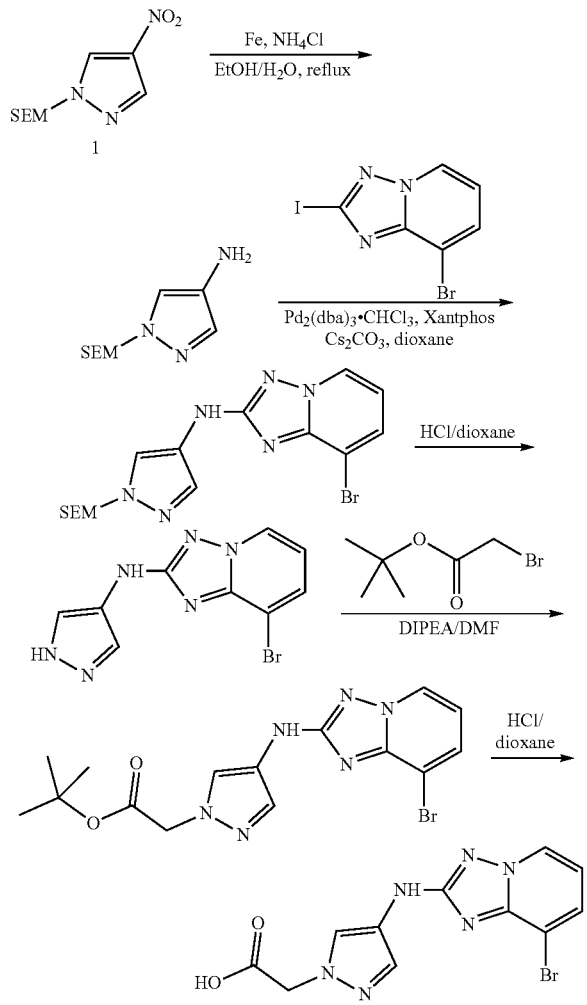

To a solution of 4-nitro-1-[[2-(trimethylsilyl)ethoxy]methyl]-1H-pyrazole (70.0 g, 288 mmol) in ethanol (1000 mL) and water (100 mL) was added iron powder (161 g, 2.88 mol) and NH$_4$Cl (76.9 g, 1.44 mol). The resulting solution was stirred for 3 h under refluxing in an oil bath. The solids were filtered out. The resulting mixture was concentrated under vacuum. The residue was dissolved in 2000 mL of ethyl acetate. The resulting mixture was washed with brine (500 mL), dried over anhydrous sodium sulfate and concentrated under vacuum. This resulted in 65 g (crude) of 1-[[2-(trimethyl silyl)ethoxy]methyl]-1H-pyrazol-4-amine as yellow oil, which was used for next step without purification. LC/MS (Method G, ESI): [M+H]$^+$ =214.1, R$_T$=0.65 min.

To a solution of 8-bromo-2-iodo-[1,2,4]triazolo[1,5-a]pyridine (42.0 g, 130 mmol) in dioxane (500 mL) was added 1-[[2-(trimethylsilyl)ethoxy]methyl]-1H-pyrazol-4-amine (30.0 g, 141 mmol) Pd$_2$(dba)$_3$.CHCl$_3$ (7.20 g, 6.96 mmol), XantPhos (8.10 g, 14.0 mmol) and Cs$_2$CO$_3$ (92.0 g, 282 mmol) under nitrogen. The resulting solution was stirred overnight at 60° C. under nitrogen and concentrated under reduced pressure. The residue was dissolved in 2000 mL of ethyl acetate. The resulting mixture was washed with 1×500 mL of brine, dried over anhydrous sodium sulfate and concentrated under vacuum. The residue was purified by flash chromatography on silica gel eluting with ethyl acetate/petroleum ether (2:3). The appropriate fractions were combined and concentrated under vacuum to give 50.0 g (87%) of N-[8-bromo-[1,2,4]triazolo[1,5-a]pyridin-2-yl]-1-[[2-(trimethylsilyl)ethoxy]methyl]-1H-pyrazol-4-amine as a yellow solid. LC/MS (Method G, ESI): [M+H]$^+$=409.0, R$_T$=1.00 min.

To a solution of N-[8-bromo-[1,2,4]triazolo[1,5-a]pyridin-2-yl]-1-[[2-(trimethylsilyl)ethoxy]methyl]-1H-pyrazol-4-amine (56.0 g, 137 mmol) in dioxane (500 mL) was added HCl/dioxane (4M, 400 mL). The resulting solution was stirred for 4 h at room temperature. The resulting mixture was concentrated under vacuum. Saturated sodium hydrogen carbonate solution was added to the residue with stirring until the pH value >9. The solids were collected by filtration, washed with water and dried to afford 38.5 g of N-[8-bromo-[1,2,4]triazolo[1,5-a]pyridin-2-yl]-1H-pyrazol-4-amine as an off-white solid. The crude product was used for next step without further purification. LC/MS (Method G, ESI): [M+H]$^+$=279.0, R$_T$=0.61 min.

To a solution of N-[8-bromo-[1,2,4]triazolo[1,5-a]pyridin-2-yl]-1H-pyrazol-4-amine (33.0 g, 118 mmol) in DMF (400 mL) was added tert-butyl 2-bromoacetate (48.0 g, 246 mmol), DIPEA (46.0 g, 356 mmol). The resulting solution was stirred overnight at 60° C. in an oil bath. The reaction was then quenched by the addition of 1000 mL of water. The resulting solution was extracted with 3×1000 mL of ethyl acetate and the organic layers combined. The resulting mixture was washed with 1×500 mL of brine. The mixture was dried over anhydrous sodium sulfate and concentrated under vacuum. The residue was purified by flash chromatography on silica gel eluting with ethyl acetate/petroleum ether (1/1). The appropriate fractions were combined and concentrated under vacuum to obtain 28.1 g (60%) of tert-butyl 2-[4-([8-bromo-[1,2,4]triazolo[1,5-a]pyridin-2-yl] amino)-1H-pyrazol-1-yl]acetate as a yellow solid. LC/MS (Method G, ESI): [M+H]$^+$=393.0, R$_T$=0.85 min.

To a solution of hydrogen chloride in dioxane (4M, 500 mL) was added tert-butyl 2-[4-([8-bromo-[1,2,4]triazolo[1,5-a]pyridin-2-yl]amino)-1H-pyrazol-1-yl]acetate (30 g, 76.3 mmol) in small portions. The resulting solution was stirred overnight at room temperature and concentrated under vacuum. This resulted in 18.1 g (70%) of 2-[4-([8-bromo-[1,2,4]triazolo[1,5-a]pyridin-2-yl]amino)-1H-pyrazol-1-yl] acetic acid hydrochloride salt as an off-white solid. $^1$H NMR (400 MHz, DMSO-d$_6$): δ (ppm) 12.41 (br, 1H), 9.52 (s, 1H), 8.73 (dd, J=6.4, 0.8 Hz, 1H), 7.86-7.84 (m, 2H), 7.50 (s, 1H), 6.91 (dd, J=7.8, 6.6 Hz, 1H), 4.94 (s, 2H).

Example 137

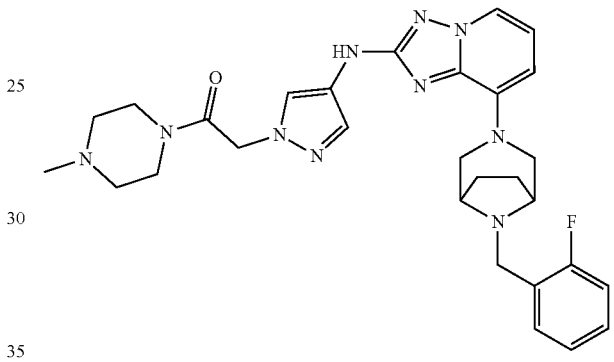

2-(4-((8-((1R,5 S)-8-(2-fluorobenzyl)-3,8-diazabicyclo[3.2.1]octan-3-yl)-[1,2,4]triazolo[1,5-a]pyridin-2-yl)amino)-1H-pyrazol-1l-yl)-1-(4-methylpiperazin-1-yl)ethan-1-one A solution 2-[4-[[8-(3,8-diazabicyclo[3.2.1]octan-3-yl)-[1,2,4]triazolo[1,5-a]pyridin-2-yl]amino]pyrazol-1-yl]-1-(4-methylpiperazin-1-yl)ethanone hydrochloride (25 mg, 0.0513 mmol), 1-(bromomethyl)-2-fluoro-benzene (9.70 mg, 0.0513 mmol) and DIPEA (20.3 mg, 0.0268 mL, 0.154 mmol) in DMF (0.257 ml) was stirred for 16 h at room temperature. The resulting mixture was purified by Prep-HPLC using the following conditions: Column, Gemini-NX C18 OBD Column, 50*30 mm, 5 um; mobile phase A, 10 mmol/L NH$_4$HCO$_3$ in water; mobile phase B, MeCN; (20% to 60% B over 10 min); Detector, UV 220 nm. Appropriate fractions were combined and evaporated to afford 2-(4-((8-((1R,5 S)-8-(2-fluorobenzyl)-3,8-diazabicyclo[3.2.1]octan-3-yl)-[1,2,4]triazolo[1,5-a]pyridin-2-yl)amino)-1H-pyrazol-1-yl)-1-(4-methylpiperazin-1-yl)ethan-1-one (9.4 mg, 33%). LC/MS (Method L, ESI): [M+H]$^+$=559.3, R$_T$=2.47 min.

Example 145

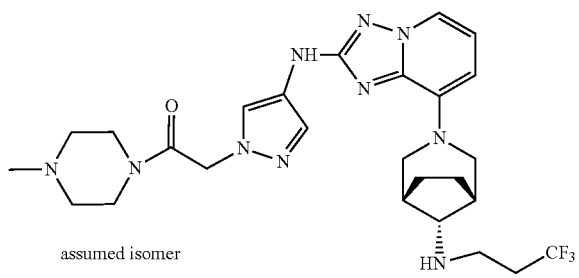 [SMILES: CN1CCN(C(=O)Cn2cc(Nc3nc4c(N5C[C@H]6CC[C@@H](C5)[C@H]6NCCC(F)(F)F)cccn4n3)cn2)CC1]

assumed isomer 1-(4-methylpiperazin-1-yl)-2-(4-((8-((1R,5 S,8r)-8-((3,3,3-trifluoropropyl)amino)-3-azabicyclo[3.2.1]octan-3-yl)-[1,2,4]triazolo[1,5-a]pyridin-2-yl)amino)-1H-pyrazol-1-yl)ethanone 3,3,3-Trifluoropropan-1-amine (201 mg, 1.77 mmol) was added to a solution of tert-butyl 8-oxo-3-azabicyclo[3.2.1]octane-3-carboxylate (200 mg, 0.888 mmol) in dichloromethane (15 mL) and the resultant solution was stirred for 6 h at room temperature. NaBH(OAc)$_3$ (471 mg, 2.22 mmol) was added and the solution stirred overnight at room temperature then concentrated under vacuum. The residue was purified by silica gel column chromatography eluting with ethyl acetate:petroleum ether (1:4). The appropriate fractions were combined and concentrated to afford tert-butyl trans-8-[(3,3,3-trifluoropropyl)amino]-3-azabicyclo[3.2.1]octane-3-carboxylate (270 mg, 94%) as a white solid. TLC: R$_f$=0.2; DCM:MeOH=10:1.

A mixture of tert-butyl trans-8-[(3,3,3-trifluoropropyl)amino]-3-azabicyclo[3.2.1]octane-3-carboxylate (270 mg, 0.838 mmol) in HCl/dioxane (10 mL, 4 M) was stirred for 4 h at room temperature. The resulting mixture was concentrated under vacuum. The residue was dissolved in water (10 mL), the pH of the solution was adjusted to 9 with aqueous saturated sodium bicarbonate solution then concentrated under vacuum. A mixture of DCM and MeOH was added and the precipitated solid was removed by filtration. The filtrate was concentrated under vacuum to give trans-N-(3,3,3-trifluoropropyl)-3-azabicyclo[3.2.1]-octan-8-amine (150 mg, 81%) as a light yellow solid. TLC: R$_f$=0.4; DCM:MeOH=1:1.

A degassed mixture of 2-[4-([8-bromo-[1,2,4]triazolo[1,5-a]pyridin-2-yl]amino)-1H-pyrazol-1-yl]-1-(4-methylpiperazin-1-yl)ethan-1-one (130 mg, 0.310 mmol), trans-N-(3,3,3-trifluoropropyl)-3-azabicyclo[3.2.1]octan-8-amine (85.0 mg, 0.382 mmol), Pd$_2$(dba)$_3$CHCl$_3$ (64.0 mg, 0.0618 mmol), BINAP (77.0 mg, 0.124 mmol) and Cs$_2$CO$_3$ (203 mg, 0.623 mmol) in dioxane (8 mL) was heated at 100° C. in an oil bath overnight. The mixture was allowed to cool to room temperature and concentrated under vacuum. The residue was purified by silica gel column chromatography eluting with dichloromethane:methanol (85:15). The crude product was further purified by Prep-HPLC with the following conditions: Column, XBridge Shield RP18 OBD Column, 5 um, 19*150 mm; mobile phase, Water (+0.05% NH$_3$H$_2$O) and MeCN (35.0% to 56.0% over 9 min); Detector, UV 254, 220 nm. Appropriate fractions were combined and evaporated to afford 1-(4-methylpiperazin-1-yl)-2-(4-((8-((1R,5 S,8r)-8-((3,3,3-trifluoropropyl)amino)-3-azabicyclo[3.2.1]octan-3-yl)-[1,2,4]triazolo[1,5-a]pyridin-2-yl)amino)-1H-pyrazol-1-yl)ethanone (20.8 mg, 12%) as an off-white solid. LC/MS (Method P, ESI): [M+H]$^+$=561.4, R$_T$=1.13 min; $^1$H NMR (300 MHz, CD$_3$OD-d$_4$): δ (ppm) 8.01 (dd, J=6.6, 0.9 Hz, 1H), 7.89 (d, J=0.6 Hz, 1H), 7.62 (d, J=0.6 Hz, 1H), 6.81 (dd, J=7.8, 6.6, 1H), 6.70 (dd, J=7.5, 0.9 Hz, 1H), 5.10 (s, 2H), 3.95-3.90 (m, 2H), 3.63-3.61 (m, 4H), 3.30-3.24 (m, 2H), 2.95-2.90 (m, 3H), 2.49-2.41 (m, 6H), 2.32 (s, 3H), 2.31-2.27 (m, 2H), 2.00-1.96 (m, 2H), 1.87-1.84 (m, 2H).

Example 149

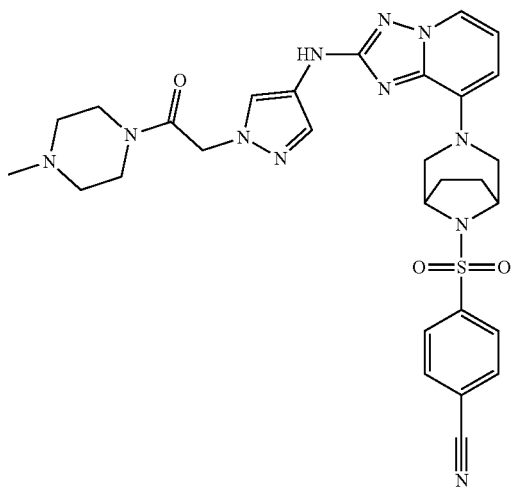 [SMILES: CN1CCN(C(=O)Cn2cc(Nc3nc4c(N5CC6CCC(C5)N6S(=O)(=O)c5ccc(C#N)cc5)cccn4n3)cn2)CC1]

4-[3-[2-([1-[2-(4-methylpiperazin-1-yl)-2-oxoethyl]-1H-pyrazol-4-yl]amino)-[1,2,4]triazolo[1,5-a]pyridin-8-yl]-3,8-diazabicyclo[3.2.1]octane-8-sulfonyl]benzonitrile To a solution of 2-[4-[(8-[3,8-diazabicyclo[3.2.1]octan-3-yl]-[1,2,4]triazolo[1,5-a]pyridin-2-yl)amino]-1H-pyrazol-1-yl]-1-(4-methylpiperazin-1-yl)ethan-1-one (70 mg, 0.155 mmol) in dichloromethane (3 mL) was added 4-cyanobenzene-1-sulfonyl chloride (37.5 mg, 0.186 mmol) and DIPEA (120 mg, 0.932 mmol) and the resultant solution was stirred overnight at room temperature. The mixture was partitioned between water and ethyl acetate and the phases separated. The organic layer was washed with water and brine, dried over anhydrous sodium sulfate and concentrated under vacuum. The residue was purified by Prep-HPLC using the following conditions: Column, XBridge Shield RP18 OBD Column, 5 um, 19*150 mm; mobile phase, Water (+0.05% NH$_3$H$_2$O) and MeCN (25% to 43.0% over 11 min); Detector, UV 254, 220 nm. Appropriate fractions were combined and evaporated to 10.1 mg (11%) of 4-[3-[2-([1-[2-(4-methylpiperazin-1-yl)-2-oxoethyl]-1H-pyrazol-4-yl]amino)-[1,2,4]triazolo[1,5-a]pyridin-8-yl]-3,8-diazabicyclo[3.2.1]octane-8-sulfonyl]benzonitrile as a white solid. LC/MS (Method H, ESI): [M+H]$^+$=616.3, R$_T$=2.39 min; $^1$H NMR (400 MHz, CD$_3$OD-d$_4$): δ (ppm) 8.13 (d, J=8.4 Hz, 2H), 8.07 (d, J=6.8 Hz, 1H), 7.97 (d, J=8.4, 2H), 7.88 (s, 1H), 7.57 (s, 1H), 6.79 (dd, J=7.6, 6.8 Hz, 1H), 6.69 (d, J=7.6 Hz, 1H), 5.14 (s, 2H), 4.48-4.40 (m, 2H), 4.18 (dd, J=11.4, 2.2 Hz, 2H), 3.69-3.48 (m, 4H), 3.01 (d, J=11.2 Hz, 2H), 2.48-2.42 (m, 4H), 2.32 (s, 3H), 2.07-2.02 (m, 2H), 1.59-1.56 (m, 2H).

Example 189

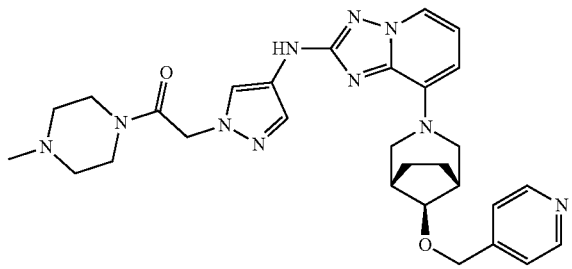 [SMILES: CN1CCN(C(=O)Cn2cc(Nc3nc4c(N5C[C@H]6CC[C@@H](C5)[C@@H]6OCc5ccncc5)cccn4n3)cn2)CC1]

1-(4-methylpiperazin-1-yl)-2-(4-((8-((1R,5 S,8s)-8-(pyridin-4-ylmethoxy)-3-azabicyclo[3.2.1]octan-3-yl)-[1,2,4]triazolo[1,5-a]pyridin-2-yl)amino)-1H-pyrazol-1-yl)ethanone To a solution of 3-benzyl-3-azabicyclo[3.2.1]octan-8-one (2.15 g, 9.98 mmol) in methanol (30 mL) was added NaBH$_4$ (570 mg, 15.0 mmol) portionwise at 0° C. under nitrogen. The resulting solution was stirred for 1 h at room temperature and carefully added to water (200 mL) with stirring. The solid was collected by filtration to afford trans-3-benzyl-3-azabicyclo[3.2.1]octan-8-ol (1.55 g, 71%) as a white solid. TLC: R$_f$=0.4; PE/EA=1/2.

To a solution of trans-3-benzyl-3-azabicyclo[3.2.1]octan-8-ol (500 mg, 2.30 mmol) in dichloromethane (10 mL) was added DIPEA (594 mg, 4.59 mmol) and Tf$_2$O (975 mg, 3.45 mmol) at 0° C. The resulting solution was stirred for 1 h at room temperature. The resulting solution was partitioned between DCM and water. The organic phase was washed with water and brine, dried over sodium sulfate and concentrated under vacuum. The residue was purified by silica gel column chromatography eluting with ethyl acetate/petroleum ether (1/10). The appropriate fractions were combined and concentrated under vacuum to give trans-3-benzyl-3-azabicyclo[3.2.1]octan-8-yl trifluoromethanesulfonate (750 mg, 93%) as light yellow oil. TLC: R$_f$=0.2; Petroleum ether:ethyl acetate=10:1.

p-Toluenesulfonic acid (555 mg, 3.22 mmol) was added to a solution of trans-3-benzyl-3-azabicyclo[3.2.1]octan-8-yl trifluoromethanesulfonate (750 mg, 2.14 mmol) in a solvent mixture of DMSO (4.0 mL), water (1.0 mL) and toluene (10 mL). The reaction mixture was heated under reflux for 3 days and allowed to cool to room temperature. Saturated potassium carbonate solution (100 mL) was added and the resultant solution was extracted with dichloromethane (2×50 mL). The combined organic layer was concentrated under vacuum and the residue was purified by silica gel column chromatography eluting with ethyl acetate/petroleum ether (1/4-1/2). The appropriate fractions were combined and concentrated under vacuum to obtain cis-3-benzyl-3-azabicyclo[3.2.1]octan-8-ol (240 mg, 51%) as a light yellow solid. TLC: R$_f$=0.4; Petroleum ether:ethyl acetate=1:2.

A mixture of cis-3-benzyl-3-azabicyclo[3.2.1]octan-8-ol (240 mg, 1.10 mmol) and 10% Pd/C (25 mg) in methanol (10 mL) was hydrogenated under an atmosphere of H$_2$ overnight. The solid was removed by filtration and the filtrate was concentrated under vacuum to give cis-3-azabicyclo[3.2.1]octan-8-ol (130 mg, 93%) as a light yellow solid. TLC: R$_f$=0.3; DCM:MeOH=1:5.

To a solution of cis-3-azabicyclo[3.2.1]octan-8-ol (130 mg, 1.02 mmol) in dichloromethane (4.0 mL) was added DIPEA (263 mg, 2.03 mmol) and di-tert butyl dicarbonate (335 mg, 1.53 mmol). The mixture was stirred for 3 h at room temperature and concentrated under vacuum. The residue was purified by silica gel column chromatography eluting with ethyl acetate:petroleum ether (1:4 to 1:2). The appropriate fractions were combined and concentrated under vacuum to afford tert-butyl cis-8-hydroxy-3-azabicyclo[3.2.1]octane-3-carboxylate (130 mg, 56%) as a light yellow solid. TLC: R$_f$=0.5; Petroleum ether:ethyl acetate=1:2.

To a suspension of NaH (117 mg, 60% dispersion in mineral oil, 2.91 mmol) in N,N-dimethylformamide (6.0 mL) was added tert-butyl cis-8-hydroxy-3-azabicyclo[3.2.1]octane-3-carboxylate (130 mg, 0.572 mmol) at 0° C. under nitrogen. The resulting solution was allowed to warm to room temperature, stirred for 20 min at room temperature then cooled to 0° C. 4-(chloromethyl)pyridine hydrochloride (140 mg, 0.853 mmol) was added and the resultant solution was stirred for 2 h at room temperature. The reaction was quenched by the addition of water (1.0 mL) and the resulting mixture was concentrated under vacuum. The residue was purified by silica gel column chromatography eluting with ethyl acetate:petroleum ether (1:2 to 1:1). The appropriate fractions were combined and concentrated under vacuum to give tert-butyl cis-8-(pyridin-4-ylmethoxy)-3-azabicyclo[3.2.1]octane-3-carboxylate (125 mg, 69%) as colorless oil. TLC: R$_f$=0.2; Petroleum ether:ethyl acetate=1:2.

A mixture of tert-butyl cis-8-(pyridin-4-ylmethoxy)-3-azabicyclo[3.2.1]octane-3-carboxylate (125 mg, 0.393 mmol) in HCl/dioxane (5.0 mL, 4 M) was stirred for 2 h at room temperature. The resulting mixture was concentrated under vacuum. The pH of the solution was adjusted to 9 by the addition of saturated potassium carbonate solution. The resulting mixture was concentrated under vacuum. A mixture of DCM:MeOH (2:1, 20 mL) was added and the resultant solid removed by filtration. The filtrate was concentrated under vacuum to obtain cis-8-(pyridin-4-ylmethoxy)-3-azabicyclo[3.2.1]octane (80 mg, 93%) as a light yellow solid. TLC: R$_f$=0.2; DCM:MeOH=1:5.

A degassed mixture of 2-[4-([8-bromo-[1,2,4]triazolo[1,5-a]pyridin-2-yl]amino)-1H-pyrazol-1-yl]-1-(4-methylpiperazin-1-yl)ethan-1-one (110 mg, 0.262 mmol), cis-8-(pyridin-4-ylmethoxy)-3-azabicyclo[3.2.1]octane (68.0 mg, 0.312 mmol), Pd$_2$(dba)$_3$ (48.0 mg, 0.052 mmol), BINAP (65.0 mg, 0.104 mmol) and Cs$_2$CO$_3$ (170 mg, 0.522 mmol) in dioxane (5 mL) was heated at 100° C. in an oil bath overnight. The reaction mixture was allowed to cool to room temperature and concentrated under vacuum. The residue was purified by silica gel column chromatography eluting with a gradient of methanol in dichloromethane (10 to 20%). The appropriate fractions were combined and concentrated under vacuum. The residue was re-crystallized from methanol to afford 1-(4-methylpiperazin-1-yl)-2-(4-((8-((1R,5S,8s)-8-(pyridin-4-ylmethoxy)-3-azabicyclo[3.2.1]octan-3-yl)-[1,2,4]triazolo[1,5-a]pyridin-2-yl)amino)-1H-pyrazol-1-yl)ethanone (64.9 mg, 44%) as a yellow solid. LC/MS (Method P, ESI): [M+H]$^+$=557, R$_T$=1.17 min; $^1$H NMR (300 MHz, DMSO-d$_6$): δ (ppm) 9.20 (s, 1H), 8.54 (dd, J=4.5, 1.5 Hz, 2H), 8.18 (dd, J=6.3, 1.2 Hz, 1H), 7.73 (s, 1H), 7.44 (s, 1H), 7.35 (dd, J=4.5, 1.5 Hz, 2H), 6.79 (dd, J=7.8, 6.3 Hz, 1H), 6.63 (dd, J=7.8, 1.2 Hz, 1H), 5.06 (s, 2H), 4.60 (s, 2H), 4.17-4.11 (m, 2H), 3.75 (s, 1H), 3.48-3.42 (m, 4H), 2.89-2.73 (m, 2H), 2.51-2.49 (m, 2H), 2.31-2.26 (m, 4H), 2.17 (s, 3H), 1.85-1.82 (m, 2H), 1.77-1.73 (m, 2H).

Using procedures similar to those described herein, compounds of Table 1 were prepared. In Table 1, certain chemical structures may be shown more than once, for example, see Examples 190-191, 192-193, and 197-198. It is understood that these separate Examples represent single diastereomers that have been separated as shown in Table 2, wherein the absolute stereochemistry of each diastereomer has not been elucidated.

Enzymatic Assays

JAK Enzyme Assays were Carried Out as Follows:

The activity of the isolated recombinant JAK1 and JAK2 kinase domain was measured by monitoring phosphorylation of a peptide derived from JAK3 (Val-Ala-Leu-Val-Asp-Gly-Tyr-Phe-Arg-Leu-Thr-Thr, fluorescently labeled on the N-terminus with 5-carboxyfluorescein) using the Caliper LabChip® technology (Caliper Life Sciences, Hopkinton, Mass.). To determine inhibition constants (K$_i$), compounds were diluted serially in DMSO and added to 50 μL kinase reactions containing purified enzyme (1.5 nM JAK1, or 0.2 nM JAK2), 100 mM HEPES buffer (pH 7.2), 0.015% Brij-35, 1.5 μM peptide substrate, ATP (25 μM), 10 mM MgCl$_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM HEPES buffer (pH 7.2), 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip® 3000 according to the manufacturer's specifications. K$_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)) modified for ATP-competitive inhibition [K$_i$=K$_{i,app}$/(1+[ATP]/K$_{m,app}$)].

JAK1 Pathway Assay in Cell Lines was Carried Out as Follows:

Inhibitor potency (EC$_{50}$) was determined in cell-based assays designed to measure JAK1 dependent STAT phosphorylation. As noted above, inhibition of IL-4, IL-13, and IL-9 signalling by blocking the Jak/Stat signaling pathway can alleviate asthmatic symptoms in pre-clinical lung inflammation models (Mathew et al., 2001, J Exp Med 193(9): 1087-1096; Kudlacz et. al., 2008, Eur J. Pharmacol 582(1-3): 154-161). In one assay approach, TF-1 human erythroleukemia cells obtained from the American Type Culture Collection (ATCC; Manassas, Va.) were used to measure JAK1-dependent STAT6 phosphorylation downstream of IL-13 stimulation. Prior to use in the assays, TF-1 cells were starved of GM-CSF overnight in OptiMEM medium (Life Technologies, Grand Island, N.Y.) supplemented with 0.5% charcoal/dextran stripped fetal bovine serum (FBS), 0.1 mM non-essential amino acids (NEAA), and 1 mM sodium pyruvate. The assays were run in 384-well plates in serum-free OptiMEM medium using 300,000 cells per well. In a second assay approach, BEAS-2B human bronchial epithelial cells obtained from ATCC were plated at 100,000 cells per well of a 96-well plate one day prior to the experiment. The BEAS-2B assay was run in complete growth medium (bronchial epithelial basal medium plus bulletkit; Lonza; Basel, Switzerland).

Test compounds were serially diluted 1:2 in DMSO and then diluted 1:50 in medium just before use. Diluted compounds were added to the cells, for a final DMSO concentration of 0.2%, and incubated for 30 min (for the TF-1 assay) or 1 hr (for the BEAS-2B assay) at 37° C. Then, cells were stimulated with human recombinant cytokine at their respective EC$_{90}$ concentrations, as previously determined for each individual lot. Cells were stimulated with IL-13 (R&D Systems, Minneapolis, Minn.) for 15 min at 37° C. The TF-1 cell reactions were stopped by the direct addition of 10× lysis buffer (Cell Signaling Technologies, Danvers, Mass.), whereas the BEAS-2B cell incubations were halted by the removal of medium and addition of 1× lysis buffer. The resultant samples were frozen in the plates at −80 OC. Compound mediated inhibition of STAT6 phosphorylation was measured in the cell lysates using MesoScale Discovery (MSD) technology (Gaithersburg, Md.). EC$_{50}$ values were determined as the concentration of compound required for 50% inhibition of STAT phosphorylation relative to that measured for the DMSO control.

Table 2 provides JAK1 K$_i$, JAK2 K$_i$ and IL-13-pSTAT6 IC$_{50}$ information for the noted Examples. It is understood that separate Examples of Table 1 represent single diastereomers that have been separated as shown in Table 2, wherein the absolute stereochemistry of each diastereomer has not been elucidated.

TABLE 2

LCMS and Potency Data

| Example | LCMS (ESI) m/z [M + H]+ | LCMS RT (Min) | LCMS Method | JAK1 Ki (μM) | JAK2 Ki (μM) | IL13-pSTAT6 BEAS2B IC50 (μM) |
|---|---|---|---|---|---|---|
| 1 | 556.4 | 2.06 | J | 0.0002 | 0.0006 | 0.01165 |
| 2 | 602.4 | 2.2 | H | 0.0005 | 0.0004 | 0.0485 |
| 3 | 551.3 | 2.99 | L | 0.0005 | 0.0006 | 0.0368 |
| 4 | 589 | 1.5 | A | 0.0005 | 0.0008 | 0.0132 |
| 5 | 575.4 | 1.69 | A | 0.0006 | 0.0012 | 0.02695 |
| 6 | 601.4 | 1.47 | C | 0.0007 | 0.0006 | 0.0155 |
| 7 | 574.3 | 1.85 | A | 0.0007 | 0.0007 | 0.181 |
| 8 | 583.3 | 3.23 | L | 0.0006 | 0.0007 | 0.0366 |
| 9 | 611.3 | 3.25 | L | 0.0006 | 0.0009 | 0.0592 |
| 10 | 645.4 | 2.24 | D | 0.0007 | 0.0012 | 0.0666 |
| 11 | 645.5 | 1.69 | A | 0.0007 | 0.0014 | 0.126 |
| 12 | 561.3 | 2.96 | L | 0.0007 | 0.0017 | 0.0366 |
| 13 | 572.3 | 3.22 | L | 0.0009 | 0.0010 | 0.02145 |
| 14 | 587.3 | 3.36 | L | 0.0010 | 0.0011 | 0.02795 |
| 15 | 601.4 | 1.14 | K | 0.0011 | 0.0037 | 0.0295 |
| 16 | 569.3 | 3.09 | L | 0.0010 | 0.0018 | 0.0833 |
| 17 | 572.4 | 2.53 | I | 0.0012 | 0.0015 | 0.0249 |
| 18 | 594.3 | 3.08 | L | 0.0015 | 0.0046 | 0.278 |
| 19 | 598.4 | 1.48 | C | 0.0015 | 0.0015 | 0.0384 |
| 20 | 530.3 | 1.9 | L | 0.0018 | 0.0021 | 0.0332 |
| 21 | 575.3 | 1.85 | A | 0.0023 | 0.0086 | 0.0523 |
| 22 | 544.3 | 2.94 | L | 0.0022 | 0.0049 | 0.199 |
| 23 | 598.4 | 1.52 | A | 0.0025 | 0.0030 | 0.0401 |
| 24 | 575.4 | 2.29 | J | 0.0025 | 0.0254 | 0.323 |
| 25 | 572.3 | 3.21 | L | 0.0027 | 0.0050 | 0.0364 |
| 26 | 561.4 | 1.58 | A | 0.0053 | 0.0487 | 0.112 |

TABLE 2-continued

LCMS and Potency Data

| Example | LCMS (ESI) m/z [M + H]+ | LCMS RT (Min) | LCMS Method | JAK1 Ki (μM) | JAK2 Ki (μM) | IL13-pSTAT6 BEAS2B IC50 (μM) |
|---|---|---|---|---|---|---|
| 27 | 575.4 | 1.4 | A | 0.0066 | 0.0506 | |
| 28 | 561.4 | 1.27 | C | 0.0102 | 0.1055 | |
| 29 | 573 | 0.97 | A | 0.0198 | 0.0529 | |
| 30 | 572.4 | 1.26 | A | 0.0288 | 0.0650 | |
| 31 | 601.4 | 1.18 | C | 0.0466 | 0.0726 | |
| 32 | 505.3 | 2.04 | L | 0.0557 | 0.1282 | |
| 33 | 561.4 | 1.21 | A | 0.0607 | >0.32 | |
| 34 | 574.4 | 2.44 | I | 0.0688 | 0.2713 | |
| 35 | 561.3 | 1.32 | C | 0.1482 | >0.32 | |
| 36 | 551.2 | 1.18 | B | 0.1725 | 0.1101 | |
| 37 | 555.3 | 2.96 | L | 0.0013 | 0.0018 | 0.0726 |
| 38 | 587.3 | 3.23 | L | 0.0013 | 0.0018 | 0.0525 |
| 39 | 672.5 | 1.45 | A | 0.0007 | 0.0004 | 0.0815 |
| 40 | 615.4 | 2.36 | J | 0.0006 | 0.0006 | 0.0214 |
| 41 | 659.4 | 1.47 | C | 0.0026 | 0.0046 | 0.0514 |
| 42 | 570.3 | 2.15 | L | 0.0016 | 0.0057 | 0.232 |
| 43 | 601.4 | 2.31 | H | 0.0011 | 0.0019 | 0.0581 |
| 44 | 672.5 | 1.38 | C | 0.0009 | 0.0006 | 0.0575 |
| 45 | 591.3 | 3.12 | L | 0.0010 | 0.0035 | 0.0671 |
| 46 | 569.3 | 3.15 | L | 0.0014 | 0.0017 | 0.0738 |
| 47 | 589.3 | 3.27 | L | 0.0018 | 0.0020 | 0.068 |
| 48 | 561.4 | 1.22 | C | >0.56 | >0.32 | |
| 49 | 595.3 | 3.34 | L | 0.0015 | 0.0041 | 0.0579 |
| 50 | 565.3 | 3.05 | L | 0.0012 | 0.0015 | 0.0347 |
| 51 | 597.3 | 3.33 | L | 0.0020 | 0.0048 | 0.0704 |
| 52 | 579.3 | 3.1 | L | 0.0031 | 0.0052 | 0.223 |
| 53 | 575.3 | 2.86 | L | 0.0019 | 0.0028 | 0.133 |
| 54 | 577.2 | 3.1 | L | 0.0016 | 0.0049 | 0.0557 |
| 55 | 566.3 | 2.2 | L | 0.0019 | 0.0040 | 0.0302 |
| 56 | 566.3 | 2.23 | L | 0.0014 | 0.0051 | 0.651 |
| 57 | 595.3 | 3.4 | L | 0.0048 | 0.0127 | 0.0868 |
| 58 | 583.3 | 3.21 | L | 0.0016 | 0.0025 | 0.098 |
| 59 | 616.4 | 1.43 | C | 0.0008 | 0.0005 | 0.0379 |
| 60 | 611.2 | 3.52 | L | 0.0007 | 0.0015 | 0.0245 |
| 61 | 591.2 | 3.51 | L | 0.0006 | 0.0010 | 0.01475 |
| 62 | 672.5 | 1.35 | C | 0.0007 | 0.0005 | 0.0984 |
| 63 | 566.3 | 2.27 | L | 0.0018 | 0.0024 | 0.0472 |
| 64 | 587.3 | 3.35 | L | 0.0019 | 0.0072 | 0.0534 |
| 65 | 615.4 | 2.44 | J | 0.0006 | 0.0008 | 0.0295 |
| 66 | 587.3 | 3.36 | L | 0.0007 | 0.0014 | 0.0323 |
| 67 | 589.3 | 3.42 | L | 0.0008 | 0.0014 | 0.0409 |
| 68 | 594.3 | 3.33 | V | 0.0029 | 0.0091 | 0.1131 |
| 69 | 594.3 | 3.15 | V | 0.0023 | 0.0093 | 0.3038 |
| 70 | 555.3 | 3.22 | V | 0.0042 | 0.0129 | 0.1167 |
| 71 | 603.3 | 3.51 | V | 0.0018 | 0.0018 | 0.0440 |
| 72 | 545.3 | 2.06 | V | 0.0024 | 0.0044 | 0.0553 |
| 73 | 561.3 | 2.24 | V | 0.0088 | 0.0354 | |
| 74 | 645.4 | 1.12 | C | 0.0010 | 0.0027 | 0.1001 |
| 75 | 743.5 | 1.40 | C | 0.0014 | 0.0039 | 0.4363 |
| 76 | 561.2 | 3.22 | V | 0.0008 | 0.0013 | 0.0326 |
| 77 | 603.3 | 3.61 | V | 0.0017 | 0.0023 | 0.0598 |
| 78 | 562.2 | 2.82 | V | 0.0008 | 0.0013 | 0.0758 |
| 79 | 716.4 | 1.50 | C | 0.0008 | 0.0016 | 0.0600 |
| 80 | 508.3 | 1.46 | P | 0.0015 | 0.0031 | 0.0835 |
| 81 | 770.5 | 1.03 | D | 0.0010 | 0.0008 | 0.5901 |
| 82 | 659.3 | 2.24 | Q | 0.0004 | 0.0003 | 0.0386 |
| 83 | 659.3 | 2.34 | Q | 0.0016 | 0.0040 | 0.1610 |
| 84 | 557.4 | 1.65 | R | 0.0004 | 0.0008 | 0.0171 |
| 85 | 556.3 | 2.52 | V | 0.0130 | 0.1182 | |
| 86 | 541.3 | 2.36 | V | 0.0192 | 0.1049 | |
| 87 | 562.3 | 3.00 | V | 0.0006 | 0.0009 | 0.0250 |
| 88 | 625.2 | 3.90 | V | 0.0003 | 0.0003 | 0.0142 |
| 89 | 589.3 | 3.58 | V | 0.0031 | 0.0134 | 0.1384 |
| 90 | 589.3 | 3.58 | V | 0.0008 | 0.0023 | 0.0373 |
| 91 | 619.3 | 3.52 | V | 0.0008 | 0.0009 | 0.0392 |
| 92 | 558.3 | 2.93 | V | 0.0009 | 0.0017 | 0.1793 |
| 93 | 625.2 | 3.89 | V | 0.0003 | 0.0008 | 0.0141 |
| 94 | 660.4 | 2.31 | S | 0.0006 | 0.0004 | 0.0549 |
| 95 | 560.3 | 1.95 | Q | 0.0023 | 0.0050 | 0.0988 |
| 96 | 565.3 | 1.38 | P | 0.0004 | 0.0005 | 0.0178 |
| 97 | 597.3 | 2.31 | H | 0.0006 | 0.0005 | 0.0325 |
| 98 | 533.3 | 3.10 | V | 0.0021 | 0.0041 | 0.0780 |
| 99 | 601.3 | 3.62 | V | 0.0016 | 0.0054 | 0.1019 |
| 100 | 601.3 | 3.61 | V | 0.0012 | 0.0042 | 0.1091 |
| 101 | 630.3 | 2.41 | V | 0.0029 | 0.0103 | 0.4143 |
| 102 | 590.3 | 2.37 | V | 0.0034 | 0.0079 | 0.4203 |
| 103 | 589.4 | 2.94 | U | 0.0015 | 0.0017 | 0.0400 |
| 104 | 589.4 | 2.93 | U | 0.0017 | 0.0008 | 0.0669 |
| 105 | 603.4 | 3.13 | U | 0.0010 | 0.0008 | 0.0412 |
| 106 | 603.4 | 3.13 | U | 0.0016 | 0.0007 | 0.0462 |
| 107 | 637.2 | 3.89 | V | 0.0004 | 0.0008 | 0.0274 |
| 108 | 605.3 | 3.66 | V | 0.0010 | 0.0027 | 0.1192 |
| 109 | 597.3 | 2.14 | V | 0.0048 | 0.0070 | >1 |
| 110 | 576.3 | 3.01 | V | 0.0009 | 0.0034 | 0.1382 |
| 111 | 625.3 | 1.57 | P | 0.0005 | 0.0005 | 0.0214 |
| 112 | 597.2 | 3.54 | V | 0.0005 | 0.0007 | 0.0250 |
| 113 | 561.3 | 2.49 | T | 0.0002 | 0.0003 | 0.0158 |
| 114 | 589.2 | 3.41 | V | 0.0017 | 0.0048 | 0.0958 |
| 115 | 601.3 | 3.46 | V | 0.0010 | 0.0021 | 0.1321 |
| 116 | 558.4 | 1.38 | P | 0.0025 | 0.0035 | 0.1574 |
| 117 | 583.4 | 3.15 | U | 0.0183 | 0.0242 | 0.4616 |
| 118 | 487.3 | 2.88 | U | 0.0005 | 0.0015 | 0.0234 |
| 119 | 681.4 | 2.38 | M | 0.0008 | 0.0008 | 0.3306 |
| 120 | 680.4 | 1.45 | P | 0.0006 | 0.0007 | 0.0758 |
| 121 | 686.4 | 2.24 | H | 0.0007 | 0.0007 | 0.1008 |
| 122 | 616.4 | 1.46 | P | 0.0004 | 0.0003 | 0.0484 |
| 123 | 615.5 | 3.09 | U | 0.0005 | 0.0005 | 0.0511 |
| 124 | 615.5 | 3.19 | U | 0.0019 | 0.0037 | 0.1746 |
| 125 | 615.4 | 3.10 | U | 0.0006 | 0.0004 | 0.0712 |
| 126 | 615.4 | 3.19 | U | 0.0025 | 0.0016 | 0.1652 |
| 127 | 575.3 | 1.14 | P | 0.0046 | 0.0115 | 0.1798 |
| 128 | 581.3 | 2.73 | H | 0.0004 | 0.0010 | 0.0206 |
| 129 | 581.4 | 2.74 | H | 0.0006 | 0.0023 | 0.0315 |
| 130 | 591.4 | 2.06 | M | 0.0119 | 0.0266 | |
| 131 | 683.5 | 2.30 | H | 0.0011 | 0.0007 | 0.0479 |
| 132 | 637.2 | 3.73 | V | 0.0004 | 0.0004 | 0.4729 |
| 133 | 659.2 | 4.08 | V | 0.0008 | 0.0015 | 0.0519 |
| 134 | 609.2 | 3.68 | V | 0.0004 | 0.0005 | 0.0336 |
| 135 | 659.2 | 4.09 | V | 0.0002 | 0.0004 | 0.0147 |
| 136 | 643.1 | 3.98 | V | 0.0020 | 0.0062 | 0.0370 |
| 137 | 559.3 | 2.47 | V | 0.0010 | 0.0007 | 0.0420 |
| 138 | 612.2 | 3.49 | V | 0.0007 | 0.0008 | 0.0270 |
| 139 | 612.2 | 3.71 | V | 0.0008 | 0.0006 | 0.0186 |
| 140 | 580.2 | 3.08 | V | 0.0004 | 0.0008 | 0.0246 |
| 141 | 618.4 | 2.08 | M | 0.0002 | 0.0003 | 0.0111 |
| 142 | 581.4 | 2.72 | H | 0.0007 | 0.0017 | 0.0354 |
| 143 | 616.3 | 2.36 | H | 0.0005 | 0.0011 | 0.0341 |
| 144 | 557.4 | 1.17 | P | 0.0008 | 0.0013 | 0.0392 |
| 145 | 561.4 | 1.13 | P | 0.0013 | 0.0029 | 0.4405 |
| 146 | 632.4 | 2.41 | M | 0.0061 | 0.0061 | |
| 147 | 616.3 | 1.48 | P | 0.0004 | 0.0003 | 0.0513 |
| 148 | 659.3 | 1.63 | P | 0.0019 | 0.0031 | 0.1050 |
| 149 | 616.3 | 2.39 | H | 0.0011 | 0.0020 | 0.0345 |
| 150 | 609.3 | 1.52 | P | 0.0007 | 0.0015 | 0.0317 |
| 151 | 571.3 | 1.21 | P | 0.0006 | 0.0012 | 0.0239 |
| 152 | 615.4 | 1.48 | P | 0.0006 | 0.0017 | 0.0226 |
| 153 | 643.4 | 2.43 | H | 0.0002 | 0.0003 | 0.0073 |
| 154 | 591.3 | 1.3 | P | 0.0005 | 0.0009 | 0.0384 |
| 155 | 572.4 | 1.45 | P | 0.0117 | 0.0210 | |
| 156 | 609.3 | 1.54 | P | 0.0013 | 0.0037 | 0.0617 |
| 157 | 561.3 | 2.13 | M | 0.0004 | 0.0014 | 0.0269 |
| 158 | 623.4 | 1.55 | P | 0.0009 | 0.0028 | 0.0732 |
| 159 | 623.4 | 1.56 | P | 0.0007 | 0.0029 | 0.0561 |
| 160 | 623.4 | 1.55 | P | 0.0006 | 0.0009 | 0.0285 |
| 161 | 639.4 | 1.61 | P | 0.0006 | 0.0007 | 0.0987 |
| 162 | 575.3 | 1.58 | P | 0.0006 | 0.0006 | 0.0855 |
| 163 | 586.4 | 1.7 | P | 0.0006 | 0.0006 | 0.0621 |
| 164 | 589.4 | 1.44 | P | 0.0007 | 0.0010 | 0.0661 |
| 165 | 639.3 | 1.62 | P | 0.0004 | 0.0008 | 0.0382 |
| 166 | 639.3 | 1.63 | P | 0.0007 | 0.0009 | 0.0835 |
| 167 | 673.4 | 2.73 | H | 0.0006 | 0.0010 | 0.1718 |
| 168 | 630.4 | 1.49 | P | 0.0027 | 0.0044 | 0.2261 |
| 169 | 637.3 | 1.62 | P | 0.0006 | 0.0006 | 0.0312 |
| 170 | 552.4 | 1.95 | M | 0.0003 | 0.0002 | 0.0141 |

TABLE 2-continued

LCMS and Potency Data

| Example | LCMS (ESI) m/z [M + H]+ | LCMS RT (Min) | LCMS Method | JAK1 Ki (μM) | JAK2 Ki (μM) | IL13-pSTAT6 BEAS2B IC50 (μM) |
| --- | --- | --- | --- | --- | --- | --- |
| 171 | 580.4 | 2.16 | M | 0.0013 | 0.0029 | 0.2385 |
| 172 | 594.4 | 2.3 | M | 0.0006 | 0.0009 | 0.0258 |
| 173 | 570.3 | 2.13 | M | 0.0005 | 0.0005 | 0.0274 |
| 174 | 625.4 | 2.45 | H | 0.0007 | 0.0011 | 0.0885 |
| 175 | 592.3 | 1.34 | P | 0.0006 | 0.0009 | 0.0399 |
| 176 | 582.4 | 1.32 | P | 0.0007 | 0.0034 | 0.0254 |
| 177 | 555.3 | 1.34 | P | 0.0021 | 0.0075 | 0.3094 |
| 178 | 597.4 | 1.59 | P | 0.0018 | 0.0015 | 0.0679 |
| 179 | 681.4 | 1.44 | P | 0.0016 | 0.0013 | 0.0672 |
| 180 | 608.4 | 2.36 | H | 0.0013 | 0.0026 | 0.0959 |
| 181 | 616.4 | 2.36 | H | 0.0008 | 0.0013 | 0.0363 |
| 182 | 587.4 | 1.34 | P | 0.0006 | 0.0009 | 0.0170 |
| 183 | 554.3 | 2.07 | M | 0.0004 | 0.0003 | 0.0815 |
| 184 | 673.4 | 1.68 | P | 0.0010 | 0.0023 | 0.0775 |
| 185 | 580.4 | 1.38 | P | 0.0005 | 0.0006 | 0.0252 |
| 186 | 662.4 | 1.48 | P | 0.0002 | 0.0002 | 0.0136 |
| 187 | 627.5 | 1.51 | P | 0.0006 | 0.0011 | 0.0363 |
| 188 | 598.4 | 1.47 | P | 0.0002 | 0.0002 | 0.0168 |
| 189 | 557.4 | 1.17 | P | 0.0005 | 0.0003 | 0.0858 |
| 190 | 680.4 | 1.51 | P | 0.0010 | 0.0018 | 0.1205 |
| 191 | 680.5 | 1.54 | P | 0.0035 | 0.0078 | 0.2361 |
| 192 | 694.4 | 1.51 | P | 0.0009 | 0.0011 | 0.1183 |
| 193 | 694.4 | 1.55 | P | 0.0006 | 0.0007 | 0.0467 |
| 194 | 644.4 | 2.22 | H | 0.0009 | 0.0004 | 0.1229 |
| 195 | 586.4 | 1.12 | N | 0.0004 | 0.0007 | 0.0366 |
| 196 | 644.3 | 1.42 | O | 0.0006 | 0.0011 | 0.0517 |
| 197 | 661.4 | 2.42 | H | 0.0003 | 0.0003 | 0.0231 |
| 198 | 661.4 | 1.55 | P | 0.0008 | 0.0021 | 0.0334 |
| 199 | 580.4 | 1.37 | P | 0.0013 | 0.0021 | 0.0914 |

What is claimed is:

1. A compound of Formula (I):

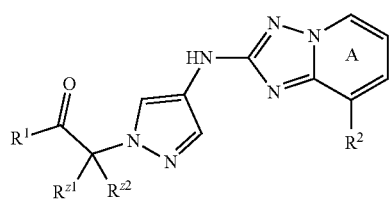

(I)

or a salt or stereoisomer thereof, wherein:

$R^1$ is a 3-11 membered heterocyclyl that is optionally substituted with one or more $R^a$;

$R^2$ is selected from the group consisting of:

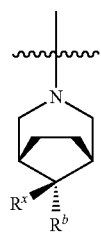

(a)

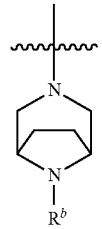

(b)

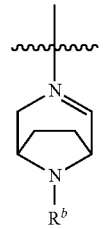

(c)

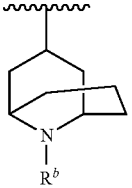

(d)

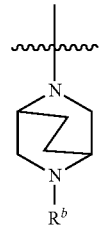

(e)

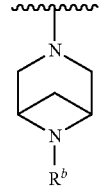

(f)

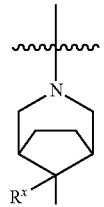

(g)

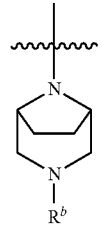

(h)

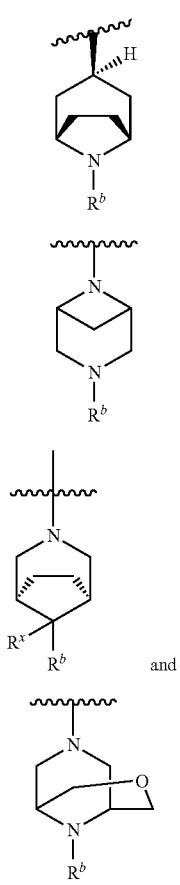

(i), (j), (o), (p)

each $R^a$ is independently selected from the group consisting of OH, halo, $C_1$-$C_6$alkyl, $C_3$-$C_8$cycloalkyl, 6-10 membered aryl, 3-11 membered heterocyclyl, C(O)NR$^c$R$^d$, NR$^c$R$^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, ($C_1$-$C_6$alkyl)S—, $C_3$-$C_8$cycloalkyl, 3-11 membered heterocyclyl that is optionally substituted with one or more groups independently selected from the group consisting of —C(O)—NR$^c$R$^d$, —C(O)—OR$^k$, —($C_1$-$C_6$alkyl)-C(O)—NR$^c$R$^d$, and —($C_1$-$C_6$alkyl)-C(O)—OR$^k$, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —OR$^k$, —CN, $C_1$-$C_6$alkyl, $C_3$-$C_8$cycloalkyl, 6-10 membered aryl, 3-11 membered heterocyclyl, —NR$^s$R$^t$, —C(O)NR$^f$R$^g$, —S(O)$_n$R$^e$, —S(O)$_2$NR$^f$R$^g$, —NR$^c$C(O)R$^m$, and —C(O)R$^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from R$^h$; and R$^x$ is selected from the group consisting of hydrogen and $C_1$-$C_6$alkyl that is optionally substituted with one or more groups independently selected from halo, cyano, and $C_1$-$C_6$alkoxy; or R$^b$ and R$^x$ taken together form a $C_1$-$C_6$alkenylene that is optionally substituted with one or more groups independently selected from halo, cyano, and $C_1$-$C_6$alkoxy;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl; or alternatively R$^c$ and R$^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, cyano, hydroxy, $C_1$-$C_6$alkoxy, —SH, ($C_1$-$C_6$alkyl)S—, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, R$^p$, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively R$^f$ and R$^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, ($C_1$-$C_6$alkyl)S—, cyano, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, cyano, S(O)$_2$NR$^f$R$^g$, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, —S(O)$_2$($C_1$-$C_6$alkyl), $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, 6-10 membered aryl and 3-11 membered heterocyclyl, wherein any said 6-10 aryl and 3-11 membered heterocyclyl is optionally substituted with halo, cyano, (C$_1$-C$_6$alkyl)$_2$NC(O)—, or C$_1$-C$_6$alkyl that is optionally substituted with one or more groups independently selected from the group consisting of halo, C$_1$-C$_6$alkoxy, cyano, hydroxy, and C$_3$-C$_8$cycloalkyl;

R$^m$ is selected from the group consisting of C$_1$-C$_6$alkyl, C$_1$-C$_6$alkoxy, C$_3$-C$_8$cycloalkyl, (C$_3$-C$_8$cycloalkyl)oxy, 6-10 membered aryl, and 3-11 membered heterocyclyl, wherein any C$_1$-C$_6$alkyl, C$_1$-C$_6$alkoxy, C$_3$-C$_8$cycloalkyl, (C$_3$-C$_8$cycloalkyl)oxy, 6-10 membered aryl, and 3-11 membered heterocyclyl is optionally substituted with one or more groups R$^n$;

each R$^n$ is independently selected from the group consisting of halo, cyano, hydroxy, C$_1$-C$_6$alkyl, C$_1$-C$_6$alkoxy, C$_3$-C$_8$cycloalkyl, —SH, —NR$^u$R$^v$, C$_1$-C$_6$alkylthio, 6-10 membered aryl, and 3-11 membered heterocyclyl, wherein any C$_1$-C$_6$alkyl, C$_1$-C$_6$alkoxy, C$_3$-C$_8$cycloalkyl, C$_1$-C$_6$alkylthio, 6-10 membered aryl, and 3-11 membered heterocyclyl is optionally substituted with one or more groups independently selected from the group consisting of halo, cyano, and C$_1$-C$_6$alkyl that is optionally substituted with one or more groups independently selected from the group consisting of halo and cyano;

each R$^p$ is independently selected from the group consisting of C$_3$-C$_8$cycloalkyl, 6-10 membered aryl, and 3-11 membered heterocyclyl, wherein any C$_3$-C$_8$cycloalkyl, 6-10 membered aryl, and 3-11 membered heterocyclyl is optionally substituted with one or more groups independently selected from the group consisting of halo, cyano, hydroxy, C$_1$-C$_6$alkoxy, C$_3$-C$_8$cycloalkyl, —SH, (C$_1$-C$_6$alkyl)S—, and C$_1$-C$_6$alkyl that is optionally substituted with one or more groups independently selected from the group consisting of halo, hydroxy, C$_1$-C$_6$alkoxy, cyano, and C$_3$-C$_8$cycloalkyl;

R$^s$ and R$^t$, independently at each occurrence, are selected from the group consisting of hydrogen, C$_1$-C$_6$alkyl, C$_3$-C$_8$cycloalkyl, 6-10 membered aryl, and 3-11 membered heterocyclyl, wherein each C$_1$-C$_6$alkyl is independently optionally substituted with one or more groups independently selected from the group consisting of halo, cyano, C$_3$-C$_8$cycloalkyl, 6-10 membered aryl, and 3-11 membered heterocyclyl;

R$^u$ and R$^v$, independently at each occurrence, are selected from the group consisting of hydrogen, C$_1$-C$_6$alkyl, C$_3$-C$_8$cycloalkyl, 6-10 membered aryl, and 3-11 membered heterocyclyl, wherein each C$_1$-C$_6$alkyl is independently optionally substituted with one or more groups independently selected from the group consisting of halo, cyano, C$_3$-C$_8$cycloalkyl, 6-10 membered aryl, and 3-11 membered heterocyclyl;

n is 0, 1, or 2;

R$^{z1}$ and R$^{z2}$ are each independently selected from hydrogen and C$_1$-C$_6$alkyl; and ring A is optionally further substituted with one or more substituents selected from the group consisting of CH$_3$, CH$_2$CH$_3$, OCH$_3$, OCHF$_2$, OCH$_2$F, OCF$_3$, CF$_3$, CHF$_2$, CH$_2$F, F and Cl.

2. The compound of claim 1 or a salt or stereoisomer thereof, wherein:

R$^1$ is a 3-11 membered heterocyclyl that is optionally substituted with one or more R$^a$;

R$^2$ is selected from the group consisting of:

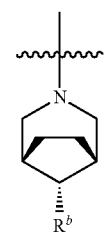

(a)

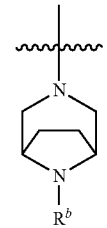

(b)

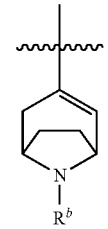

(c)

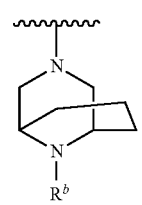

(d)

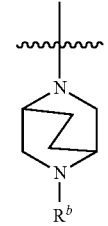

(e)

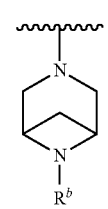

(f)

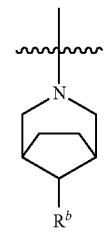

(g)

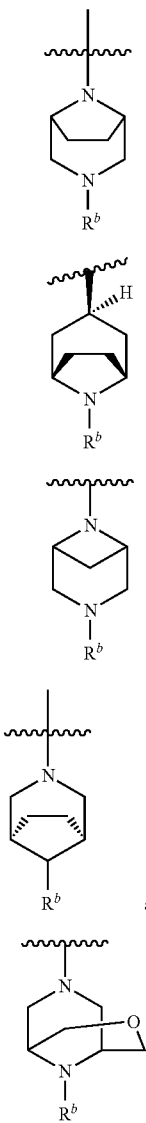

(h), (i), (j), (o), and (p)

each $R^a$ is independently selected from the group consisting of OH, halo, $C_1$-$C_6$alkyl, $C_3$-$C_8$cycloalkyl, 6-10 membered aryl, 3-11 membered heterocyclyl, C(O)NR$^c$R$^d$, NR$^c$R$^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, $C_3$-$C_8$cycloalkyl, 3-11 membered heterocyclyl that is optionally substituted with —($C_1$-$C_6$alkyl)-C(O)—NR$^c$R$^d$ or —($C_1$-$C_6$alkyl)-C(O)—OR$^k$, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —OR$^k$, —CN, $C_1$-$C_6$alkyl, $C_3$-$C_8$cycloalkyl, 6-10 membered aryl, 3-11 membered heterocyclyl, NR$^c$R$^d$, —C(O)NR$^f$R$^g$, —S(O)$_n$R$^e$, —S(O)$_2$NR$^f$R$^g$, and —C(O)R$^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from R$^h$;

R$^c$ and R$^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, cyano, $C_3$-$C_8$cycloalkyl, 6-10 membered aryl, and 3-11 membered heterocyclyl; or alternatively R$^c$ and R$^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each R$^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, $C_1$-$C_6$alkoxy, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

R$^f$ and R$^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively R$^f$ and R$^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each R$^h$ is independently selected from the group consisting of halo, cyano, S(O)$_2$NR$^f$R$^g$, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, $C_1$-$C_6$alkoxy, cyano, and $C_3$-$C_8$cycloalkyl;

each R$^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, 6-10 membered aryl and 3-11 membered heterocyclyl, wherein any said 6-10 aryl and 3-11 membered heterocyclyl is optionally substituted with halo, cyano, or $C_1$-$C_6$alkyl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl is optionally substituted with one or more groups $R^n$;

each $R^n$ is independently selected from the group consisting of halo, cyano, $C_1$-$C_6$alkyl, $C_1$-$C_6$alkoxy, $C_3$-$C_8$cycloalkyl, —SH, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano;

n is 0, 1, or 2;

$R^{z1}$ and $R^{z2}$ are each independently selected from hydrogen and $C_1$-$C_6$alkyl; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl.

3. A compound of claim 1 wherein the compound of Formula (I) is a compound of Formula (I-I):

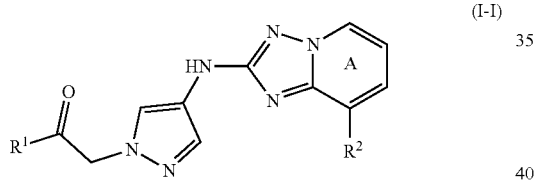

(I-I)

or a salt or stereoisomer thereof, wherein:

$R^1$ is a 3-11 membered heterocyclyl that is optionally substituted with one or more $R^a$;

$R^2$ is selected from the group consisting of:

(a)

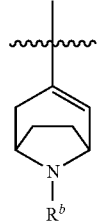

(b)

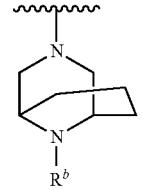

(c)

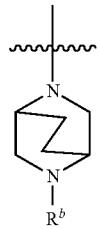

(d)

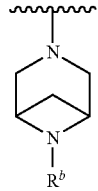

(e)

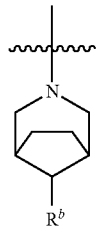

(f)

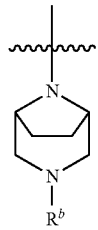

(g)

(h)

(i)

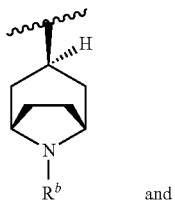

and

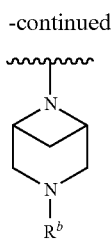
(j)

each $R^a$ is independently selected from the group consisting of OH, halo, $C_1$-$C_6$alkyl, $C_3$-$C_8$cycloalkyl, 6-10 membered aryl, 3-11 membered heterocyclyl, C(O)NR$^c$R$^d$, NR$^c$R$^d$, and $C_1$-$C_6$alkanoyl, wherein said alkyl, cycloalkyl, alkanoyl, 6-10 membered aryl, and 3-11 membered heterocyclyl are optionally substituted with one or more groups independently selected from the group consisting of halo, $C_1$-$C_6$alkoxy, $C_3$-$C_8$cycloalkyl, 3-11 membered heterocyclyl, and $C_1$-$C_6$alkyl that is optionally substituted with one or more groups independently selected from the group consisting of halo, $C_1$-$C_6$alkoxy, and $C_3$-$C_8$cycloalkyl;

$R^b$ is selected from the group consisting of hydrogen, —OR$^k$, —CN, $C_1$-$C_6$alkyl, $C_3$-$C_8$cycloalkyl, 6-10 membered aryl, 3-11 membered heterocyclyl, —C(O)NR$^f$R$^g$, —S(O)$_n$R$^e$, —S(O)$_2$NR$^f$R$^g$, and —C(O)R$^m$, wherein said $C_1$-$C_6$alkyl, $C_3$-$C_8$cycloalkyl, $C_1$-$C_6$alkanoyl, 6-10 membered aryl, and 3-11 membered heterocyclyl are each independently optionally substituted with one or more groups independently selected from R$^h$;

$R^c$ and $R^d$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively $R^c$ and $R^d$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^e$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from halo, $C_1$-$C_6$alkoxy, $C_3$-$C_8$cycloalkyl, and $C_1$-$C_6$alkyl that is optionally substituted with one or more groups independently selected from the group consisting of halo, $C_1$-$C_6$alkoxy, and $C_3$-$C_8$cycloalkyl;

$R^f$ and $R^g$, independently at each occurrence, are selected from the group consisting of hydrogen, $C_1$-$C_6$alkyl, $C_3$-$C_8$cycloalkyl, 6-10 membered aryl, and 3-11 membered heterocyclyl, wherein each $C_1$-$C_6$alkyl is independently optionally substituted with one or more groups independently selected from the group consisting of halo, $C_3$-$C_8$cycloalkyl, 6-10 membered aryl, and 3-11 membered heterocyclyl; or alternatively $R^f$ and $R^g$ may be joined together with the nitrogen atom to which they are attached to form an optionally substituted 3-11 membered heterocyclyl that is optionally substituted with one or more groups independently selected from the group consisting of halo, $C_3$-$C_8$cycloalkyl, 6-10 membered aryl, and $C_1$-$C_6$alkyl that is optionally substituted with one or more groups independently selected from the group consisting of halo, $C_1$-$C_6$alkoxy, and $C_3$-$C_8$cycloalkyl;

each $R^h$ is independently selected from the group consisting of halo, $C_1$-$C_6$alkoxy, $C_1$-$C_6$alkanoyl, $C_3$-$C_8$cycloalkyl, 6-10 membered aryl, and 3-11 membered heterocyclyl, wherein any $C_1$-$C_6$alkoxy, $C_1$-$C_6$alkanoyl, $C_3$-$C_8$cycloalkyl, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo, $C_1$-$C_6$alkoxy, cyano, and $C_3$-$C_8$cycloalkyl;

each $R^k$ is independently selected from the group consisting of hydrogen, $C_1$-$C_6$alkyl, $C_3$-$C_8$cycloalkyl, 6-10 membered aryl, and 3-11 membered heterocyclyl, wherein any $C_1$-$C_6$alkyl, $C_3$-$C_8$cycloalkyl, 6-10 membered aryl, and 3-11 membered heterocyclyl is optionally substituted with one or more groups independently selected from the group consisting of halo, cyano, and 3-11 membered heterocyclyl;

$R^m$ is selected from the group consisting of $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl, wherein any $C_1$-$C_6$alkyl, $C_1$-$C_6$alkoxy, $C_3$-$C_8$cycloalkyl, ($C_3$-$C_8$cycloalkyl)oxy, 6-10 membered aryl, and 3-11 membered heterocyclyl is optionally substituted with one or more groups $R^n$;

each $R^n$ is independently selected from the group consisting of halo, cyano, $C_1$-$C_6$alkyl, $C_1$-$C_6$alkoxy, $C_3$-$C_8$cycloalkyl, —SH, $C_1$-$C_6$alkylthio, 6-10 membered aryl, and 3-11 membered heterocyclyl, wherein any $C_1$-$C_6$alkyl, $C_1$-$C_6$alkoxy, $C_3$-$C_8$cycloalkyl, $C_1$-$C_6$alkylthio, 6-10 membered aryl, and 3-11 membered heterocyclyl is optionally substituted with one or more groups independently selected from the group consisting of halo, cyano, and $C_1$-$C_6$alkyl that is optionally substituted with one or more groups independently selected from the group consisting of halo and cyano;

n is 0, 1, or 2; and ring A is optionally further substituted with one or more substituents selected from the group consisting of $CH_3$, $CH_2CH_3$, $OCH_3$, $OCHF_2$, $OCH_2F$, $OCF_3$, $CF_3$, $CHF_2$, $CH_2F$, F and Cl.

4. The compound of claim 1, or a salt or stereoisomer thereof, wherein ring A is not optionally substituted.

5. The compound of claim 1, or a salt or stereoisomer thereof, wherein $R^{z1}$ and $R^{z2}$ are each hydrogen.

6. The compound of claim 1, or a salt or stereoisomer thereof, wherein $R^{z1}$ is hydrogen and $R^{z2}$ is $C_1$-$C_6$alkyl.

7. The compound, salt or stereoisomer of claim 1, wherein $R^1$ is selected from the group consisting of:

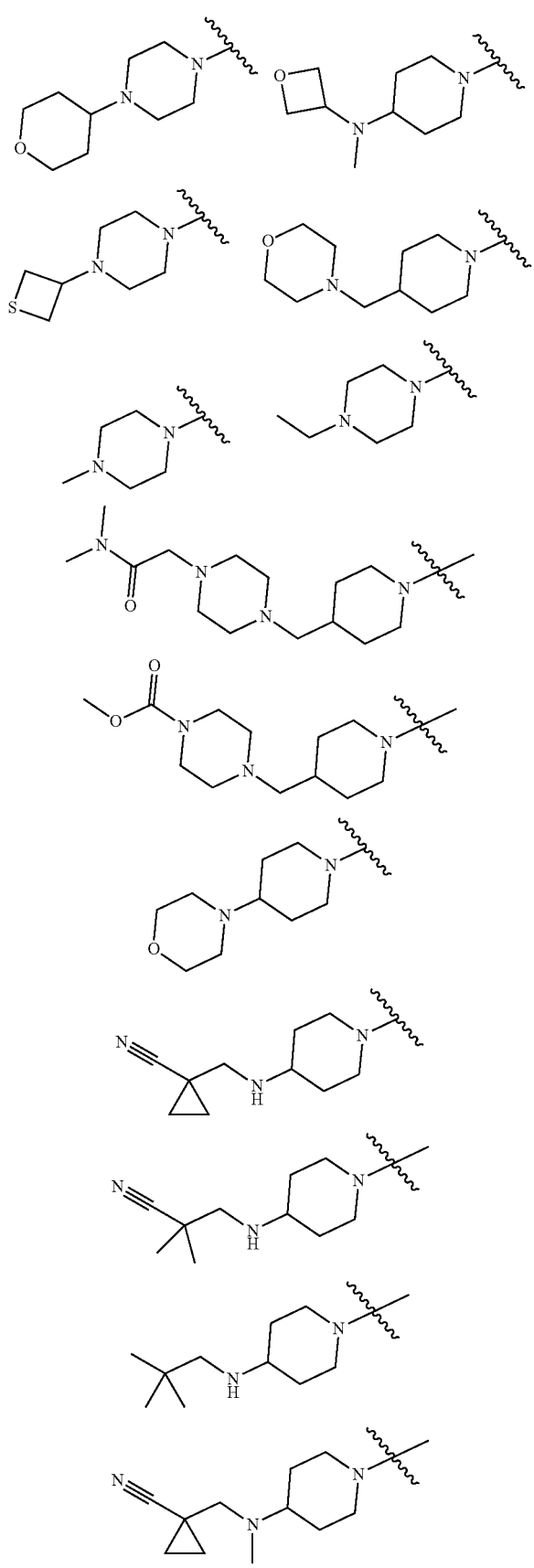
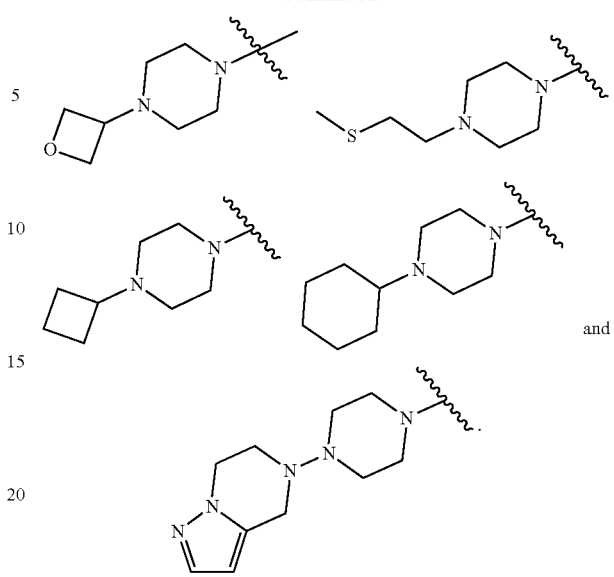
8. The compound, salt or stereoisomer of claim 1, wherein $R^2$ is selected from the group consisting of:
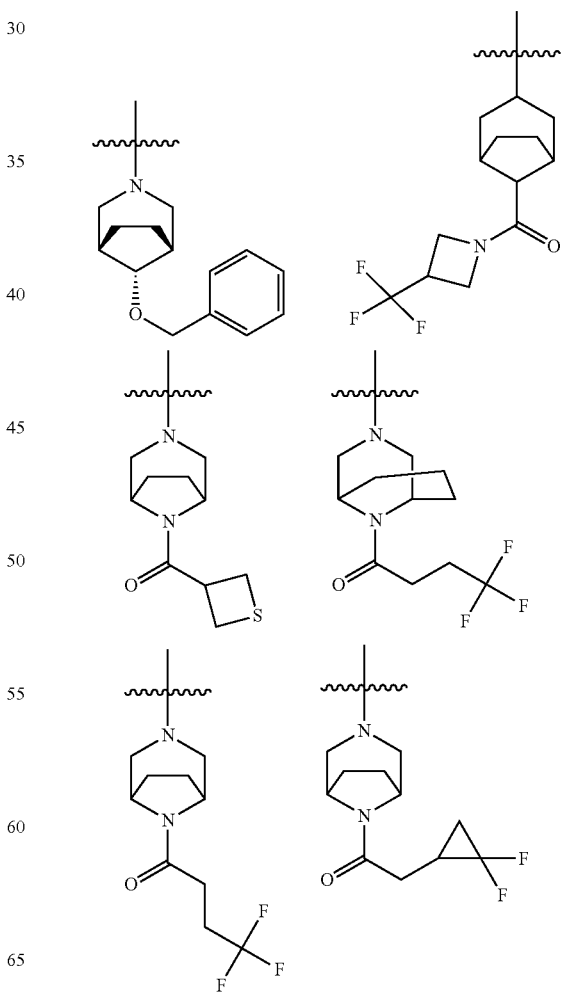

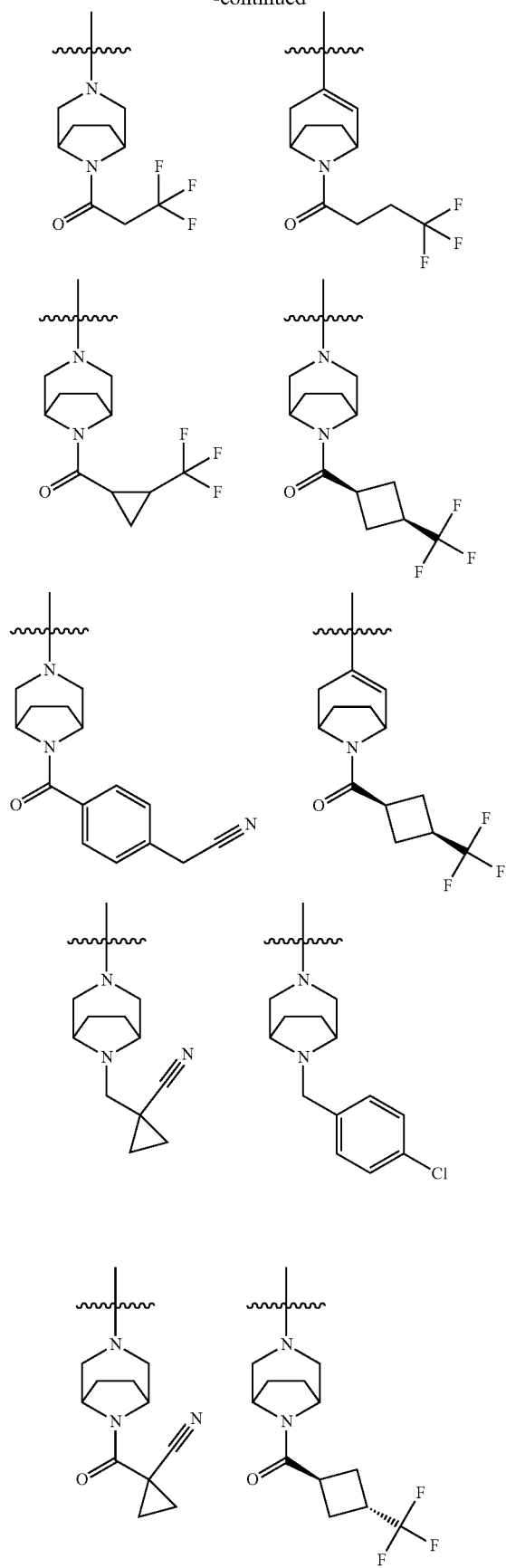
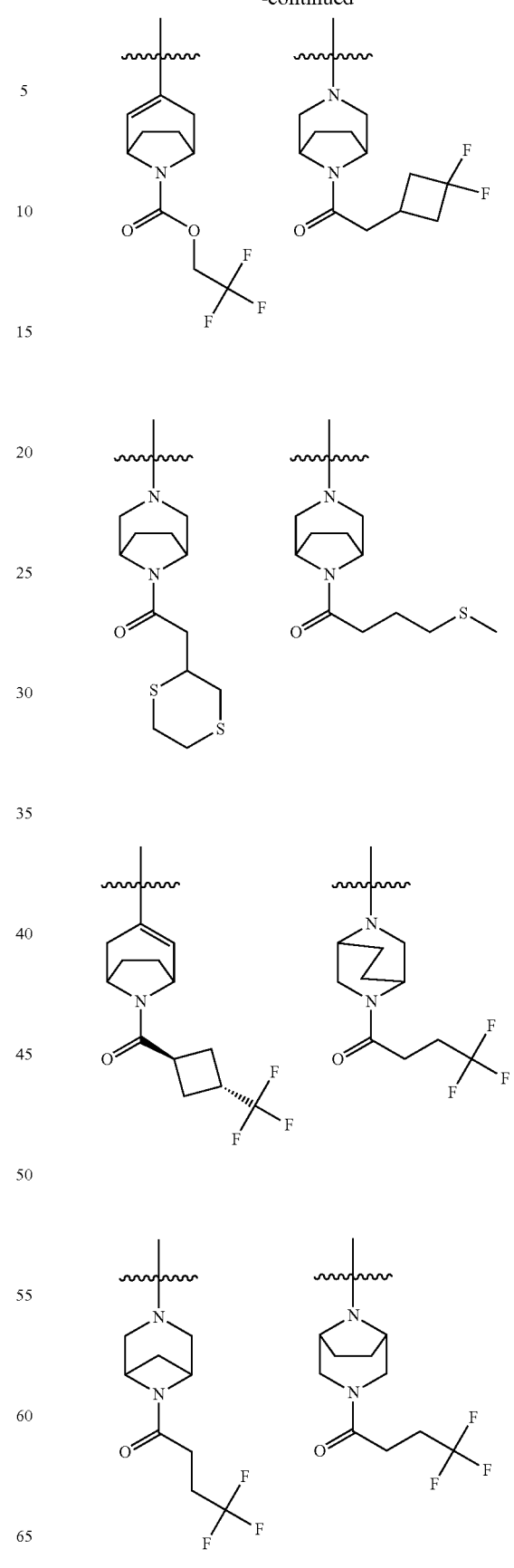

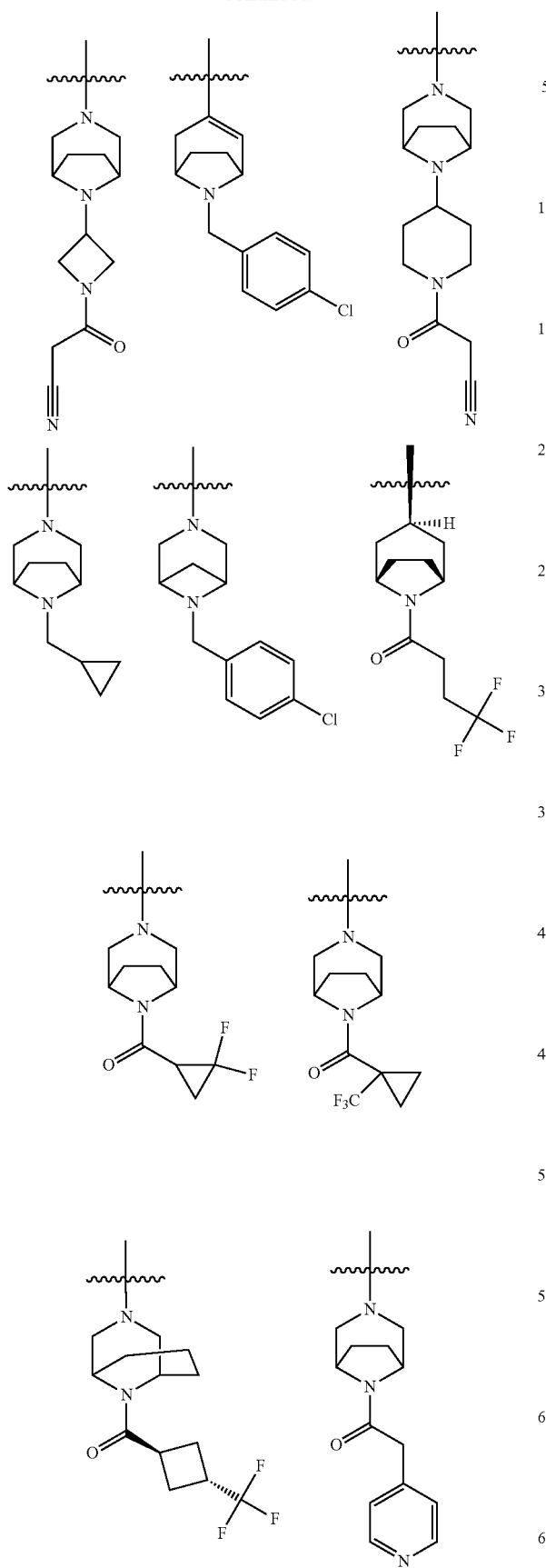
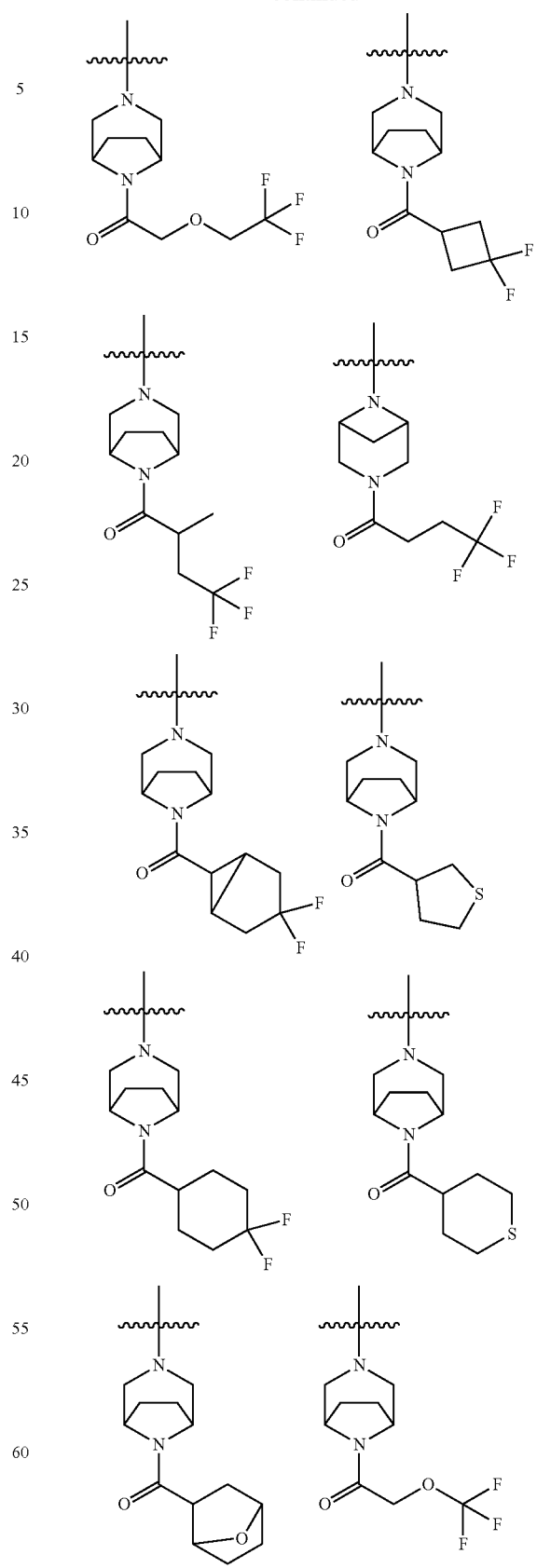

249
-continued
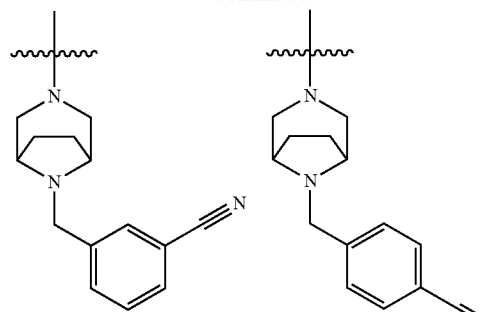
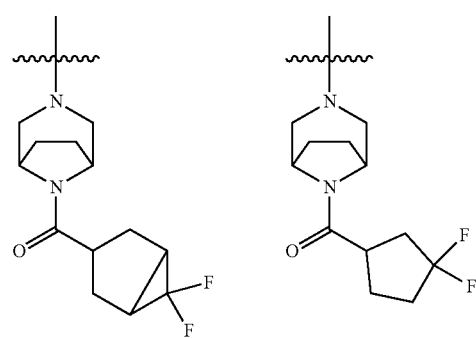
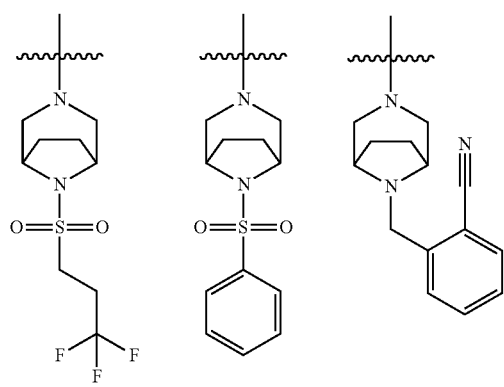
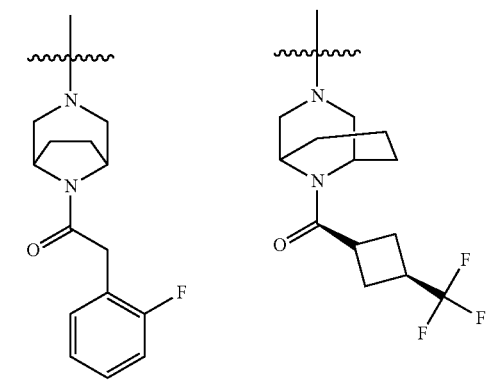
250
-continued
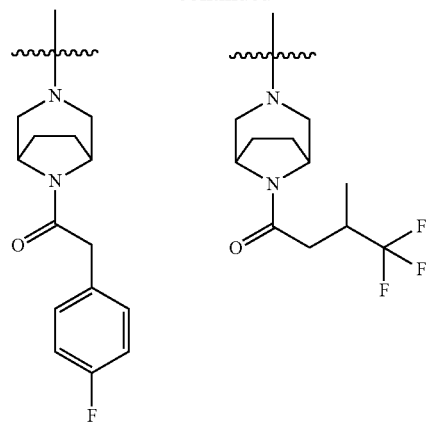
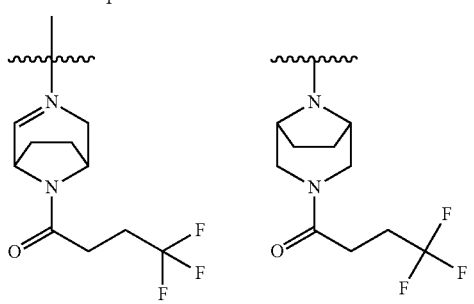
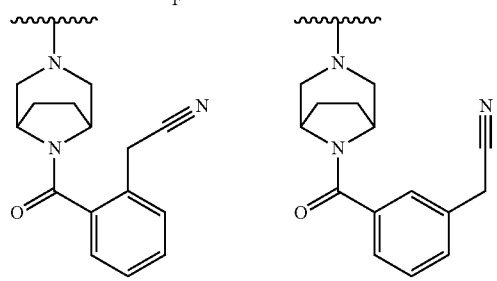
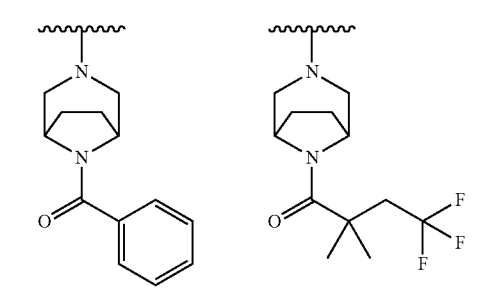
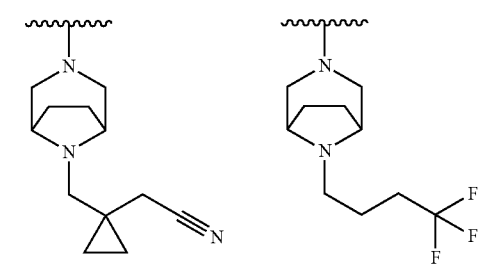

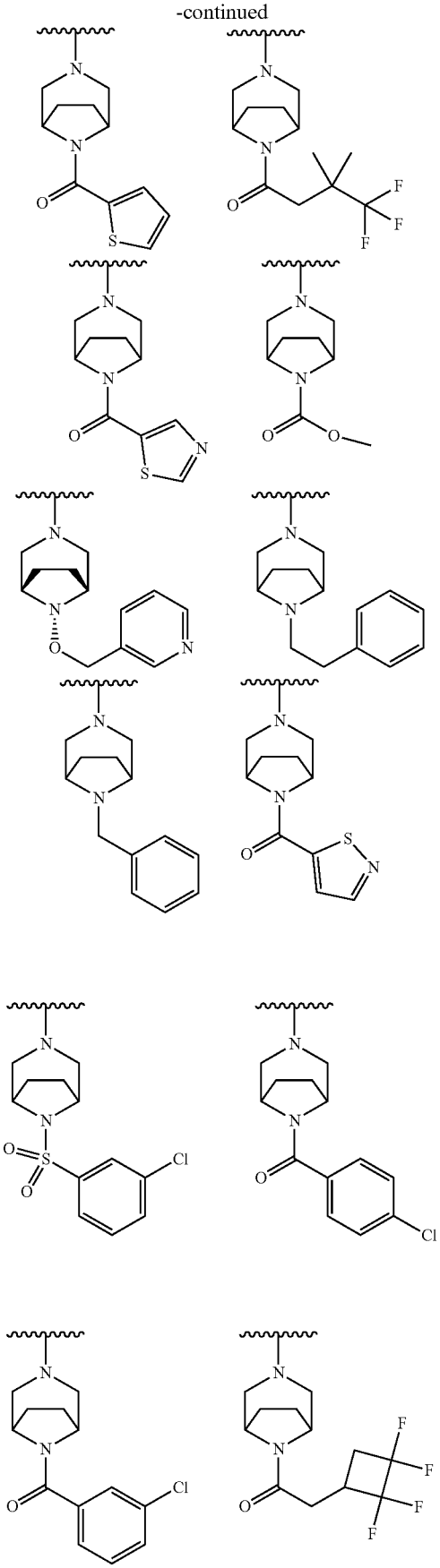
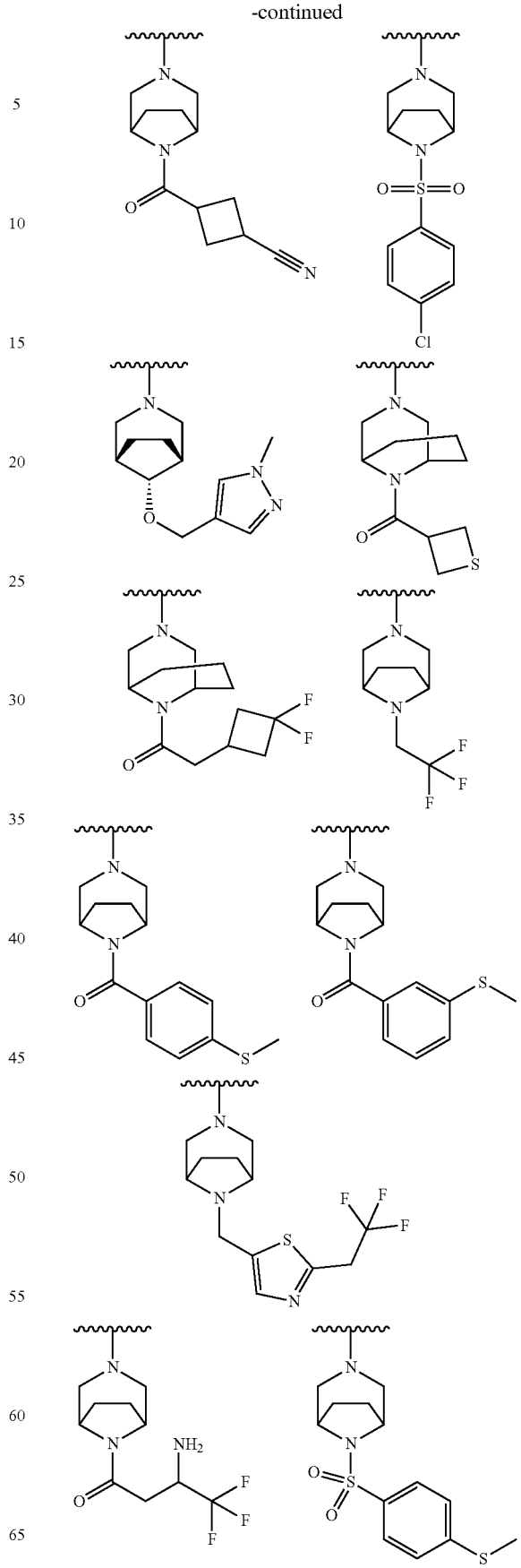

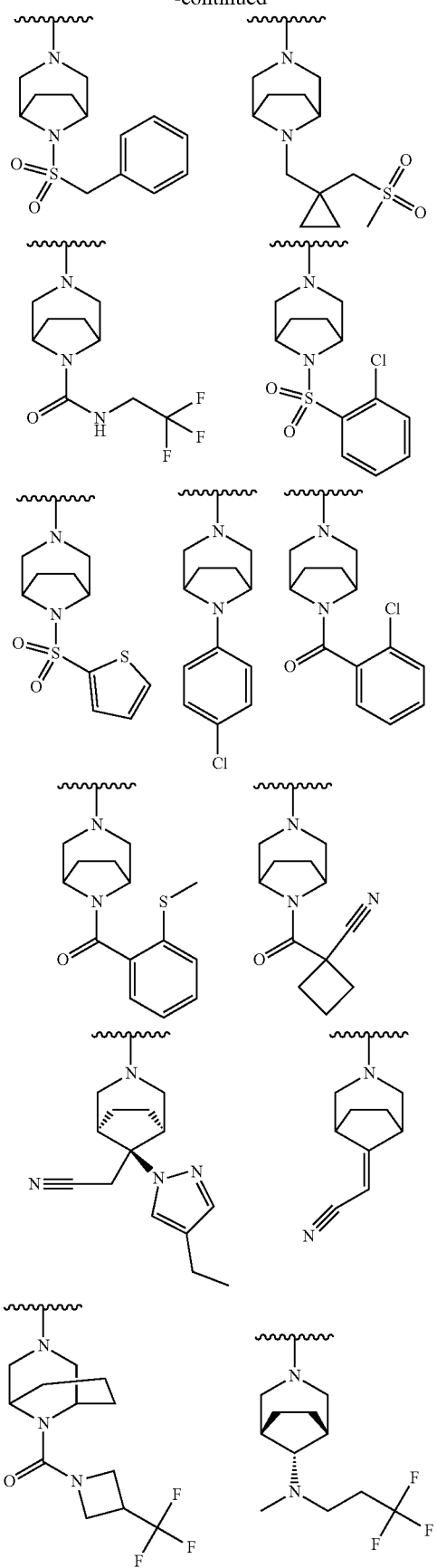
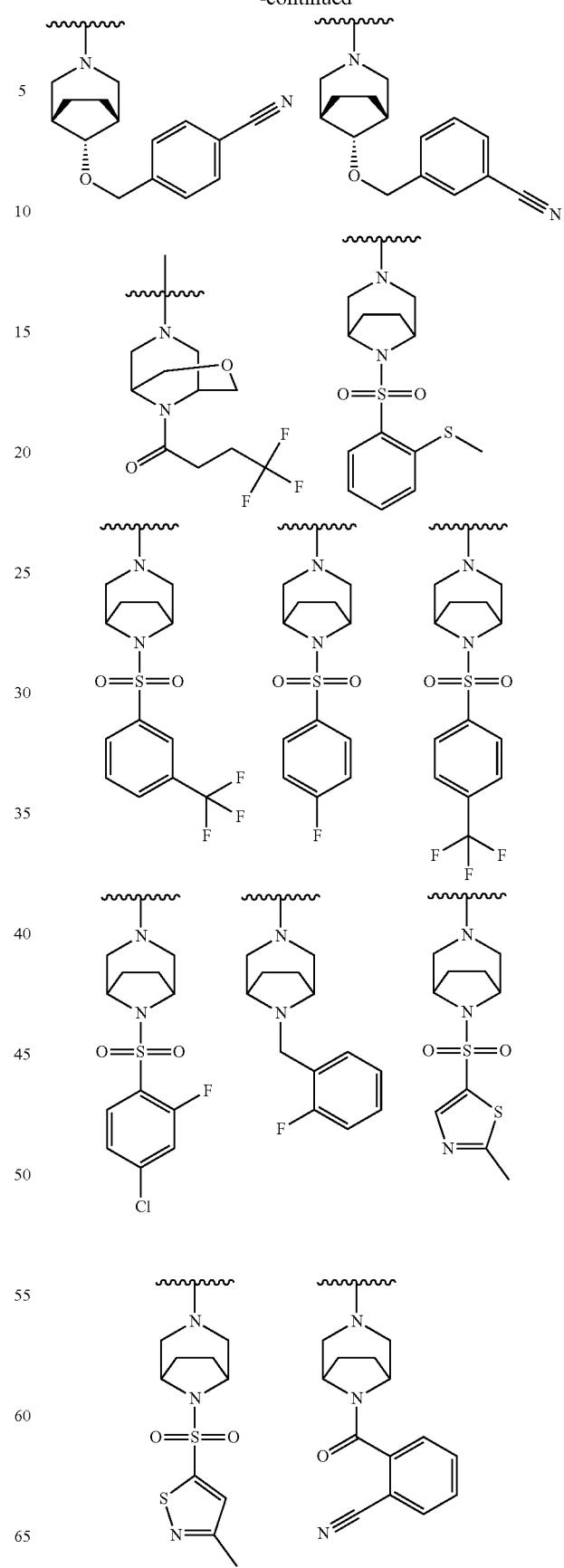

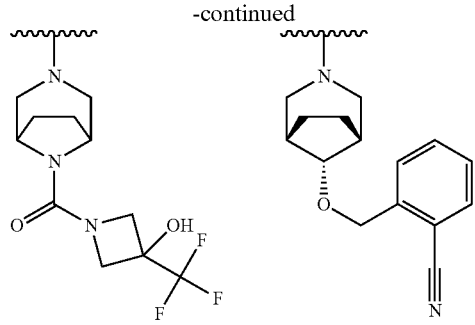
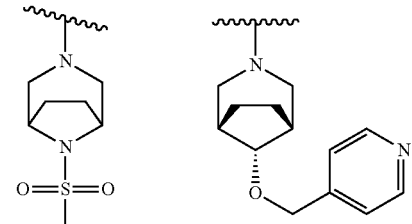
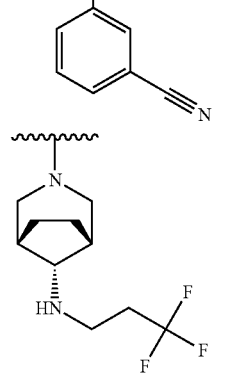
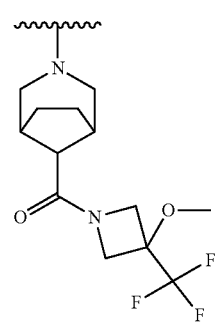
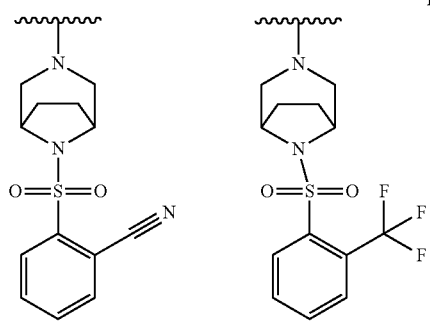
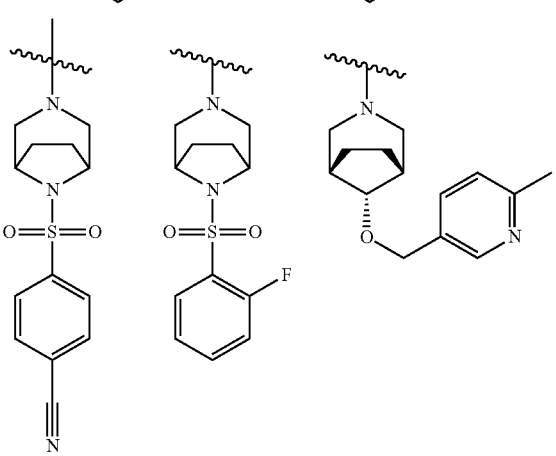
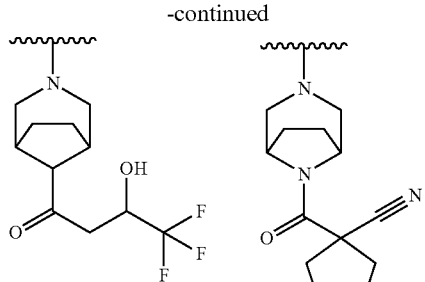
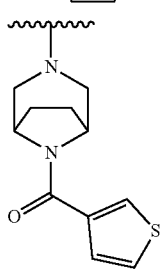
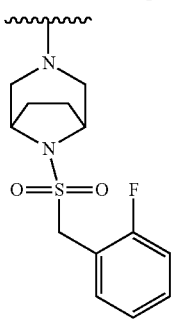
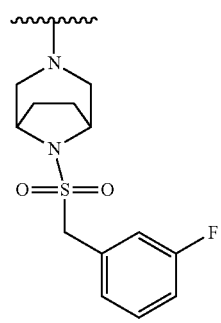
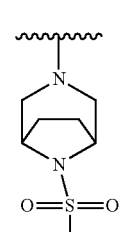
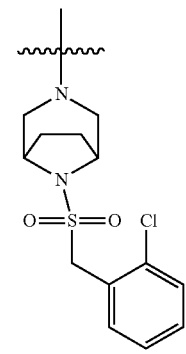
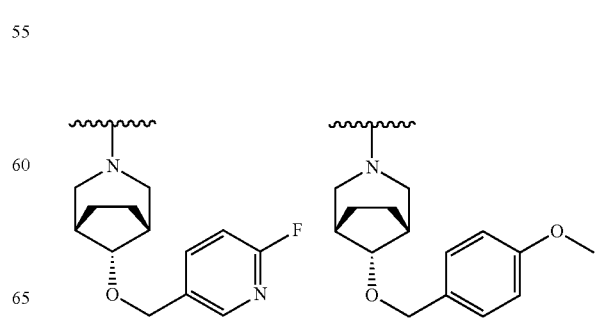

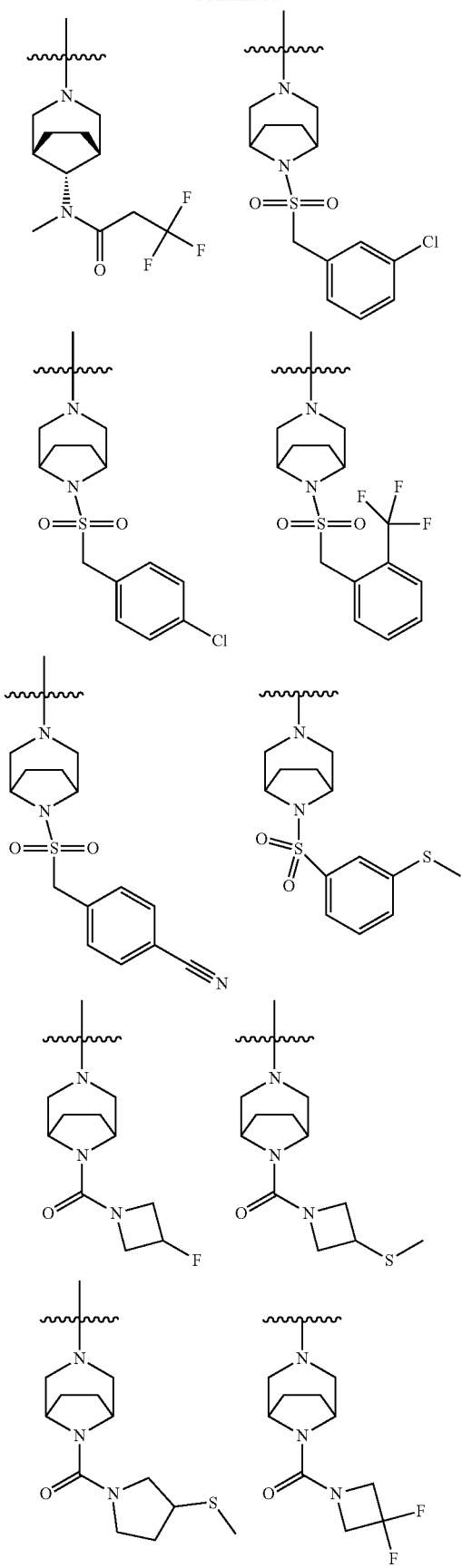
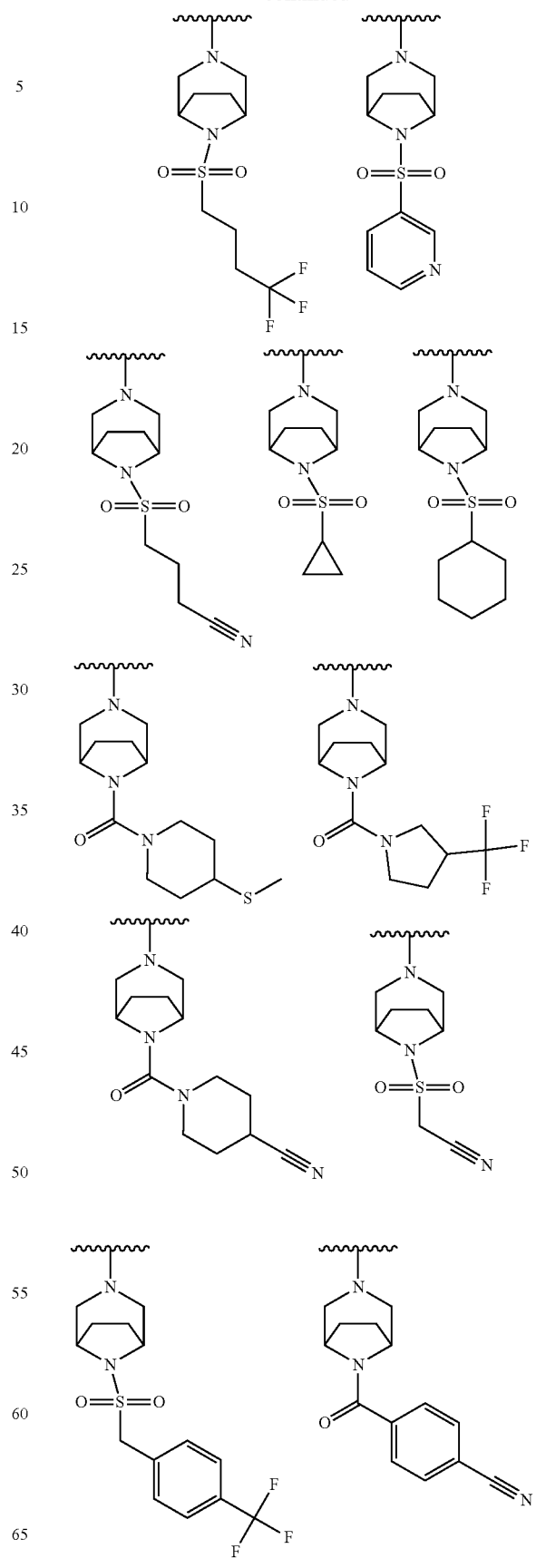

-continued
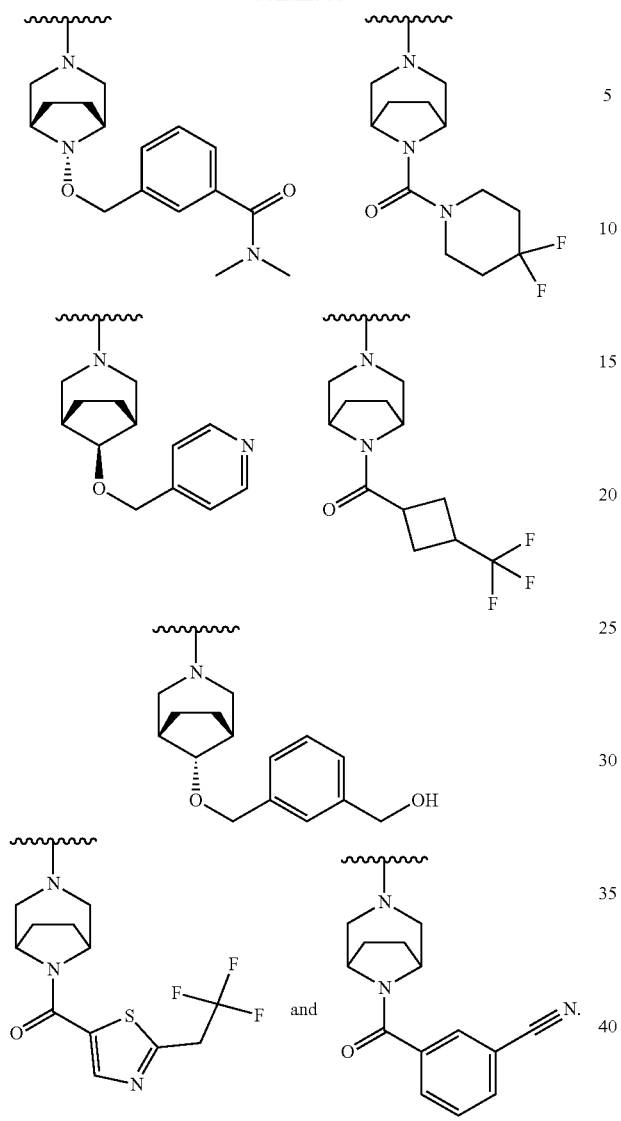
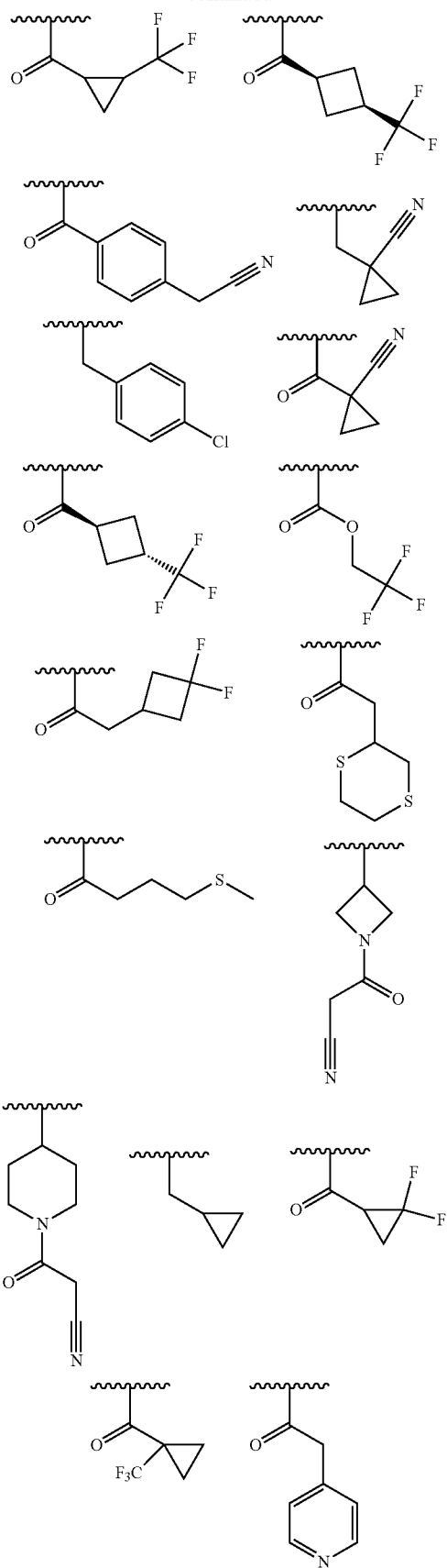
9. The compound, salt or stereoisomer of claim 1, wherein $R^b$ is —C(O)NR$^f$R$^g$ or —C(O)R$^m$.
10. The compound, salt or stereoisomer of claim 1, wherein $R^b$ is selected from the group consisting of:
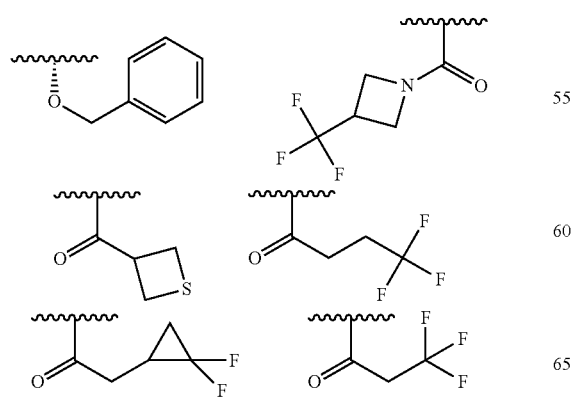

-continued
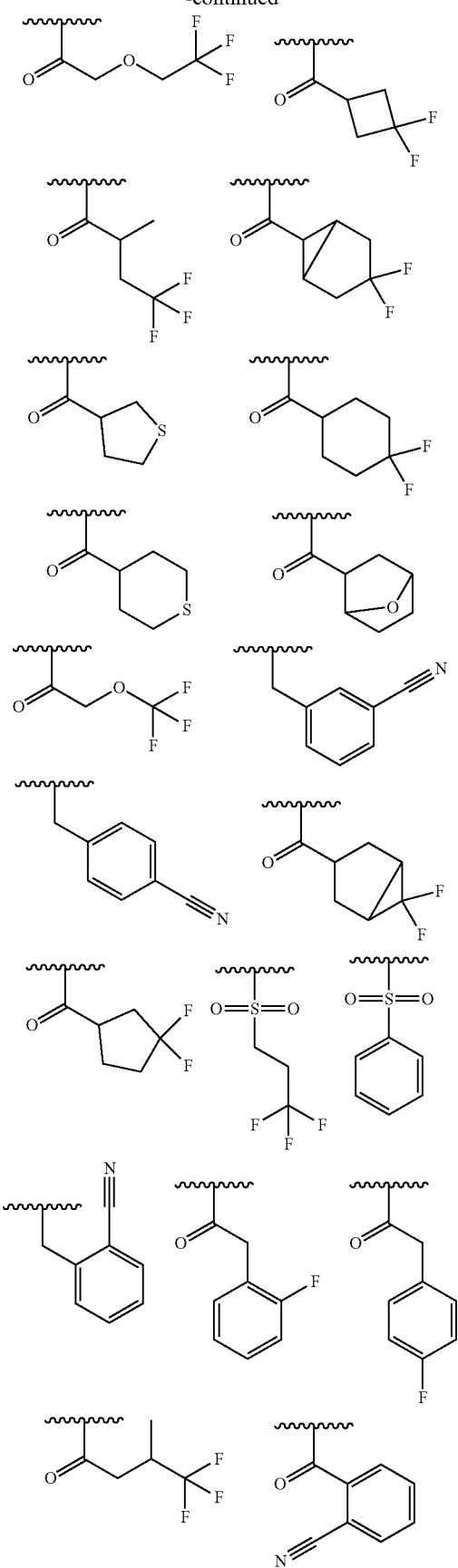
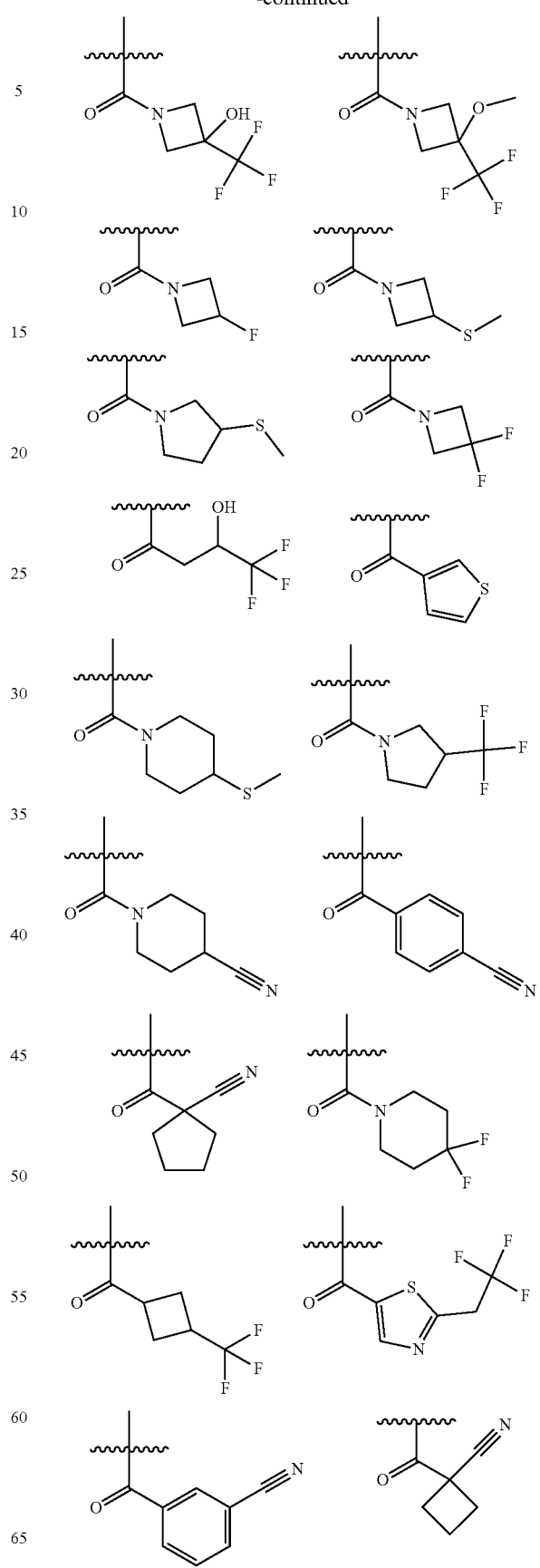

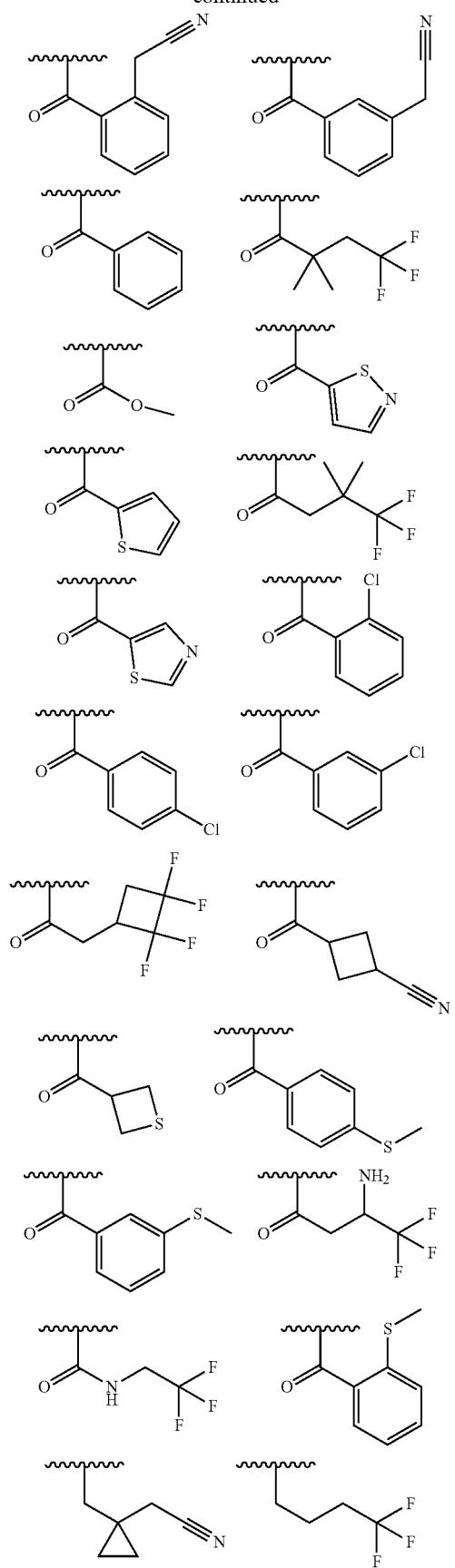
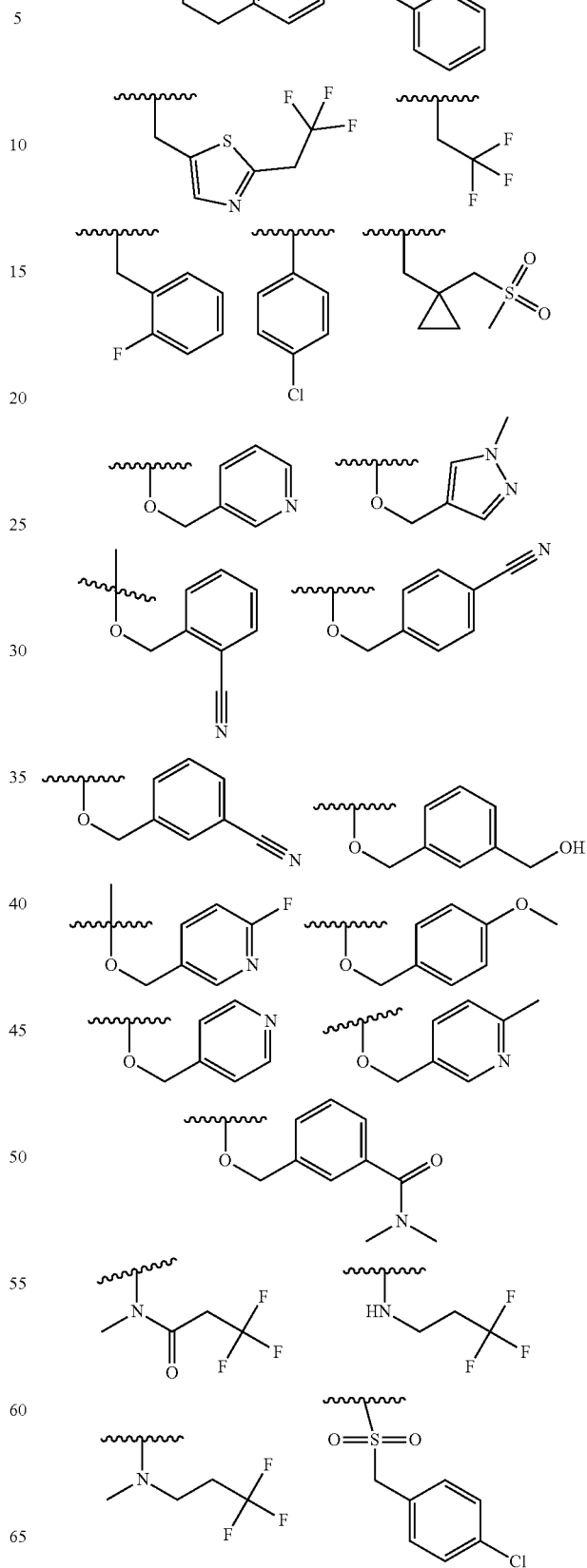

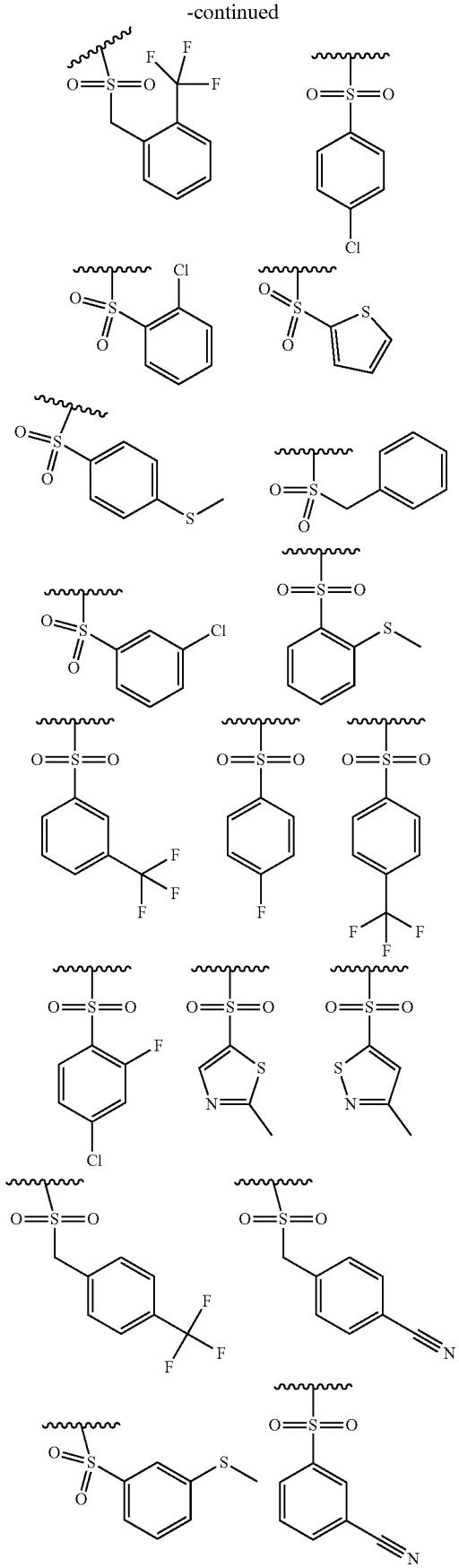
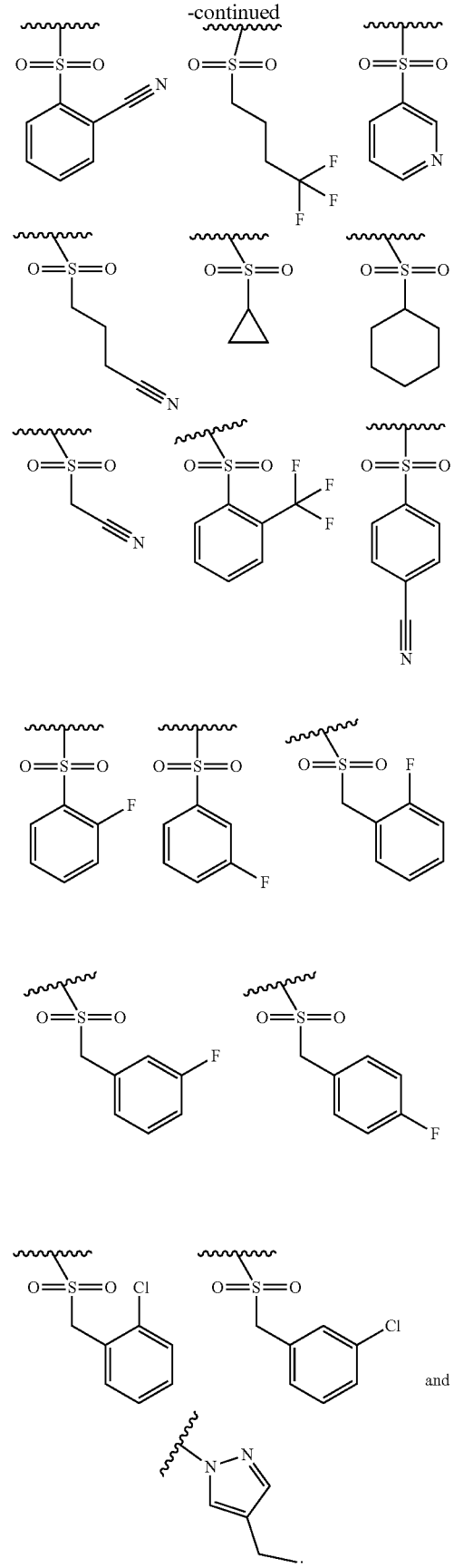

11. A compound selected from the group consisting of:
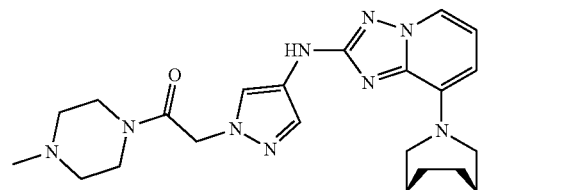
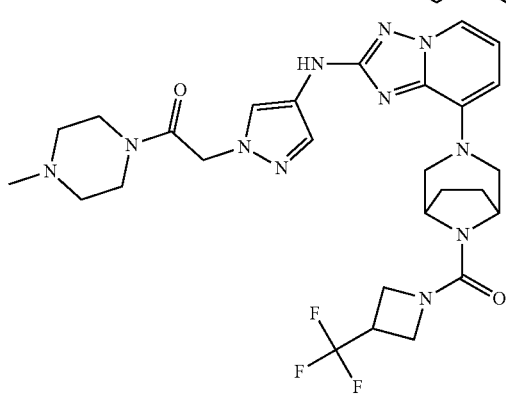
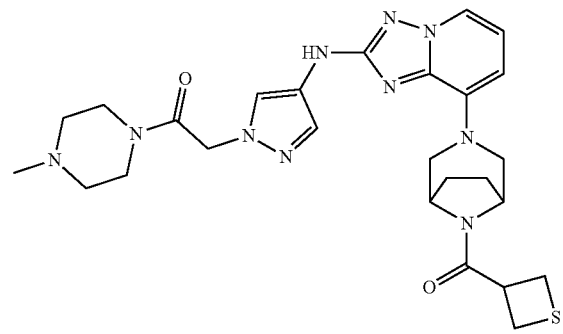
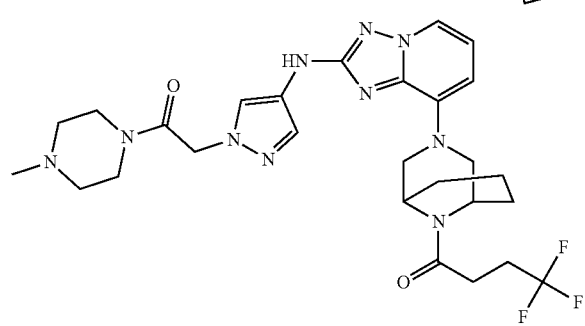
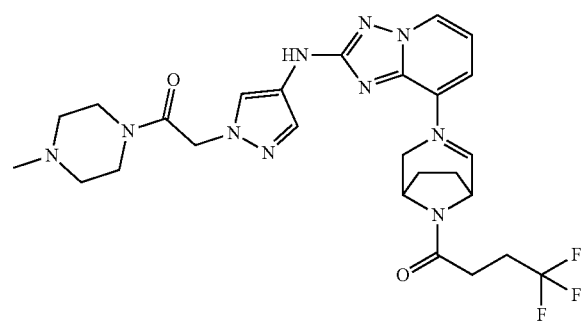
-continued
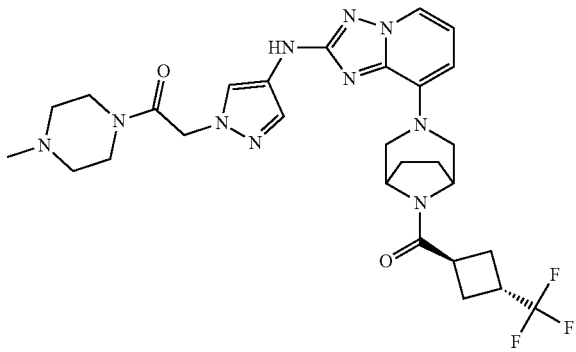
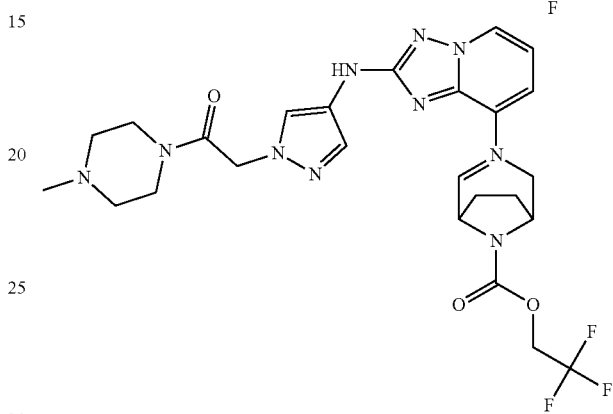
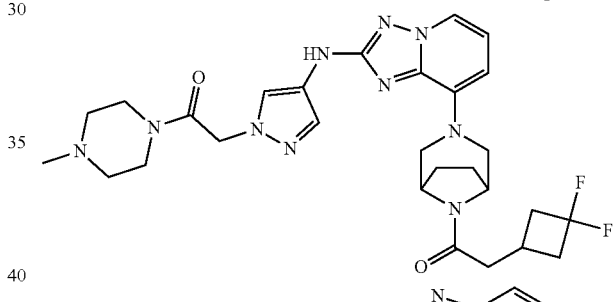
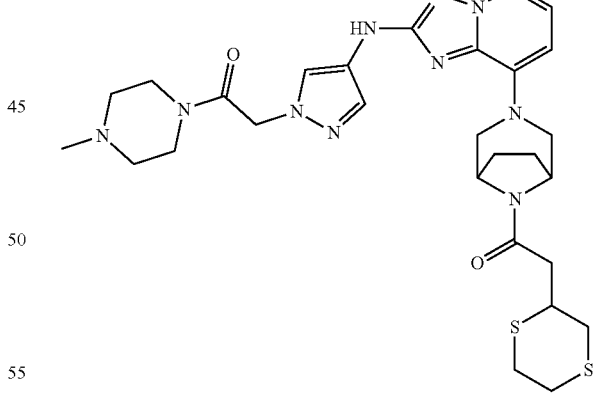
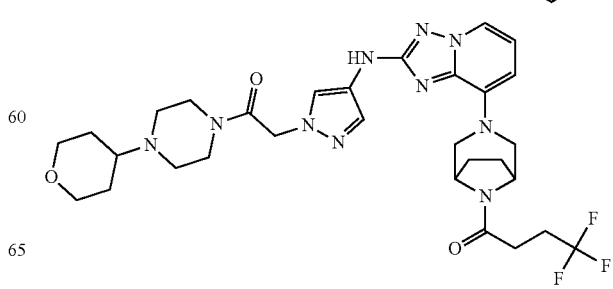

269
-continued
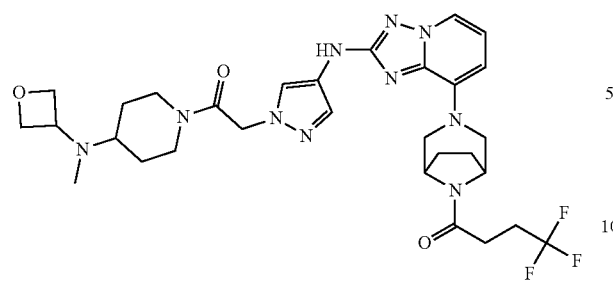
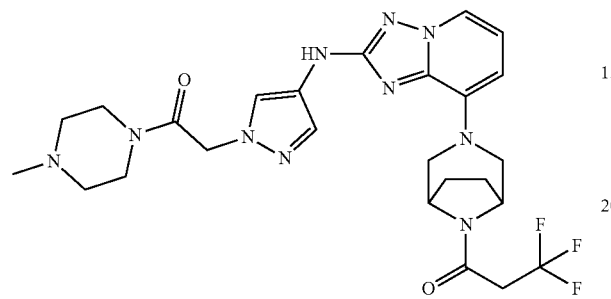
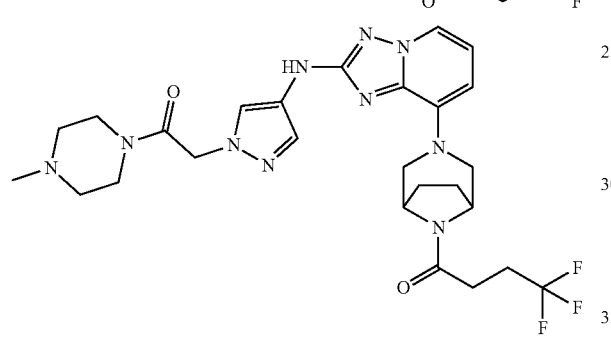
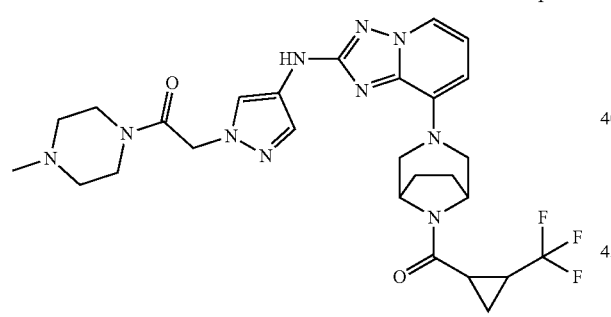
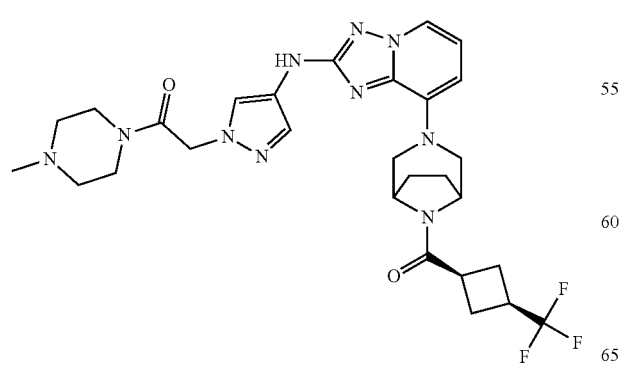
270
-continued
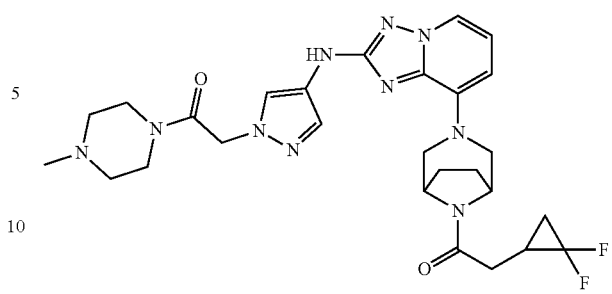
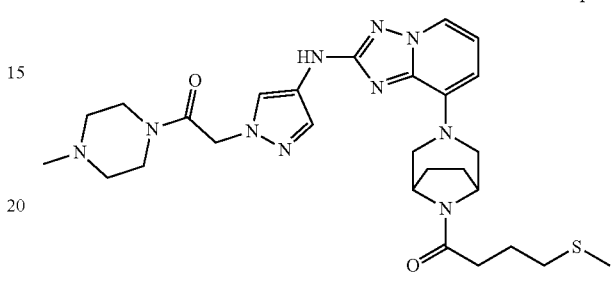
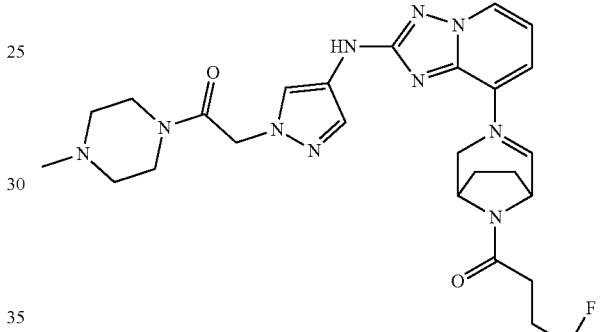
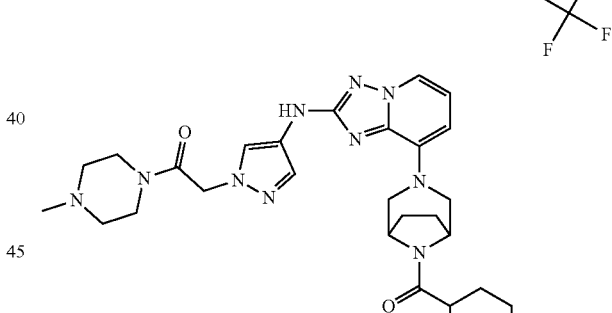

271
-continued
272
-continued
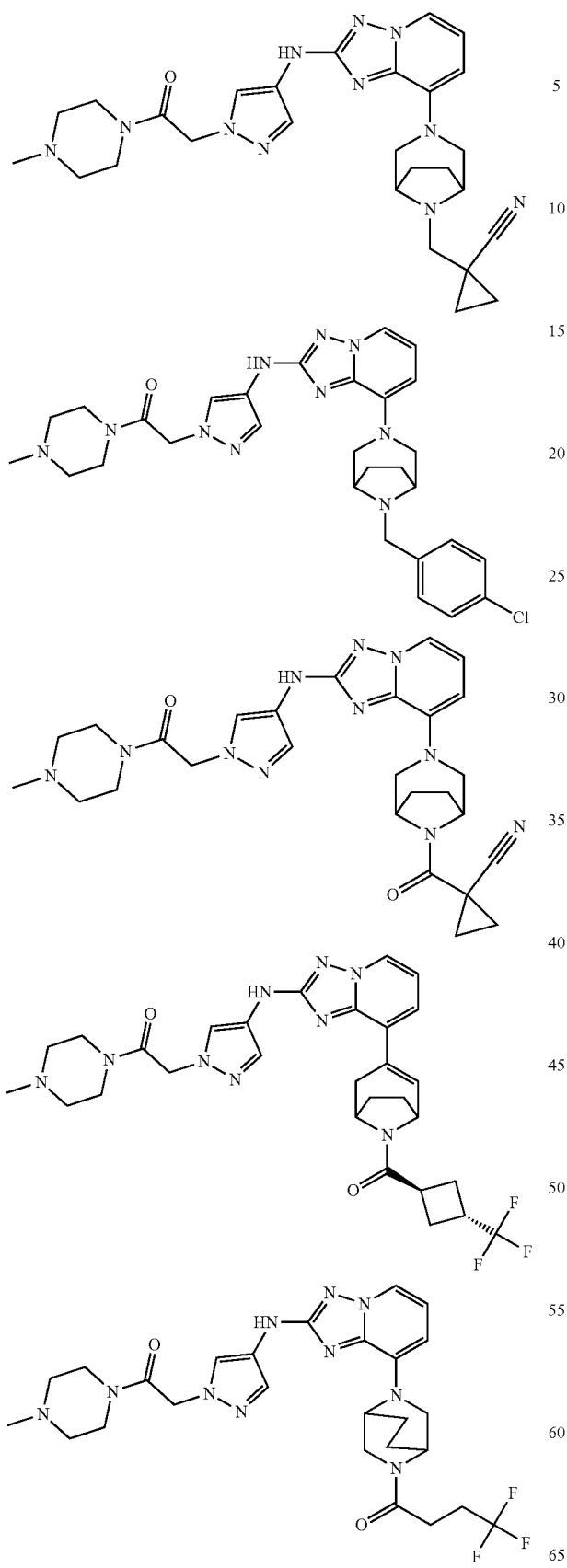
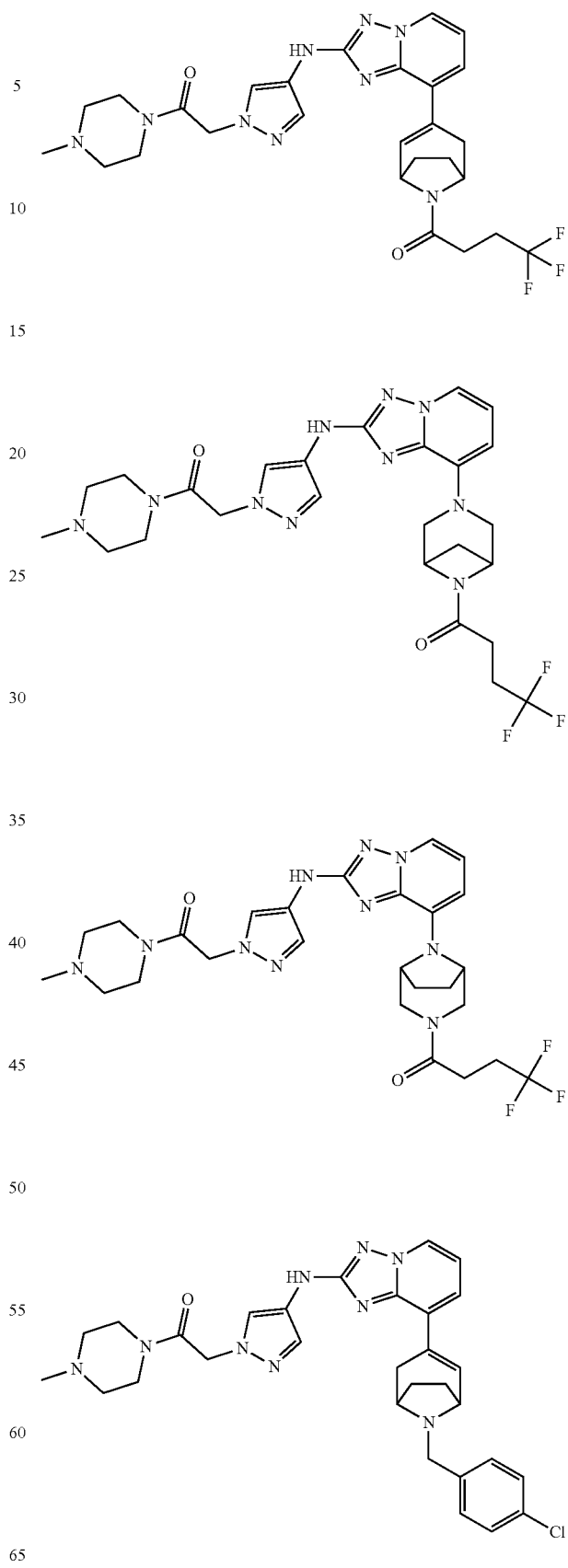

273
-continued
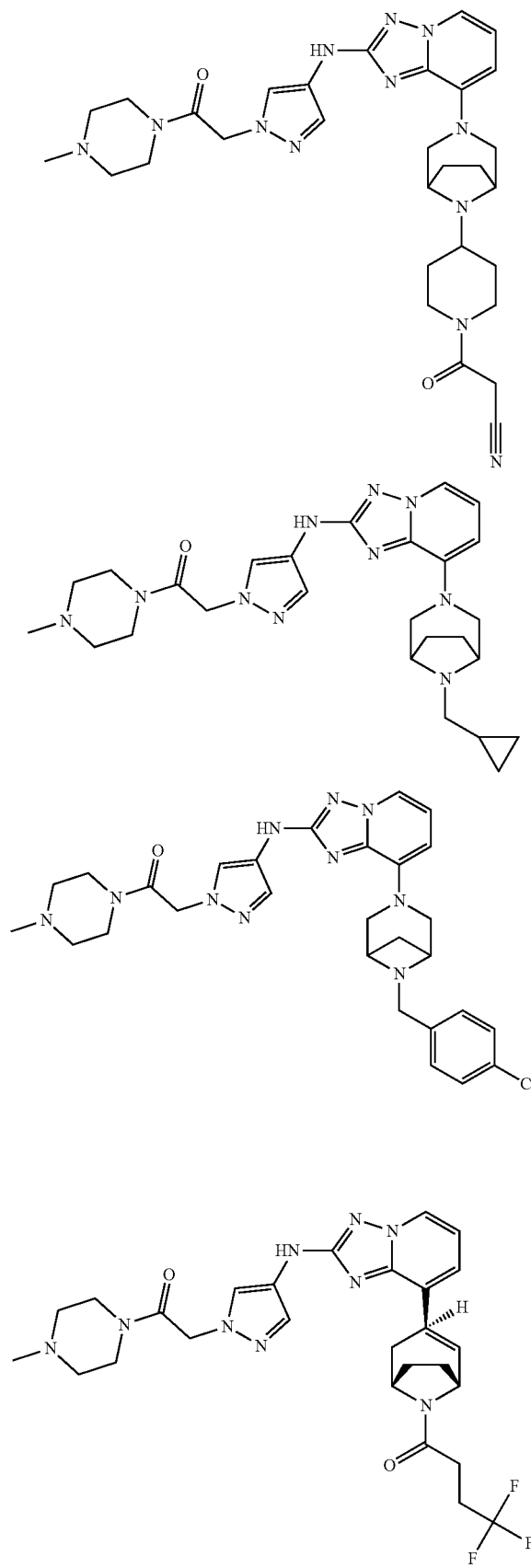
274
-continued
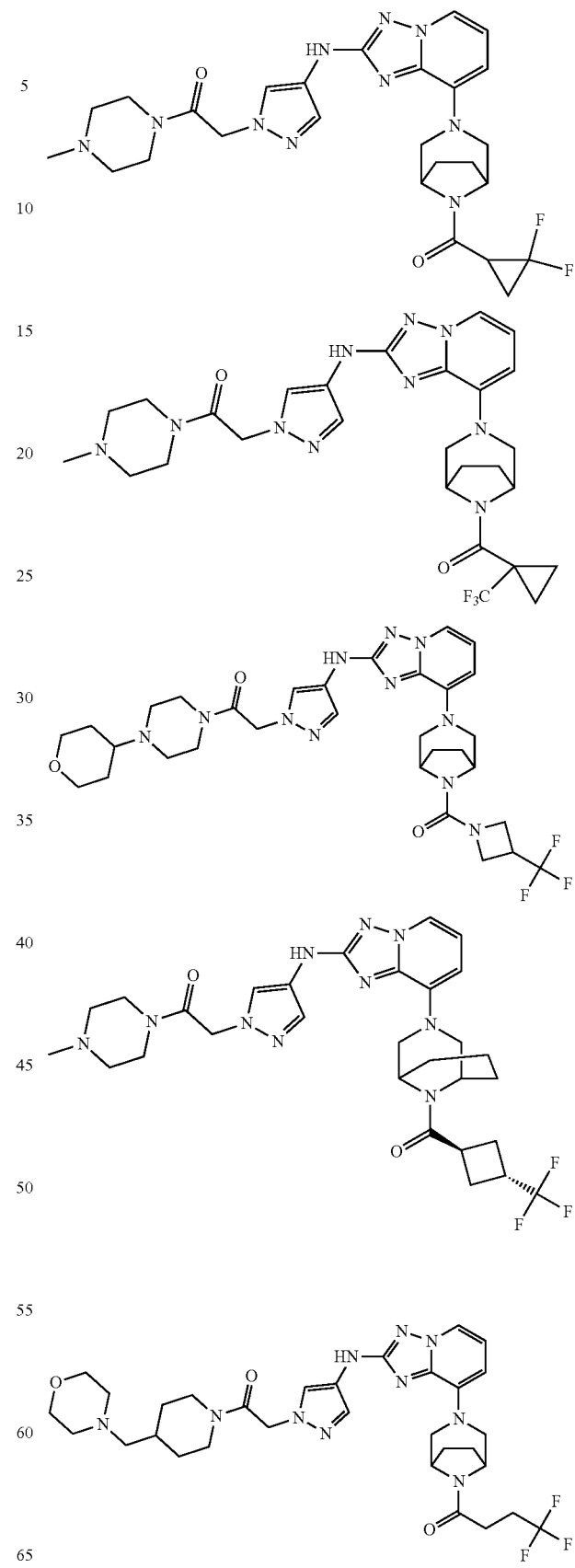

275
-continued

276
-continued

277
-continued
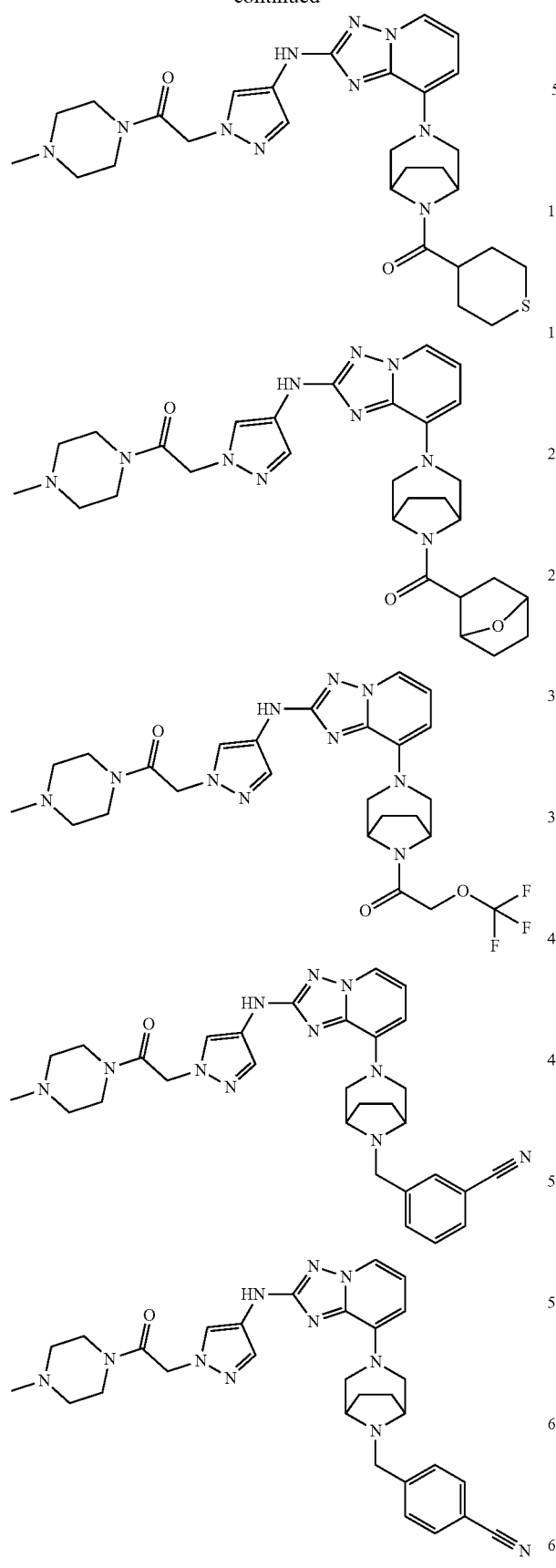
278
-continued
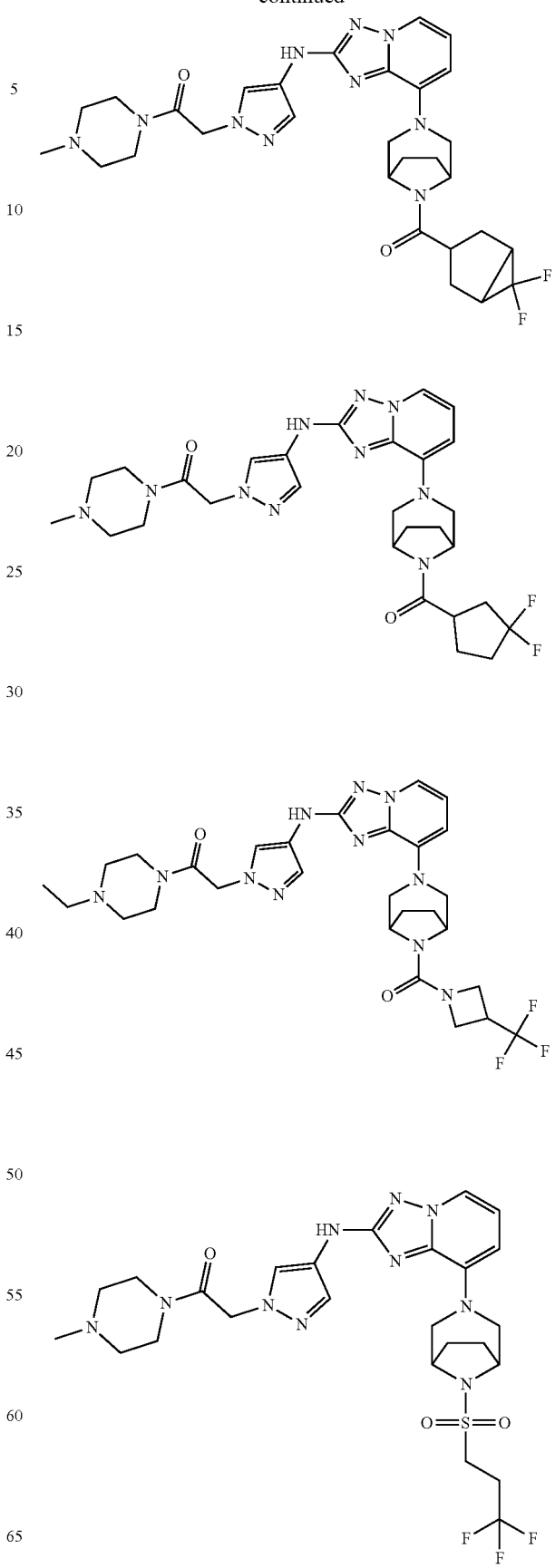

-continued
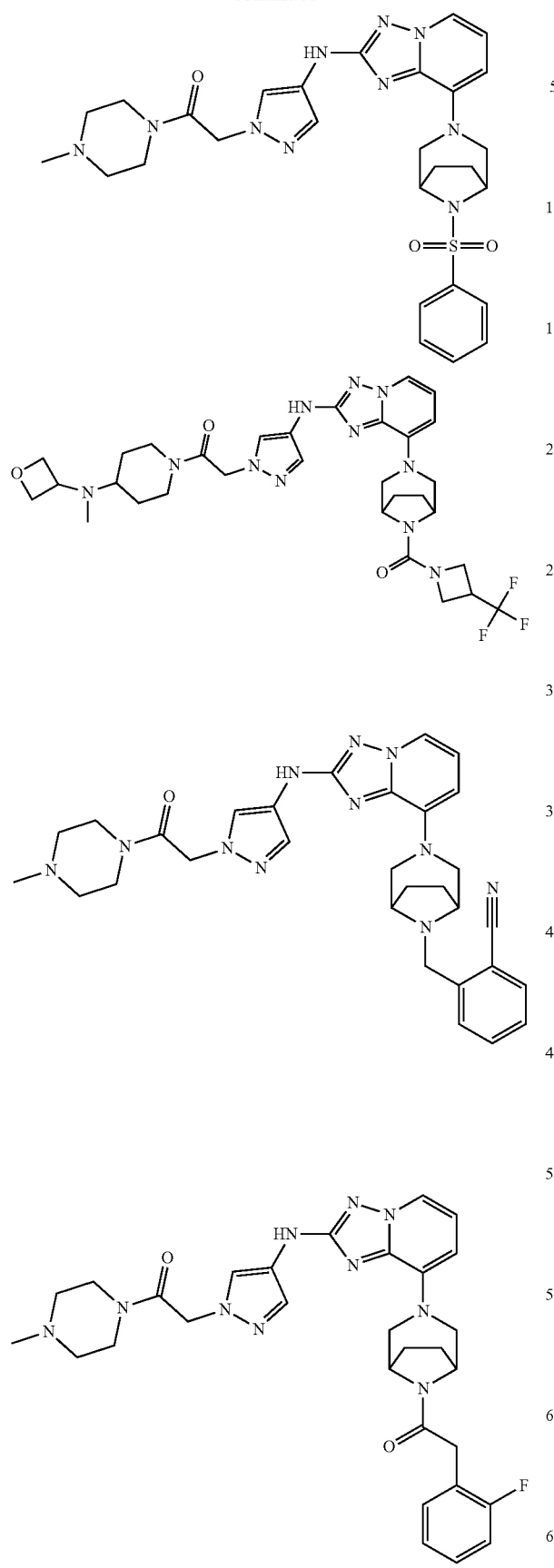
-continued
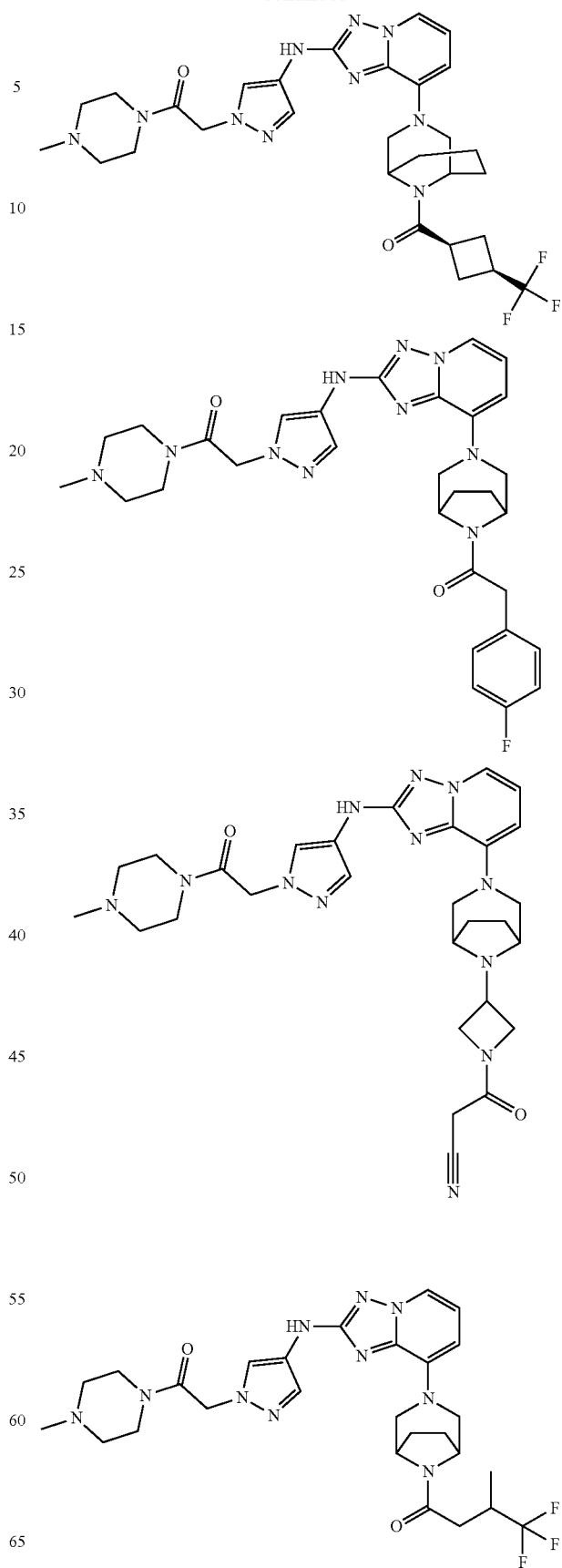

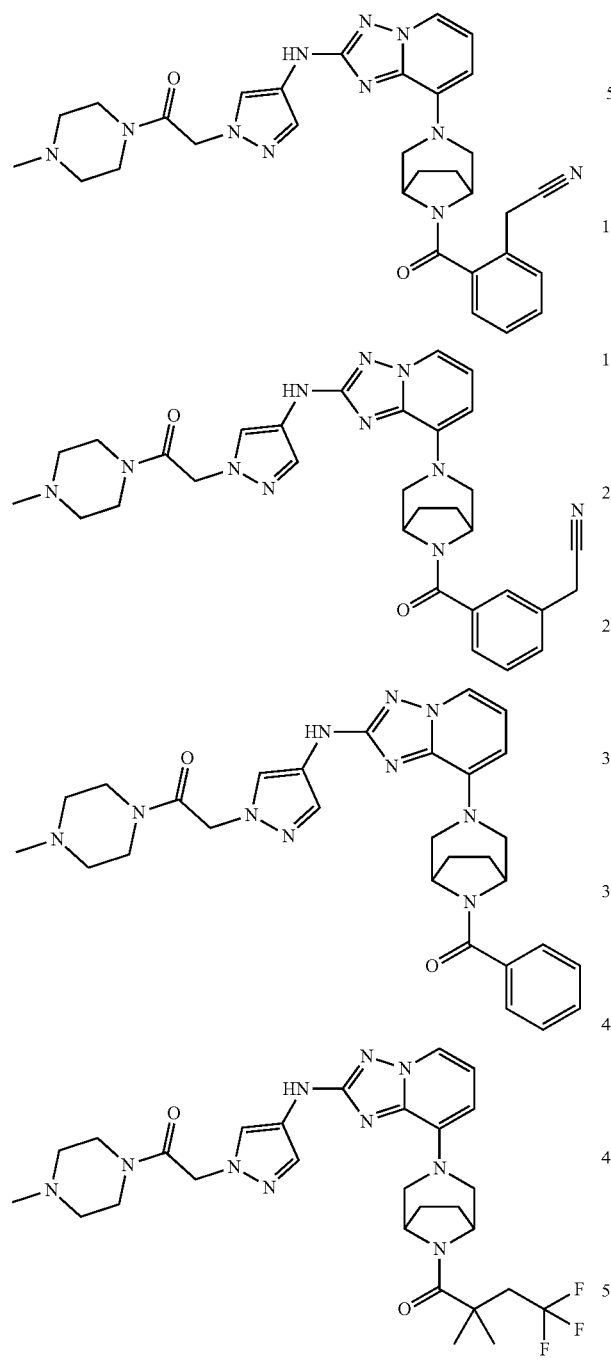
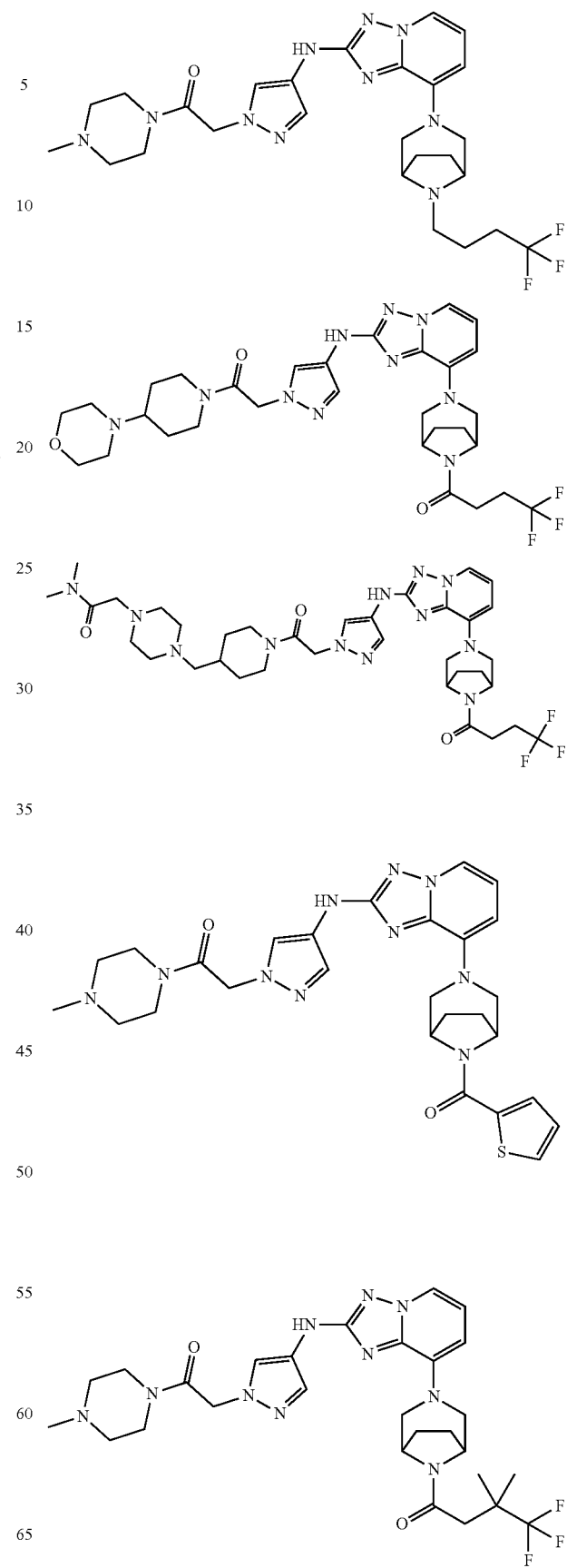

283
-continued
284
-continued
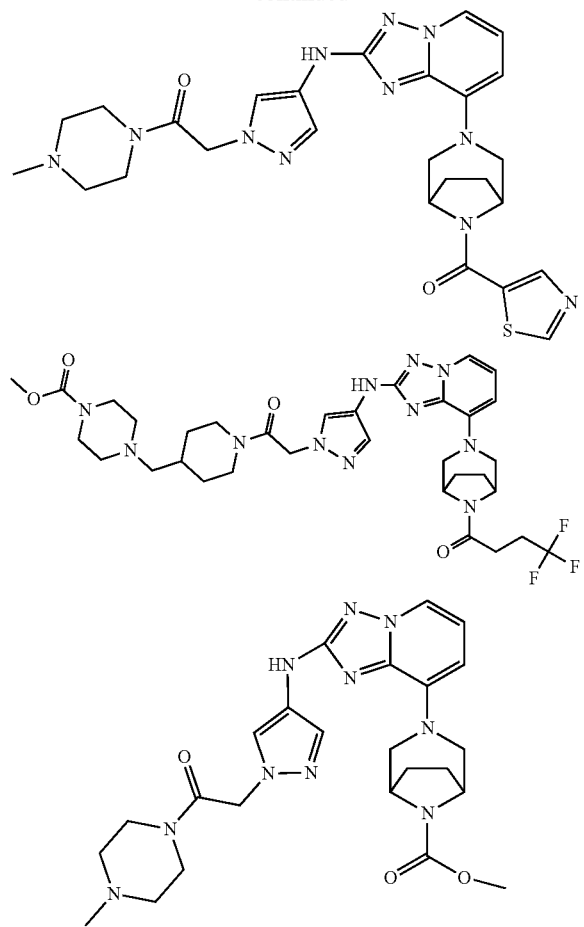
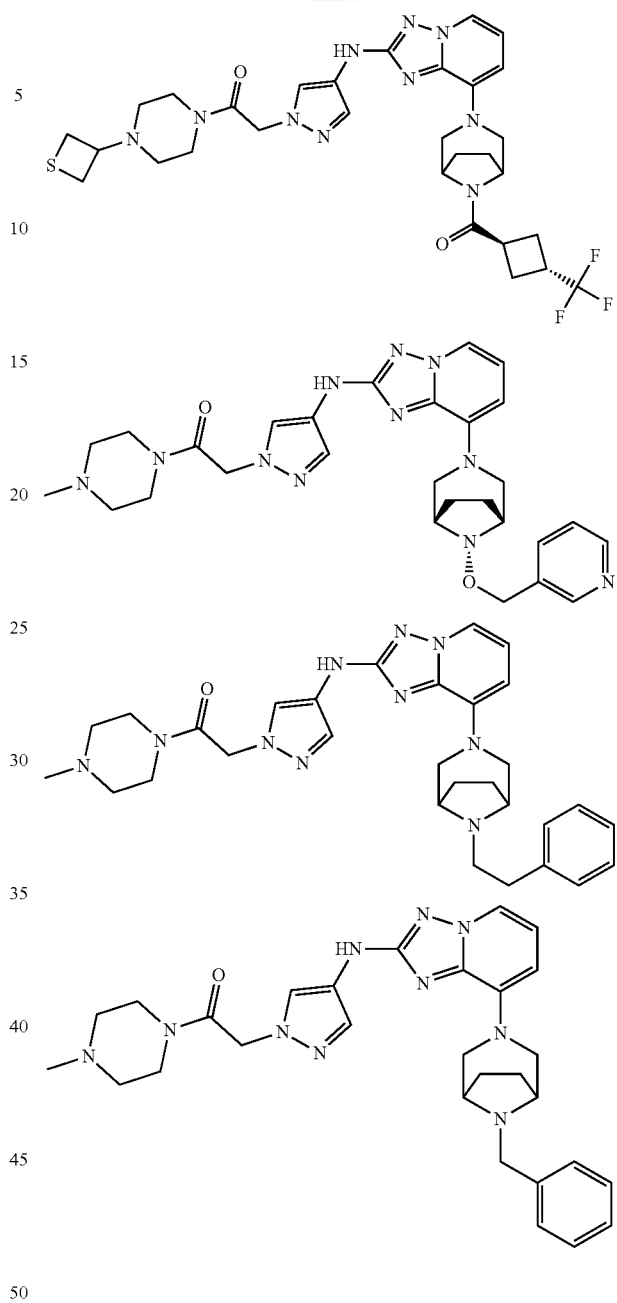
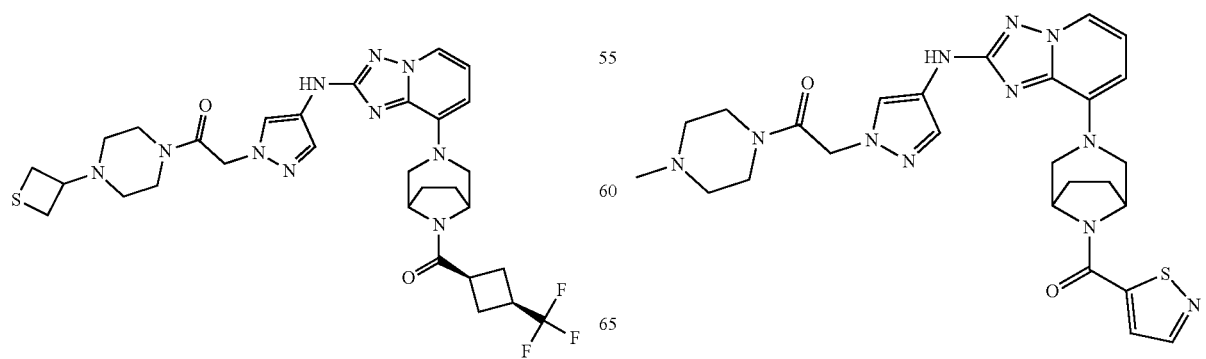

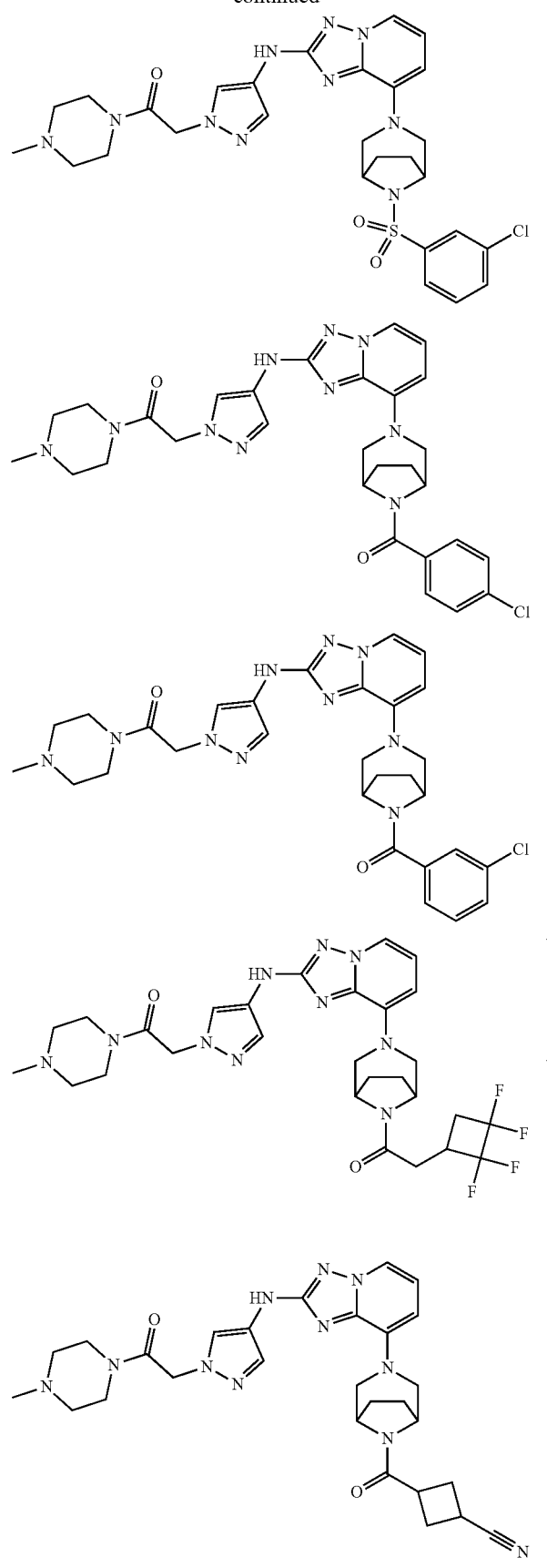
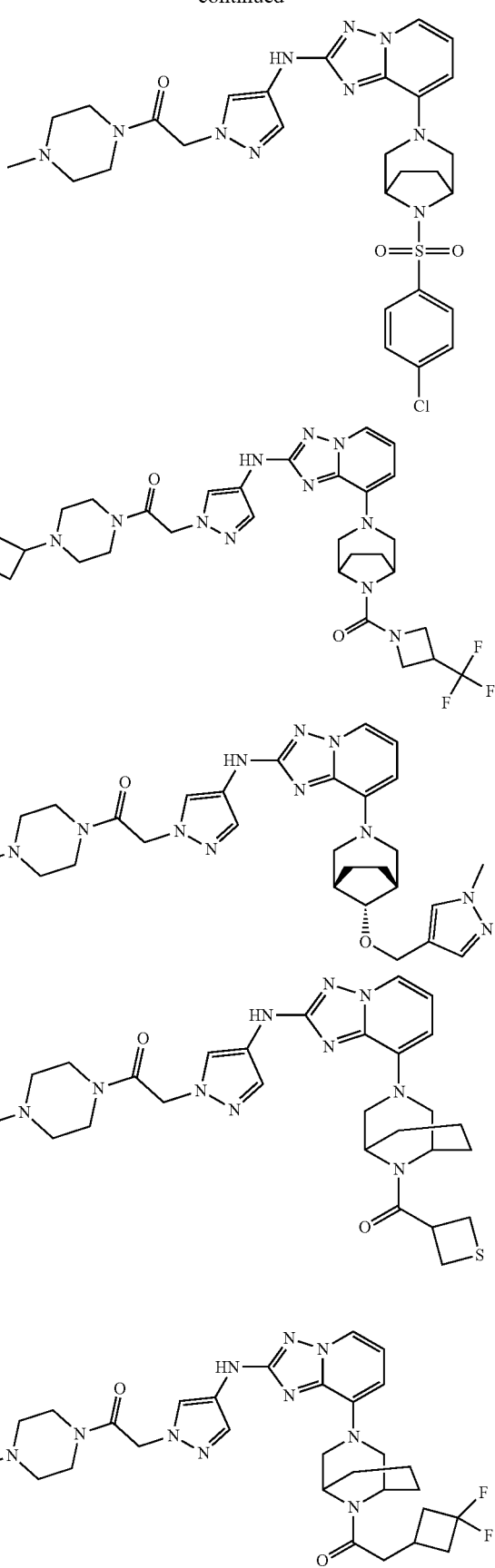

287
-continued
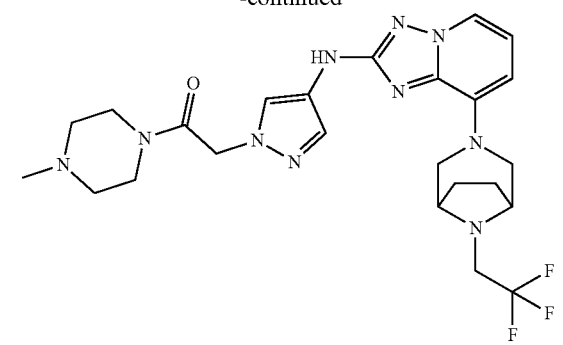
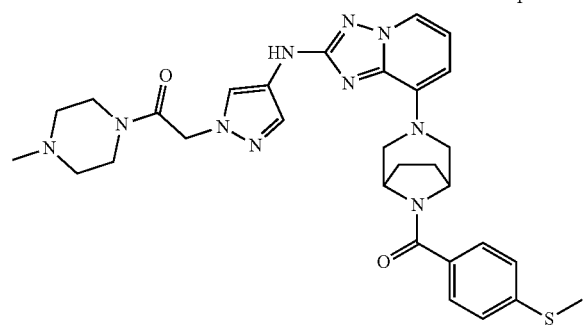
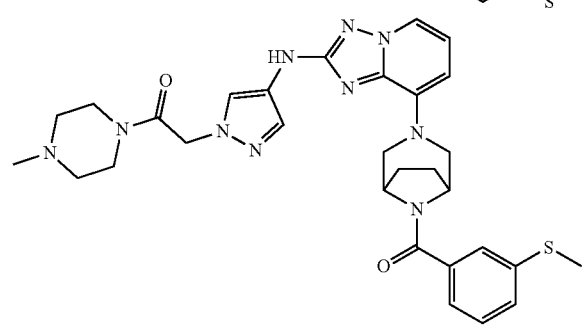
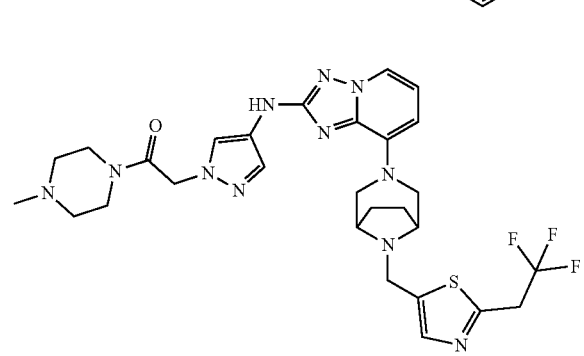
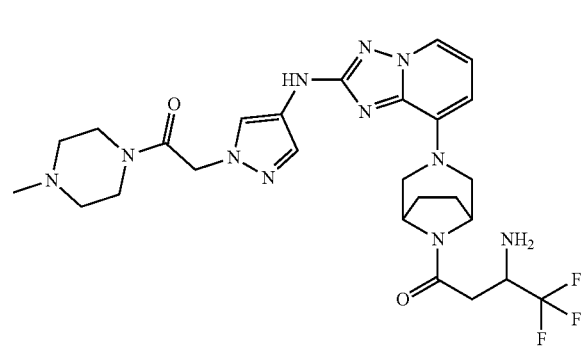
288
-continued
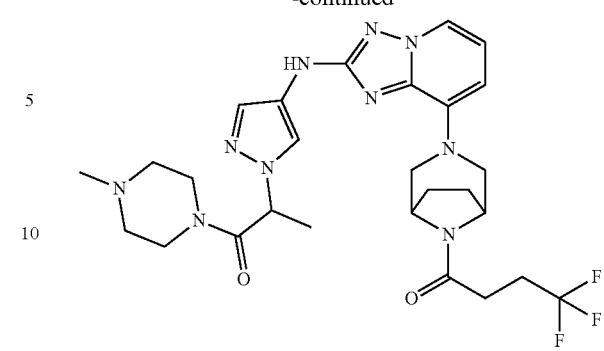
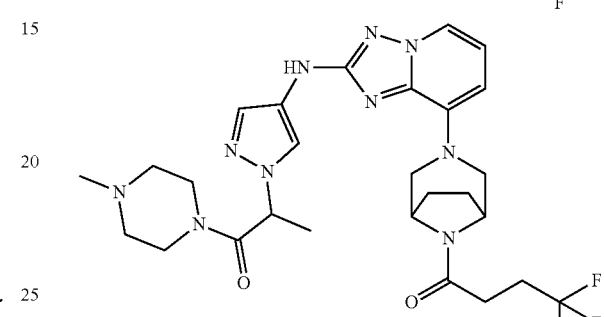
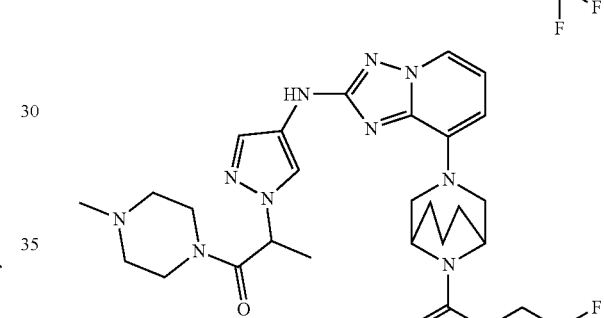
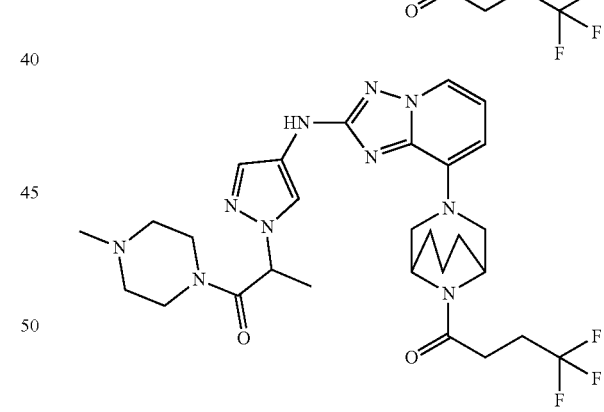
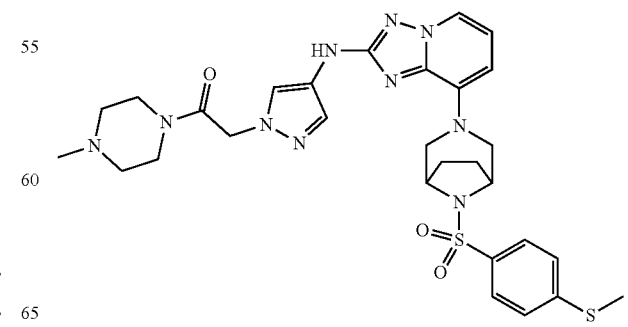

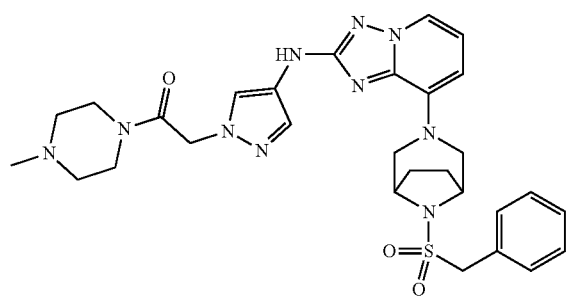
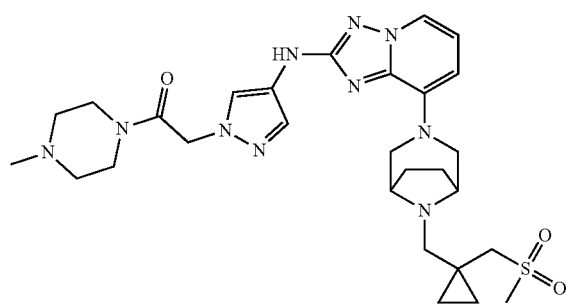
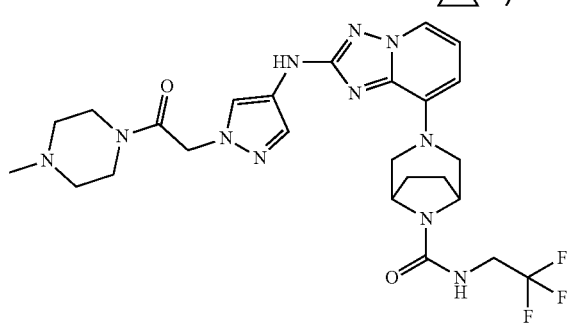
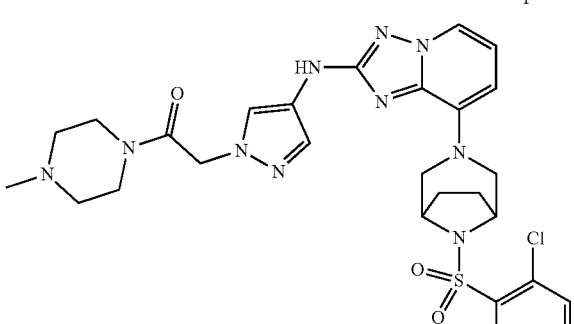
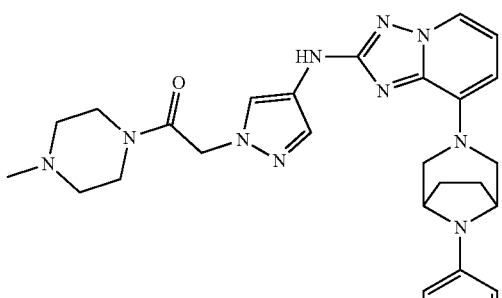
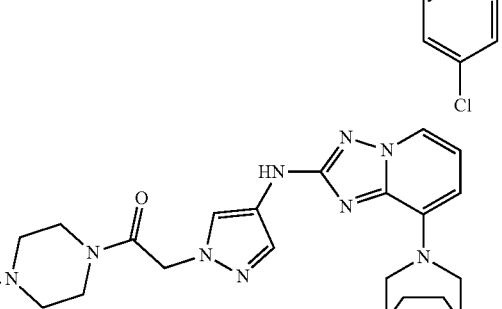
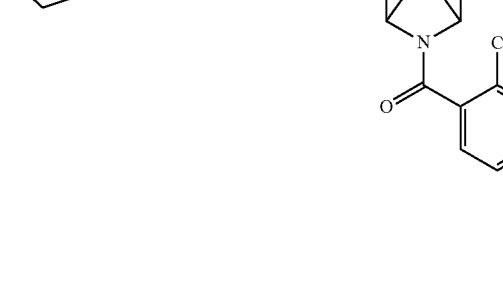
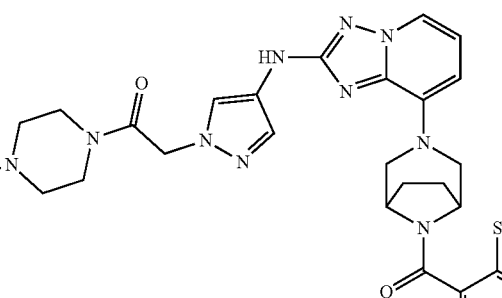
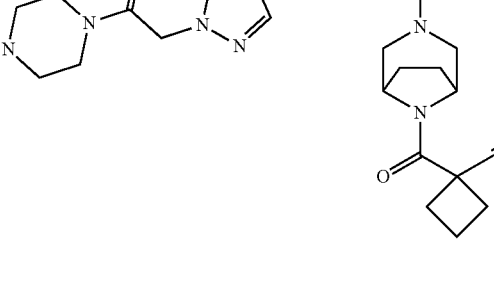

291
-continued
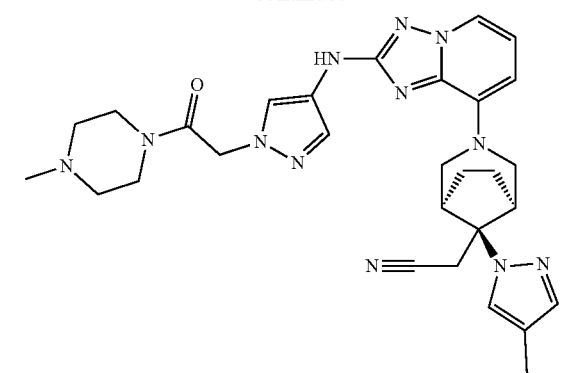
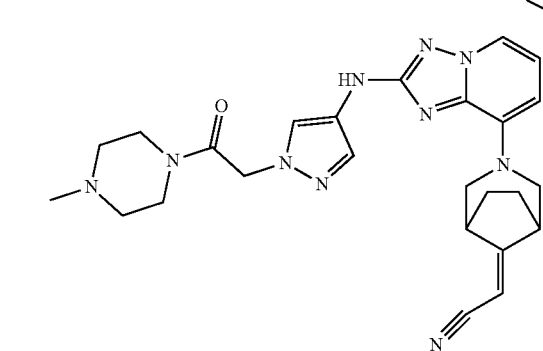
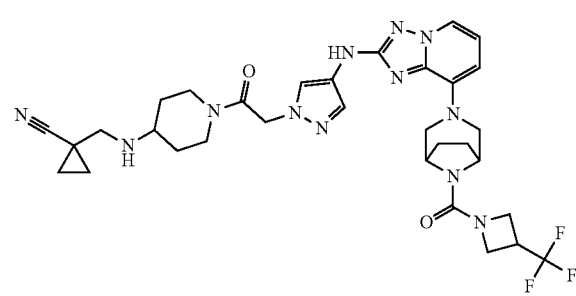
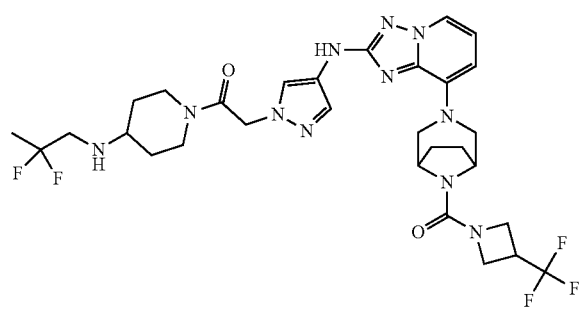
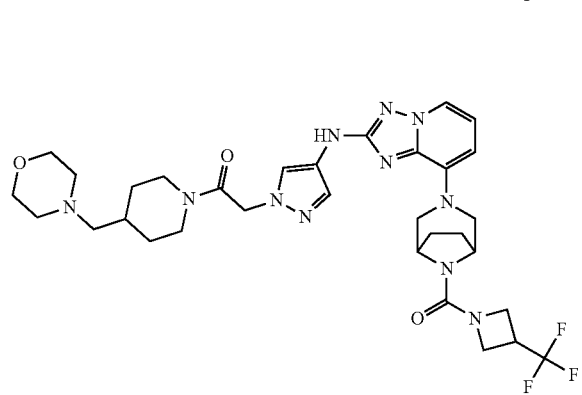
292
-continued
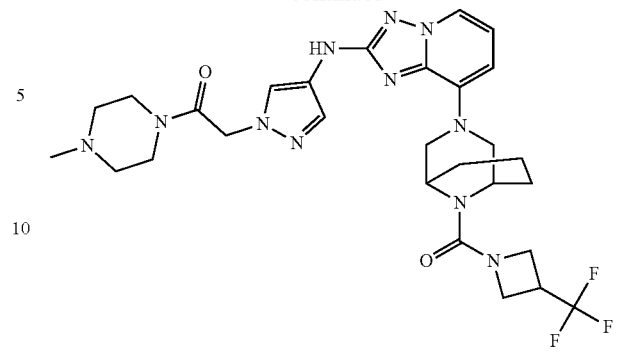
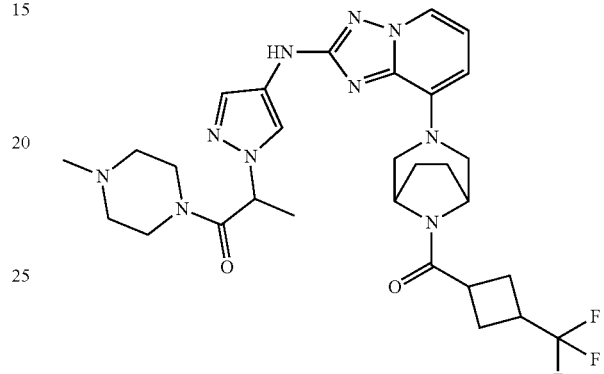
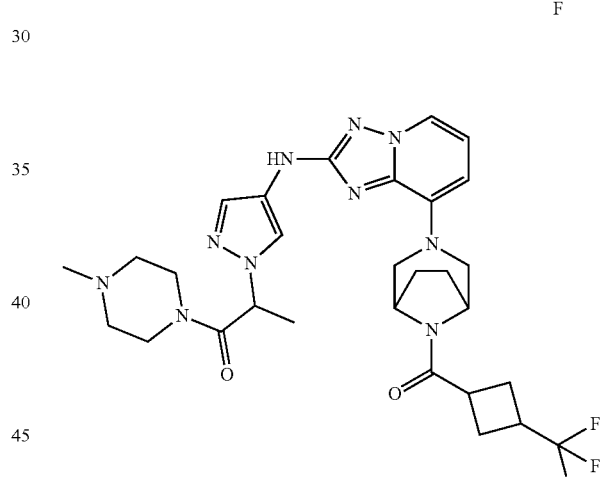
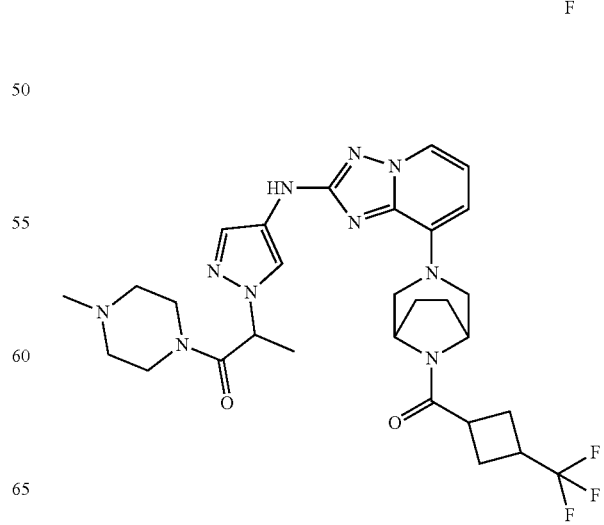

293
-continued
294
-continued
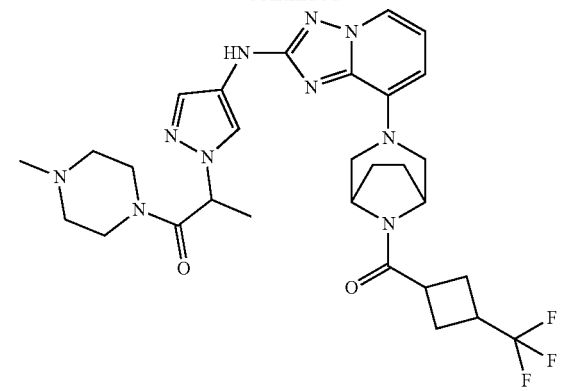
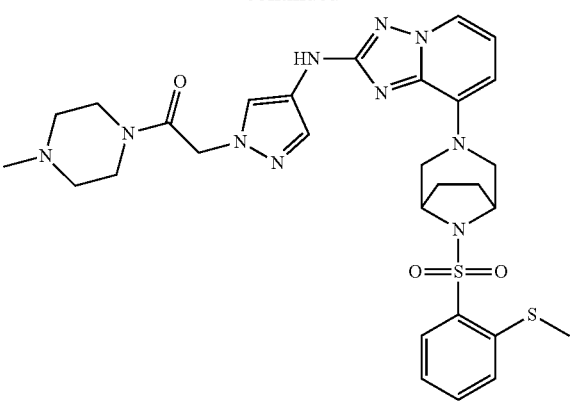
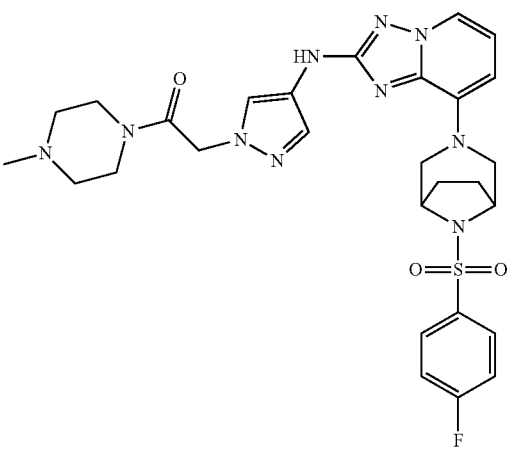

295
-continued
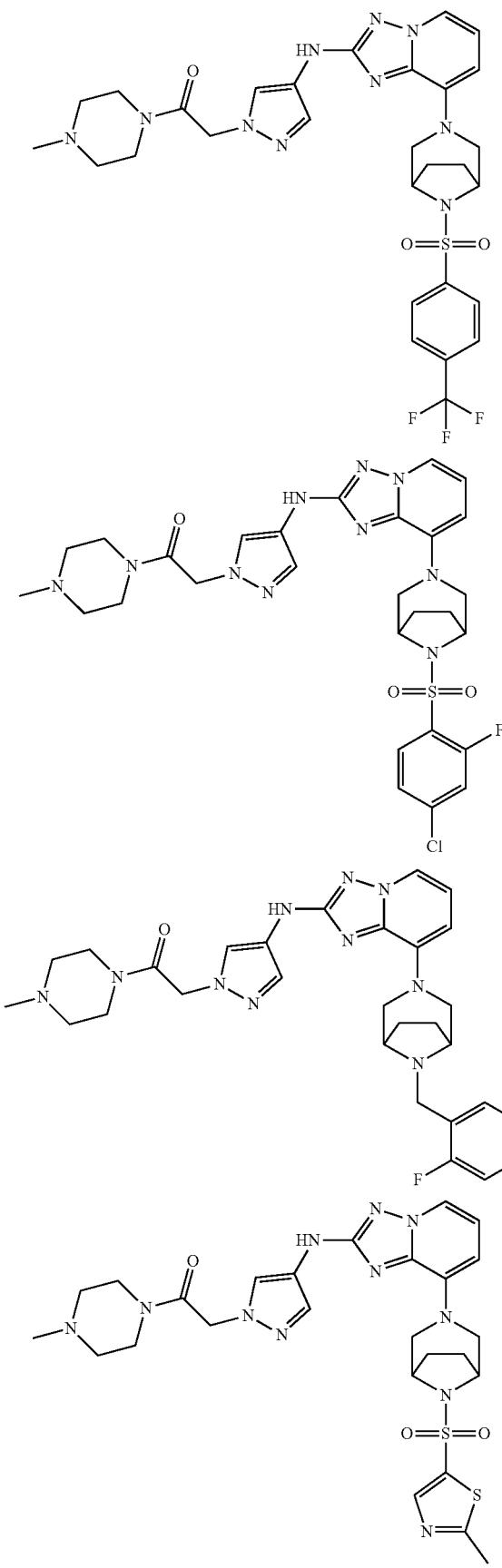
296
-continued
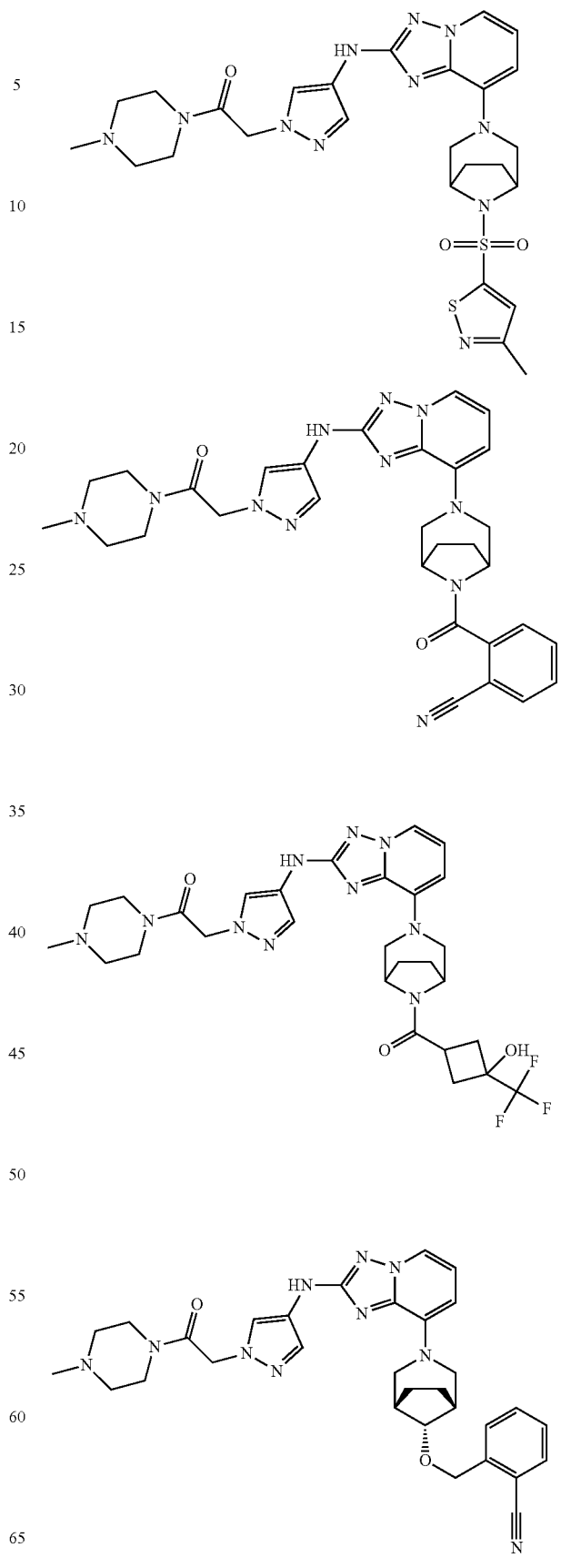

-continued
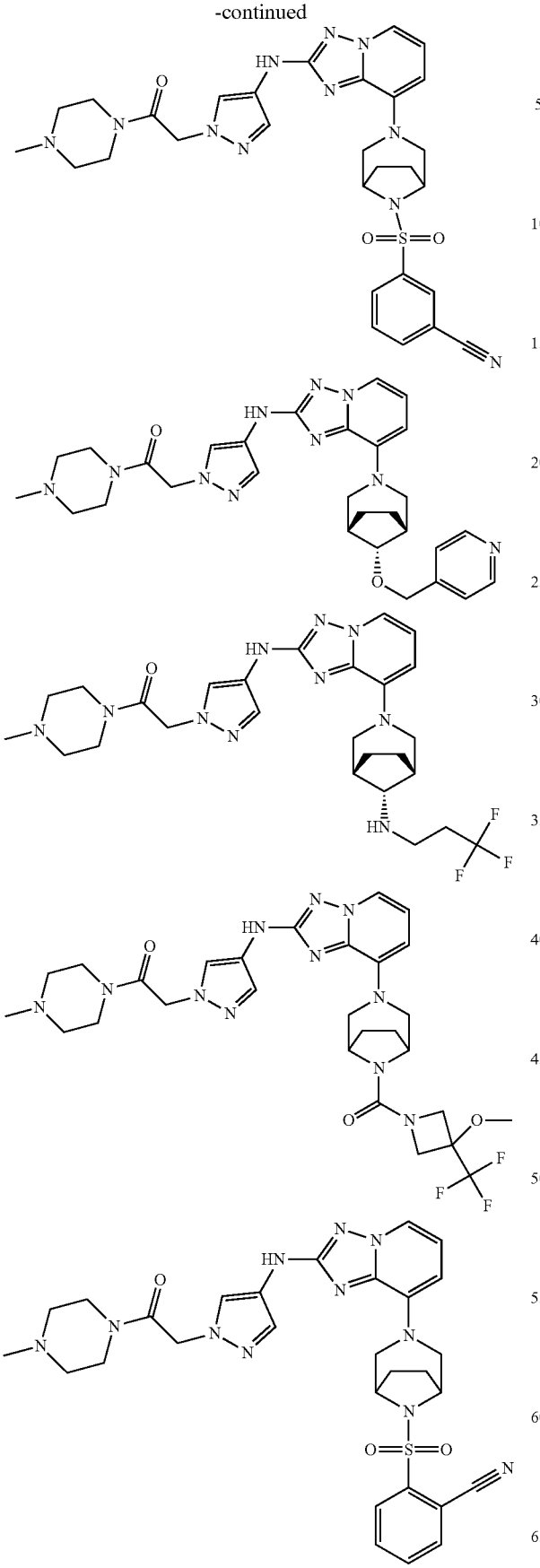
-continued
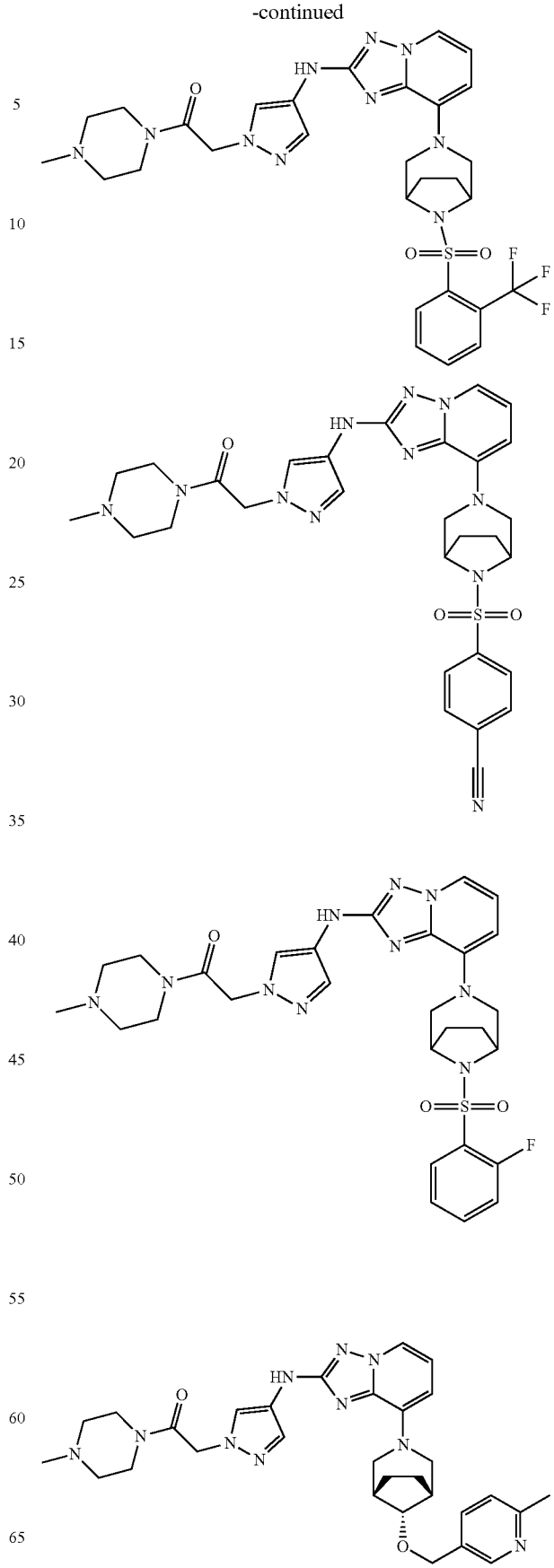

299
-continued
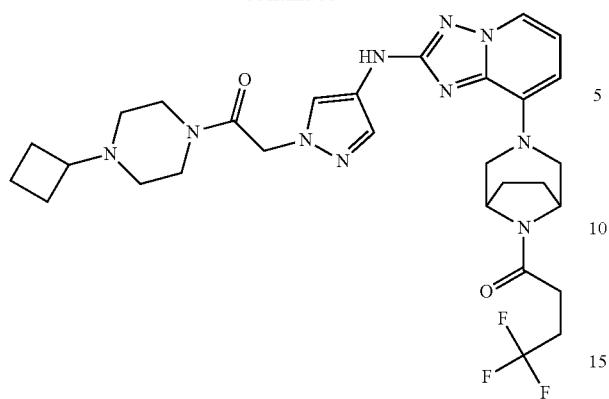
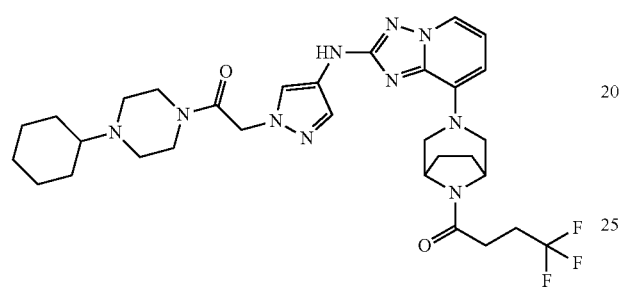
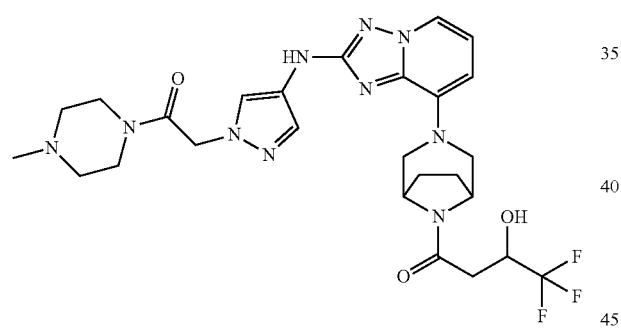
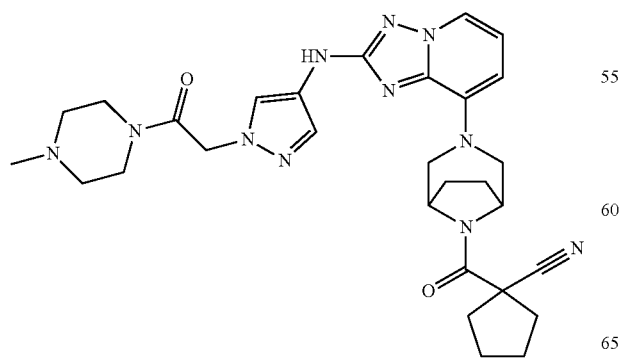
300
-continued
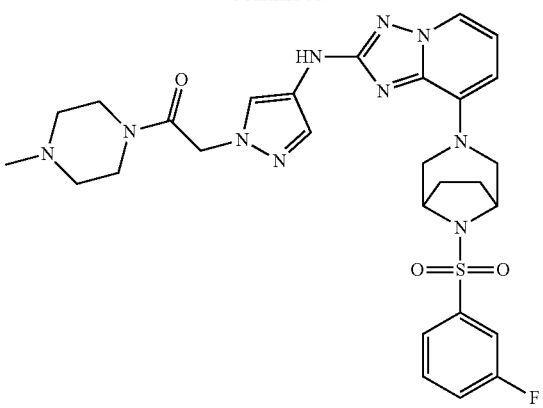
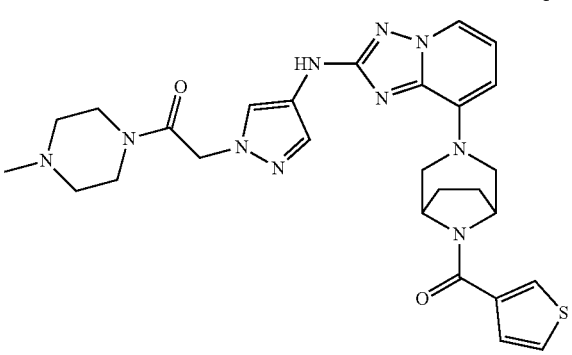
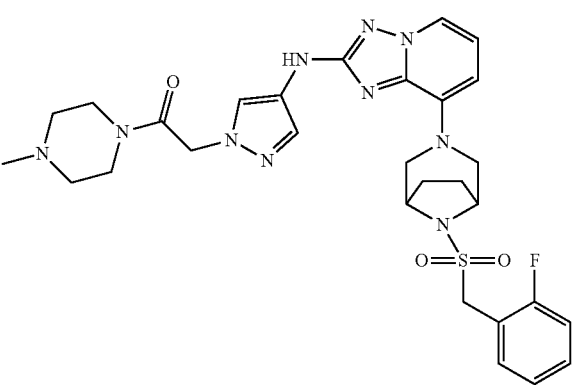
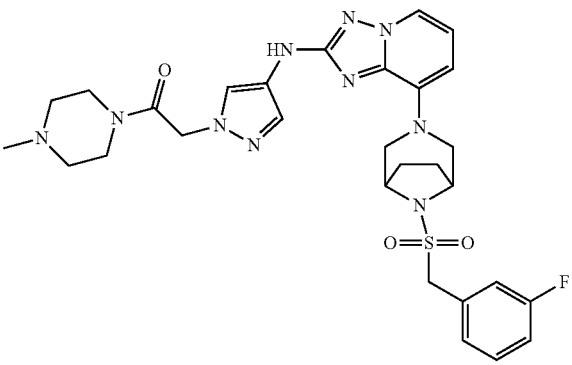

301
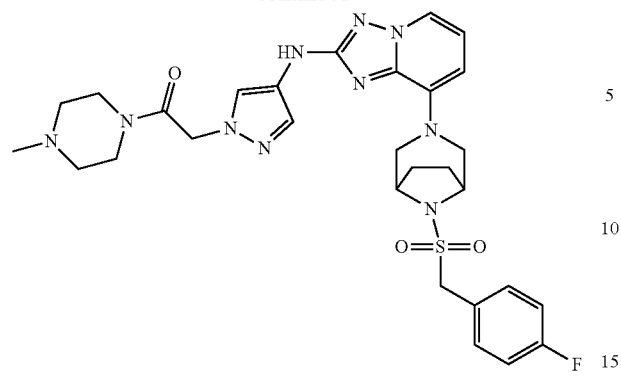
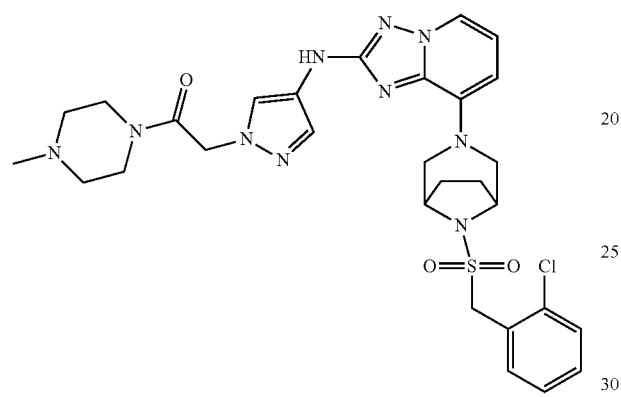
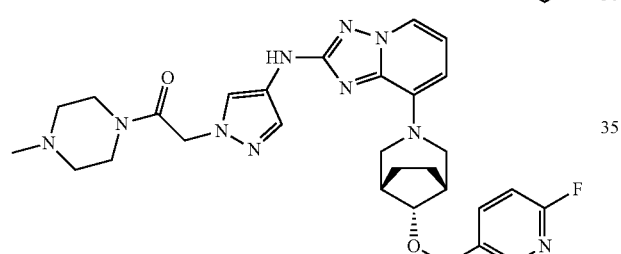
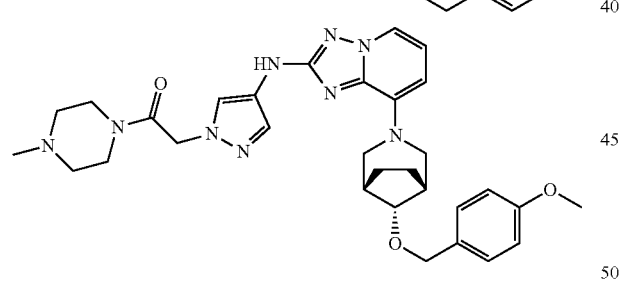
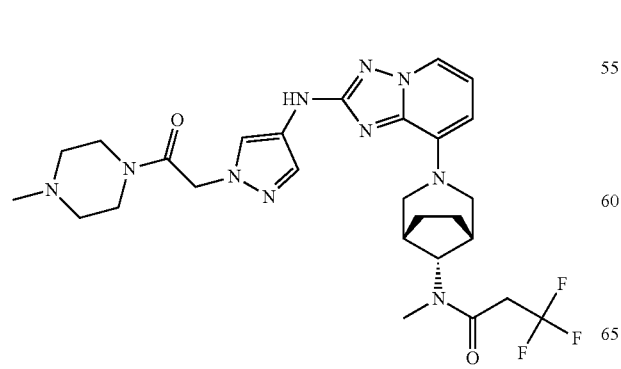
302
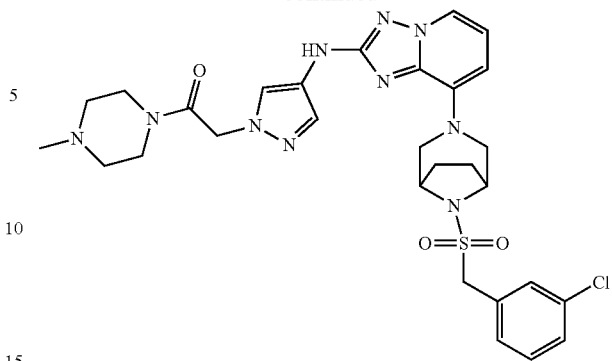
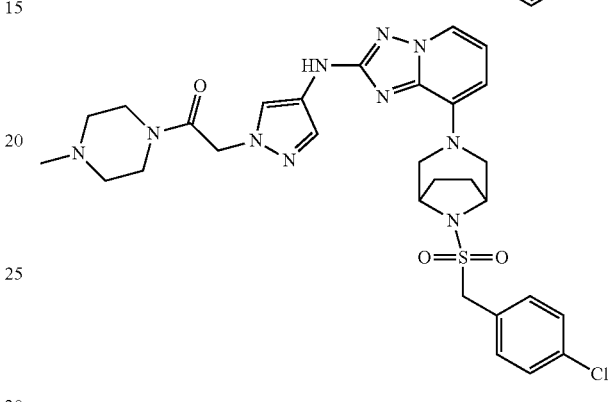
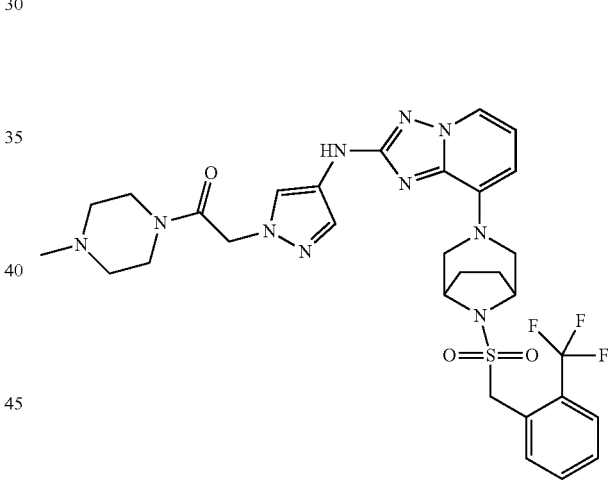
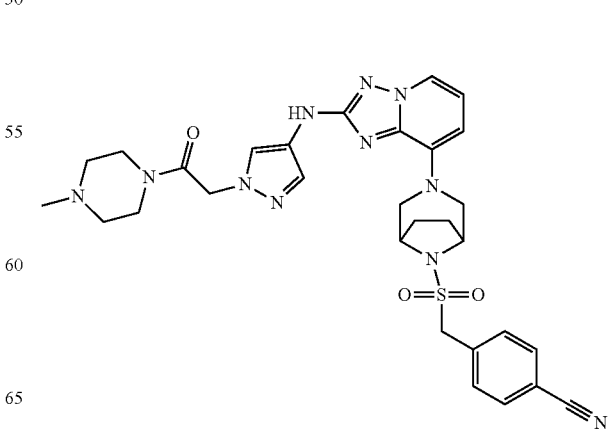

303
-continued
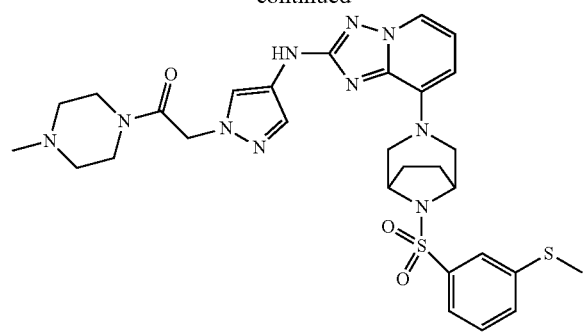
304
-continued
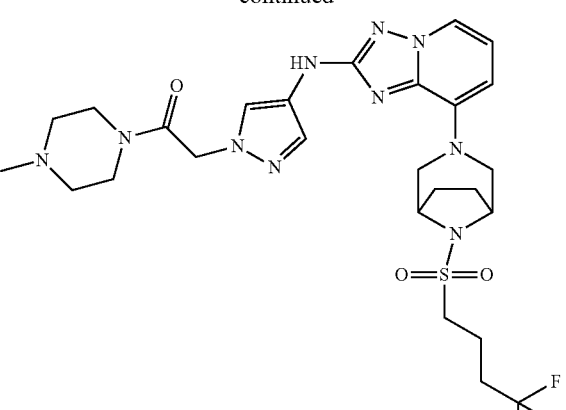
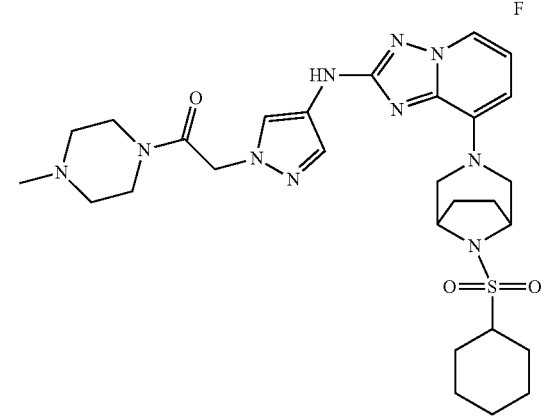
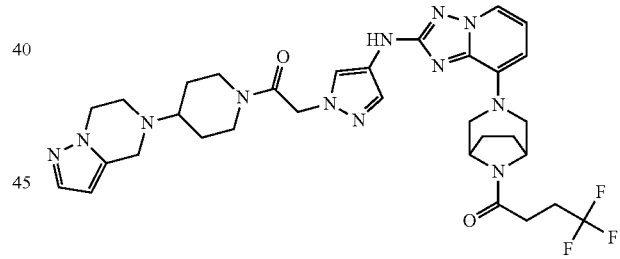
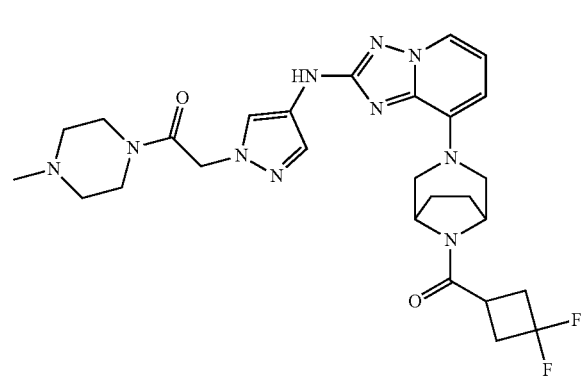

305
-continued
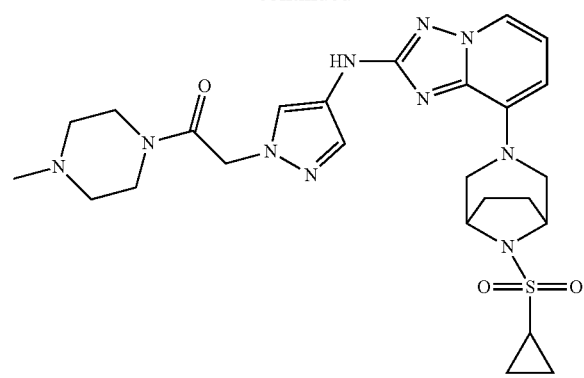
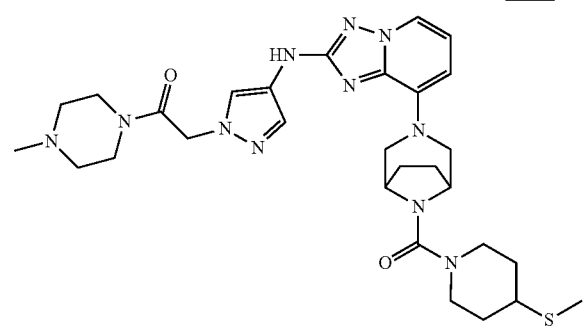
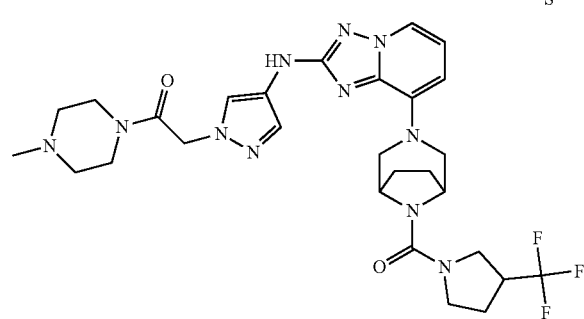
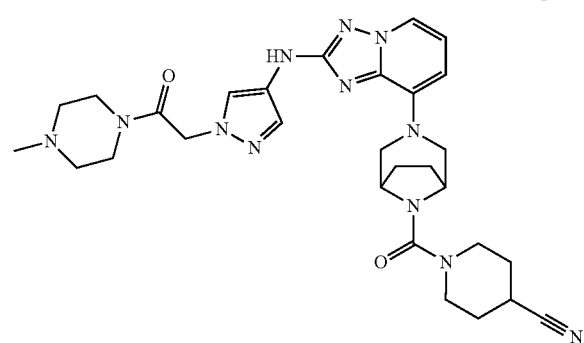
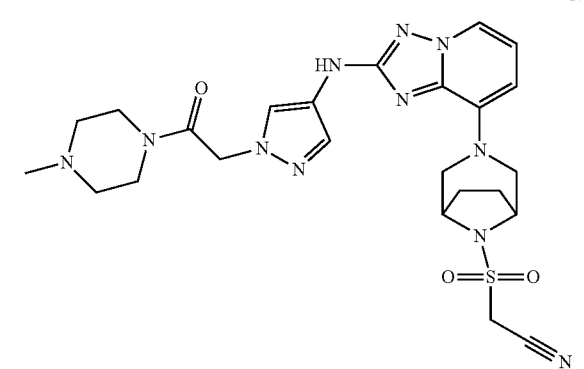
306
-continued
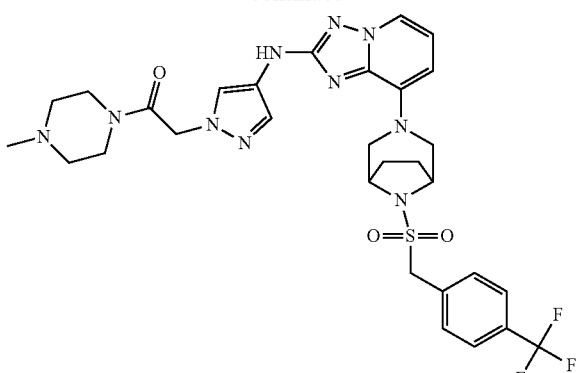
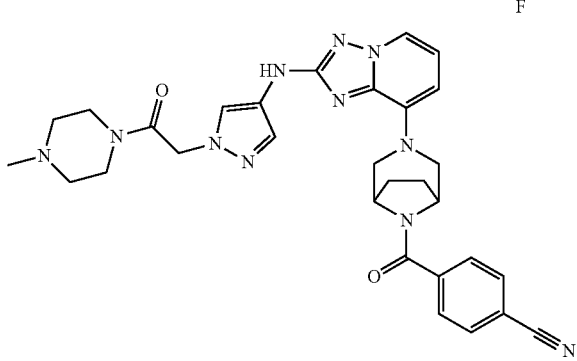
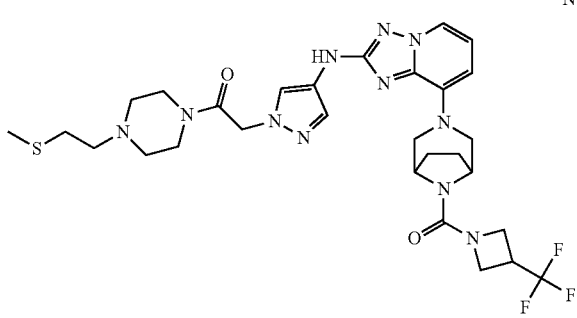
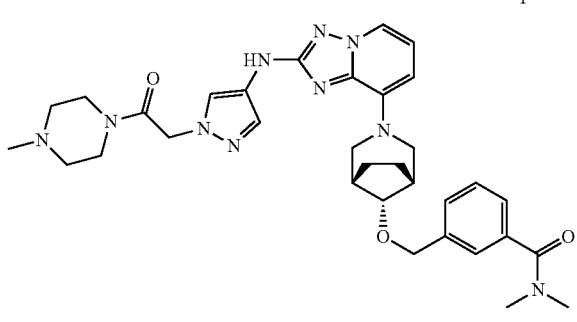
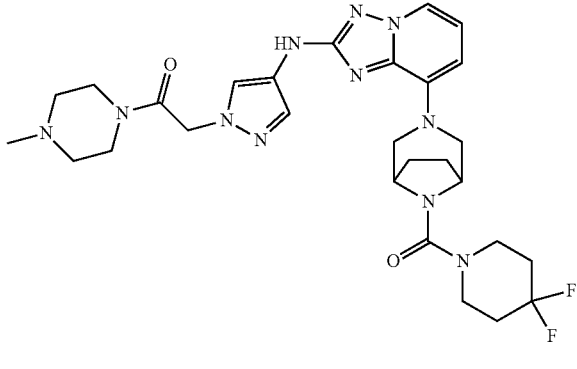

307
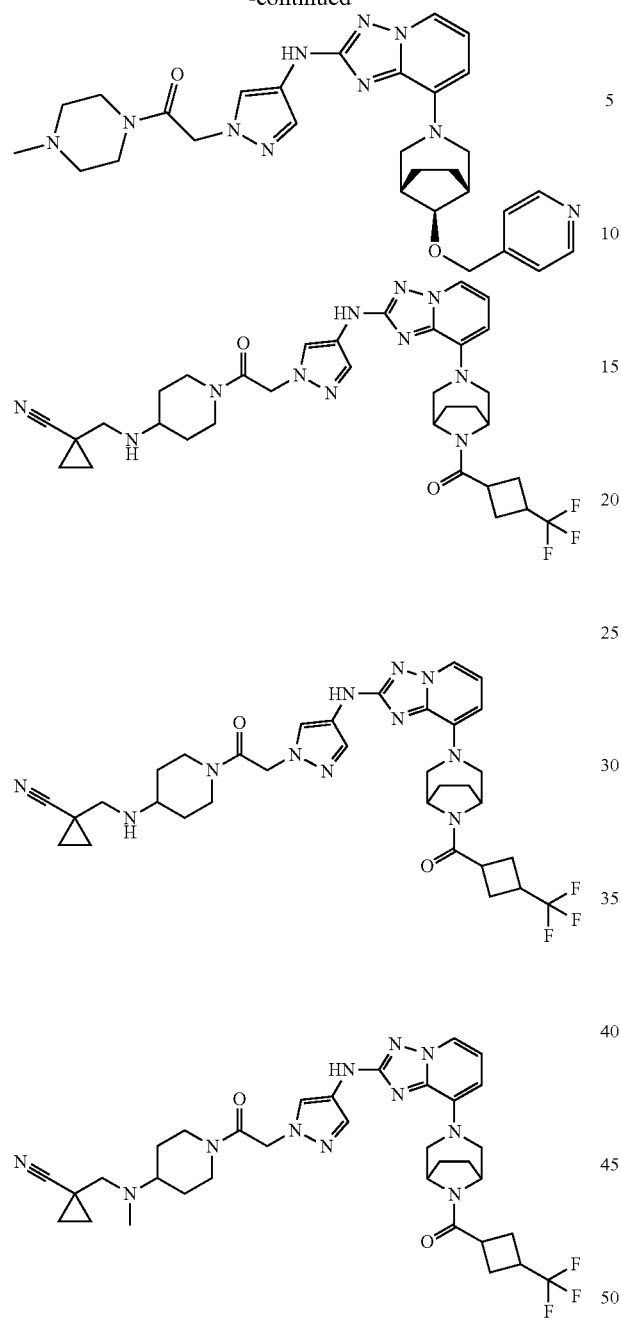
308
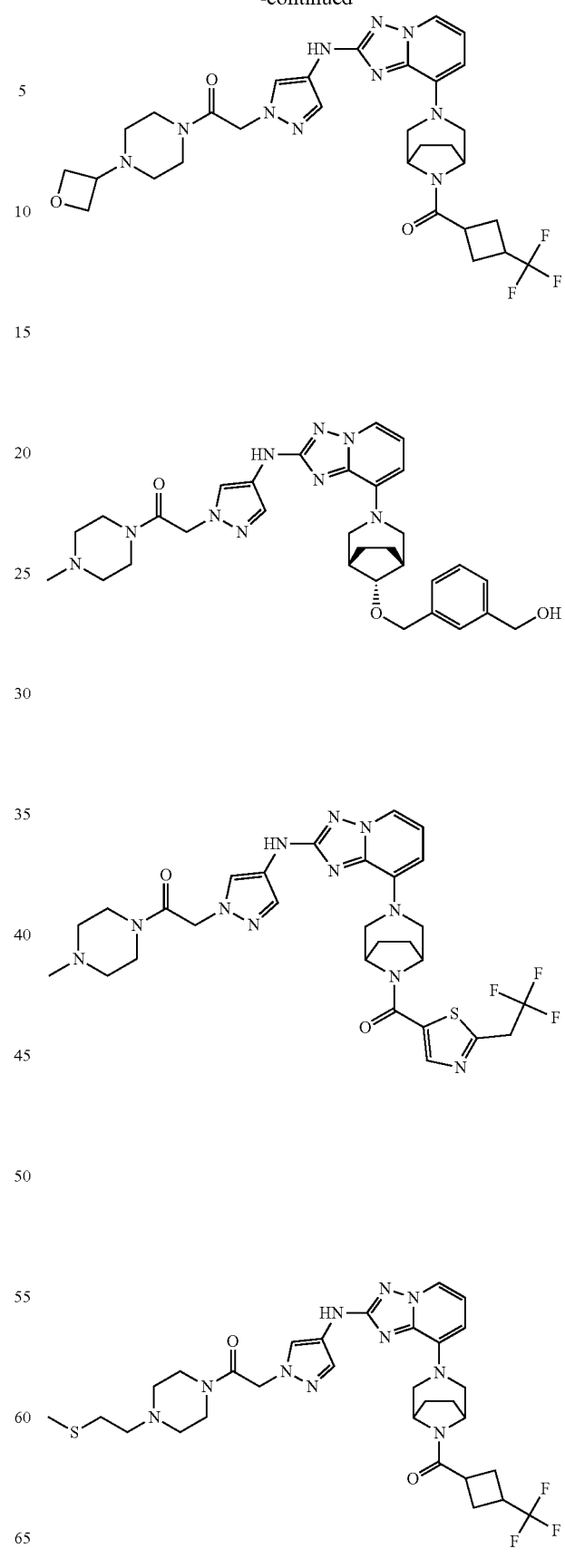

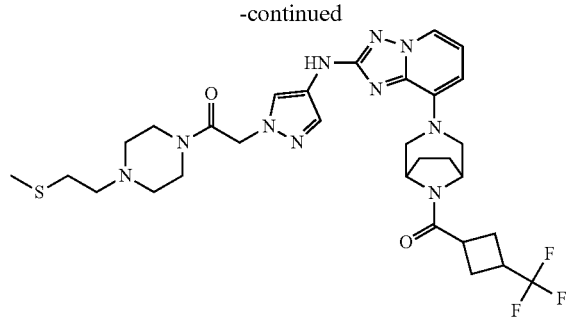

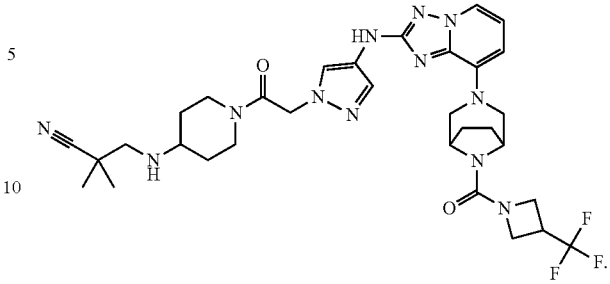

or a salt or stereoisomer thereof.

12. A pharmaceutical composition comprising a compound of claim 1, or a salt or stereoisomer thereof, and a pharmaceutically acceptable carrier, diluent or excipient.

13. A method of preventing, treating or lessening the severity of a disease or condition responsive to the inhibition of a Janus kinase activity in a patient, comprising administering to the patient a therapeutically effective amount of a compound of claim 1 or a stereoisomer thereof, or a pharmaceutically acceptable salt thereof.

14. The method of claim 13, wherein the disease or condition is asthma.

15. The method of claim 13, wherein the Janus kinase is JAK1.

* * * * *